(12) United States Patent
Sentman et al.

(10) Patent No.: US 12,060,394 B2
(45) Date of Patent: Aug. 13, 2024

(54) NUCLEIC ACID CONSTRUCTS FOR CO-EXPRESSION OF CHIMERIC ANTIGEN RECEPTOR AND TRANSCRIPTION FACTOR, CELLS CONTAINING AND THERAPEUTIC USE THEREOF

(71) Applicant: THE TRUSTEES OF DARTMOUTH COLLEGE, Hanover, NH (US)

(72) Inventors: Charles L. Sentman, Grantham, NH (US); Albert Gacerez, Lebanon, NH (US)

(73) Assignee: THE TRUSTEES OF DARTMOUTH COLLEGE, Hanover, NH (US)

( * ) Notice: Subject to any disclaimer, the term of this patent is extended or adjusted under 35 U.S.C. 154(b) by 611 days.

(21) Appl. No.: 16/096,562

(22) PCT Filed: Apr. 28, 2017

(86) PCT No.: PCT/US2017/030284
§ 371 (c)(1),
(2) Date: Oct. 25, 2018

(87) PCT Pub. No.: WO2017/190100
PCT Pub. Date: Nov. 2, 2017

(65) Prior Publication Data
US 2022/0025001 A1 Jan. 27, 2022

Related U.S. Application Data

(60) Provisional application No. 62/328,936, filed on Apr. 28, 2016.

(51) Int. Cl.
| | |
|---|---|
| *C07K 14/47* | (2006.01) |
| *A61K 35/17* | (2015.01) |
| *A61P 35/00* | (2006.01) |
| *C07K 14/705* | (2006.01) |
| *C07K 14/725* | (2006.01) |
| *C07K 16/28* | (2006.01) |
| *C12N 15/86* | (2006.01) |

(52) U.S. Cl.
CPC .......... *C07K 14/4702* (2013.01); *A61K 35/17* (2013.01); *A61P 35/00* (2018.01); *C07K 14/7051* (2013.01); *C07K 14/70521* (2013.01); *C07K 16/2827* (2013.01); *C12N 15/86* (2013.01); *C07K 2317/622* (2013.01); *C07K 2319/03* (2013.01); *C07K 2319/33* (2013.01); *C12N 2740/10043* (2013.01)

(58) Field of Classification Search
CPC ............ C07K 14/4702; C07K 14/7051; C07K 14/70521; C07K 16/2827; C07K 2317/622; C07K 2319/03; C07K 2319/33; C07K 16/00; A61K 35/17; A61K 38/1796; A61K 39/39558; A61K 48/005; A61P 35/00; C12N 15/86; C12N 2740/10043
See application file for complete search history.

(56) References Cited

U.S. PATENT DOCUMENTS

| | | | | |
|---|---|---|---|---|
| 2003/0186377 A1* | 10/2003 | Glimcher | ........... | G01N 33/6872 514/6.9 |
| 2004/0120945 A1* | 6/2004 | Tamatani | ................ | A61P 37/08 424/133.1 |
| 2014/0120622 A1 | 5/2014 | Gregory et al. | | |
| 2015/0024482 A1 | 1/2015 | Frigault et al. | | |
| 2016/0264665 A1* | 9/2016 | Lim | ....................... | C07K 14/71 |
| 2018/0044424 A1* | 2/2018 | June | ..................... | C12N 5/0636 |

FOREIGN PATENT DOCUMENTS

| | | | | |
|---|---|---|---|---|
| WO | 2015/157432 | 10/2015 | | |
| WO | WO-2015157432 A1 * | 10/2015 | ............. | A61K 35/17 |

OTHER PUBLICATIONS

Garcia et al. Science, vol. 279, Issue 5354, pp. 1166-1172 (Year: 1998).*
Tong Zhang et. al., J Immunol, 189 (5): 2290-2299 (Year: 2012).*
Gabriella Pietra et al. Journal of Biomedicine and Biotechnology vol. 2010, Article ID 907092, 8 pages (Year: 2010).*
Rudikoff et al. (Proceedings of the National Academy of Sciences USA, vol. 79, p. 1979). (Year: 1980).*
Panka et al. (Proceedings of the National Academy of Sciences USA, vol. 85, 1988) (Year: 1988).*
Lewis et al. (Mol Cell Biol. 27(24): 8510-8521). (Year: 2007).*
M-R Wu et al (Gene Therapy 22, 675-684 (Year: 2015).*
Miriam B. F. Werneck et al.; T-Bet Plays a Key Role in NK-Mediated Control of Melanoma Metastatic Disease; J Immunol (2008) 180 (12): 8004-8010 (Year: 2008).*
Vanja Lazarevic et al., T-bet: a bridge between innate and adaptive immunity; Nat Rev Immunol. Nov. 2013 ; 13(11): 777-789. doi:10. 1038/nri3536. (Year: 2013).*

(Continued)

*Primary Examiner* — James D Schultz
*Assistant Examiner* — Masudur Rahman
(74) *Attorney, Agent, or Firm* — Robin L. Teskin; Baker, Donelson, Bearman, Caldwell & Berkowitz PC

(57) ABSTRACT

Nucleic acid constructs, vectors, and recombinant cells harboring the nucleic acid constructs or vectors are disclosed. The nucleic acid constructs include genes encoding a chimeric antigen receptor (CAR) and/or one or more transcription factors, optionally mutated. The transcription factors include those that mediate proinflammatory cytokine expression, e.g., T-bet, STAT1, or STAT4. Methods are disclosed of co-expression of the CAR and the transcription factor in a human or non-human immune cell, preferably human T cells. Also disclosed are methods for using these cells for immunotherapy, e.g., in treating cancer, infection, autoimmunity, allergy or inflammation diseases by the administration of a prophylactically or therapeutically effective amount of one or more of the nucleic acid constructs, vectors, and/or immune cells, e.g., human CAR-T cells, described herein.

20 Claims, 17 Drawing Sheets

Specification includes a Sequence Listing.

(56) References Cited

OTHER PUBLICATIONS

Frigault MJ, et al. "Identification of chimeric antigen receptors that mediate constitutive or inducible proliferation of T cells," Cancer Immunol Res. Apr. 2015;3(4):356-67.

* cited by examiner

FIG. 2B

| Position | Modification | Physiological effect |
|---|---|---|
| Y219/Y265/Y304 | c-Abl-mediated phosphorylation | Induction of Th1 cell development<br>Suppression of Th2 cell development |
| T302 | Phosphorylation | Interaction with NFAT<br>Suppression of IL-2 and Th2 cytokines |
| Y304 | — | Interaction with RUNX1<br>Inhibition of Th17 cell development |
| K313 | Ubiquitination | Binding to DNA sequence<br>Control of protein stability |
| S508 | GSK-3-mediated phosphorylation | Interaction with NF-κB p65<br>Inhibition of IL-2 |
| Y525 | ITK-induced phosphorylation | Interaction with GATA-3<br>Suppression of Th2 cytokines |

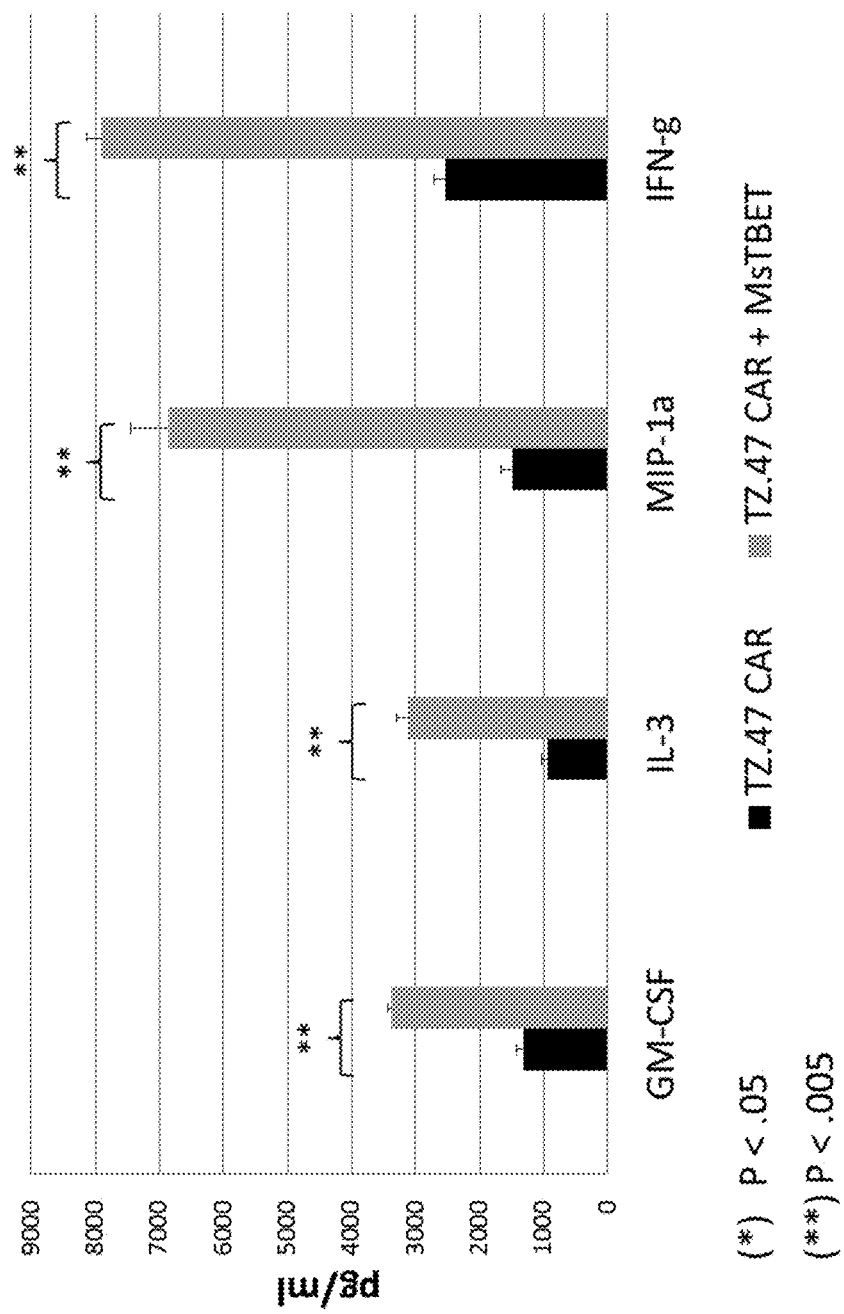

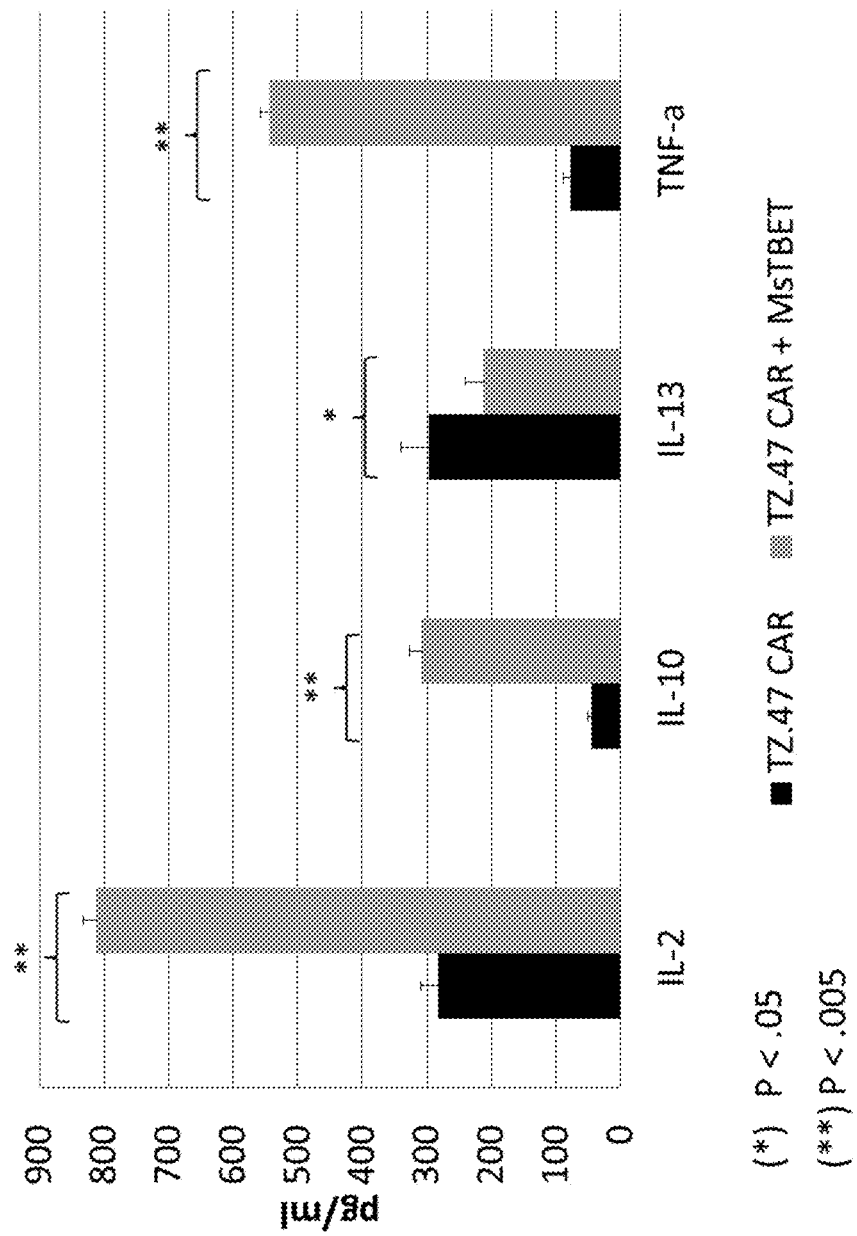

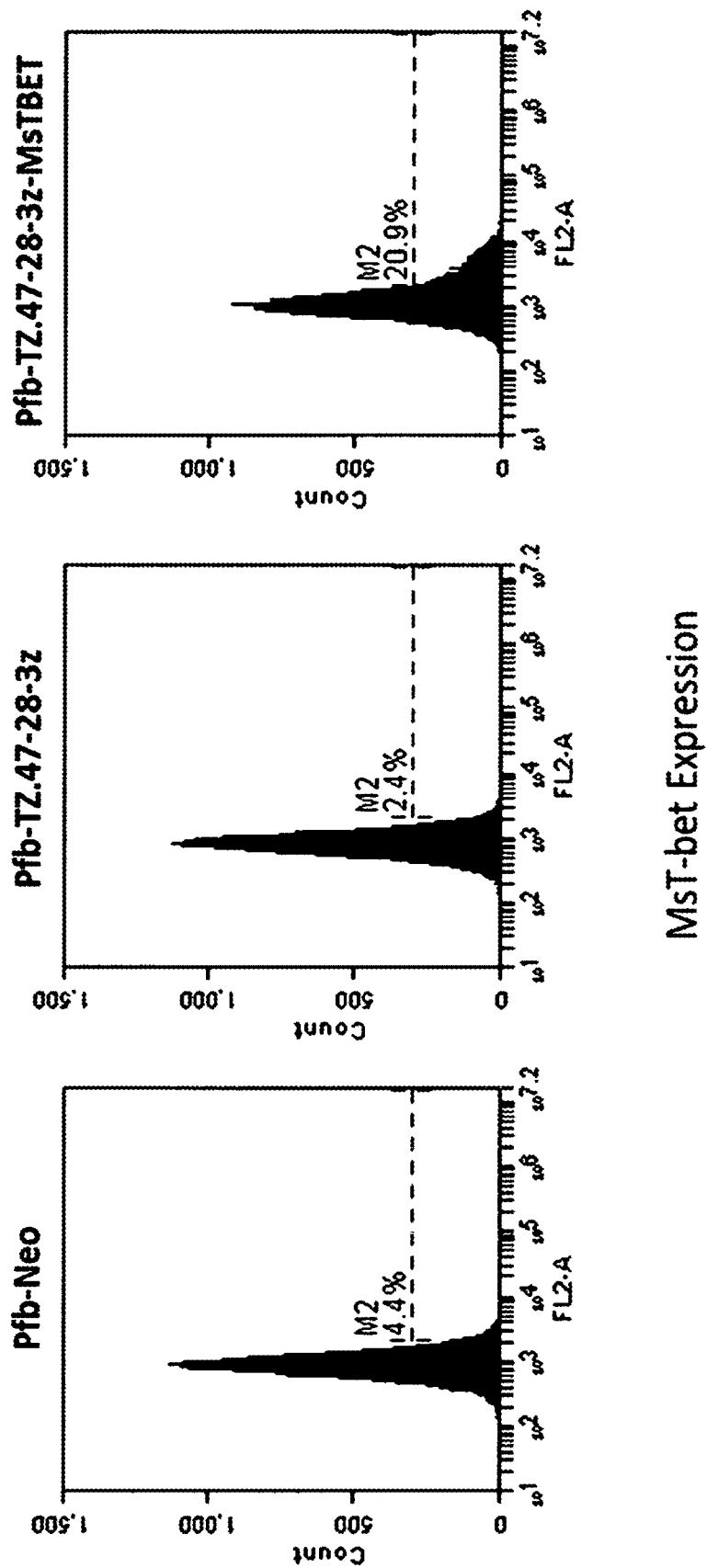

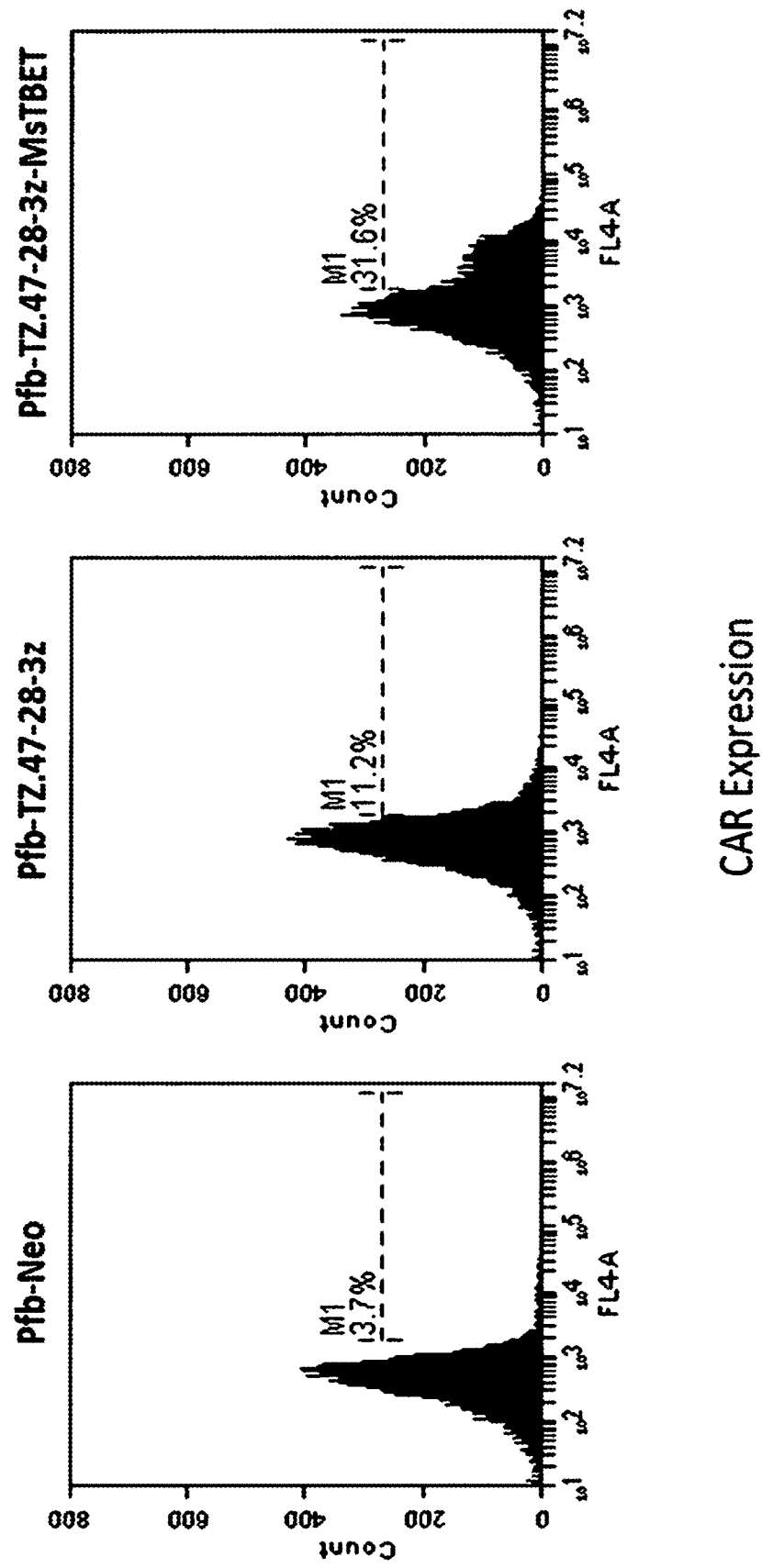

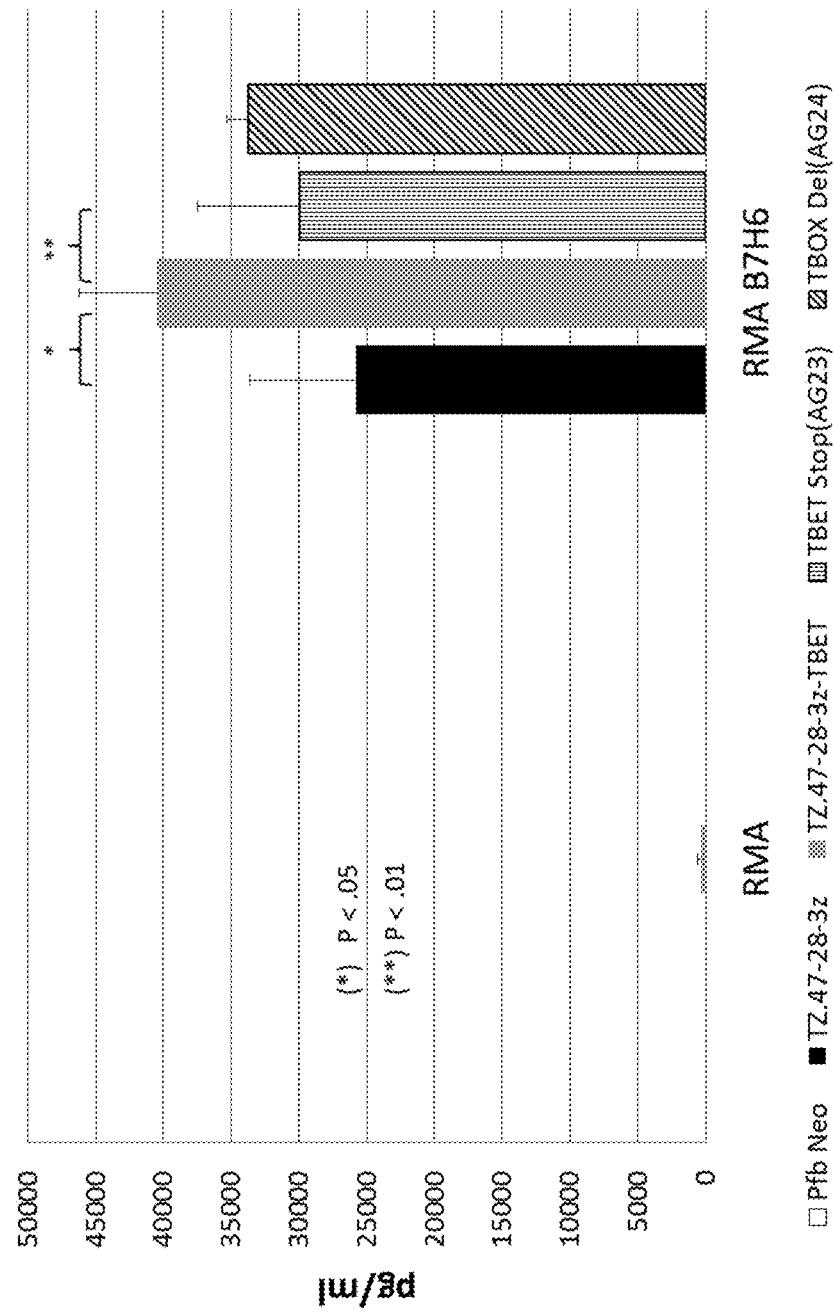

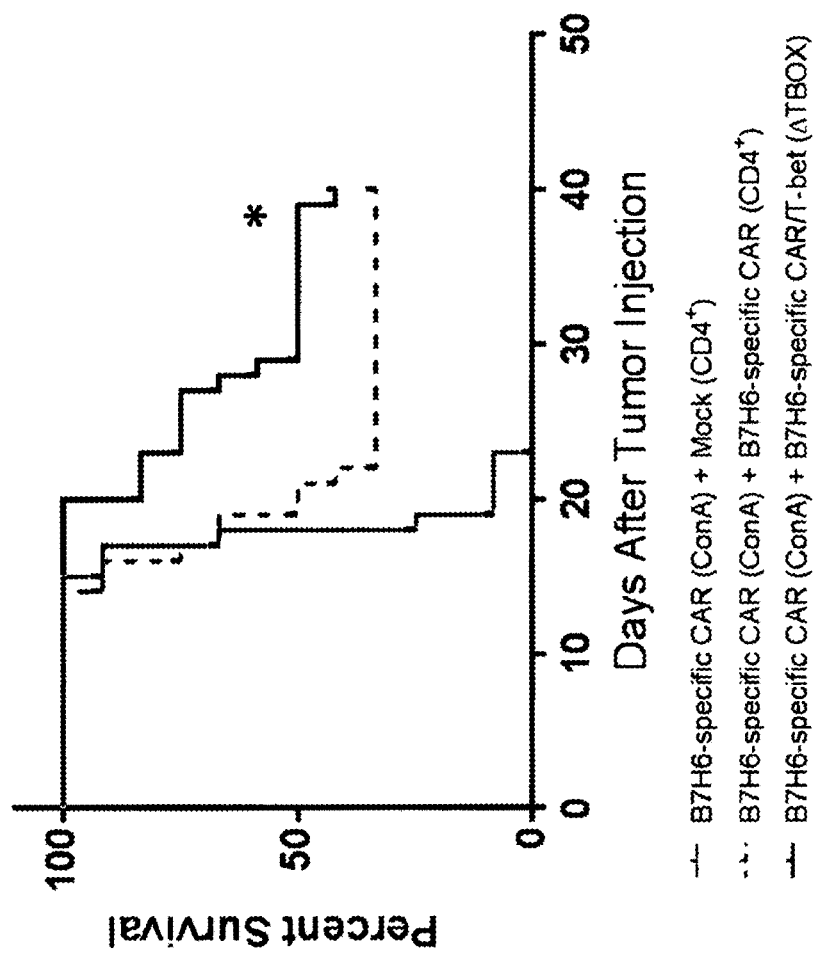

SEQUENCE LISTING

```
<160> NUMBER OF SEQ ID NOS: 59

<210> SEQ ID NO 1
<211> LENGTH: 19
<212> TYPE: PRT
<213> ORGANISM: Artificial
<220> FEATURE:
<223> OTHER INFORMATION: ITAM consensus
<220> FEATURE:
<221> NAME/KEY: MISC_FEATURE
<222> LOCATION: (1)..(1)
<223> OTHER INFORMATION: Xaa = Asp or Glu
<220> FEATURE:
<221> NAME/KEY: MISC_FEATURE
<222> LOCATION: (2)..(3)
<223> OTHER INFORMATION: Xaa = Any amino acid
<220> FEATURE:
<221> NAME/KEY: MISC_FEATURE
<222> LOCATION: (5)..(6)
<223> OTHER INFORMATION: Xaa = Any amino acid
<220> FEATURE:
```

-continued

```
<221> NAME/KEY: MISC_FEATURE
<222> LOCATION: (7)..(7)
<223> OTHER INFORMATION: Xaa = Ile or Leu
<220> FEATURE:
<221> NAME/KEY: MISC_FEATURE
<222> LOCATION: (8)..(15)
<223> OTHER INFORMATION: Xaa = Any amino acid
<220> FEATURE:
<221> NAME/KEY: MISC_FEATURE
<222> LOCATION: (14)..(15)
<223> OTHER INFORMATION: Any or all of the amino acids may be absent or
      present.
<220> FEATURE:
<221> NAME/KEY: MISC_FEATURE
<222> LOCATION: (17)..(18)
<223> OTHER INFORMATION: Xaa = Any amino acid
<220> FEATURE:
<221> NAME/KEY: MISC_FEATURE
<222> LOCATION: (19)..(19)
<223> OTHER INFORMATION: Xaa = Ile or Leu

<400> SEQUENCE: 1

Xaa Xaa Xaa Tyr Xaa Xaa Xaa Xaa Xaa Xaa Xaa Xaa Xaa Xaa Xaa Tyr
1               5                   10                  15

Xaa Xaa Xaa

<210> SEQ ID NO 2
<211> LENGTH: 63
<212> TYPE: PRT
<213> ORGANISM: Foot-and-mouth disease virus

<400> SEQUENCE: 2

Gly Ser Gly Ser Arg Val Thr Glu Leu Leu Tyr Arg Met Lys Arg Ala
1               5                   10                  15

Glu Thr Tyr Cys Pro Arg Pro Leu Leu Ala Ile His Pro Thr Glu Ala
            20                  25                  30

Arg His Lys Gln Lys Ile Val Ala Pro Val Lys Gln Leu Leu Asn Phe
        35                  40                  45

Asp Leu Leu Lys Leu Ala Gly Asp Val Glu Ser Asn Pro Gly Pro
    50                  55                  60

<210> SEQ ID NO 3
<211> LENGTH: 25
<212> TYPE: PRT
<213> ORGANISM: Strongylocentrotus purpuratus

<400> SEQUENCE: 3

Asp Gly Phe Cys Ile Leu Tyr Leu Leu Leu Ile Leu Leu Met Arg Ser
1               5                   10                  15

Gly Asp Val Glu Thr Asn Pro Gly Pro
            20                  25

<210> SEQ ID NO 4
<211> LENGTH: 20
<212> TYPE: PRT
<213> ORGANISM: Amphimedon queenslandica

<400> SEQUENCE: 4

Leu Leu Cys Phe Met Leu Leu Leu Leu Ser Gly Asp Val Glu Leu
1               5                   10                  15

Asn Pro Gly Pro
            20

<210> SEQ ID NO 5
<211> LENGTH: 20
```

```
<212> TYPE: PRT
<213> ORGANISM: Amphimedon queenslandica

<400> SEQUENCE: 5

His His Phe Met Phe Leu Leu Leu Leu Ala Gly Asp Ile Glu Leu
1               5                   10                  15

Asn Pro Gly Pro
            20

<210> SEQ ID NO 6
<211> LENGTH: 20
<212> TYPE: PRT
<213> ORGANISM: Saccoglossus kowalevskii

<400> SEQUENCE: 6

Trp Phe Leu Val Leu Leu Ser Phe Ile Leu Ser Gly Asp Ile Glu Val
1               5                   10                  15

Asn Pro Gly Pro
            20

<210> SEQ ID NO 7
<211> LENGTH: 20
<212> TYPE: PRT
<213> ORGANISM: Branchiostoma floridae

<400> SEQUENCE: 7

Lys Asn Cys Ala Met Tyr Met Leu Leu Leu Ser Gly Asp Val Glu Thr
1               5                   10                  15

Asn Pro Gly Pro
            20

<210> SEQ ID NO 8
<211> LENGTH: 20
<212> TYPE: PRT
<213> ORGANISM: Branchiostoma floridae

<400> SEQUENCE: 8

Met Val Ile Ser Gln Leu Met Leu Lys Leu Ala Gly Asp Val Glu Glu
1               5                   10                  15

Asn Pro Gly Pro
            20

<210> SEQ ID NO 9
<211> LENGTH: 22
<212> TYPE: PRT
<213> ORGANISM: Teschovirus teschovirus A

<400> SEQUENCE: 9

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 10
<211> LENGTH: 21
<212> TYPE: PRT
<213> ORGANISM: Alphapermutotetravirus thosea asigna virus

<400> SEQUENCE: 10

Gly Ser Gly Glu Gly Arg Gly Ser Leu Leu Thr Cys Gly Asp Val Glu
1               5                   10                  15

Glu Asn Pro Gly Pro
```

20

<210> SEQ ID NO 11
<211> LENGTH: 23
<212> TYPE: PRT
<213> ORGANISM: Aphthovirus equine rhinitis A virus

<400> SEQUENCE: 11

Gly Ser Gly Gln Cys Thr Asn Tyr Ala Leu Leu Lys Leu Ala Gly Asp
1               5                   10                  15

Val Glu Ser Asn Pro Gly Pro
            20

<210> SEQ ID NO 12
<211> LENGTH: 8
<212> TYPE: PRT
<213> ORGANISM: Artificial Sequence
<220> FEATURE:
<223> OTHER INFORMATION: 2A consensus
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid

<400> SEQUENCE: 12

Asp Xaa Glu Xaa Asn Pro Gly Pro
1               5

<210> SEQ ID NO 13
<211> LENGTH: 259
<212> TYPE: PRT
<213> ORGANISM: Artificial Sequence
<220> FEATURE:
<223> OTHER INFORMATION: TZ47 scFv

<400> SEQUENCE: 13

Met Glu Trp Thr Trp Val Phe Leu Phe Leu Leu Ser Val Thr Ala Gly
1               5                   10                  15

Val His Ser Gln Val Gln Leu Gln Gln Ser Gly Ala Glu Leu Met Lys
            20                  25                  30

Pro Gly Ala Ser Val Lys Leu Ser Cys Lys Ala Thr Gly Tyr Thr Phe
        35                  40                  45

Thr Gly Tyr Trp Ile Glu Trp Ile Lys Gln Arg Pro Gly His Gly Leu
    50                  55                  60

Glu Trp Ile Gly Glu Ile Leu Pro Gly Thr Gly Ser Thr Asn Tyr Asn
65                  70                  75                  80

Glu Lys Phe Lys Gly Lys Ala Thr Phe Thr Ala Asp Thr Ser Ser Asn
                85                  90                  95

Thr Ala Tyr Met Gln Leu Ser Ser Leu Thr Thr Glu Asp Ser Ala Ile
            100                 105                 110

Tyr Tyr Cys Ala Ile Pro Gly Pro Met Asp Tyr Trp Gly Gln Gly Thr
        115                 120                 125

Ser Val Thr Val Ser Ser Ala Gly Gly Gly Ser Gly Gly Gly Gly
    130                 135                 140

Ser Gly Gly Gly Gly Ser Glu Phe Asp Ile Lys Met Thr Gln Ser Pro
145                 150                 155                 160

Ser Ser Met Tyr Ala Ser Leu Gly Glu Arg Val Thr Ile Thr Cys Lys
                165                 170                 175

Ala Ser Gln Asp Ile Asn Ser Tyr Leu Ser Trp Phe Gln Gln Lys Pro
            180                 185                 190

Gly Lys Ser Pro Lys Thr Leu Ile Tyr Arg Ala Asn Arg Leu Val Asp
            195                 200                 205

Gly Val Pro Ser Arg Phe Ser Gly Ser Gly Ser Gly Gln Asp Tyr Ser
            210                 215                 220

Leu Thr Ile Ser Ser Leu Glu Tyr Glu Asp Met Gly Ile Tyr Tyr Cys
225                 230                 235                 240

Leu Gln Tyr Asp Glu Phe Pro Tyr Thr Phe Gly Gly Gly Thr Lys Leu
            245                 250                 255

Glu Ile Lys

<210> SEQ ID NO 14
<211> LENGTH: 220
<212> TYPE: PRT
<213> ORGANISM: Homo sapiens

<400> SEQUENCE: 14

Met Leu Arg Leu Leu Ala Leu Asn Leu Phe Pro Ser Ile Gln Val
1               5                   10                  15

Thr Gly Asn Lys Ile Leu Val Lys Gln Ser Pro Met Leu Val Ala Tyr
            20                  25                  30

Asp Asn Ala Val Asn Leu Ser Cys Lys Tyr Ser Tyr Asn Leu Phe Ser
            35                  40                  45

Arg Glu Phe Arg Ala Ser Leu His Lys Gly Leu Asp Ser Ala Val Glu
            50                  55                  60

Val Cys Val Val Tyr Gly Asn Tyr Ser Gln Gln Leu Gln Val Tyr Ser
65                  70                  75                  80

Lys Thr Gly Phe Asn Cys Asp Gly Lys Leu Gly Asn Glu Ser Val Thr
            85                  90                  95

Phe Tyr Leu Gln Asn Leu Tyr Val Asn Gln Thr Asp Ile Tyr Phe Cys
            100                 105                 110

Lys Ile Glu Val Met Tyr Pro Pro Pro Tyr Leu Asp Asn Glu Lys Ser
            115                 120                 125

Asn Gly Thr Ile Ile His Val Lys Gly Lys His Leu Cys Pro Ser Pro
            130                 135                 140

Leu Phe Pro Gly Pro Ser Lys Pro Phe Trp Val Leu Val Val Val Gly
145                 150                 155                 160

Gly Val Leu Ala Cys Tyr Ser Leu Leu Val Thr Val Ala Phe Ile Ile
            165                 170                 175

Phe Trp Val Arg Ser Lys Arg Ser Arg Leu Leu His Ser Asp Tyr Met
            180                 185                 190

Asn Met Thr Pro Arg Arg Pro Gly Pro Thr Arg Lys His Tyr Gln Pro
            195                 200                 205

Tyr Ala Pro Pro Arg Asp Phe Ala Ala Tyr Arg Ser
            210                 215                 220

<210> SEQ ID NO 15
<211> LENGTH: 218
<212> TYPE: PRT
<213> ORGANISM: Mus musculus

<400> SEQUENCE: 15

Met Thr Leu Arg Leu Leu Phe Leu Ala Leu Asn Phe Phe Ser Val Gln
1               5                   10                  15

```
Val Thr Glu Asn Lys Ile Leu Val Lys Gln Ser Pro Leu Leu Val Val
            20                  25                  30

Asp Ser Asn Glu Val Ser Leu Ser Cys Arg Tyr Ser Tyr Asn Leu Leu
        35                  40                  45

Ala Lys Glu Phe Arg Ala Ser Leu Tyr Lys Gly Val Asn Ser Asp Val
    50                  55                  60

Glu Val Cys Val Gly Asn Gly Asn Phe Thr Tyr Gln Pro Gln Phe Arg
65                  70                  75                  80

Ser Asn Ala Glu Phe Asn Cys Asp Gly Asp Phe Asp Asn Glu Thr Val
                85                  90                  95

Thr Phe Arg Leu Trp Asn Leu His Val Asn His Thr Asp Ile Tyr Phe
            100                 105                 110

Cys Lys Ile Glu Phe Met Tyr Pro Pro Pro Tyr Leu Asp Asn Glu Arg
        115                 120                 125

Ser Asn Gly Thr Ile Ile His Ile Lys Glu Lys His Leu Cys His Thr
    130                 135                 140

Gln Ser Ser Pro Lys Leu Phe Trp Ala Leu Val Val Val Ala Gly Val
145                 150                 155                 160

Leu Phe Cys Tyr Gly Leu Leu Val Thr Val Ala Leu Cys Val Ile Trp
                165                 170                 175

Thr Asn Ser Arg Arg Asn Arg Leu Leu Gln Ser Asp Tyr Met Asn Met
            180                 185                 190

Thr Pro Arg Arg Pro Gly Leu Thr Arg Lys Pro Tyr Gln Pro Tyr Ala
        195                 200                 205

Pro Ala Arg Asp Phe Ala Ala Tyr Arg Pro
    210                 215

<210> SEQ ID NO 16
<211> LENGTH: 164
<212> TYPE: PRT
<213> ORGANISM: Homo sapiens

<400> SEQUENCE: 16

Met Lys Trp Lys Ala Leu Phe Thr Ala Ala Ile Leu Gln Ala Gln Leu
1               5                   10                  15

Pro Ile Thr Glu Ala Gln Ser Phe Gly Leu Leu Asp Pro Lys Leu Cys
            20                  25                  30

Tyr Leu Leu Asp Gly Ile Leu Phe Ile Tyr Gly Val Ile Leu Thr Ala
        35                  40                  45

Leu Phe Leu Arg Val Lys Phe Ser Arg Ser Ala Asp Ala Pro Ala Tyr
    50                  55                  60

Gln Gln Gly Gln Asn Gln Leu Tyr Asn Glu Leu Asn Leu Gly Arg Arg
65                  70                  75                  80

Glu Glu Tyr Asp Val Leu Asp Lys Arg Arg Gly Arg Asp Pro Glu Met
                85                  90                  95

Gly Gly Lys Pro Gln Arg Arg Lys Asn Pro Gln Glu Gly Leu Tyr Asn
            100                 105                 110

Glu Leu Gln Lys Asp Lys Met Ala Glu Ala Tyr Ser Glu Ile Gly Met
        115                 120                 125

Lys Gly Glu Arg Arg Arg Gly Lys Gly His Asp Gly Leu Tyr Gln Gly
    130                 135                 140

Leu Ser Thr Ala Thr Lys Asp Thr Tyr Asp Ala Leu His Met Gln Ala
145                 150                 155                 160

Leu Pro Pro Arg
```

<210> SEQ ID NO 17
<211> LENGTH: 164
<212> TYPE: PRT
<213> ORGANISM: Mus musculus

<400> SEQUENCE: 17

Met Lys Trp Lys Val Ser Val Leu Ala Cys Ile Leu His Val Arg Phe
1               5                   10                  15

Pro Gly Ala Glu Ala Gln Ser Phe Gly Leu Leu Asp Pro Lys Leu Cys
            20                  25                  30

Tyr Leu Leu Asp Gly Ile Leu Phe Ile Tyr Gly Val Ile Ile Thr Ala
        35                  40                  45

Leu Tyr Leu Arg Ala Lys Phe Ser Arg Ser Ala Glu Thr Ala Ala Asn
    50                  55                  60

Leu Gln Asp Pro Asn Gln Leu Tyr Asn Glu Leu Asn Leu Gly Arg Arg
65                  70                  75                  80

Glu Glu Tyr Asp Val Leu Glu Lys Lys Arg Ala Arg Asp Pro Glu Met
                85                  90                  95

Gly Gly Lys Gln Gln Arg Arg Arg Asn Pro Gln Glu Gly Val Tyr Asn
            100                 105                 110

Ala Leu Gln Lys Asp Lys Met Ala Glu Ala Tyr Ser Glu Ile Gly Thr
        115                 120                 125

Lys Gly Glu Arg Arg Arg Gly Lys Gly His Asp Gly Leu Tyr Gln Gly
    130                 135                 140

Leu Ser Thr Ala Thr Lys Asp Thr Tyr Asp Ala Leu His Met Gln Thr
145                 150                 155                 160

Leu Ala Pro Arg

<210> SEQ ID NO 18
<211> LENGTH: 750
<212> TYPE: PRT
<213> ORGANISM: Homo sapiens

<400> SEQUENCE: 18

Met Ser Gln Trp Tyr Glu Leu Gln Gln Leu Asp Ser Lys Phe Leu Glu
1               5                   10                  15

Gln Val His Gln Leu Tyr Asp Asp Ser Phe Pro Met Glu Ile Arg Gln
            20                  25                  30

Tyr Leu Ala Gln Trp Leu Glu Lys Gln Asp Trp Glu His Ala Ala Asn
        35                  40                  45

Asp Val Ser Phe Ala Thr Ile Arg Phe His Asp Leu Leu Ser Gln Leu
    50                  55                  60

Asp Asp Gln Tyr Ser Arg Phe Ser Leu Glu Asn Asn Phe Leu Leu Gln
65                  70                  75                  80

His Asn Ile Arg Lys Ser Lys Arg Asn Leu Gln Asp Asn Phe Gln Glu
                85                  90                  95

Asp Pro Ile Gln Met Ser Met Ile Ile Tyr Ser Cys Leu Lys Glu Glu
            100                 105                 110

Arg Lys Ile Leu Glu Asn Ala Gln Arg Phe Asn Gln Ala Gln Ser Gly
        115                 120                 125

Asn Ile Gln Ser Thr Val Met Leu Asp Lys Gln Lys Glu Leu Asp Ser
    130                 135                 140

Lys Val Arg Asn Val Lys Asp Lys Val Met Cys Ile Glu His Glu Ile
145                 150                 155                 160

Lys Ser Leu Glu Asp Leu Gln Asp Glu Tyr Asp Phe Lys Cys Lys Thr

-continued

```
            165                 170                 175
Leu Gln Asn Arg Glu His Glu Thr Asn Gly Val Ala Lys Ser Asp Gln
            180                 185                 190
Lys Gln Glu Gln Leu Leu Lys Lys Met Tyr Leu Met Leu Asp Asn
            195                 200             205
Lys Arg Lys Glu Val Val His Lys Ile Ile Glu Leu Leu Asn Val Thr
    210                 215                 220
Glu Leu Thr Gln Asn Ala Leu Ile Asn Asp Glu Leu Val Glu Trp Lys
225                 230                 235                 240
Arg Arg Gln Gln Ser Ala Cys Ile Gly Gly Pro Pro Asn Ala Cys Leu
                245                 250                 255
Asp Gln Leu Gln Asn Trp Phe Thr Ile Val Ala Glu Ser Leu Gln Gln
            260                 265                 270
Val Arg Gln Gln Leu Lys Lys Leu Glu Glu Leu Glu Gln Lys Tyr Thr
        275                 280                 285
Tyr Glu His Asp Pro Ile Thr Lys Asn Lys Gln Val Leu Trp Asp Arg
    290                 295                 300
Thr Phe Ser Leu Phe Gln Gln Leu Ile Gln Ser Ser Phe Val Val Glu
305                 310                 315                 320
Arg Gln Pro Cys Met Pro Thr His Pro Gln Arg Pro Leu Val Leu Lys
                325                 330                 335
Thr Gly Val Gln Phe Thr Val Lys Leu Arg Leu Leu Val Lys Leu Gln
            340                 345                 350
Glu Leu Asn Tyr Asn Leu Lys Val Lys Val Leu Phe Asp Lys Asp Val
        355                 360                 365
Asn Glu Arg Asn Thr Val Lys Gly Phe Arg Lys Phe Asn Ile Leu Gly
    370                 375                 380
Thr His Thr Lys Val Met Asn Met Glu Glu Ser Thr Asn Gly Ser Leu
385                 390                 395                 400
Ala Ala Glu Phe Arg His Leu Gln Leu Lys Glu Gln Lys Asn Ala Gly
                405                 410                 415
Thr Arg Thr Asn Glu Gly Pro Leu Ile Val Thr Glu Glu Leu His Ser
            420                 425                 430
Leu Ser Phe Glu Thr Gln Leu Cys Gln Pro Gly Leu Val Ile Asp Leu
        435                 440                 445
Glu Thr Thr Ser Leu Pro Val Val Val Ile Ser Asn Val Ser Gln Leu
    450                 455                 460
Pro Ser Gly Trp Ala Ser Ile Leu Trp Tyr Asn Met Leu Val Ala Glu
465                 470                 475                 480
Pro Arg Asn Leu Ser Phe Phe Leu Thr Pro Pro Cys Ala Arg Trp Ala
                485                 490                 495
Gln Leu Ser Glu Val Leu Ser Trp Gln Phe Ser Ser Val Thr Lys Arg
            500                 505                 510
Gly Leu Asn Val Asp Gln Leu Asn Met Leu Gly Glu Lys Leu Leu Gly
        515                 520                 525
Pro Asn Ala Ser Pro Asp Gly Leu Ile Pro Trp Thr Arg Phe Cys Lys
    530                 535                 540
Glu Asn Ile Asn Asp Lys Asn Phe Pro Phe Trp Leu Trp Ile Glu Ser
545                 550                 555                 560
Ile Leu Glu Leu Ile Lys Lys His Leu Leu Pro Leu Trp Asn Asp Gly
                565                 570                 575
Cys Ile Met Gly Phe Ile Ser Lys Glu Arg Glu Arg Ala Leu Leu Lys
            580                 585                 590
```

```
Asp Gln Gln Pro Gly Thr Phe Leu Leu Arg Phe Ser Glu Ser Ser Arg
            595                 600                 605

Glu Gly Ala Ile Thr Phe Thr Trp Val Glu Arg Ser Gln Asn Gly Gly
610                 615                 620

Glu Pro Asp Phe His Ala Val Glu Pro Tyr Thr Lys Lys Glu Leu Ser
625                 630                 635                 640

Ala Val Thr Phe Pro Asp Ile Ile Arg Asn Tyr Lys Val Met Ala Ala
            645                 650                 655

Glu Asn Ile Pro Glu Asn Pro Leu Lys Tyr Leu Tyr Pro Asn Ile Asp
            660                 665                 670

Lys Asp His Ala Phe Gly Lys Tyr Tyr Ser Arg Pro Lys Glu Ala Pro
            675                 680                 685

Glu Pro Met Glu Leu Asp Gly Pro Lys Gly Thr Gly Tyr Ile Lys Thr
            690                 695                 700

Glu Leu Ile Ser Val Ser Glu Val His Pro Ser Arg Leu Gln Thr Thr
705                 710                 715                 720

Asp Asn Leu Leu Pro Met Ser Pro Glu Glu Phe Asp Glu Val Ser Arg
            725                 730                 735

Ile Val Gly Ser Val Glu Phe Asp Ser Met Met Asn Thr Val
            740                 745                 750
```

<210> SEQ ID NO 19
<211> LENGTH: 749
<212> TYPE: PRT
<213> ORGANISM: Mus musculus

<400> SEQUENCE: 19

```
Met Ser Gln Trp Phe Glu Leu Gln Gln Leu Asp Ser Lys Phe Leu Glu
1               5                   10                  15

Gln Val His Gln Leu Tyr Asp Asp Ser Phe Pro Met Glu Ile Arg Gln
            20                  25                  30

Tyr Leu Ala Gln Trp Leu Glu Lys Gln Asp Trp Glu His Ala Ala Tyr
        35                  40                  45

Asp Val Ser Phe Ala Thr Ile Arg Phe His Asp Leu Leu Ser Gln Leu
    50                  55                  60

Asp Asp Gln Tyr Ser Arg Phe Ser Leu Glu Asn Asn Phe Leu Leu Gln
65                  70                  75                  80

His Asn Ile Arg Lys Ser Lys Arg Asn Leu Gln Asp Asn Phe Gln Glu
                85                  90                  95

Asp Pro Val Gln Met Ser Met Ile Ile Tyr Asn Cys Leu Lys Glu Glu
            100                 105                 110

Arg Lys Ile Leu Glu Asn Ala Gln Arg Phe Asn Gln Ala Gln Glu Gly
        115                 120                 125

Asn Ile Gln Asn Thr Val Met Leu Asp Lys Gln Lys Glu Leu Asp Ser
    130                 135                 140

Lys Val Arg Asn Val Lys Asp Gln Val Met Cys Ile Glu Gln Glu Ile
145                 150                 155                 160

Lys Thr Leu Glu Glu Leu Gln Asp Glu Tyr Asp Phe Lys Cys Lys Thr
                165                 170                 175

Ser Gln Asn Arg Glu Gly Glu Ala Asn Gly Val Ala Lys Ser Asp Gln
            180                 185                 190

Lys Gln Glu Gln Leu Leu Leu His Lys Met Phe Leu Met Leu Asp Asn
        195                 200                 205

Lys Arg Lys Glu Ile Ile His Lys Ile Arg Glu Leu Leu Asn Ser Ile
```

```
            210                 215                 220
Glu Leu Thr Gln Asn Thr Leu Ile Asn Asp Glu Leu Val Glu Trp Lys
225                 230                 235                 240

Arg Arg Gln Gln Ser Ala Cys Ile Gly Gly Pro Pro Asn Ala Cys Leu
                245                 250                 255

Asp Gln Leu Gln Thr Trp Phe Thr Ile Val Ala Glu Thr Leu Gln Gln
                260                 265                 270

Ile Arg Gln Gln Leu Lys Lys Leu Glu Glu Leu Glu Gln Lys Phe Thr
            275                 280                 285

Tyr Glu Pro Asp Pro Ile Thr Lys Asn Lys Gln Val Leu Ser Asp Arg
290                 295                 300

Thr Phe Leu Leu Phe Gln Gln Leu Ile Gln Ser Ser Phe Val Val Glu
305                 310                 315                 320

Arg Gln Pro Cys Met Pro Thr His Pro Gln Arg Pro Leu Val Leu Lys
                325                 330                 335

Thr Gly Val Gln Phe Thr Val Lys Ser Arg Leu Leu Val Lys Leu Gln
                340                 345                 350

Glu Ser Asn Leu Leu Thr Lys Val Lys Cys His Phe Asp Lys Asp Val
            355                 360                 365

Asn Glu Lys Asn Thr Val Lys Gly Phe Arg Lys Phe Asn Ile Leu Gly
370                 375                 380

Thr His Thr Lys Val Met Asn Met Glu Glu Ser Thr Asn Gly Ser Leu
385                 390                 395                 400

Ala Ala Glu Leu Arg His Leu Gln Leu Lys Glu Gln Lys Asn Ala Gly
                405                 410                 415

Asn Arg Thr Asn Glu Gly Pro Leu Ile Val Thr Glu Glu Leu His Ser
                420                 425                 430

Leu Ser Phe Glu Thr Gln Leu Cys Gln Pro Gly Leu Val Ile Asp Leu
            435                 440                 445

Glu Thr Thr Ser Leu Pro Val Val Val Ile Ser Asn Val Ser Gln Leu
450                 455                 460

Pro Ser Gly Trp Ala Ser Ile Leu Trp Tyr Asn Met Leu Val Thr Glu
465                 470                 475                 480

Pro Arg Asn Leu Ser Phe Phe Leu Asn Pro Pro Cys Ala Trp Trp Ser
                485                 490                 495

Gln Leu Ser Glu Val Leu Ser Trp Gln Phe Ser Ser Val Thr Lys Arg
                500                 505                 510

Gly Leu Asn Ala Asp Gln Leu Ser Met Leu Gly Glu Lys Leu Leu Gly
            515                 520                 525

Pro Asn Ala Gly Pro Asp Gly Leu Ile Pro Trp Thr Arg Phe Cys Lys
530                 535                 540

Glu Asn Ile Asn Asp Lys Asn Phe Ser Phe Trp Pro Trp Ile Asp Thr
545                 550                 555                 560

Ile Leu Glu Leu Ile Lys Asn Asp Leu Leu Cys Leu Trp Asn Asp Gly
                565                 570                 575

Cys Ile Met Gly Phe Ile Ser Lys Glu Arg Glu Arg Ala Leu Leu Lys
                580                 585                 590

Asp Gln Gln Pro Gly Thr Phe Leu Leu Arg Phe Ser Glu Ser Ser Arg
            595                 600                 605

Glu Gly Ala Ile Thr Phe Thr Trp Val Glu Arg Ser Gln Asn Gly Gly
610                 615                 620

Glu Pro Asp Phe His Ala Val Glu Pro Tyr Thr Lys Lys Glu Leu Ser
625                 630                 635                 640
```

```
Ala Val Thr Phe Pro Asp Ile Ile Arg Asn Tyr Lys Val Met Ala Ala
                645                 650                 655

Glu Asn Ile Pro Glu Asn Pro Leu Lys Tyr Leu Tyr Pro Asn Ile Asp
            660                 665                 670

Lys Asp His Ala Phe Gly Lys Tyr Tyr Ser Arg Pro Lys Glu Ala Pro
        675                 680                 685

Glu Pro Met Glu Leu Asp Asp Pro Lys Arg Thr Gly Tyr Ile Lys Thr
    690                 695                 700

Glu Leu Ile Ser Val Ser Glu Val His Pro Ser Arg Leu Gln Thr Thr
705                 710                 715                 720

Asp Asn Leu Leu Pro Met Ser Pro Glu Glu Phe Asp Glu Met Ser Arg
                725                 730                 735

Ile Val Gly Pro Glu Phe Asp Ser Met Met Ser Thr Val
                740                 745
```

<210> SEQ ID NO 20
<211> LENGTH: 748
<212> TYPE: PRT
<213> ORGANISM: Homo sapiens

<400> SEQUENCE: 20

```
Met Ser Gln Trp Asn Gln Val Gln Gln Leu Glu Ile Lys Phe Leu Glu
1               5                   10                  15

Gln Val Asp Gln Phe Tyr Asp Asp Asn Phe Pro Met Glu Ile Arg His
                20                  25                  30

Leu Leu Ala Gln Trp Ile Glu Asn Gln Asp Trp Glu Ala Ala Ser Asn
            35                  40                  45

Asn Glu Thr Met Ala Thr Ile Leu Leu Gln Asn Leu Leu Ile Gln Leu
        50                  55                  60

Asp Glu Gln Leu Gly Arg Val Ser Lys Glu Lys Asn Leu Leu Leu Ile
65                  70                  75                  80

His Asn Leu Lys Arg Ile Arg Lys Val Leu Gln Gly Lys Phe His Gly
                85                  90                  95

Asn Pro Met His Val Ala Val Val Ile Ser Asn Cys Leu Arg Glu Glu
                100                 105                 110

Arg Arg Ile Leu Ala Ala Ala Asn Met Pro Val Gln Gly Pro Leu Glu
            115                 120                 125

Lys Ser Leu Gln Ser Ser Ser Val Ser Glu Arg Gln Arg Asn Val Glu
        130                 135                 140

His Lys Val Ala Ala Ile Lys Asn Ser Val Gln Met Thr Glu Gln Asp
145                 150                 155                 160

Thr Lys Tyr Leu Glu Asp Leu Gln Asp Glu Phe Asp Tyr Arg Tyr Lys
                165                 170                 175

Thr Ile Gln Thr Met Asp Gln Ser Asp Lys Asn Ser Ala Met Val Asn
            180                 185                 190

Gln Glu Val Leu Thr Leu Gln Glu Met Leu Asn Ser Leu Asp Phe Lys
        195                 200                 205

Arg Lys Glu Ala Leu Ser Lys Met Thr Gln Ile Ile His Glu Thr Asp
    210                 215                 220

Leu Leu Met Asn Thr Met Leu Ile Glu Glu Leu Gln Asp Trp Lys Arg
225                 230                 235                 240

Arg Gln Gln Ile Ala Cys Ile Gly Gly Pro Leu His Asn Gly Leu Asp
                245                 250                 255

Gln Leu Gln Asn Cys Phe Thr Leu Leu Ala Glu Ser Leu Phe Gln Leu
```

```
                260             265             270
Arg Arg Gln Leu Glu Lys Leu Glu Glu Gln Ser Thr Lys Met Thr Tyr
            275             280             285
Glu Gly Asp Pro Ile Pro Met Gln Arg Thr His Met Leu Glu Arg Val
            290             295             300
Thr Phe Leu Ile Tyr Asn Leu Phe Lys Asn Ser Phe Val Val Glu Arg
305             310             315             320
Gln Pro Cys Met Pro Thr His Pro Gln Arg Pro Leu Val Leu Lys Thr
            325             330             335
Leu Ile Gln Phe Thr Val Lys Leu Arg Leu Leu Ile Lys Leu Pro Glu
            340             345             350
Leu Asn Tyr Gln Val Lys Val Lys Ala Ser Ile Asp Lys Asn Val Ser
            355             360             365
Thr Leu Ser Asn Arg Arg Phe Val Leu Cys Gly Thr Asn Val Lys Ala
            370             375             380
Met Ser Ile Glu Glu Ser Ser Asn Gly Ser Leu Ser Val Glu Phe Arg
385             390             395             400
His Leu Gln Pro Lys Glu Met Lys Ser Ser Ala Gly Gly Lys Gly Asn
            405             410             415
Glu Gly Cys His Met Val Thr Glu Glu Leu His Ser Ile Thr Phe Glu
            420             425             430
Thr Gln Ile Cys Leu Tyr Gly Leu Thr Ile Asp Leu Glu Thr Ser Ser
            435             440             445
Leu Pro Val Val Met Ile Ser Asn Val Ser Gln Leu Pro Asn Ala Trp
            450             455             460
Ala Ser Ile Ile Trp Tyr Asn Val Ser Thr Asn Asp Ser Gln Asn Leu
465             470             475             480
Val Phe Phe Asn Asn Pro Pro Ala Thr Leu Ser Gln Leu Leu Glu
            485             490             495
Val Met Ser Trp Gln Phe Ser Ser Tyr Val Gly Arg Gly Leu Asn Ser
            500             505             510
Asp Gln Leu His Met Leu Ala Glu Lys Leu Thr Val Gln Ser Ser Tyr
            515             520             525
Ser Asp Gly His Leu Thr Trp Ala Lys Phe Cys Lys Glu His Leu Pro
            530             535             540
Gly Lys Ser Phe Thr Phe Trp Thr Trp Leu Glu Ala Ile Leu Asp Leu
545             550             555             560
Ile Lys Lys His Ile Leu Pro Leu Trp Ile Asp Gly Tyr Val Met Gly
            565             570             575
Phe Val Ser Lys Glu Lys Glu Arg Leu Leu Leu Lys Asp Lys Met Pro
            580             585             590
Gly Thr Phe Leu Leu Arg Phe Ser Glu Ser His Leu Gly Gly Ile Thr
            595             600             605
Phe Thr Trp Val Asp His Ser Glu Ser Gly Glu Val Arg Phe His Ser
            610             615             620
Val Glu Pro Tyr Asn Lys Gly Arg Leu Ser Ala Leu Pro Phe Ala Asp
625             630             635             640
Ile Leu Arg Asp Tyr Lys Val Ile Met Ala Glu Asn Ile Pro Glu Asn
            645             650             655
Pro Leu Lys Tyr Leu Tyr Pro Asp Ile Pro Lys Asp Lys Ala Phe Gly
            660             665             670
Lys His Tyr Ser Ser Gln Pro Cys Glu Val Ser Arg Pro Thr Glu Arg
            675             680             685
```

```
Gly Asp Lys Gly Tyr Val Pro Ser Val Phe Ile Pro Ile Ser Thr Ile
        690                 695                 700

Arg Ser Asp Ser Thr Glu Pro His Ser Pro Ser Asp Leu Leu Pro Met
705                 710                 715                 720

Ser Pro Ser Val Tyr Ala Val Leu Arg Glu Asn Leu Ser Pro Thr Thr
                725                 730                 735

Ile Glu Thr Ala Met Lys Ser Pro Tyr Ser Ala Glu
            740                 745

<210> SEQ ID NO 21
<211> LENGTH: 749
<212> TYPE: PRT
<213> ORGANISM: Mus musculus

<400> SEQUENCE: 21

Met Ser Gln Trp Asn Gln Val Gln Gln Leu Glu Ile Lys Phe Leu Glu
1               5                   10                  15

Gln Val Asp Gln Phe Tyr Asp Asp Asn Phe Pro Met Glu Ile Arg His
            20                  25                  30

Leu Leu Ala Gln Trp Ile Glu Thr Gln Asp Trp Glu Val Ala Ser Asn
        35                  40                  45

Asn Glu Thr Met Ala Thr Ile Leu Leu Gln Asn Leu Leu Ile Gln Leu
50                  55                  60

Asp Glu Gln Leu Gly Arg Val Ser Lys Glu Lys Asn Leu Leu Leu Ile
65                  70                  75                  80

His Asn Leu Lys Arg Ile Arg Lys Val Leu Gln Gly Lys Phe His Gly
                85                  90                  95

Asn Pro Met His Val Ala Val Val Ile Ser Asn Cys Leu Arg Glu Glu
            100                 105                 110

Arg Arg Ile Leu Ala Ala Ala Asn Met Pro Ile Gln Gly Pro Leu Glu
        115                 120                 125

Lys Ser Leu Gln Ser Ser Val Ser Glu Arg Gln Arg Asn Val Glu
130                 135                 140

His Lys Val Ser Ala Ile Lys Asn Ser Val Gln Met Thr Glu Gln Asp
145                 150                 155                 160

Thr Lys Tyr Leu Glu Asp Leu Gln Asp Glu Phe Asp Tyr Arg Tyr Lys
                165                 170                 175

Thr Ile Gln Thr Met Asp Gln Gly Asp Lys Asn Ser Ile Leu Val Asn
            180                 185                 190

Gln Glu Val Leu Thr Leu Leu Gln Glu Met Leu Asn Ser Leu Asp Phe
        195                 200                 205

Lys Arg Lys Glu Ala Leu Ser Lys Met Thr Gln Ile Val Asn Glu Thr
210                 215                 220

Asp Leu Leu Met Asn Ser Met Leu Leu Glu Glu Leu Gln Asp Trp Lys
225                 230                 235                 240

Lys Arg Gln Gln Ile Ala Cys Ile Gly Gly Pro Leu His Asn Gly Leu
                245                 250                 255

Asp Gln Leu Gln Asn Cys Phe Thr Leu Leu Ala Glu Ser Leu Phe Gln
            260                 265                 270

Leu Arg Gln Gln Leu Glu Lys Leu Gln Glu Gln Ser Thr Lys Met Thr
        275                 280                 285

Tyr Glu Gly Asp Pro Ile Pro Ala Gln Arg Ala His Leu Leu Glu Arg
290                 295                 300

Ala Thr Phe Leu Ile Tyr Asn Leu Phe Lys Asn Ser Phe Val Val Glu
```

-continued

```
                305                 310                 315                 320
Arg Gln Pro Cys Met Pro Thr His Pro Gln Arg Pro Met Val Leu Lys
                    325                 330                 335

Thr Leu Ile Gln Phe Thr Val Lys Leu Arg Leu Ile Lys Leu Pro
                340                 345                 350

Glu Leu Asn Tyr Gln Val Lys Val Lys Ala Ser Ile Asp Lys Asn Val
                    355                 360                 365

Ser Thr Leu Ser Asn Arg Arg Phe Val Leu Cys Gly Thr His Val Lys
    370                 375                 380

Ala Met Ser Ser Glu Glu Ser Ser Asn Gly Ser Leu Ser Val Glu Phe
385                 390                 395                 400

Arg His Leu Gln Pro Lys Glu Met Lys Cys Ser Thr Gly Ser Lys Gly
                    405                 410                 415

Asn Glu Gly Cys His Met Val Thr Glu Leu His Ser Ile Thr Phe
                420                 425                 430

Glu Thr Gln Ile Cys Leu Tyr Gly Leu Thr Ile Asn Leu Glu Thr Ser
                    435                 440                 445

Ser Leu Pro Val Val Met Ile Ser Asn Val Ser Gln Leu Pro Asn Ala
    450                 455                 460

Trp Ala Ser Ile Ile Trp Tyr Asn Val Ser Thr Asn Asp Ser Gln Asn
465                 470                 475                 480

Leu Val Phe Phe Asn Asn Pro Pro Ser Val Thr Leu Gly Gln Leu Leu
                    485                 490                 495

Glu Val Met Ser Trp Gln Phe Ser Ser Tyr Val Gly Arg Gly Leu Asn
                500                 505                 510

Ser Glu Gln Leu Asn Met Leu Ala Glu Lys Leu Thr Val Gln Ser Asn
                    515                 520                 525

Tyr Asn Asp Gly His Leu Thr Trp Ala Lys Phe Cys Lys Glu His Leu
    530                 535                 540

Pro Gly Lys Thr Phe Thr Phe Trp Thr Trp Leu Glu Ala Ile Leu Asp
545                 550                 555                 560

Leu Ile Lys Lys His Ile Leu Pro Leu Trp Ile Asp Gly Tyr Ile Met
                565                 570                 575

Gly Phe Val Ser Lys Glu Lys Glu Arg Leu Leu Leu Lys Asp Lys Met
                580                 585                 590

Pro Gly Thr Phe Leu Leu Arg Phe Ser Glu Ser His Leu Gly Gly Ile
                    595                 600                 605

Thr Phe Thr Trp Val Asp Gln Ser Glu Asn Gly Glu Val Arg Phe His
                610                 615                 620

Ser Val Glu Pro Tyr Asn Lys Gly Arg Leu Ser Ala Leu Ala Phe Ala
625                 630                 635                 640

Asp Ile Leu Arg Asp Tyr Lys Val Ile Met Ala Glu Asn Ile Pro Glu
                    645                 650                 655

Asn Pro Leu Lys Tyr Leu Tyr Pro Asp Ile Pro Lys Asp Lys Ala Phe
                660                 665                 670

Gly Lys His Tyr Ser Ser Gln Pro Cys Glu Val Ser Arg Pro Thr Glu
                    675                 680                 685

Arg Gly Asp Lys Gly Tyr Val Pro Ser Val Phe Ile Pro Ile Ser Thr
                690                 695                 700

Ile Arg Ser Asp Ser Thr Glu Pro Gln Ser Pro Ser Asp Leu Leu Pro
705                 710                 715                 720

Met Ser Pro Ser Ala Tyr Ala Val Leu Arg Glu Asn Leu Ser Pro Thr
                    725                 730                 735
```

```
Thr Ile Glu Thr Ala Met Asn Ser Pro Tyr Ser Ala Glu
            740                 745

<210> SEQ ID NO 22
<211> LENGTH: 530
<212> TYPE: PRT
<213> ORGANISM: Mus musculus

<400> SEQUENCE: 22

Met Gly Ile Val Glu Pro Gly Cys Gly Asp Met Leu Thr Gly Thr Glu
1               5                   10                  15

Pro Met Pro Ser Asp Glu Gly Arg Gly Pro Gly Ala Asp Gln Gln His
            20                  25                  30

Arg Phe Phe Tyr Pro Glu Pro Gly Ala Gln Asp Pro Thr Asp Arg Arg
        35                  40                  45

Ala Gly Ser Ser Leu Gly Thr Pro Tyr Ser Gly Gly Ala Leu Val Pro
    50                  55                  60

Ala Ala Pro Gly Arg Phe Leu Gly Ser Phe Ala Tyr Pro Pro Arg Ala
65                  70                  75                  80

Gln Val Ala Gly Phe Pro Gly Pro Gly Glu Phe Phe Pro Pro Pro Ala
                85                  90                  95

Gly Ala Glu Gly Tyr Pro Pro Val Asp Gly Tyr Pro Ala Pro Asp Pro
            100                 105                 110

Arg Ala Gly Leu Tyr Pro Gly Pro Arg Glu Asp Tyr Ala Leu Pro Ala
        115                 120                 125

Gly Leu Glu Val Ser Gly Lys Leu Arg Val Ala Leu Ser Asn His Leu
    130                 135                 140

Leu Trp Ser Lys Phe Asn Gln His Gln Thr Glu Met Ile Ile Thr Lys
145                 150                 155                 160

Gln Gly Arg Arg Met Phe Pro Phe Leu Ser Phe Thr Val Ala Gly Leu
                165                 170                 175

Glu Pro Thr Ser His Tyr Arg Met Phe Val Asp Val Val Leu Val Asp
            180                 185                 190

Gln His His Trp Arg Tyr Gln Ser Gly Lys Trp Val Gln Cys Gly Lys
        195                 200                 205

Ala Glu Gly Ser Met Pro Gly Asn Arg Leu Tyr Val His Pro Asp Ser
    210                 215                 220

Pro Asn Thr Gly Ala His Trp Met Arg Gln Glu Val Ser Phe Gly Lys
225                 230                 235                 240

Leu Lys Leu Thr Asn Asn Lys Gly Ala Ser Asn Asn Val Thr Gln Met
                245                 250                 255

Ile Val Leu Gln Ser Leu His Lys Tyr Gln Pro Arg Leu His Ile Val
            260                 265                 270

Glu Val Asn Asp Gly Glu Pro Glu Ala Ala Cys Ser Ala Ser Asn Thr
        275                 280                 285

His Val Phe Thr Phe Gln Glu Thr Gln Phe Ile Ala Val Thr Ala Tyr
    290                 295                 300

Gln Asn Ala Glu Ile Thr Gln Leu Lys Ile Asp Asn Asn Pro Phe Ala
305                 310                 315                 320

Lys Gly Phe Arg Glu Asn Phe Glu Ser Met Tyr Ala Ser Val Asp Thr
                325                 330                 335

Ser Val Pro Ser Pro Gly Pro Asn Cys Gln Leu Leu Gly Gly Asp
            340                 345                 350

Pro Phe Ser Pro Leu Leu Ser Asn Gln Tyr Pro Val Pro Ser Arg Phe
```

-continued

```
              355                 360                 365
Tyr Pro Asp Leu Pro Gly Gln Pro Lys Asp Met Ile Ser Gln Pro Tyr
370                 375                 380

Trp Leu Gly Thr Pro Arg Glu His Ser Tyr Glu Ala Glu Phe Arg Ala
385                 390                 395                 400

Val Ser Met Lys Pro Thr Leu Leu Pro Ser Ala Pro Gly Pro Thr Val
                405                 410                 415

Pro Tyr Tyr Arg Gly Gln Asp Val Leu Ala Pro Gly Ala Gly Trp Pro
            420                 425                 430

Val Ala Pro Gln Tyr Pro Pro Lys Met Ser Pro Ala Gly Trp Phe Arg
        435                 440                 445

Pro Met Arg Thr Leu Pro Met Asp Pro Gly Leu Gly Ser Ser Glu Glu
    450                 455                 460

Gln Gly Ser Ser Pro Ser Leu Trp Pro Glu Val Thr Ser Leu Gln Pro
465                 470                 475                 480

Glu Pro Ser Asp Ser Gly Leu Gly Glu Gly Asp Thr Lys Arg Arg Arg
                485                 490                 495

Ile Ser Pro Tyr Pro Ser Ser Gly Asp Ser Ser Ser Pro Ala Gly Ala
            500                 505                 510

Pro Ser Pro Phe Asp Lys Glu Thr Glu Gly Gln Phe Tyr Asn Tyr Phe
        515                 520                 525

Pro Asn
    530

<210> SEQ ID NO 23
<211> LENGTH: 535
<212> TYPE: PRT
<213> ORGANISM: Homo sapiens

<400> SEQUENCE: 23

Met Gly Ile Val Glu Pro Gly Cys Gly Asp Met Leu Thr Gly Thr Glu
1               5                   10                  15

Pro Met Pro Gly Ser Asp Glu Gly Arg Ala Pro Gly Ala Asp Pro Gln
                20                  25                  30

His Arg Tyr Phe Tyr Pro Glu Pro Gly Ala Gln Asp Ala Asp Glu Arg
            35                  40                  45

Arg Gly Gly Gly Ser Leu Gly Ser Pro Tyr Pro Gly Gly Ala Leu Val
        50                  55                  60

Pro Ala Pro Pro Ser Arg Phe Leu Gly Ala Tyr Ala Tyr Pro Pro Arg
65                  70                  75                  80

Pro Gln Ala Ala Gly Phe Pro Gly Ala Gly Glu Ser Phe Pro Pro Pro
                85                  90                  95

Ala Asp Ala Glu Gly Tyr Gln Pro Gly Glu Gly Tyr Ala Ala Pro Asp
            100                 105                 110

Pro Arg Ala Gly Leu Tyr Pro Gly Pro Arg Glu Asp Tyr Ala Leu Pro
        115                 120                 125

Ala Gly Leu Glu Val Ser Gly Lys Leu Arg Val Ala Leu Asn Asn His
    130                 135                 140

Leu Leu Trp Ser Lys Phe Asn Gln His Gln Thr Glu Met Ile Ile Thr
145                 150                 155                 160

Lys Gln Gly Arg Arg Met Phe Pro Phe Leu Ser Phe Thr Val Ala Gly
                165                 170                 175

Leu Glu Pro Thr Ser His Tyr Arg Met Phe Val Asp Val Val Leu Val
            180                 185                 190
```

| | | | | | | | | | | | |
|---|---|---|---|---|---|---|---|---|---|---|---|
|Asp|Gln|His|His|Trp|Arg|Tyr|Gln|Ser|Gly|Lys|Trp|Val|Gln|Cys|Gly|
| | | | |195| | | | |200| | | | |205| |

Lys Ala Glu Gly Ser Met Pro Gly Asn Arg Leu Tyr Val His Pro Asp
210                     215                     220

Ser Pro Asn Thr Gly Ala His Trp Met Arg Gln Glu Val Ser Phe Gly
225                     230                     235                 240

Lys Leu Lys Leu Thr Asn Asn Lys Gly Ala Ser Asn Asn Val Thr Gln
            245                     250                     255

Met Ile Val Leu Gln Ser Leu His Lys Tyr Gln Pro Arg Leu His Ile
                260                     265                     270

Val Glu Val Asn Asp Gly Glu Pro Glu Ala Ala Cys Asn Ala Ser Asn
            275                     280                     285

Thr His Ile Phe Thr Phe Gln Glu Thr Gln Phe Ile Ala Val Thr Ala
    290                     295                     300

Tyr Gln Asn Ala Glu Ile Thr Gln Leu Lys Ile Asp Asn Asn Pro Phe
305                     310                     315                 320

Ala Lys Gly Phe Arg Glu Asn Phe Glu Ser Met Tyr Thr Ser Val Asp
                325                     330                     335

Thr Ser Ile Pro Ser Pro Pro Gly Pro Asn Cys Gln Phe Leu Gly Gly
            340                     345                     350

Asp His Tyr Ser Pro Leu Leu Pro Asn Gln Tyr Pro Val Pro Ser Arg
    355                     360                     365

Phe Tyr Pro Asp Leu Pro Gly Gln Ala Lys Asp Val Val Pro Gln Ala
    370                     375                     380

Tyr Trp Leu Gly Ala Pro Arg Asp His Ser Tyr Glu Ala Glu Phe Arg
385                     390                     395                 400

Ala Val Ser Met Lys Pro Ala Phe Leu Pro Ser Ala Pro Gly Pro Thr
                405                     410                     415

Met Ser Tyr Tyr Arg Gly Gln Glu Val Leu Ala Pro Gly Ala Gly Trp
            420                     425                     430

Pro Val Ala Pro Gln Tyr Pro Pro Lys Met Gly Pro Ala Ser Trp Phe
    435                     440                     445

Arg Pro Met Arg Thr Leu Pro Met Glu Pro Gly Pro Gly Gly Ser Glu
450                     455                     460

Gly Arg Gly Pro Glu Asp Gln Gly Pro Pro Leu Val Trp Thr Glu Ile
465                     470                     475                 480

Ala Pro Ile Arg Pro Glu Ser Ser Asp Ser Gly Leu Gly Glu Gly Asp
                485                     490                     495

Ser Lys Arg Arg Arg Val Ser Pro Tyr Pro Ser Ser Gly Asp Ser Ser
            500                     505                     510

Ser Pro Ala Gly Ala Pro Ser Pro Phe Asp Lys Glu Ala Glu Gly Gln
    515                     520                     525

Phe Tyr Asn Tyr Phe Pro Asn
530                     535

<210> SEQ ID NO 24
<211> LENGTH: 777
<212> TYPE: DNA
<213> ORGANISM: Homo sapiens

<400> SEQUENCE: 24
atggaatgga cctgggtctt tctcttcctc ctgtcagtaa ctgcaggtgt ccactcccag      60
gttcagctgc agcagtctgg agctgagctg atgaagcctg gggcctcagt gaagctttcc     120
tgcaaggcta ctggctacac attcactggc tactggatag agtggataaa gcagaggcct     180

-continued

```
ggacatggcc ttgagtggat tggagagatt ttacctggaa ctggtagtac taactacaat    240
gagaagttca agggcaaggc cacattcact gcagatacat cctccaacac agcctacatg    300
caactcagca gcctgacaac tgaggactct gccatctatt actgtgcaat cccggggcct    360
atggactact ggggtcaagg aacctcagtc accgtctcct cagccggcgg aggcggatca    420
ggaggaggag gatcaggcgg aggaggatca gaattcgaca tcaagatgac ccagtctcca    480
tcttccatgt atgcatctct aggagagaga gtcactatca cttgcaaggc gagtcaggac    540
attaatagct atttaagctg gttccagcag aaaccaggga atctcctaa gaccctgatc     600 tatcgtgcaa acagattggt agatggggtc ccatcaaggt tcagtggcag tggatctggg    660
caagattatt ctctcaccat cagcagcctg gagtatgaag atatgggaat ttattattgt    720
ctacagtatg atgagtttcc gtacacgttc ggaggggga ccaagctgga aataaaa       777
```

<210> SEQ ID NO 25
<211> LENGTH: 461
<212> TYPE: PRT
<213> ORGANISM: Artificial Sequence
<220> FEATURE:
<223> OTHER INFORMATION: Tz.47-28-3z
<400> SEQUENCE: 25

```
Met Glu Trp Thr Trp Val Phe Leu Phe Leu Leu Ser Val Thr Ala Gly
1               5                   10                  15

Val His Ser Gln Val Gln Leu Gln Gln Ser Gly Ala Glu Leu Met Lys
            20                  25                  30

Pro Gly Ala Ser Val Lys Leu Ser Cys Lys Ala Thr Gly Tyr Thr Phe
        35                  40                  45

Thr Gly Tyr Trp Ile Glu Trp Ile Lys Gln Arg Pro Gly His Gly Leu
    50                  55                  60

Glu Trp Ile Gly Glu Ile Leu Pro Gly Thr Gly Ser Thr Asn Tyr Asn
65                  70                  75                  80

Glu Lys Phe Lys Gly Lys Ala Thr Phe Thr Ala Asp Thr Ser Ser Asn
                85                  90                  95

Thr Ala Tyr Met Gln Leu Ser Ser Leu Thr Thr Glu Asp Ser Ala Ile
            100                 105                 110

Tyr Tyr Cys Ala Ile Pro Gly Pro Met Asp Tyr Trp Gly Gln Gly Thr
        115                 120                 125

Ser Val Thr Val Ser Ser Ala Gly Gly Gly Ser Gly Gly Gly Gly
    130                 135                 140

Ser Gly Gly Gly Gly Ser Glu Phe Asp Ile Lys Met Thr Gln Ser Pro
145                 150                 155                 160

Ser Ser Met Tyr Ala Ser Leu Gly Glu Arg Val Thr Ile Thr Cys Lys
                165                 170                 175

Ala Ser Gln Asp Ile Asn Ser Tyr Leu Ser Trp Phe Gln Gln Lys Pro
            180                 185                 190

Gly Lys Ser Pro Lys Thr Leu Ile Tyr Arg Ala Asn Arg Leu Val Asp
        195                 200                 205

Gly Val Pro Ser Arg Phe Ser Gly Ser Gly Ser Gly Gln Asp Tyr Ser
    210                 215                 220

Leu Thr Ile Ser Ser Leu Glu Tyr Glu Asp Met Gly Ile Tyr Tyr Cys
225                 230                 235                 240

Leu Gln Tyr Asp Glu Phe Pro Tyr Thr Phe Gly Gly Thr Lys Leu
                245                 250                 255
```

```
Glu Ile Lys Ala Ser Val Lys Gly Lys His Leu Cys Pro Ser Pro Leu
                260                 265                 270

Phe Pro Gly Pro Ser Lys Pro Phe Trp Val Leu Val Val Gly Gly
            275                 280                 285

Val Leu Ala Cys Tyr Ser Leu Leu Val Thr Val Ala Phe Ile Ile Phe
        290                 295                 300

Trp Val Arg Ser Lys Arg Ser Arg Leu Leu His Ser Asp Tyr Met Asn
305                 310                 315                 320

Met Thr Pro Arg Arg Pro Gly Pro Thr Arg Lys His Tyr Gln Pro Tyr
                325                 330                 335

Ala Pro Pro Arg Asp Phe Ala Ala Tyr Arg Ser Lys Leu Arg Val Lys
            340                 345                 350

Phe Ser Arg Ser Ala Asp Ala Pro Ala Tyr Gln Gln Gly Gln Asn Gln
        355                 360                 365

Leu Tyr Asn Glu Leu Asn Leu Gly Arg Arg Glu Glu Tyr Asp Val Leu
    370                 375                 380

Asp Lys Arg Arg Gly Arg Asp Pro Glu Met Gly Gly Lys Pro Arg Arg
385                 390                 395                 400

Lys Asn Pro Gln Glu Gly Leu Tyr Asn Glu Leu Gln Lys Asp Lys Met
                405                 410                 415

Ala Glu Ala Tyr Ser Glu Ile Gly Met Lys Gly Glu Arg Arg Arg Gly
            420                 425                 430

Lys Gly His Asp Gly Leu Tyr Gln Gly Leu Ser Thr Ala Thr Lys Asp
        435                 440                 445

Thr Tyr Asp Ala Leu His Met Gln Ala Leu Pro Pro Arg
    450                 455                 460

<210> SEQ ID NO 26
<211> LENGTH: 1383
<212> TYPE: DNA
<213> ORGANISM: Artificial Sequence
<220> FEATURE:
<223> OTHER INFORMATION: Tz.47-28-3z DNA

<400> SEQUENCE: 26
atggaatgga cctgggtctt tctcttcctc ctgtcagtaa ctgcaggtgt ccactcccag      60
gttcagctgc agcagtctgg agctgagctg atgaagcctg gggcctcagt gaagctttcc     120
tgcaaggcta ctggctacac attcactggc tactggatag agtggataaa gcagaggcct     180
ggacatggcc ttgagtggat tggagagatt ttacctggaa ctggtagtac taactacaat     240
gagaagttca gggcaaggc cacattcact gcagatacac ctccaacac agcctacatg      300 caactcagca gcctgacaac tgaggactct gccatctatt actgtgcaat cccggggcct     360
atggactact ggggtcaagg aacctcagtc accgtctcct cagccggcgg aggcggatca     420
ggaggaggag gatcaggcgg aggaggatca gaattcgaca tcaagatgac ccagtctcca     480
tcttccatgt atgcatctct aggagagaga gtcactatca cttgcaaggc gagtcaggac     540
attaatagct atttaagctg gttccagcag aaaccaggga atctcctaa gaccctgatc     600 tatcgtgcaa acagattggt agatggggtc ccatcaaggt tcagtggcag tggatctggg     660
caagattatt ctctcaccat cagcagcctg gagtatgaag atatgggaat ttattattgt     720
ctacagtatg atgagtttcc gtacacgttc ggagggggga ccaagctgga aataaaagct     780
agcgtgaaag ggaacaccct tgtccaagt cccctatttc ccggaccttc taagcccttt     840
tgggtgctgg tggtggttgg tggagtcctg gcttgctata gcttgctagt aacagtggcc     900
```

-continued

```
tttattattt tctgggtgag gagtaagagg agcaggctcc tgcacagtga ctacatgaac    960
atgactcccc gccgcccggg cccacccgc aagcattacc agccctatgc cccaccacgc    1020
gacttcgcag cctatcgctc caagcttaga gtgaagttca gcaggagcgc agacgccccc    1080
gcgtaccagc agggccagaa ccagctctat aacgagctca atctaggacg aagagaggag    1140
tacgatgttt tggacaagag acgtggccgg gaccctgaga tggggggaaa gccgagaagg    1200
aagaaccctc aggaaggcct gtacaatgaa ctgcagaaag ataagatggc ggaggcctac    1260
agtgagattg ggatgaaagg cgagcgccgg aggggcaagg ggcacgatgg cctttaccag    1320
ggtctcagta cagccaccaa ggacacctac gacgcccttc acatgcaggc cctgccccct    1380
cgc                                                                 1383
```

<210> SEQ ID NO 27
<211> LENGTH: 26
<212> TYPE: PRT
<213> ORGANISM: Artificial Sequence
<220> FEATURE:
<223> OTHER INFORMATION: Furin T2A

<400> SEQUENCE: 27

Arg Ala Lys Arg Ser Gly Ser Gly Glu Gly Arg Gly Ser Leu Ile Thr
1               5                   10                  15

Cys Gly Asp Val Glu Glu Asn Pro Gly Pro
            20                  25

<210> SEQ ID NO 28
<211> LENGTH: 78
<212> TYPE: DNA
<213> ORGANISM: Artificial Sequence
<220> FEATURE:
<223> OTHER INFORMATION: Furin T2A DNA

<400> SEQUENCE: 28

```
agagccaaaa ggtctggctc cggtgagggc agaggaagtc ttataacatg cggtgacgtg    60
gaggagaatc ccggccct                                                 78
```

<210> SEQ ID NO 29
<211> LENGTH: 71
<212> TYPE: PRT
<213> ORGANISM: Artificial Sequence
<220> FEATURE:
<223> OTHER INFORMATION: T-bet STOP

<400> SEQUENCE: 29

Met Gly Ile Val Glu Pro Gly Cys Gly Asp Met Leu Thr Gly Thr Glu
1               5                   10                  15

Pro Met Pro Ser Asp Glu Gly Arg Gly Pro Gly Ala Asp Gln Gln His
            20                  25                  30

Arg Phe Phe Tyr Pro Glu Pro Gly Ala Gln Asp Pro Thr Asp Arg Arg
        35                  40                  45

Ala Gly Ser Ser Leu Gly Thr Pro Tyr Ser Gly Gly Ala Leu Val Pro
    50                  55                  60

Ala Ala Pro Gly Arg Phe Leu
65                  70

<210> SEQ ID NO 30
<211> LENGTH: 1593
<212> TYPE: DNA
<213> ORGANISM: Artificial Sequence
<220> FEATURE:

<223> OTHER INFORMATION: T-bet STOP DNA

<400> SEQUENCE: 30

| | |
|---|---|
| atgggcatcg tggagccggg ctgcggagac atgctgaccg gcaccgagcc gatgccgagt | 60 |
| gacgagggcc gggggcccgg agcggaccaa cagcatcgtt tcttctatcc cgagccgggc | 120 |
| gcacaggacc cgaccgatcg ccgcgcaggt agcagcctgg ggacgcccta ctctgggggc | 180 |
| gccctggtgc ctgccgcgcc gggtcgcttc ctttgatcct tcgcctaccc gccccgggct | 240 |
| caggtggctg gctttcccgg gcctggcgag ttcttcccgc cgcccgcggg tgcggagggc | 300 |
| tacccgcccg tggatggcta ccctgcccct gacccgcgcg cggggctcta cccagggccg | 360 |
| cgcgaggact acgcattgcc cgcggggttg gaggtgtctg ggaagctgag agtcgcgctc | 420 |
| agcaaccacc tgttgtggtc caagttcaac cagcaccaga cagagatgat catcactaag | 480 |
| caaggacggc gaatgttccc attcctgtcc ttcaccgtgg ccgggctgga gcccacaagc | 540 |
| cattacagga tgtttgtgga tgtggtcttg tggaccagc accactggcg gtaccagagc | 600 |
| ggcaagtggg tgcagtgtgg aaaggcagaa ggcagcatgc cagggaaccg cttatatgtc | 660 |
| cacccagact cccccaacac cggagcccac tggatgcgcc aggaagtttc atttgggaag | 720 |
| ctaaagctca ccaacaacaa gggggcttcc aacaatgtga cccagatgat cgtcctgcag | 780 |
| tctctccaca gtaccagcc ccggctgcac atcgtggagg tgaatgatgg agagccagag | 840 |
| gctgcctgca gtgcttctaa cacacacgtc tttactttcc aagagaccca gttcattgca | 900 |
| gtgactgcct accagaacgc agagatcact cagctgaaaa tcgacaacaa ccccttgcc | 960 |
| aaaggattcc gggagaactt tgagtccatg tacgcatctg ttgatacgag tgtcccctcg | 1020 |
| ccacctggac ccaactgtca actgcttggg ggagacccct tctcacctct tctatccaac | 1080 |
| cagtatcctg ttcccagccg tttctacccc gaccttccag gccagcccaa ggatatgatc | 1140 |
| tcacagcctt actggctggg gacacctcgg gaacacagtt atgaagcgga gttccgagct | 1200 |
| gtgagcatga gcccacact cctaccctct gccccggggc ccactgtgcc ctactaccgg | 1260 |
| ggccaagacg tcctggcgcc tggagctggt tggcccgtgg cccctcaata cccgcccaag | 1320 |
| atgagcccag ctggctggtt ccggcccatg cgaactctgc ccatggaccc gggcctggga | 1380 |
| tcctcagagg aacagggctc ctcccctcg ctgtggcctg aggtcacctc cctccagccg | 1440 |
| gagcccagcg actcaggact aggcgaagga gacactaaga ggaggaggat atcccctat | 1500 |
| ccttccagtg gcgacagctc ctctcccgct ggggcccctt ctccttttga taaggaaacc | 1560 |
| gaaggccagt tttataatta ttttcccaac tga | 1593 |

<210> SEQ ID NO 31
<211> LENGTH: 338
<212> TYPE: PRT
<213> ORGANISM: Artificial Sequence
<220> FEATURE:
<223> OTHER INFORMATION: TBOX DEL

<400> SEQUENCE: 31

Met Gly Ile Val Glu Pro Gly Cys Gly Asp Met Leu Thr Gly Thr Glu
1               5                   10                  15

Pro Met Pro Ser Asp Glu Gly Arg Gly Pro Gly Ala Asp Gln Gln His
                20                  25                  30

Arg Phe Phe Tyr Pro Glu Pro Gly Ala Gln Asp Pro Thr Asp Arg Arg
            35                  40                  45

Ala Gly Ser Ser Leu Gly Thr Pro Tyr Ser Gly Gly Ala Leu Val Pro
        50                  55                  60

Ala Ala Pro Gly Arg Phe Leu Gly Ser Phe Tyr Pro Pro Arg Ala
65                  70                  75                  80

Gln Val Ala Gly Phe Pro Gly Pro Gly Glu Phe Phe Pro Pro Ala
            85                  90                  95

Gly Ala Glu Gly Tyr Pro Pro Val Asp Gly Tyr Pro Ala Pro Asp Pro
            100                 105                 110

Arg Ala Gly Leu Tyr Pro Gly Pro Arg Glu Asp Tyr Ala Leu Pro Ala
            115                 120                 125

Gly Leu Glu Val Ser Gly Phe Glu Ser Met Tyr Ala Ser Val Asp Thr
130                 135                 140

Ser Val Pro Ser Pro Pro Gly Pro Asn Cys Gln Leu Leu Gly Gly Asp
145                 150                 155                 160

Pro Phe Ser Pro Leu Leu Ser Asn Gln Tyr Pro Val Pro Ser Arg Phe
                165                 170                 175

Tyr Pro Asp Leu Pro Gly Gln Pro Lys Asp Met Ile Ser Gln Pro Tyr
            180                 185                 190

Trp Leu Gly Thr Pro Arg Glu His Ser Tyr Glu Ala Glu Phe Arg Ala
            195                 200                 205

Val Ser Met Lys Pro Thr Leu Leu Pro Ser Ala Pro Gly Pro Thr Val
210                 215                 220

Pro Tyr Tyr Arg Gly Gln Asp Val Leu Ala Pro Gly Ala Gly Trp Pro
225                 230                 235                 240

Val Ala Pro Gln Tyr Pro Pro Lys Met Ser Pro Ala Gly Trp Phe Arg
                245                 250                 255

Pro Met Arg Thr Leu Pro Met Asp Pro Gly Leu Gly Ser Ser Glu Glu
            260                 265                 270

Gln Gly Ser Ser Pro Ser Leu Trp Pro Glu Val Thr Ser Leu Gln Pro
            275                 280                 285

Glu Pro Ser Asp Ser Gly Leu Gly Glu Gly Asp Thr Lys Arg Arg Arg
290                 295                 300

Ile Ser Pro Tyr Pro Ser Ser Gly Asp Ser Ser Ser Pro Ala Gly Ala
305                 310                 315                 320

Pro Ser Pro Phe Asp Lys Glu Thr Glu Gly Gln Phe Tyr Asn Tyr Phe
                325                 330                 335

Pro Asn

<210> SEQ ID NO 32
<211> LENGTH: 1017
<212> TYPE: DNA
<213> ORGANISM: Artificial Sequence
<220> FEATURE:
<223> OTHER INFORMATION: TBOX DEL DNA

<400> SEQUENCE: 32
atgggcatcg tggagccggg ctgcggagac atgctgaccg gcaccgagcc gatgccgagt    60
gacgagggcc gggggcccgg agcggaccaa cagcatcgtt tcttctatcc cgagccgggc   120
gcacaggacc cgaccgatcg ccgcgcaggt agcagcctgg gacgcccta ctctgggggc    180 gccctggtgc ctgccgcgcc gggtcgcttc cttggatcct cgcctaccc gccccgggct    240 caggtggctg gctttccggg cctggcgag ttcttcccgc cgcccgcggg tgcggagggc    300
tacccgcccg tggatggcta ccctgcccct gacccgcgcg cgggctcta cccagggccg   360 cgcgaggact acgcattgcc cgcggggttg gaggtgtctg ggtttgagtc catgtacgca   420
tctgttgata cgagtgtccc ctcgccacct ggacccaact gtcaactgct ggggggagac    480

```
cccttctcac ctcttctatc caaccagtat cctgttccca gccgtttcta ccccgacctt    540
ccaggccagc ccaaggatat gatctcacag ccttactggc tggggacacc tcgggaacac    600
agttatgaag cggagttccg agctgtgagc atgaagccca cactcctacc ctctgccccg    660
gggcccactg tgccctacta ccggggccaa gacgtcctgg cgcctggagc tggttggccc    720
gtggcccctc aatacccgcc aagatgagc ccagctggct ggttccggcc catgcgaact    780
ctgcccatgg acccgggcct gggatcctca gaggaacagg gctcctcccc ctcgctgtgg    840
cctgaggtca cctccctcca gccggagccc agcgactcag gactaggcga aggagacact    900
aagaggagga ggatatcccc ctatccttcc agtggcgaca gctcctctcc cgctggggcc    960
ccttctcctt tgataagga aaccgaaggc cagtttttata attattttcc caactga     1017
```

<210> SEQ ID NO 33
<211> LENGTH: 6572
<212> TYPE: DNA
<213> ORGANISM: Artificial Sequence
<220> FEATURE:
<223> OTHER INFORMATION: Pfb vector

<400> SEQUENCE: 33

```
gaattgctag caattgctag caattgctag caattcatac cagatcaccg aaaactgtcc     60
tccaaatgtg tcccctcac actcccaaat tcgcgggctt ctgcctctta gaccactcta    120
ccctattccc cacactcacc ggagccaaag ccgcgggaca tatacatgtg aaagacccca    180
cctgtaggtt tggcaagcta gcttaagtaa cgccattttg caaggcatgg aaaaatacat    240
aactgagaat agaaaagttc agatcaaggt caggaacaga tggaacagct gaatatgggc    300
caaagcggat atctgtggta agcagttcct gccccggctc agggccaaga acagatggaa    360
cagctgaata tgggccaaac aggatatctg tggtaagcag ttcctgcccc ggctcagggc    420
caagaacaga tggtccccag atgcggtcca gccctcagca gtttctagag aaccatcaga    480
tgtttccagg gtgcccaag gacctgaaat gaccctgtgc cttatttgaa ctaaccaatc    540
agttcgcttc tcgcttctgt tcgcgcgctt ctgctcccg agctcaataa aagagcccac    600 aaccctcac tcggggcgcc agtcctccga ttgactgagt cgcccgggta cccgtgtatc    660
caataaaccc tcttgcagtt gcatccgact tgtggtctcg ctgttccttg ggagggtctc    720
ctctgagtga ttgactaccc gtcagcgggg gtctttcatt tgggggctcg tccgggatcg    780
ggagacccct gcccagggac caccgaccca ccacgggag gtaagctggc cagcaactta    840
tctgtgtctg tccgattgtc tagtgtctat gactgatttt atgcgcctgc gtcggtacta    900
gttagctaac tagctctgta tctggcggac ccgtggtgga actgacgagt tcggaacacc    960
cggccgcaac cctgggagac gtcccaggga cttcgggggc cgttttttgtg gcccgacctg   1020 agtccaaaaa tcccgatcgt tttggactct ttggtgcacc ccccttagag gagggatatg   1080
tggttctggt aggagacgag aacctaaaac agttcccgcc tccgtctgaa tttttgcttt   1140
cggtttggga ccgaagccgc gccgcgcgtc ttgtctgctg cagcatcgtt ctgtgttgtc   1200
tctgtctgac tgtgtttctg tatttgtctg aaaatatggg cccgggccag actgttacca   1260
ctcccttaag tttgacctta ggtcactgga agatgtcga gcagatcgct cacaaccagt   1320
cggtagatgt caagaagaga cgttgggtta ccttctgctc tgcagaatgg ccaaccttta   1380
acgtcggatg gccgcgagac ggcacctttaa accgagacct catcacccag gttaagatca   1440
aggtcttttc acctggcccg catggacacc cagaccaggt ccctacatc gtgacctggg   1500
```

```
aagccttggc tttttgacccc cctccctggg tcaagccctt tgtacaccct aagcctccgc    1560
ctcctcttcc tccatccgcc ccgtctctcc cccttgaacc tcctcgttcg accccgcctc    1620
gatcctccct ttatccagcc ctcactcctt ctctaggcgc ccccatatgg ccatatgaga    1680
tcttatatgg ggcaccccg ccccttgtaa acttccctga ccctgacatg acaagagtta     1740
ctaacagccc ctctctccaa gctcacttac aggctctcta cttagtccag cacgaagtct    1800
ggagacctct ggcggcagcc taccaagaac aactggaccg accggtggta cctcaccctt    1860
accgagtcgg cgacacagtg tgggtccgcc gacaccagac taagaaccta gaacctcgct    1920
ggaaaggacc ttacacagtc ctgctgacca cccccaccgc cctcaaagta gacggcatcg    1980
cagcttggat acacgccgcc cacgtgaagg ctgccgaccc cggggtgga ccatcctcta     2040
gactgccgga tcgaattgtc gacgaattcg gatcctcgag cggccgcgat ccggttattt    2100
tccaccatat tgccgtcttt tggcaatgtg agggcccgga aacctggccc tgtcttcttg    2160
acgagcattc ctaggggtct ttcccctctc gccaaaggaa tgcaaggtct gttgaatgtc    2220
gtgaaggaag cagttcctct ggaagcttct tgaagacaaa caacgtctgt agcgacccct    2280
tgcaggcagc ggaaccccc acctggcgac aggtgcctct gcggccaaaa gccacgtgta     2340
taagatacac ctgcaaaggc ggcacaaccc cagtgccacg ttgtgagttg atagttgtg     2400
gaaagagtca aatggctctc ctcaagcgta ttcaacaagg ggctgaagga tgcccagaag    2460
gtacccatt gtatgggatc tgatctgggg cctcggtgca catgctttac atgtgtttag     2520
tcgaggttaa aaaacgtcta ggccccccga accacgggga cgtggttttc ctttgaaaaa    2580
cacgatcgat aatatggaac aaaaacttat ttctgaagaa gacttggaca ccaaactttc    2640
ctgccgctcg atttctccac ccaggtgaac tcctccctca cctccccgac ggggcgaggc    2700
tccatggctg cccctcgct gcaccgtcc ctggtccac gcggttccat gggatcgttt       2760
cgcatgattg aacaagatgg attgcacgca ggttctccgg ccgcttgggt ggagaggcta    2820
ttcggctatg actgggcaca acagacaatc ggctgctctg atgccgccgt gttccggctg    2880
tcagcgcagg ggcgcccggt tctttttgtc aagaccgacc tgtccggtgc cctgaatgaa    2940
ctgcaggacg aggcagcgcg gctatcgtgg ctggccacga cgggcgttcc ttgcgcagct    3000
gtgctcgacg ttgtcactga agcgggaagg gactggctgc tattgggcga agtgccgggg    3060
caggatctcc tgtcatctca ccttgctcct gccgagaaag tatccatcat ggctgatgca    3120
atgcggcggc tgcatacgct tgatccggct acctgcccat tcgaccacca agcgaaacat    3180
cgcatcgagc gagcacgtac tcggatgaa gccgtcttg tcgatcagga tgatctggac      3240
gaagagcatc aggggctcgc gccagccgaa ctgttcgcca ggctcaaggc gcgcatgccc    3300
gacggcgagg atctcgtcgt gacccatggc gatgcctgct tgccgaatat catggtggaa    3360
aatggccgct tttctggatt catcgactgt ggccggctgg gtgtggcgga ccgctatcag    3420
gacatagcgt tggctacccg tgatattgct gaagagcttg gcggcgaatg gctgaccgc     3480
ttcctcgtgc tttacggtat cgccgctccc gattcgcagc gcatcgcctt ctatcgcctt    3540
cttgacgagt tcttctgagc gggactctgg ggttcgataa aataaaagat tttatttagt    3600
ctccagaaaa aggggggaat gaaagacccc acctgtaggt ttggcaagct agcttaagta    3660
acgccatttt gcaaggcatg gaaaaataca taactgagaa tagagaagtt cagatcaagg    3720
tcaggaacag atggaacagc tgaatatggg ccaaacagga tatctgtggt aagcagttcc    3780
tgccccggct cagggccaag aacagatgga acagctgaat atgggccaaa caggatatct    3840
gtggtaagca gttcctgccc cggctcaggg ccaagaacag atggtcccca gatgcggtcc    3900
```

```
agccctcagc agtttctaga gaaccatcag atgtttccag ggtgccccaa ggacctgaaa   3960
tgaccctgtg ccttatttga actaaccaat cagttcgctt ctcgcttctg ttcgcgcgct   4020
tctgctcccc gagctcaata aaagagccca aacccctca ctcggggcgc cagtcctccg    4080
attgactgag tcgcccgggt acccgtgtat ccaataaacc ctcttgcagt tgcatccgac   4140
ttgtggtctc gctgttcctt gggagggtct cctctgagtg attgactacc cgtcagcggg   4200
ggtctttcat ttgggggctc gtccgggatc gggagacccc tgcccaggga ccaccgaccc   4260
accaccggga ggtaagctgg ctgcctcgcg cgtttcggtg atgacggtga aaacctctga   4320
cacatgcagc tcccggagac ggtcacagct tgtctgtaag cggatgccgg gagcagacaa   4380
gcccgtcagg gcgcgtcagc gggtgttggc gggtgtcggg gcgcagccat gacccagtca   4440
cgtagcgata gcggagtgta tactggctta actatgcggc atcagagcag attgtactga   4500
gagtgcacca tatgcggtgt gaaataccgc acagatgcgt aaggagaaaa taccgcatca   4560
ggcgctcttc cgcttcctcg ctcactgact cgctgcgctc ggtcgttcgg ctgcggcgag   4620
cggtatcagc tcactcaaag gcggtaatac ggttatccac agaatcaggg gataacgcag   4680
gaaagaacat gtgagcaaaa ggccagcaaa aggccaggaa ccgtaaaaag gccgcgttgc   4740
tggcgttttt ccataggctc cgcccccctg acgagcatca caaaaatcga cgctcaagtc   4800
agaggtggcg aaacccgaca ggactataaa gataccaggc gtttccccct ggaagctccc   4860
tcgtgcgctc tcctgttccg accctgccgc ttaccggata cctgtccgcc tttctccctt   4920
cgggaagcgt ggcgctttct catagctcac gctgtaggta tctcagttcg gtgtaggtcg   4980
ttcgctccaa gctgggctgt gtgcacgaac cccccgttca gcccgaccgc tgcgccttat   5040
ccggtaacta tcgtcttgag tccaacccgg taagacacga cttatcgcca ctggcagcag   5100
ccactggtaa caggattagc agagcgaggt atgtaggcgg tgctacagag ttcttgaagt   5160
ggtggcctaa ctacggctac actagaagga cagtatttgg tatctgcgct ctgctgaagc   5220
cagttacctt cggaaaaaga gttggtagct cttgatccgg caaacaaacc accgctggta   5280
gcggtggttt ttttgtttgc aagcagcaga ttacgcgcag aaaaaaagga tctcaagaag   5340
atcctttgat cttttctacg gggtctgacg ctcagtggaa cgaaaactca cgttaaggga   5400
ttttggtcat gagattatca aaaaggatct tcacctagat ccttttaaat taaaaatgaa   5460
gttttaaatc aatctaaagt atatatgagt aaacttggtc tgacagttac caatgcttaa   5520
tcagtgaggc acctatctca gcgatctgtc tatttcgttc atccatagtt gcctgactcc   5580
ccgtcgtgta gataactacg atacgggagg gcttaccatc tggccccagt gctgcaatga   5640
taccgcgaga cccacgctca ccggctccag atttatcagc aataaaccag ccagccggaa   5700
gggccgagcg cagaagtggt cctgcaactt tatccgcctc catccagtct attaattgtt   5760
gccgggaagc tagagtaagt agttcgccag ttaatagttt gcgcaacgtt gttgccattg   5820
ctgcaggcat cgtggtgtca cgctcgtcgt ttggtatggc ttcattcagc tccgttccc    5880
aacgatcaag gcgagttaca tgatccccca tgttgtgcaa aaaagcggtt agctccttcg   5940
gtcctccgat cgttgtcaga agtaagttgg ccgcagtgtt atcactcatg gttatggcag   6000
cactgcataa ttctcttact gtcatgccat ccgtaagatg cttttctgtg actggtgagt   6060
actcaaccaa gtcattctga gaatagtgta tgcggcgacc gagttgctct tgcccggcgt   6120
caacacggga taataccgcg ccacatagca gaactttaaa agtgctcatc attggaaaac   6180
gttcttcggg gcgaaaactc tcaaggatct taccgctgtt gagatccagt tcgatgtaac   6240
```

-continued

```
ccactcgtgc acccaactga tcttcagcat cttttacttt caccagcgtt tctgggtgag    6300
caaaaacagg aaggcaaaat gccgcaaaaa agggaataag ggcgacacgg aaatgttgaa    6360
tactcatact cttccttttt caatattatt gaagcattta tcagggttat tgtctcatga    6420
gcggatacat atttgaatgt atttagaaaa ataaacaaat aggggttccg cgcacatttc    6480
cccgaaaagt gccacctgac gtctaagaaa ccattattat catgacatta acctataaaa    6540
ataggcgtat cacgaggccc tttcgtcttc aa                                  6572

<210> SEQ ID NO 34
<211> LENGTH: 1017
<212> TYPE: PRT
<213> ORGANISM: Artificial Sequence
<220> FEATURE:
<223> OTHER INFORMATION: Tz.47-28-3z-MsTBET

<400> SEQUENCE: 34
```

Met Glu Trp Thr Trp Val Phe Leu Phe Leu Leu Ser Val Thr Ala Gly
1               5                   10                  15

Val His Ser Gln Val Gln Leu Gln Gln Ser Gly Ala Glu Leu Met Lys
                20                  25                  30

Pro Gly Ala Ser Val Lys Leu Ser Cys Lys Ala Thr Gly Tyr Thr Phe
            35                  40                  45

Thr Gly Tyr Trp Ile Glu Trp Ile Lys Gln Arg Pro Gly His Gly Leu
        50                  55                  60

Glu Trp Ile Gly Glu Ile Leu Pro Gly Thr Gly Ser Thr Asn Tyr Asn
65                  70                  75                  80

Glu Lys Phe Lys Gly Lys Ala Thr Phe Thr Ala Asp Thr Ser Ser Asn
                85                  90                  95

Thr Ala Tyr Met Gln Leu Ser Ser Leu Thr Thr Glu Asp Ser Ala Ile
            100                 105                 110

Tyr Tyr Cys Ala Ile Pro Gly Pro Met Asp Tyr Trp Gly Gln Gly Thr
        115                 120                 125

Ser Val Thr Val Ser Ser Ala Gly Gly Gly Ser Gly Gly Gly Gly
        130                 135                 140

Ser Gly Gly Gly Gly Ser Glu Phe Asp Ile Lys Met Thr Gln Ser Pro
145                 150                 155                 160

Ser Ser Met Tyr Ala Ser Leu Gly Glu Arg Val Thr Ile Thr Cys Lys
                165                 170                 175

Ala Ser Gln Asp Ile Asn Ser Tyr Leu Ser Trp Phe Gln Gln Lys Pro
            180                 185                 190

Gly Lys Ser Pro Lys Thr Leu Ile Tyr Arg Ala Asn Arg Leu Val Asp
        195                 200                 205

Gly Val Pro Ser Arg Phe Ser Gly Ser Gly Ser Gly Gln Asp Tyr Ser
    210                 215                 220

Leu Thr Ile Ser Ser Leu Glu Tyr Glu Asp Met Gly Ile Tyr Tyr Cys
225                 230                 235                 240

Leu Gln Tyr Asp Glu Phe Pro Tyr Thr Phe Gly Gly Gly Thr Lys Leu
                245                 250                 255

Glu Ile Lys Ala Ser Val Lys Gly Lys His Leu Cys Pro Ser Pro Leu
            260                 265                 270

Phe Pro Gly Pro Ser Lys Pro Phe Trp Val Leu Val Val Val Gly Gly
        275                 280                 285

Val Leu Ala Cys Tyr Ser Leu Leu Val Thr Val Ala Phe Ile Ile Phe
    290                 295                 300

```
Trp Val Arg Ser Lys Arg Ser Arg Leu Leu His Ser Asp Tyr Met Asn
305                 310                 315                 320

Met Thr Pro Arg Arg Pro Gly Pro Thr Arg Lys His Tyr Gln Pro Tyr
            325                 330                 335

Ala Pro Pro Arg Asp Phe Ala Ala Tyr Arg Ser Lys Leu Arg Val Lys
            340                 345                 350

Phe Ser Arg Ser Ala Asp Ala Pro Ala Tyr Gln Gln Gly Gln Asn Gln
        355                 360                 365

Leu Tyr Asn Glu Leu Asn Leu Gly Arg Arg Glu Tyr Asp Val Leu
    370                 375                 380

Asp Lys Arg Arg Gly Arg Asp Pro Glu Met Gly Gly Lys Pro Arg Arg
385                 390                 395                 400

Lys Asn Pro Gln Glu Gly Leu Tyr Asn Glu Leu Gln Lys Asp Lys Met
                405                 410                 415

Ala Glu Ala Tyr Ser Glu Ile Gly Met Lys Gly Glu Arg Arg Arg Gly
            420                 425                 430

Lys Gly His Asp Gly Leu Tyr Gln Gly Leu Ser Thr Ala Thr Lys Asp
        435                 440                 445

Thr Tyr Asp Ala Leu His Met Gln Ala Leu Pro Pro Arg Arg Ala Lys
    450                 455                 460

Arg Ser Gly Ser Gly Glu Gly Arg Gly Ser Leu Ile Thr Cys Gly Asp
465                 470                 475                 480

Val Glu Glu Asn Pro Gly Pro Met Gly Ile Val Glu Pro Gly Cys Gly
                485                 490                 495

Asp Met Leu Thr Gly Thr Glu Pro Met Pro Ser Asp Glu Gly Arg Gly
            500                 505                 510

Pro Gly Ala Asp Gln Gln His Arg Phe Phe Tyr Pro Glu Pro Gly Ala
        515                 520                 525

Gln Asp Pro Thr Asp Arg Arg Ala Gly Ser Ser Leu Gly Thr Pro Tyr
    530                 535                 540

Ser Gly Gly Ala Leu Val Pro Ala Ala Pro Gly Arg Phe Leu Gly Ser
545                 550                 555                 560

Phe Ala Tyr Pro Pro Arg Ala Gln Val Ala Gly Phe Pro Gly Pro Gly
                565                 570                 575

Glu Phe Phe Pro Pro Ala Gly Ala Glu Gly Tyr Pro Pro Val Asp
            580                 585                 590

Gly Tyr Pro Ala Pro Asp Pro Arg Ala Gly Leu Tyr Pro Gly Pro Arg
        595                 600                 605

Glu Asp Tyr Ala Leu Pro Ala Gly Leu Glu Val Ser Gly Lys Leu Arg
    610                 615                 620

Val Ala Leu Ser Asn His Leu Leu Trp Ser Lys Phe Asn Gln His Gln
625                 630                 635                 640

Thr Glu Met Ile Ile Thr Lys Gln Gly Arg Arg Met Phe Pro Phe Leu
                645                 650                 655

Ser Phe Thr Val Ala Gly Leu Glu Pro Thr Ser His Tyr Arg Met Phe
            660                 665                 670

Val Asp Val Val Leu Val Asp Gln His His Trp Arg Tyr Gln Ser Gly
        675                 680                 685

Lys Trp Val Gln Cys Gly Lys Ala Glu Gly Ser Met Pro Gly Asn Arg
    690                 695                 700

Leu Tyr Val His Pro Asp Ser Pro Asn Thr Gly Ala His Trp Met Arg
705                 710                 715                 720

Gln Glu Val Ser Phe Gly Lys Leu Lys Leu Thr Asn Asn Lys Gly Ala
```

|     |     |     |     |     | 725 |     |     |     | 730 |     |     |     |     | 735 |
| --- | --- | --- | --- | --- | --- | --- | --- | --- | --- | --- | --- | --- | --- | --- |
| Ser | Asn | Asn | Val | Thr | Gln | Met | Ile | Val | Leu | Gln | Ser | Leu | His | Lys | Tyr |

Gln Pro Arg Leu His Ile Val Glu Val Asn Asp Gly Glu Pro Glu Ala
        755                      760                 765

Ala Cys Ser Ala Ser Asn Thr His Val Phe Thr Phe Gln Glu Thr Gln
       770                   775                 780

Phe Ile Ala Val Thr Ala Tyr Gln Asn Ala Glu Ile Thr Gln Leu Lys
785                   790               795                800

Ile Asp Asn Asn Pro Phe Ala Lys Gly Phe Arg Glu Asn Phe Glu Ser
               805                 810              815

Met Tyr Ala Ser Val Asp Thr Ser Val Pro Ser Pro Gly Pro Asn
       820                   825              830

Cys Gln Leu Leu Gly Gly Asp Pro Phe Ser Pro Leu Leu Ser Asn Gln
               835                 840              845

Tyr Pro Val Pro Ser Arg Phe Tyr Pro Asp Leu Pro Gly Gln Pro Lys
850                   855               860

Asp Met Ile Ser Gln Pro Tyr Trp Leu Gly Thr Pro Arg Glu His Ser
865                   870               875               880

Tyr Glu Ala Glu Phe Arg Ala Val Ser Met Lys Pro Thr Leu Leu Pro
               885                 890              895

Ser Ala Pro Gly Pro Thr Val Pro Tyr Tyr Arg Gly Asn Val Leu
       900                   905              910

Ala Pro Gly Ala Gly Trp Pro Val Ala Pro Gln Tyr Pro Pro Lys Met
               915                 920              925

Ser Pro Ala Gly Trp Phe Arg Pro Met Arg Thr Leu Pro Met Asp Pro
       930                   935              940

Gly Leu Gly Ser Ser Glu Gln Gly Ser Ser Pro Ser Leu Trp Pro
945                   950               955                960

Glu Val Thr Ser Leu Gln Pro Glu Pro Ser Asp Ser Gly Leu Gly Glu
               965                 970              975

Gly Asp Thr Lys Arg Arg Arg Ile Ser Pro Tyr Pro Ser Ser Gly Asp
             980                 985              990

Ser Ser Ser Pro Ala Gly Ala Pro Ser Pro Phe Asp Lys Glu Thr Glu
       995                  1000              1005

Gly Gln Phe Tyr Asn Tyr Phe Pro Asn
    1010                    1015

```
<210> SEQ ID NO 35
<211> LENGTH: 3054
<212> TYPE: DNA
<213> ORGANISM: Artificial Sequence
<220> FEATURE:
<223> OTHER INFORMATION: Tz.47-28-3z-MsTBET DNA

<400> SEQUENCE: 35
```

| | | |
|---|---|---|
| atggaatgga cctgggtctt tctcttcctc ctgtcagtaa ctgcaggtgt ccactcccag | 60 |
| gttcagctgc agcagtctgg agctgagctg atgaagcctg gggcctcagt gaagctttcc | 120 |
| tgcaaggcta ctggctacac attcactggc tactggatag agtggataaa gcagaggcct | 180 |
| ggacatggcc ttgagtggat tggagagatt ttacctggaa ctggtagtac taactacaat | 240 |
| gagaagttca aggcaaggc cacattcact gcagatacat cctccaacac agcctacatg | 300 |
| caactcagca gcctgacaac tgaggactct gccatctatt actgtgcaat cccggggcct | 360 |
| atggactact ggggtcaagg aacctcagtc accgtctcct cagccggcgg aggcggatca | 420 |

```
ggaggaggag gatcaggcgg aggaggatca gaattcgaca tcaagatgac ccagtctcca    480
tcttccatgt atgcatctct aggagagaga gtcactatca cttgcaaggc gagtcaggac    540
attaatagct atttaagctg gttccagcag aaaccaggga atctcctaa gaccctgatc     600 tatcgtgcaa acagattggt agatggggtc ccatcaaggt tcagtggcag tggatctggg    660
caagattatt ctctcaccat cagcagcctg gagtatgaag atatgggaat ttattattgt    720
ctacagtatg atgagtttcc gtacacgttc ggagggggga ccaagctgga aataaaagct    780
agcgtgaaag gaaacacct ttgtccaagt ccctatttc ccggaccttc taagcccttt      840
tgggtgctgg tggtggttgg tggagtcctg gcttgctata gcttgctagt aacagtggcc    900
tttattattt tctgggtgag gagtaagagg agcaggctcc tgcacagtga ctacatgaac    960
atgactcccc gccgcccgg gcccacccgc aagcattacc agcctatgc cccaccacgc     1020 gacttcgcag cctatcgctc aagcttaga gtgaagttca gcaggagcgc agacgccccc    1080
gcgtaccagc agggccagaa ccagctctat aacgagctca atctaggacg aagagaggag    1140
tacgatgttt tggacaagag acgtggccgg gaccctgaga tggggggaaa gccgagaagg    1200
aagaaccctc aggaaggcct gtacaatgaa ctgcagaaag ataagatggc ggaggcctac    1260
agtgagattg ggatgaaagg cgagcgccgg aggggcaagg ggcacgatgg cctttaccag    1320
ggtctcagta cagccaccaa ggacacctac gacgccttc acatgcaggc cctgccccct    1380
cgcagagcca aaggtctgg ctccggtgag ggcagaggaa gtcttataac atgcggtgac     1440
gtggaggaga atcccggccc tatgggcatc gtggagccgg gctgcggaga catgctgacc    1500
ggcaccgagc cgatgccgag tgacgagggc cggggggccg gagcggacca acagcatcgt    1560
ttcttctatc ccgagccggg cgcacaggac ccgaccgatc gccgcgcagg tagcagcctg    1620
gggacgccct actctggggg cgccctggtg cctgccgcgc cgggtcgctt ccttggatcc    1680
ttcgcctacc cgccccgggc tcaggtggct ggctttcccg ggcctggcga gttcttcccg    1740
ccgcccgcgg gtgcggaggg ctacccgccc gtggatggct accctgcccc tgacccgcgc    1800
gcggggctct acccagggcc gcgcgaggac tacgcattgc ccgcggggtt ggaggtgtct    1860
gggaagctga gagtcgcgct cagcaaccac ctgttgtggt ccaagttcaa ccagcaccag    1920
acagagatga tcatcactaa gcaaggacgg cgaatgttcc cattcctgtc cttcaccgtg    1980
gccgggctga gcccacaag ccattacagg atgtttgtgg atgtggtctt ggtggaccag     2040
caccactggc ggtaccagag cggcaagtgg gtgcagtgtg aaaggcaga aggcagcatg     2100 ccagggaacc gcttatatgt ccacccagac tcccccaaca ccggagccca ctggatgcgc    2160
caggaagttt catttgggaa gctaaagctc accaacaaca aggggcttc caacaatgtg     2220 acccagatga tcgtcctgca gtctctccac aagtaccagc ccggctgca catcgtggag     2280 gtgaatgatg agagccaga ggctgcctgc agtgcttcta acacacacgt ctttactttc     2340
caagagaccc agttcattgc agtgactgcc taccagaacg cagagatcac tcagctgaaa    2400
atcgacaaca ccccctttgc caaggattc cgggagaact ttgagtccat gtacgcatct     2460
gttgatacga gtgtcccctc gccacctgga cccaactgtc aactgcttgg gggagacccc    2520
ttctcacctc ttctatccaa ccagtatcct gttcccagcc gtttctaccc cgaccttcca    2580
ggccagccca aggatatgat ctcacagcct tactggctgg ggacacctcg ggaacacagt    2640
tatgaagcga agttccgagc tgtgagcatg aagcccacac tcctaccctc tgccccgggg    2700
cccactgtgc cctactaccg gggccaagac gtcctggcgc ctggagctgg ttggcccgtg    2760
```

```
gcccctcaat acccgcccaa gatgagccca gctggctggt tccggcccat gcgaactctg    2820
cccatggacc cgggcctggg atcctcagag gaacagggct cctccccctc gctgtggcct    2880
gaggtcacct cccctccagcc ggagcccagc gactcaggac taggcgaagg agacactaag   2940
aggaggagga tatcccccta tccttccagt ggcgacagct cctctcccgc tggggcccct    3000
tctccttttg ataaggaaac cgaaggccag ttttataatt attttcccaa ctga          3054
```

<210> SEQ ID NO 36
<211> LENGTH: 558
<212> TYPE: PRT
<213> ORGANISM: Artificial Sequence
<220> FEATURE:
<223> OTHER INFORMATION: Tz.47-28-3z-MsTBET-STOP

<400> SEQUENCE: 36

```
Met Glu Trp Thr Trp Val Phe Leu Phe Leu Leu Ser Val Thr Ala Gly
1               5                   10                  15

Val His Ser Gln Val Gln Leu Gln Gln Ser Gly Ala Glu Leu Met Lys
            20                  25                  30

Pro Gly Ala Ser Val Lys Leu Ser Cys Lys Ala Thr Gly Tyr Thr Phe
        35                  40                  45

Thr Gly Tyr Trp Ile Glu Trp Ile Lys Gln Arg Pro Gly His Gly Leu
    50                  55                  60

Glu Trp Ile Gly Glu Ile Leu Pro Gly Thr Gly Ser Thr Asn Tyr Asn
65                  70                  75                  80

Glu Lys Phe Lys Gly Lys Ala Thr Phe Thr Ala Asp Thr Ser Ser Asn
                85                  90                  95

Thr Ala Tyr Met Gln Leu Ser Ser Leu Thr Thr Glu Asp Ser Ala Ile
            100                 105                 110

Tyr Tyr Cys Ala Ile Pro Gly Pro Met Asp Tyr Trp Gly Gln Gly Thr
        115                 120                 125

Ser Val Thr Val Ser Ser Ala Gly Gly Gly Ser Gly Gly Gly Gly
    130                 135                 140

Ser Gly Gly Gly Gly Ser Glu Phe Asp Ile Lys Met Thr Gln Ser Pro
145                 150                 155                 160

Ser Ser Met Tyr Ala Ser Leu Gly Glu Arg Val Thr Ile Thr Cys Lys
                165                 170                 175

Ala Ser Gln Asp Ile Asn Ser Tyr Leu Ser Trp Phe Gln Gln Lys Pro
            180                 185                 190

Gly Lys Ser Pro Lys Thr Leu Ile Tyr Arg Ala Asn Arg Leu Val Asp
        195                 200                 205

Gly Val Pro Ser Arg Phe Ser Gly Ser Gly Ser Gly Gln Asp Tyr Ser
    210                 215                 220

Leu Thr Ile Ser Ser Leu Glu Tyr Glu Asp Met Gly Ile Tyr Tyr Cys
225                 230                 235                 240

Leu Gln Tyr Asp Glu Phe Pro Tyr Thr Phe Gly Gly Gly Thr Lys Leu
                245                 250                 255

Glu Ile Lys Ala Ser Val Lys Gly Lys His Leu Cys Pro Ser Pro Leu
            260                 265                 270

Phe Pro Gly Pro Ser Lys Pro Phe Trp Val Leu Val Val Val Gly Gly
        275                 280                 285

Val Leu Ala Cys Tyr Ser Leu Leu Val Thr Val Ala Phe Ile Ile Phe
    290                 295                 300

Trp Val Arg Ser Lys Arg Ser Arg Leu Leu His Ser Asp Tyr Met Asn
305                 310                 315                 320
```

```
Met Thr Pro Arg Arg Pro Gly Pro Thr Arg Lys His Tyr Gln Pro Tyr
            325                 330                 335

Ala Pro Pro Arg Asp Phe Ala Ala Tyr Arg Ser Lys Leu Arg Val Lys
            340                 345                 350

Phe Ser Arg Ser Ala Asp Ala Pro Ala Tyr Gln Gln Gly Gln Asn Gln
            355                 360                 365

Leu Tyr Asn Glu Leu Asn Leu Gly Arg Arg Glu Glu Tyr Asp Val Leu
            370                 375                 380

Asp Lys Arg Arg Gly Arg Asp Pro Glu Met Gly Gly Lys Pro Arg Arg
385                 390                 395                 400

Lys Asn Pro Gln Glu Gly Leu Tyr Asn Glu Leu Gln Lys Asp Lys Met
                405                 410                 415

Ala Glu Ala Tyr Ser Glu Ile Gly Met Lys Gly Glu Arg Arg Arg Gly
            420                 425                 430

Lys Gly His Asp Gly Leu Tyr Gln Gly Leu Ser Thr Ala Thr Lys Asp
            435                 440                 445

Thr Tyr Asp Ala Leu His Met Gln Ala Leu Pro Pro Arg Arg Ala Lys
    450                 455                 460

Arg Ser Gly Ser Gly Glu Gly Arg Gly Ser Leu Ile Thr Cys Gly Asp
465                 470                 475                 480

Val Glu Glu Asn Pro Gly Pro Met Gly Ile Val Glu Pro Gly Cys Gly
                485                 490                 495

Asp Met Leu Thr Gly Thr Glu Pro Met Pro Ser Asp Glu Gly Arg Gly
            500                 505                 510

Pro Gly Ala Asp Gln Gln His Arg Phe Phe Tyr Pro Glu Pro Gly Ala
            515                 520                 525

Gln Asp Pro Thr Asp Arg Arg Ala Gly Ser Ser Leu Gly Thr Pro Tyr
            530                 535                 540

Ser Gly Gly Ala Leu Val Pro Ala Ala Pro Gly Arg Phe Leu
545                 550                 555

<210> SEQ ID NO 37
<211> LENGTH: 3054
<212> TYPE: DNA
<213> ORGANISM: Artificial Sequence
<220> FEATURE:
<223> OTHER INFORMATION: Tz.47-28-3z-MsTBET-STOP DNA

<400> SEQUENCE: 37
atggaatgga cctgggtctt tctcttcctc ctgtcagtaa ctgcaggtgt ccactcccag    60
gttcagctgc agcagtctgg agctgagctg atgaagcctg gggcctcagt gaagctttcc   120
tgcaaggcta ctggctacac attcactggc tactggatag agtggataaa gcagaggcct   180
ggacatggcc ttgagtggat tggagagatt ttacctggaa ctggtagtac taactacaat   240
gagaagttca aggcaaggc cacattcact gcagatacat cctccaacac agcctacatg   300
caactcagca gcctgacaac tgaggactct gccatctatt actgtgcaat cccgggggcct   360 atggactact ggggtcaagg aacctcagtc accgtctcct cagccggcgg aggcggatca   420
ggaggaggag gatcaggcgg aggaggatca gaattcgaca tcaagatgac ccagtctcca   480
tcttccatgt atgcatctct aggagagaga gtcactatca cttgcaaggc gagtcaggac   540
attaatagct atttaagctg gttccagcag aaaccaggga atctcctaa gaccctgatc   600 tatcgtgcaa acagattggt agatggggtc ccatcaaggt tcagtggcag tggatctggg   660
caagattatt ctctcaccat cagcagcctg gagtatgaag atatgggaat ttattattgt   720
```

```
ctacagtatg atgagtttcc gtacacgttc ggagggggga ccaagctgga aataaaagct    780
agcgtgaaag ggaaacacct ttgtccaagt cccctatttc ccggaccttc taagcccttt    840
tgggtgctgg tggtggttgg tggagtcctg gcttgctata gcttgctagt aacagtggcc    900
tttattattt tctgggtgag gagtaagagg agcaggctcc tgcacagtga ctacatgaac    960
atgactcccc gccgcccggg gcccacccgc aagcattacc agccctatgc cccaccacgc   1020
gacttcgcag cctatcgctc caagcttaga gtgaagttca gcaggagcgc agacgccccc   1080
gcgtaccagc agggccagaa ccagctctat aacgagctca atctaggacg aagagaggag   1140
tacgatgttt tggacaagag acgtggccgg gaccctgaga tgggggggaaa gccgagaagg   1200 aagaaccctc aggaaggcct gtacaatgaa ctgcagaaag ataagatggc ggaggcctac   1260
agtgagattg ggatgaaagg cgagcgccgg aggggcaagg ggcacgatgg cctttaccag   1320
ggtctcagta cagccaccaa ggacacctac gacgcccttc acatgcaggc cctgcccct    1380 cgcagagcca aaaggtctgg ctccggtgag ggcagaggaa gtcttataac atgcggtgac   1440
gtggaggaga atcccggccc tatgggcatc gtggagccgg gctgcggaga catgctgacc   1500
ggcaccgagc cgatgccgag tgacgagggc cgggggcccg agcggaccac acagcatcgt   1560
ttcttctatc ccgagccggg cgcacaggac ccgaccgatc gccgcgcagg tagcagcctg   1620
gggacgccct actctggggg cgccctggtg cctgccgcgc cgggtcgctt cctttgatcc   1680
ttcgcctacc cgccccgggc tcaggtggct ggctttcccg ggcctggcga gttcttcccg   1740
ccgcccgcgg gtgcggaggg ctacccgccc gtggatggct accctgcccc tgacccgcgc   1800
gcggggctct acccagggcc gcgcgaggac tacgcattgc ccgcgggggtt ggaggtgtct   1860 gggaagctga gagtcgcgct cagcaaccac ctgttgtggt ccaagttcaa ccagcaccag   1920
acagagatga tcatcactaa gcaaggacgg cgaatgttcc cattcctgtc cttcaccgtg   1980
gccgggctgg agcccacaag ccattacagg atgtttgtgg atgtggtctt ggtggaccag   2040
caccactggc ggtaccagag cggcaagtgg gtgcagtgtg aaaggcaga aggcagcatg   2100 ccagggaacc gcttatatgt ccacccagac tccccaaca ccggagccca ctggatgcgc   2160
caggaagttt catttgggaa gctaaagctc accaacaaca agggggcttc caacaatgtg   2220
acccagatga tcgtcctgca gtctctccac aagtaccagc cccggctgca catcgtggag   2280
gtgaatgatg gagagccaga ggctgcctgc agtgcttcta acacacacgt ctttactttc   2340
caagagaccc agttcattgc agtgactgcc taccagaacg cagagatcac tcagctgaaa   2400
atcgacaaca ccccctttgc caaaggattc cgggagaact ttgagtccat gtacgcatct   2460
gttgatacga gtgtccccctc gccacctgga cccaactgtc aactgcttgg gggagacccc   2520
ttctcacctc ttctatccaa ccagtatcct gttcccagcc gtttctaccc cgaccttcca   2580
ggccagccca aggatatgat ctcacagcct tactggctgg ggacacctcg gaacacagt    2640 tatgaagcgt agttccgagc tgtgagcatg aagcccacac tcctaccctc tgccccgggg   2700
cccactgtgc cctactaccg gggccaagac gtcctggcgc ctggagctgg ttggcccgtg   2760 gccctcaat acccgcccaa gatgagccca gctggctggt tccggcccat gcgaactctg   2820
cccatggacc cgggctgggg atcctcagag gaacagggct cctccccctc gctgtggcct   2880
gaggtcacct ccctccagcc ggagcccagc gactcaggac taggcgaagg agacactaag   2940
aggaggagga tatcccccta tccttccagt ggcgacagct cctctcccgc tggggccct    3000 tctccttttg ataaggaaac cgaaggccag ttttataatt attttcccaa ctga          3054
```

-continued

```
<210> SEQ ID NO 38
<211> LENGTH: 825
<212> TYPE: PRT
<213> ORGANISM: Artificial Sequence
<220> FEATURE:
<223> OTHER INFORMATION: Tz.47-28-3z-MsTBET-TBOX Del

<400> SEQUENCE: 38

Met Glu Trp Thr Trp Val Phe Leu Phe Leu Leu Ser Val Thr Ala Gly
1               5                   10                  15

Val His Ser Gln Val Gln Leu Gln Gln Ser Gly Ala Glu Leu Met Lys
            20                  25                  30

Pro Gly Ala Ser Val Lys Leu Ser Cys Lys Ala Thr Gly Tyr Thr Phe
        35                  40                  45

Thr Gly Tyr Trp Ile Glu Trp Ile Lys Gln Arg Pro Gly His Gly Leu
    50                  55                  60

Glu Trp Ile Gly Glu Ile Leu Pro Gly Thr Gly Ser Thr Asn Tyr Asn
65                  70                  75                  80

Glu Lys Phe Lys Gly Lys Ala Thr Phe Thr Ala Asp Thr Ser Ser Asn
                85                  90                  95

Thr Ala Tyr Met Gln Leu Ser Ser Leu Thr Thr Glu Asp Ser Ala Ile
            100                 105                 110

Tyr Tyr Cys Ala Ile Pro Gly Pro Met Asp Tyr Trp Gly Gln Gly Thr
        115                 120                 125

Ser Val Thr Val Ser Ser Ala Gly Gly Gly Ser Gly Gly Gly Gly
    130                 135                 140

Ser Gly Gly Gly Gly Ser Glu Phe Asp Ile Lys Met Thr Gln Ser Pro
145                 150                 155                 160

Ser Ser Met Tyr Ala Ser Leu Gly Glu Arg Val Thr Ile Thr Cys Lys
                165                 170                 175

Ala Ser Gln Asp Ile Asn Ser Tyr Leu Ser Trp Phe Gln Gln Lys Pro
            180                 185                 190

Gly Lys Ser Pro Lys Thr Leu Ile Tyr Arg Ala Asn Arg Leu Val Asp
        195                 200                 205

Gly Val Pro Ser Arg Phe Ser Gly Ser Gly Ser Gly Gln Asp Tyr Ser
    210                 215                 220

Leu Thr Ile Ser Ser Leu Glu Tyr Glu Asp Met Gly Ile Tyr Tyr Cys
225                 230                 235                 240

Leu Gln Tyr Asp Glu Phe Pro Tyr Thr Phe Gly Gly Gly Thr Lys Leu
                245                 250                 255

Glu Ile Lys Ala Ser Val Lys Gly Lys His Leu Cys Pro Ser Pro Leu
            260                 265                 270

Phe Pro Gly Pro Ser Lys Pro Phe Trp Val Leu Val Val Val Gly Gly
        275                 280                 285

Val Leu Ala Cys Tyr Ser Leu Leu Val Thr Val Ala Phe Ile Ile Phe
    290                 295                 300

Trp Val Arg Ser Lys Arg Ser Arg Leu Leu His Ser Asp Tyr Met Asn
305                 310                 315                 320

Met Thr Pro Arg Arg Pro Gly Pro Thr Arg Lys His Tyr Gln Pro Tyr
                325                 330                 335

Ala Pro Pro Arg Asp Phe Ala Ala Tyr Arg Ser Lys Leu Arg Val Lys
            340                 345                 350

Phe Ser Arg Ser Ala Asp Ala Pro Ala Tyr Gln Gln Gly Gln Asn Gln
        355                 360                 365
```

```
Leu Tyr Asn Glu Leu Asn Leu Gly Arg Arg Glu Glu Tyr Asp Val Leu
    370                 375                 380

Asp Lys Arg Arg Gly Arg Asp Pro Glu Met Gly Gly Lys Pro Arg Arg
385                 390                 395                 400

Lys Asn Pro Gln Glu Gly Leu Tyr Asn Glu Leu Gln Lys Asp Lys Met
                405                 410                 415

Ala Glu Ala Tyr Ser Glu Ile Gly Met Lys Gly Glu Arg Arg Arg Gly
            420                 425                 430

Lys Gly His Asp Gly Leu Tyr Gln Gly Leu Ser Thr Ala Thr Lys Asp
        435                 440                 445

Thr Tyr Asp Ala Leu His Met Gln Ala Leu Pro Pro Arg Arg Ala Lys
450                 455                 460

Arg Ser Gly Ser Gly Glu Gly Arg Gly Ser Leu Ile Thr Cys Gly Asp
465                 470                 475                 480

Val Glu Glu Asn Pro Gly Pro Met Gly Ile Val Glu Pro Gly Cys Gly
                485                 490                 495

Asp Met Leu Thr Gly Thr Glu Pro Met Pro Ser Asp Glu Gly Arg Gly
            500                 505                 510

Pro Gly Ala Asp Gln Gln His Arg Phe Phe Tyr Pro Glu Pro Gly Ala
        515                 520                 525

Gln Asp Pro Thr Asp Arg Arg Ala Gly Ser Ser Leu Gly Thr Pro Tyr
    530                 535                 540

Ser Gly Gly Ala Leu Val Pro Ala Ala Pro Gly Arg Phe Leu Gly Ser
545                 550                 555                 560

Phe Ala Tyr Pro Pro Arg Ala Gln Val Ala Gly Phe Pro Gly Pro Gly
                565                 570                 575

Glu Phe Phe Pro Pro Ala Gly Ala Glu Gly Tyr Pro Pro Val Asp
            580                 585                 590

Gly Tyr Pro Ala Pro Asp Pro Arg Ala Gly Leu Tyr Pro Gly Pro Arg
        595                 600                 605

Glu Asp Tyr Ala Leu Pro Ala Gly Leu Glu Val Ser Gly Phe Glu Ser
    610                 615                 620

Met Tyr Ala Ser Val Asp Thr Ser Val Pro Ser Pro Pro Gly Pro Asn
625                 630                 635                 640

Cys Gln Leu Leu Gly Gly Asp Pro Phe Ser Pro Leu Leu Ser Asn Gln
                645                 650                 655

Tyr Pro Val Pro Ser Arg Phe Tyr Pro Asp Leu Pro Gly Gln Pro Lys
            660                 665                 670

Asp Met Ile Ser Gln Pro Tyr Trp Leu Gly Thr Pro Arg Glu His Ser
        675                 680                 685

Tyr Glu Ala Glu Phe Arg Ala Val Ser Met Lys Pro Thr Leu Leu Pro
    690                 695                 700

Ser Ala Pro Gly Pro Thr Val Pro Tyr Tyr Arg Gly Gln Asp Val Leu
705                 710                 715                 720

Ala Pro Gly Ala Gly Trp Pro Val Ala Pro Gln Tyr Pro Pro Lys Met
                725                 730                 735

Ser Pro Ala Gly Trp Phe Arg Pro Met Arg Thr Leu Pro Met Asp Pro
            740                 745                 750

Gly Leu Gly Ser Ser Glu Glu Gln Gly Ser Pro Ser Leu Trp Pro
        755                 760                 765

Glu Val Thr Ser Leu Gln Pro Glu Pro Ser Asp Ser Gly Leu Gly Glu
    770                 775                 780

Gly Asp Thr Lys Arg Arg Arg Ile Ser Pro Tyr Pro Ser Ser Gly Asp
```

```
                785          790          795         800
Ser Ser Ser Pro Ala Gly Ala Pro Ser Pro Phe Asp Lys Glu Thr Glu
                    805             810             815
Gly Gln Phe Tyr Asn Tyr Phe Pro Asn
            820             825

<210> SEQ ID NO 39
<211> LENGTH: 2478
<212> TYPE: DNA
<213> ORGANISM: Artificial Sequence
<220> FEATURE:
<223> OTHER INFORMATION: Tz.47-28-3z-MsTBET-TBOX Del DNA

<400> SEQUENCE: 39
atggaatgga cctgggtctt tctcttcctc ctgtcagtaa ctgcaggtgt ccactcccag      60
gttcagctgc agcagtctgg agctgagctg atgaagcctg ggcctcagt gaagctttcc     120 tgcaaggcta ctggctacac attcactggc tactggatag agtggataaa gcagaggcct    180
ggacatggcc ttgagtggat tggagagatt ttacctggaa ctggtagtac taactacaat    240
gagaagttca gggcaaggc acattcact gcagatacat cctccaacac agcctacatg     300
caactcagca gcctgacaac tgaggactct gccatctatt actgtgcaat cccggggcct    360
atggactact ggggtcaagg aacctcagtc accgtctcct cagccggcgg aggcggatca    420
ggaggaggag gatcaggcgg aggaggatca gaattcgaca tcaagatgac ccagtctcca    480
tcttccatgt atgcatctct aggagagaga gtcactatca cttgcaaggc gagtcaggac    540
attaatagct atttaagctg gttccagcag aaaccaggga atctcctaa gaccctgatc     600 tatcgtgcaa acagattggt agatggggtc ccatcaaggt tcagtggcag tggatctggg    660
caagattatt ctctcaccat cagcagcctg agtatgaag atatgggaat ttattattgt     720
ctacagtatg atgagtttcc gtacacgttc ggaggggga ccaagctgga aataaaagct     780
agcgtgaaag gaaacacct tgtccaagt cccctatttc ccggaccttc taagcccttt     840
tgggtgctgg tggtggttgg tggagtcctg gcttgctata gcttgctagt aacagtggcc    900
tttattattt tctgggtgag gagtaagagg agcaggctcc tgcacagtga ctacatgaac    960
atgactcccc gccgccccgg gcccacccgc aagcattacc agcctatgc cccaccacgc    1020 gacttcgcag cctatcgctc caagcttaga gtgaagttca gcaggagcgc agacgccccc    1080
gcgtaccagc agggccagaa ccagctctat aacgagctca atctaggacg aagagaggag   1140
tacgatgttt tggacaagag acgtggccga gaccctgaga tgggggaaa gccgagaagg    1200 aagaaccctc aggaaggcct gtacaatgaa ctgcagaaag ataagatggc ggaggcctac   1260
agtgagattg ggatgaaagg cgagcgccgg aggggcaagg gcacgatgg cctttaccag    1320 ggtctcagta cagccaccaa ggacacctac gacgcccttc acatgcaggc cctgcccct    1380 cgcagagcca aaaggtctgg ctccggtgag ggcagaggaa gtcttataac atgcggtgac   1440
gtggaggaga atcccggccc tatgggcatc gtggagccgg gctgcggaga catgctgacc    1500
ggcaccgagc cgatgccgag tgacgagggc cgggggcccg gagcggacca acagcatcgt    1560
ttcttctatc ccgagccggg cgcacaggac ccgaccgatc gccgcgcagg tagcagcctg   1620
gggacgccct actctggggg cgccctggtg cctgccgcgc cggtcgctt ccttggatcc     1680 ttcgcctacc cgccccgggc tcaggtggct ggctttcccg gcctggcga gttcttcccg     1740 ccgcccgcgg gtgcggaggg ctaccccgcc gtggatggct accctgcccc tgaccccgcg    1800
gcggggctct acccagggcc gcgcgaggac tacgcattgc ccgcggggtt ggaggtgtct    1860
```

```
gggtttgagt ccatgtacgc atctgttgat acgagtgtcc cctcgccacc tggacccaac   1920
tgtcaactgc ttgggggaga cccccttctca cctcttctat ccaaccagta tcctgttccc   1980
agccgtttct accccgacct tccaggccag cccaaggata tgatctcaca gccttactgg   2040
ctggggacac ctcgggaaca cagttatgaa gcggagttcc gagctgtgag catgaagccc   2100
acactcctac cctctgcccc ggggcccact gtgccctact accggggcca agacgtcctg   2160
gcgcctggag ctggttggcc cgtggcccct caatacccgc ccaagatgag cccagctggc   2220
tggttccggc ccatgcgaac tctgcccatg gacccgggcc tgggatcctc agaggaacag   2280
ggctcctccc cctcgctgtg gcctgaggtc acctccctcc agccggagcc cagcgactca   2340
ggactaggcg aaggagacac taagaggagg aggatatccc cctatccttc cagtggcgac   2400
agctcctctc ccgctggggc cccttctcct tttgataagg aaaccgaagg ccagttttat   2460
aattattttc ccaactga                                                 2478

<210> SEQ ID NO 40
<211> LENGTH: 1418
<212> TYPE: DNA
<213> ORGANISM: Artificial
<220> FEATURE:
<223> OTHER INFORMATION: Synthetic heavy chain sequence

<400> SEQUENCE: 40
atggaatgga cctgggtctt tctcttcctc ctgtcagtaa ctgcaggtgt ccactcccag     60
gttcagctgc agcagtctgg agctgagctg atgaagcctg gggcctcagt gaagctttcc    120
tgcaaggcta ctggctacac attcactggc tactggatag agtggataaa gcagaggcct    180
ggacatggcc ttgagtggat tggagagatt ttacctggaa ctggtagtac taactacaat    240
gagaagttca agggcaaggc cacattcact gcagatacat cctccaacac agcctacatg    300
caactcagca gcctgacaac tgaggactct gccatctatt actgtgcaat cccgggggcct   360 atggactact ggggtcaagg aacctcagtc accgtctcct cagccaaaac aacagcccca    420
tcggtctatc cactggcccc tgtgtgtgga ggtacaactg ctcctcggt gactctagga     480 tgcctggtca agggttattt ccctgagcca gtgaccttga cctggaactc tggatccctg    540
tccagtggtg tgcacacctt cccagctctc ctgcagtctg gcctctacac cctcagcagc    600
tcagtgactg taacctcgaa cacctggccc agccagacca tcacctgcaa tgtggcccac    660
ccggcaagca gcaccaaagt ggacaagaaa attgagccca gagtgcccat aacacagaac    720
ccctgtcctc cactcaaaga gtgtcccca tgcgcagctc cagacctctt gggtggacca    780
tccgtcttca tcttccctcc aaagatcaag gatgtactca tgatctccct gagccccatg    840
gtcacatgtg tggtggtgga tgtgagcgag gatgacccag acgtccagat cagctggttt    900
gtgaacaacg tggaagtaca cacagctcag acacaaaccc atagagagga ttacaacagt    960
actctccggg tggtcagtgc cctccccatc cagcaccagg actggatgag tggcaaggag   1020
ttcaaatgca aggtcaacaa cagagccctc ccatccccca tcgagaaaac catctcaaaa   1080
cccagagggc agtaagagc tccacaggta tatgtcttgc ctccaccagc agaagagatg    1140
actaagaaag agttcagtct gacctgcatg atcacaggct tcttacctgc cgaaattgct   1200
gtggactgga ccagcaatgg gcgtacagag caaaactaca agaacaccgc aacagtcctg   1260
gactctgatg gttcttactt catgtacagc aagctcagag tacaaaagag cacttgggaa   1320
agaggaagtc ttttcgcctg ctcagtggtc cacgagggtc tgcacaatca ccttacgact   1380
```
aagaccatct cccggactcc gggtaaatga gcggccgc                                    1418

<210> SEQ ID NO 41
<211> LENGTH: 719
<212> TYPE: DNA
<213> ORGANISM: Artificial
<220> FEATURE:
<223> OTHER INFORMATION: Synthetic light chain sequence

<400> SEQUENCE: 41
atggacatga ggacccctgc tcagtttctt ggaatcttgt tgctctggtt tccaggtatc      60
aaatgtgaca tcaagatgac ccagtctcca tcttccatgt atgcatctct aggagagaga     120
gtcactatca cttgcaaggc gagtcaggac attaatagct atttaagctg gttccagcag     180
aaaccaggga atctcctaa gaccctgatc tatcgtgcaa acagattggt agatggggtc      240
ccatcaaggt tcagtggcag tggatctggg caagattatt ctctcaccat cagcagcctg     300
gagtatgaag atatgggaat ttattattgt ctacagtatg atgagtttcc gtacacgttc     360
ggaggggga ccaagctgga aataaaacgg gctgatgctg caccaactgt atccatcttc      420
ccaccatcca gtgagcagtt aacatctgga ggtgcctcag tcgtgtgctt cttgaacaac     480
ttctacccca agacatcaa tgtcaagtgg aagattgatg gcagtgaacg acaaaatggc      540
gtcctgaaca gttggactga tcaggacagc aaagacagca cctacagcat gagcagcacc     600
ctcacgttga ccaaggacga gtatgaacga cataacagct atacctgtga ggccactcac     660
aagacatcaa cttcacccat tgtcaagagc ttcaacagga atgagtgtta ggcggccgc      719

<210> SEQ ID NO 42
<211> LENGTH: 115
<212> TYPE: PRT
<213> ORGANISM: Artificial
<220> FEATURE:
<223> OTHER INFORMATION: Synthetic heavy chain sequence

<400> SEQUENCE: 42

Gln Val Gln Leu Gln Gln Ser Gly Ala Glu Leu Met Lys Pro Gly Ala
1               5                   10                  15

Ser Val Lys Leu Ser Cys Lys Ala Thr Gly Tyr Thr Phe Thr Gly Tyr
            20                  25                  30

Trp Ile Glu Trp Ile Lys Gln Arg Pro Gly His Gly Leu Glu Trp Ile
        35                  40                  45

Gly Glu Ile Leu Pro Gly Thr Gly Ser Thr Asn Tyr Asn Glu Lys Phe
    50                  55                  60

Lys Gly Lys Ala Thr Phe Thr Ala Asp Thr Ser Ser Asn Thr Ala Tyr
65                  70                  75                  80

Met Gln Leu Ser Ser Leu Thr Thr Glu Asp Ser Ala Ile Tyr Tyr Cys
                85                  90                  95

Ala Ile Pro Gly Pro Met Asp Tyr Trp Gly Gln Gly Thr Ser Val Thr
            100                 105                 110

Val Ser Ser
        115

<210> SEQ ID NO 43
<211> LENGTH: 107
<212> TYPE: PRT
<213> ORGANISM: Artificial
<220> FEATURE:
<223> OTHER INFORMATION: Synthetic light chain sequence

<400> SEQUENCE: 43

-continued

```
Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Ser Tyr
            20                  25                  30

Leu Ser Trp Phe Gln Lys Pro Gly Lys Ser Pro Lys Thr Leu Ile
        35                  40                  45

Tyr Arg Ala Asn Arg Leu Val Asp Gly Val Pro Ser Arg Phe Ser Gly
    50                  55                  60

Ser Gly Ser Gly Gln Asp Tyr Ser Leu Thr Ile Ser Ser Leu Glu Tyr
65                  70                  75                  80

Glu Asp Met Gly Ile Tyr Tyr Cys Leu Gln Tyr Asp Glu Phe Pro Tyr
                85                  90                  95

Thr Phe Gly Gly Gly Thr Lys Leu Glu Ile Lys
                100                 105
```

<210> SEQ ID NO 44
<211> LENGTH: 8
<212> TYPE: PRT
<213> ORGANISM: Artificial
<220> FEATURE:
<223> OTHER INFORMATION: Synthetic heavy chain variable region CDR1

<400> SEQUENCE: 44

```
Gly Tyr Thr Phe Thr Gly Tyr Trp
1               5
```

<210> SEQ ID NO 45
<211> LENGTH: 8
<212> TYPE: PRT
<213> ORGANISM: Artificial
<220> FEATURE:
<223> OTHER INFORMATION: Synthetic heavy chain variable region CDR2

<400> SEQUENCE: 45

```
Ile Leu Pro Gly Thr Gly Ser Thr
1               5
```

<210> SEQ ID NO 46
<211> LENGTH: 8
<212> TYPE: PRT
<213> ORGANISM: Artificial
<220> FEATURE:
<223> OTHER INFORMATION: Synthetic heavy chain variable region CDR3

<400> SEQUENCE: 46

```
Ala Ile Pro Gly Pro Met Asp Tyr
1               5
```

<210> SEQ ID NO 47
<211> LENGTH: 6
<212> TYPE: PRT
<213> ORGANISM: Artificial
<220> FEATURE:
<223> OTHER INFORMATION: Synthetic light chain variable region CDR1

<400> SEQUENCE: 47

```
Gln Asp Ile Asn Ser Tyr
1               5
```

<210> SEQ ID NO 48
<211> LENGTH: 3
<212> TYPE: PRT
<213> ORGANISM: Artificial

```
<220> FEATURE:
<223> OTHER INFORMATION: Synthetic light chain variable region CDR2

<400> SEQUENCE: 48

Arg Ala Asn
1

<210> SEQ ID NO 49
<211> LENGTH: 9
<212> TYPE: PRT
<213> ORGANISM: Artificial
<220> FEATURE:
<223> OTHER INFORMATION: Synthetic light chain variable region CDR3

<400> SEQUENCE: 49

Leu Gln Tyr Asp Glu Phe Pro Tyr Thr
1               5

<210> SEQ ID NO 50
<211> LENGTH: 113
<212> TYPE: PRT
<213> ORGANISM: Artificial
<220> FEATURE:
<223> OTHER INFORMATION: Synthetic CD3 zeta cytoplasmic domain

<400> SEQUENCE: 50

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Gln Arg Arg Lys Asn Pro Gln Glu Gly Leu Tyr Asn Glu Leu Gln
    50                  55                  60

Lys Asp Lys Met Ala Glu Ala Tyr Ser Glu Ile Gly Met Lys Gly Glu
65                  70                  75                  80

Arg Arg Arg Gly Lys Gly His Asp Gly Leu Tyr Gln Gly Leu Ser Thr
                85                  90                  95

Ala Thr Lys Asp Thr Tyr Asp Ala Leu His Met Gln Ala Leu Pro Pro
            100                 105                 110

Arg

<210> SEQ ID NO 51
<211> LENGTH: 86
<212> TYPE: PRT
<213> ORGANISM: Artificial
<220> FEATURE:
<223> OTHER INFORMATION: Synthetic CD28 hinge-transmembrane-cytoplasmic
      domains

<400> SEQUENCE: 51

Val Lys Gly Lys His Leu Cys Pro Ser Pro Leu Phe Pro Gly Pro Ser
1               5                   10                  15

Lys Pro Phe Trp Val Leu Val Val Val Gly Gly Val Leu Ala Cys Tyr
            20                  25                  30

Ser Leu Leu Val Thr Val Ala Phe Ile Ile Phe Trp Val Arg Ser Lys
        35                  40                  45

Arg Ser Arg Leu Leu His Ser Asp Tyr Met Asn Met Thr Pro Arg Arg
    50                  55                  60

Pro Gly Pro Thr Arg Lys His Tyr Gln Pro Tyr Ala Pro Pro Arg Asp
65                  70                  75                  80
```

```
Phe Ala Ala Tyr Arg Ser
                85
```

<210> SEQ ID NO 52
<211> LENGTH: 327
<212> TYPE: PRT
<213> ORGANISM: Artificial
<220> FEATURE:
<223> OTHER INFORMATION: Synthetic CD19

<400> SEQUENCE: 52

```
Met Pro Pro Pro Arg Leu Leu Phe Phe Leu Leu Phe Leu Thr Pro Met
1               5                   10                  15

Glu Val Arg Pro Glu Glu Pro Leu Val Val Lys Val Glu Glu Gly Asp
            20                  25                  30

Asn Ala Val Leu Gln Cys Leu Lys Gly Thr Ser Asp Gly Pro Thr Gln
        35                  40                  45

Gln Leu Thr Trp Ser Arg Glu Ser Pro Leu Lys Pro Phe Leu Lys Leu
    50                  55                  60

Ser Leu Gly Leu Pro Gly Leu Gly Ile His Met Arg Pro Leu Ala Ser
65                  70                  75                  80

Trp Leu Phe Ile Phe Asn Val Ser Gln Gln Met Gly Gly Phe Tyr Leu
                85                  90                  95

Cys Gln Pro Gly Pro Pro Ser Glu Lys Ala Trp Gln Pro Gly Trp Thr
            100                 105                 110

Val Asn Val Glu Gly Ser Gly Glu Leu Phe Arg Trp Asn Val Ser Asp
        115                 120                 125

Leu Gly Gly Leu Gly Cys Gly Leu Lys Asn Arg Ser Ser Glu Gly Pro
    130                 135                 140

Ser Ser Pro Ser Gly Lys Leu Met Ser Pro Lys Leu Tyr Val Trp Ala
145                 150                 155                 160

Lys Asp Arg Pro Glu Ile Trp Glu Gly Glu Pro Pro Cys Val Pro Pro
                165                 170                 175

Arg Asp Ser Leu Asn Gln Ser Leu Ser Gln Asp Leu Thr Met Ala Pro
            180                 185                 190

Gly Ser Thr Leu Trp Leu Ser Cys Gly Val Pro Pro Asp Ser Val Ser
        195                 200                 205

Arg Gly Pro Leu Ser Trp Thr His Val His Pro Lys Gly Pro Lys Ser
    210                 215                 220

Leu Leu Ser Leu Glu Leu Lys Asp Asp Arg Pro Ala Arg Asp Met Trp
225                 230                 235                 240

Val Met Glu Thr Gly Leu Leu Leu Pro Arg Ala Thr Ala Gln Asp Ala
                245                 250                 255

Gly Lys Tyr Tyr Cys His Arg Gly Asn Leu Thr Met Ser Phe His Leu
            260                 265                 270

Glu Ile Thr Ala Arg Pro Val Leu Trp His Trp Leu Leu Arg Thr Gly
        275                 280                 285

Gly Trp Lys Val Ser Ala Val Thr Leu Ala Tyr Leu Ile Phe Cys Leu
    290                 295                 300

Cys Ser Leu Val Gly Ile Leu His Leu Gln Arg Ala Leu Val Leu Arg
305                 310                 315                 320

Arg Lys Arg Lys Arg Met Thr
                325
```

<210> SEQ ID NO 53

```
<211> LENGTH: 15
<212> TYPE: PRT
<213> ORGANISM: Artificial
<220> FEATURE:
<223> OTHER INFORMATION: Synthetic linker peptide

<400> SEQUENCE: 53

Gly Gly Gly Gly Ser Gly Gly Gly Gly Ser Gly Gly Gly Gly Ser
1               5                   10                  15

<210> SEQ ID NO 54
<211> LENGTH: 11
<212> TYPE: PRT
<213> ORGANISM: Artificial
<220> FEATURE:
<223> OTHER INFORMATION: Synthetic CD3 HCVR CDR1

<400> SEQUENCE: 54

Ser Gly Tyr Thr Phe Thr Arg Tyr Thr Met His
1               5                   10

<210> SEQ ID NO 55
<211> LENGTH: 17
<212> TYPE: PRT
<213> ORGANISM: Artificial
<220> FEATURE:
<223> OTHER INFORMATION: Synthetic CD3 HCVR CDR2

<400> SEQUENCE: 55

Tyr Ile Asn Pro Ser Arg Gly Tyr Thr Asn Tyr Asn Gln Lys Phe Lys
1               5                   10                  15

Asp

<210> SEQ ID NO 56
<211> LENGTH: 8
<212> TYPE: PRT
<213> ORGANISM: Artificial
<220> FEATURE:
<223> OTHER INFORMATION: Synthetic CD3 HCVR CDR3

<400> SEQUENCE: 56

Tyr Tyr Asp Asp His Tyr Cys Leu
1               5

<210> SEQ ID NO 57
<211> LENGTH: 10
<212> TYPE: PRT
<213> ORGANISM: Artificial
<220> FEATURE:
<223> OTHER INFORMATION: Synthetic CD3 LCVR CDR1

<400> SEQUENCE: 57

Ser Ala Ser Ser Ser Val Ser Tyr Met Asn
1               5                   10

<210> SEQ ID NO 58
<211> LENGTH: 7
<212> TYPE: PRT
<213> ORGANISM: Artificial
<220> FEATURE:
<223> OTHER INFORMATION: Synthetic CD3 LCVR CDR2

<400> SEQUENCE: 58

Asp Thr Ser Lys Leu Ala Ser
1               5
```

```
<210> SEQ ID NO 59
<211> LENGTH: 8
<212> TYPE: PRT
<213> ORGANISM: Artificial
<220> FEATURE:
<223> OTHER INFORMATION: Synthetic CD3 LCVR CDR3

<400> SEQUENCE: 59

Gln Gln Trp Ser Ser Asn Pro Phe
1               5
```

NUCLEIC ACID CONSTRUCTS FOR CO-EXPRESSION OF CHIMERIC ANTIGEN RECEPTOR AND TRANSCRIPTION FACTOR, CELLS CONTAINING AND THERAPEUTIC USE THEREOF

CROSS-REFERENCE TO RELATED APPLICATIONS

This application is a U.S. National Phase Application submitted under 35 U.S.C. 371 based on International Application No. PCT/US2017/030284 filed Apr. 28, 2017 (published as WO2017/190100 on Nov. 2, 2017), which claims the benefit of U.S. Provisional Patent Application 62/328,936 filed Apr. 28, 2016, the disclosure of each and all of which are hereby incorporated by reference in their entirety.

STATEMENT REGARDING FEDERALLY SPONSORED RESEARCH OR DEVELOPMENT

This invention was made with government support under Grant No. P30GM103415 awarded by the National Institutes of Health. The government has certain rights in the invention.

SEQUENCE LISTING

This application includes as part of its disclosure an electronic sequence listing text file named "43252o2202.txt", created Oct. 25, 2018, which is hereby incorporated by reference in its entirety.

BACKGROUND

Field

The present invention provides novel CAR nucleic acid constructs and CAR-T cells engineered to express these nucleic acid constructs which possess enhanced properties. Particularly, the invention provides nucleic acid constructs and CAR-T cells containing, which are engineered to express at least one transcription factor, e.g. T-bet, STAT-1 or STAT-4, which transcription factor optionally may be mutated. These CAR-T cells possess one or more improved properties and are well suited for use in immunotherapy, e.g., for the treatment and prevention of cancer, infectious disease, inflammatory conditions, allergic conditions, autoimmune conditions and for alleviating the pathological side effects associated with any of the foregoing.

Description of Related Art

Chimeric antigen receptors (CARs) are typically composed of three basic parts: a recognition or antigen targeting domain, a transmembrane domain, and one or more signaling domains (Sadelain, et al. (2013) Cancer Discov. 3:388-398; Park, et al. (2011) Trends Biotechnol. 29:550-557). The recognition domain can be based on an antibody, a T cell receptor, another receptor, or a ligand for a receptor. The transmembrane domain includes an extracellular stalk region and may allow for dimerization. The signaling portion involves a protein domain that induces a primary activation signal in cells (e.g., CD3-ζ or FcεRIγ).

CAR-transduced T cells have been shown to constitute an effective means to eliminate tumors and increase patient survival (Sadelain, et al. (2009) Curr. Opin. Immunol. 21:215-23; Sadelain, et al. (2003) Nat. Rev. Cancer 3:35-45; Barber, et al. (2008) J. Immunol. 180:72-78). For example, CARs that target B-lineage-restricted antigens such as CD19 (Cooper, et al. (2003) Blood 101:1637-1644; Brentjens, et al. (2003) Nat. Med. 9:279-286) CD20 (Jensen, et al. (1998) Biol. Blood Marrow Transplant 4:75-83) and the light chain of human immunoglobulins (Vera, et al. (2006) Blood 108:3890-97) or CD30 expressed by Reed-Sternberg cells (Hombach, et al. (1999) J. Immunother. 22:473-480; Savoldo, et al. (2007) Blood 110:2620-2630) have been cloned and validated in preclinical lymphoma/leukemia models, and some have been in phase I clinical trials (Till, et al. (2008) Blood 112:2261-71; Sadelain, et al. (2009) Curr. Opin. Immunol. 21:215-223; Dotti, et al. (2009) Hum. Gene Ther. 20:1229-1239; Brentjens, et al. (2010) Mol. Ther. 18:666-668). Similarly, T cells transduced to express a chimeric NKG2D-based CAR (chNKG2D), composed of the NKG2D receptor fused to the CD3-ζ (CD3-ζ) cytoplasmic domain, kill tumor cells and secrete T-cell effector cytokines that promote endogenous antitumor immunity (Barber, et al. (2009) J. Immunol. 183:2365-72; Barber, et al. (2007) Cancer Res. 67:5003-8; Zhang, et al. (2005) Blood 106:1544-51; Zhang, et al. (2006) Cancer Res. 66:5927-33).

However, clinical trials (Till, et al. (2008) Blood 112:2261-71; Kershaw, et al. (2006) Clin. Cancer Res. 12:6106-15; Kowolik, et al. (2006) Cancer Res. 66:10995-11004) and preclinical models (Sadelain, et al. (2009) Curr. Opin. Immunol. 21:215-223; Vera, et al. (2006) Blood 108:3890-7; Kowolik, et al. (2006) Cancer Res. 66:10995-11004) have shown that the expansion and persistence of CAR-modified T cells in vivo can be hampered by the lack of costimulatory signals after engagement with target antigens, as many tumor cells down-regulate their expression of the costimulatory molecules required for optimal and sustained T-cell function, proliferation and persistence (Sadelain, et al. (2009) Curr. Opin. Immunol. 21:215-223; Dotti, et al. (2009) Hum. Gene Ther. 20:1229-1239).

This limitation has been partially resolved by the construction of 'second-generation' CARs which are engineered to comprise a costimulatory endodomain derived from costimulatory molecules such as CD28 (Vera, et al. (2006) Blood 108:3890-7; Kowolik, et al. (2006) Cancer Res. 66:10995-11004; Maher, et al. (2002) Nat. Biotechnol. 20:70-75) and 4-1BB (Imai, et al. (2004) Leukemia 18:676-84; Milone, et al. (2009) Mol. Ther. 17:1453-1464). T cells expressing these CARs reportedly retain their cytotoxic function, and upon antigen engagement produce interleukin-2 (IL-2), which helps to sustain their activation and expansion (Vera, et al. (2006) Blood 108:3890-7; Kowolik, et al. (2006) Cancer Res. 66:10995-11004; Maher, et al. (2002) Nat. Biotechnol. 20:70-75) as well as enhancing their antitumor activity (Sadelain, et al. (2009) Curr. Opin. Immunol. 21:215-223; Vera, et al. (2006) Blood 108:3890-7; Kowolik, et al. (2006) Cancer Res. 66:10995-11004).

Additionally, 'third-generation' CARs have been developed that contain multiple costimulatory endodomains derived from the same or different costimulatory molecules, e.g., CARs have been produced which contain costimulatory endodomains derived from CD28 and 4-1BB (Carpenito, et al. (2009) Proc. Natl. Acad. Sci. USA 106:3360-3365; Tammana, et al. (2010) Hum. Gene Ther. 21:75-86; Zhao, et al. (2009) J. Immunol. 183:5563-74; Wang, et al. (2007) Hum. Gene Ther. 18:712-25) and from CD28 and OX40 (Pule, et al. 2005) Mol. Ther. 12:933-41). These CARS reportedly elicit enhanced immunostimulatory activity in vitro compared with those encoding single costimulatory endodomains (Carpenito, et al. (2009) Proc. Natl. Acad. Sci. USA 106:3360-3365; Tammana, et al. (2010) Hum. Gene Ther.

21:75-86; Zhao, et al. (2009) *J. Immunol.* 183:5563-74; Pule, et al. 2005)*Mol. Ther.* 12:933-41).

Additional strategies to enhance the activity of CAR-modified T cells in vivo include the ex vivo treatment of CAR-modified T cells with cytokines (MacGregor, et al. (2006) *Cancer Res.* 66:4913; Singh, et al. (2011) *Cancer Res.* 71:3516-3527) or the engineering of CAR-modified T cells to secrete stimulatory cytokines (Chmielewski, et al. (2011) *Cancer Res.* 71:5697; Chmielewski, et al. (2014) *Immunol. Rev.* 257:83-90; Markley & Sadelain (2010) *Blood* 115:3508-19; Chinnasamy et al. (2012) *Clin. Cancer Res.* 18:1672-1683; Sadelain et al. (2013) *Cancer Discov.* 3:388-9; US 2013/0071414; US 2014/0255363).

BRIEF SUMMARY

The present invention relates to novel nucleic acid constructs and their incorporation into immune cells. Particularly, the invention relates to the discovery that immune cells, preferably T cells, e.g., primary human T cells, which are engineered to express at least one CAR and one or more transcription factors, e.g., T-bet, STAT-1 or STAT-4 or mutated forms thereof, possess properties which render these cells well suited for use in human or animal therapy. In some embodiments, the nucleic acid construct or constructs encoding the CAR and the transcription factor or variant thereof may be on the same or different vectors.

In some embodiments, the transcription factor may elicit one or more of the following effects in an immune cell containing said construct or constructs:
  i. enhances the expression of said CAR by said immune cell,
  ii. for an immune cell that may be a $CD4^+$ T cell, promotes the development of the $CD4^+$ T cell to a $T_H1$ cell,
  iii. promotes the immune cell's expression of $T_H1$ cytokines such as IL-2, IFNγ or TNFα,
  iv. suppresses the development of these immune cells or their progeny into other (non-$T_H1$) cells such as $T_H2$, $T_H17$, or $T_{FH}$ cells,
  v. suppresses the expression of $T_H2$ cytokines such as IL-13 by said immune cell or its progeny;
  vi. enhances the immune cell's killing of target cells expressing the antigen bound by the CAR; and/or
  vii. promotes the migration of $T-bet^+$ $T_{Reg}$ cells.

In some embodiments, the transcription factor may be selected from T-box 21 (T-bet), signal transducer and activator of transcription 1 (STAT1), and signal transducer and activator of transcription 4 (STAT4) or a mutated form of any one of the foregoing.

In some embodiments, the transcription factor may be T-bet, or a homologue or orthologue thereof.

In some embodiments, the transcription factor may be a mutated form of T-bet, optionally wherein the mutation comprises:
  i. a truncation, deletion, and/or mutation of at least one T-bet domain;
  ii. the incorporation of a stop codon within the T-bet coding sequence;
  iii. a mutation or deletion within the T-box domain or the transactivation domain;
  iv. the modification of one or more of the following amino acid residues: Y219, Y265, T302, Y304, K313, 5508 and Y525;
  v. a mutation resulting in altered c-Abl mediated phosphorylation, ubiquitination, GSK-3 mediated phosphorylation, and/or ITK-induced phosphorylation relative to wild-type T-bet;
  vi. the incorporation of a stop codon within, or mutation of any of the residues within, nucleic acid residues 50-450, 150-350, or 200-250 of T-bet;
  vii. the incorporation of a stop codon which replaces nucleic acid residues 214-217, optionally wherein the mutated T-bet nucleic acid sequence encodes an amino acid sequence having at least 80%, at least 85%, at least 90%, at least 95%, at least 98%, at least 99%, or 100% identity to the amino acid sequence of SEQ ID NO:29, or having at least 80%, at least 85%, at least 90%, at least 95%, at least 98%, at least 99%, or 100% identity to the amino acid sequence encoded by SEQ ID NO:30;
  viii. the deletion of all or part of the T-Box domain, e.g., the deletion of nucleic acid residues 300-400, 300-500, 400-600, 400-700, 500-800, 600-900, 400-1000, 400-1100, 400-1200, +/−1, 2, 3, 4, 5, . . . 50; 51, 52 . . . 75; 76, 77, . . . 100; 101, 102, . . . 125; or 126, 127, . . . 150 nucleic acid residues;
  ix. a deletion of nucleic acid residues 403-978; and
  x. a deletion of all or substantially all of the T-box domain, optionally wherein the mutated T-bet nucleic acid sequence encodes an amino acid sequence having at least 80%, at least 85%, at least 90%, at least 95%, at least 98%, at least 99%, or 100% identity to the amino acid sequence of SEQ ID NO:31, or having at least 80%, at least 85%, at least 90%, at least 95%, at least 98%, at least 99%, or 100% identity to the amino acid sequence encoded by SEQ ID NO:32;
wherein the foregoing mutations are indicated with respect to the mouse T-bet sequence, but are intended to further include corresponding or analogous mutations to the homologous or orthologous residues or domains of a T-bet homologue or orthologue, e.g., human T-bet or TBX21.

In some embodiments, the transcription factor may be human T-bet or a variant, chimeric, truncated or mutated form thereof.

In some embodiments, the transcription factor may be human STAT-1 or human STAT-4 or a variant, chimeric, truncated or mutated form thereof.

In some embodiments, the nucleic acid construct or constructs may comprise a CAR which comprises an antigen binding domain or receptor, a transmembrane domain, and one or more immune signaling or costimulatory endodomains.

In some embodiments, the nucleic acid construct or constructs comprise nucleic acid sequences encoding or comprising one or more of:
  i. a promoter;
  ii. a transcription enhancer;
  iii. a self-cleaving peptide cis-acting hydrolase element (CHYSEL) located between the CAR and the transcription factor;
  iv. a protein that is capable of triggering cell suicide or elimination;
  v. a suicide gene;
  vi. one or more internal ribosomal entry sites (IRES);
  vii. a gene encoding a protein whose expression allows for selection of a cell harboring the vector; and
  viii. one or more cis-acting hydrolase elements.

In some embodiments, the CAR may comprise an antigen binding domain that specifically recognizes any of: CD19, CD20, CD22, kappa light chain, CD38, receptor-tyrosine-kinase-like orphan receptor 1 (ROR1), CD30, CD33, epithelial glycoprotein (EGP) 40, tumor-associated glycoprotein 72, prostate-specific membrane antigen, prostate stem cell antigen, ganglioside (GD) 3, high molecular weight melanoma-associated antigen, HLA-A1 MAGEA1, ErbB2, mucin (MUC) 1, MUC16, folate receptor-α, CD44v7/8, carbonic anhydrase 9, G250/CAIX, GD2, CD171, nerve cell adhesion molecule, fetal acetylcholine receptor, ErB3/4, epidermal growth factor receptor VIII, carcinoembryonic antigen, EGP2, mesothelin, natural killer group 2 member D ligands, B7-H6, IL-13 receptor α2, HLA-A2 NY-ESO-1, CD44v6, α$_v$β$_6$ integrin, 8H9, vascular endothelial growth factor receptors, or 5T4.

In some embodiments, the antigen binding domain may specifically recognize B7-H6.

In some embodiments, the CAR may comprise a human, humanized, or chimeric antigen binding domain, optionally wherein the antigen binding domain comprises a human, humanized, or chimeric scFv.

In some embodiments, the construct or constructs may comprise a nucleic acid sequence encoding an amino acid sequence having at least 80%, at least 85%, at least 90%, at least 95%, at least 98%, at least 99%, or 100% identity to the amino acid sequence of TZ.47 scFv (SEQ ID NO:13), or having at least 80%, at least 85%, at least 90%, at least 95%, at least 98%, at least 99%, or 100% identity to the amino acid sequence encoded by SEQ ID NO:24.

In some embodiments, the construct or constructs may comprise a nucleic acid sequence encoding an amino acid sequence:
  i. having at least 80%, at least 85%, at least 90%, at least 95%, at least 98%, at least 99%, or 100% identity to the amino acid sequence of Tz.47-28-3z (SEQ ID NO:25), or having at least 80%, at least 85%, at least 90%, at least 95%, at least 98%, at least 99%, or 100% identity to the amino acid sequence encoded by SEQ ID NO:26;
  ii. having at least 80%, at least 85%, at least 90%, at least 95%, at least 98%, at least 99%, or 100% identity to the amino acid sequence of Tz.47-28-3z-MsTBET (SEQ ID NO:34), or having at least 80%, at least 85%, at least 90%, at least 95%, at least 98%, at least 99%, or 100% identity to the amino acid sequence encoded by SEQ ID NO:35;
  iii. having at least 80%, at least 85%, at least 90%, at least 95%, at least 98%, at least 99%, or 100% identity to the amino acid sequence of Tz.47-28-3z-MsTBET-STOP (SEQ ID NO:36), or having at least 80%, at least 85%, at least 90%, at least 95%, at least 98%, at least 99%, or 100% identity to the amino acid sequence encoded by SEQ ID NO:37; and/or
  iv. having at least 80%, at least 85%, at least 90%, at least 95%, at least 98%, at least 99%, or 100% identity to the amino acid sequence of Tz.47-28-3z-MsTBET-TBOX Deletion (SEQ ID NO:38), or having at least 80%, at least 85%, at least 90%, at least 95%, at least 98%, at least 99%, or 100% identity to the amino acid sequence encoded by SEQ ID NO:39.

In some embodiments, the CAR may comprise a transmembrane domain derived from a protein selected from the group consisting of CD28, CD3 ε, CD4, CD5, CD8, CD9, CD16, CD22, CD33, CD37, CD45, CD64, CD80, CD86, CD134, CD137, CD154, TCR α, TCR β, and CD3 ζ.

In some embodiments, the CAR may comprise a transmembrane domain of CD28 and/or an endodomain of CD28, optionally the CD28 transmembrane domain and CD28 endodomain corresponding to amino acids 135 to 220 of human CD28 (SEQ ID NO:14), or the homologous residues of another mammalian CD28, e.g., mouse CD28 (SEQ ID NO:15).

In some embodiments, the CAR may comprise at least one of the endodomains of one or more of a lymphocyte receptor chain, a TCR/CD3 complex protein, an Fc receptor subunit, an IL-2 receptor subunit, FcRγ, FcRβ, CD3γ, CD3δ, CD3ε, CD5, CD22, CD79a, CD79b, CD66d, CD2, CD4, CD5, CD8α, CD8β, CD28, CD134, CD137, ICOS, CD122, CD132, CD40, CD154, FIεRI, DAP10, DAP12 or CD3ζ.

In some embodiments, the CAR may further comprise one or more costimulatory endodomains derived from a protein selected from the group consisting of an MHC class I molecule, TNF receptor proteins, Immunoglobulin-like proteins, cytokine receptors, integrins, signaling lymphocytic activation molecules (SLAM proteins), activating NK cell receptors, a Toll ligand receptor, B7-H3, BAFFR, BTLA, BLAME (SLAMF8), CD2, CD4, CD5, CD7, CD8α, CD8β, CD11a, LFA-1 (CD11a/CD18), CD11b, CD11c, CD11d, CD18, CD19, CD19a, CD27, CD28, CD29, CD30, CD40, CD49a, CD49D, CD49f, CD69, CD84, CD96 (Tactile), CD100 (SEMA4D), CD103, OX40 (CD134), 4-1BB (CD137), SLAM (SLAMF1, CD150, IPO-3), CD160 (BY55), SELPLG (CD162), DNAM1 (CD226), Ly9 (CD229), SLAMF4 (CD244, 2B4), ICOS (CD278), CEACAM1, CDS, CRTAM, DAP10, GADS, GITR, HVEM (LIGHTR), IA4, ICAM-1, IL2R β, IL2R γ, IL7R α, ITGA4, ITGA6, ITGAD, ITGAE, ITGAL, ITGAM, ITGAX, ITGB1, ITGB2, ITGB7, KIRDS2, LAT, LFA-1, LIGHT, LTBR, NKG2C, NKG2D, NKp30, NKp44, NKp46, NKp80 (KLRF1), PAG/Cbp, PD-1, PSGL1, SLAMF6 (NTB-A, Ly108), SLAMF7, SLP-76, TNFR2, TRANCE/RANKL, VLA1, VLA-6, and a ligand that specifically binds with CD83.

In some embodiments, the nucleic acid construct or constructs include sequences encoding the endodomains of CD28 and CD3ζ.

In some embodiments, the construct or constructs may comprise:
  (a) a nucleic acid sequence encoding an anti-B7-H6 scFv;
  (b) a nucleic acid sequence encoding a CD28 transmembrane domain;
  (c) a nucleic acid sequence encoding a CD28 endodomain;
  (d) a nucleic acid sequence encoding a CD3 ζ endodomain; and/or
  (e) a nucleic acid sequence encoding one or more of T-bet, STAT1, and STAT4 or a mutated form of any one of the foregoing.

In some embodiments, the nucleic acid encoding the CAR and the nucleic acid encoding the transcription factor may be on the same vector.

In some embodiments, the nucleic acid encoding the CAR and the nucleic acid encoding the transcription factor may be on different vectors.

In some embodiments, the nucleic acid encoding the CAR may comprise a gene encoding a C-type lectin-like natural killer cell receptor and an immune signaling receptor containing an immunoreceptor tyrosine-based activation motif.

In some embodiments, the expression of the nucleic acid encoding the CAR and the nucleic acid encoding the transcription factor may be regulated by different constitutive or inducible promoters.

In some embodiments, the expression of the nucleic acid encoding the CAR and the nucleic acid encoding the transcription factor may be regulated by the same constitutive or inducible promoter.

In some embodiments, the nucleic acid encoding the CAR and the nucleic acid encoding the transcription factor are separated by a self-cleaving peptide or CHYSEL. In some embodiments, the self-cleaving peptide or CHYSEL gene may be selected from foot-and-mouth disease virus (FMDV) self-cleaving polypeptide 2A sequence (SEQ ID NO:2), sea urchin (*Strongylocentrotus purpuratus*) 2A sequence (SEQ ID NO:3), sponge (*Amphimedon queenslandica*) 2A sequence (SEQ ID NO:4 or SEQ ID NO:5), acorn worm (*Saccoglossus kowalevskii*) 2A sequence (SEQ ID NO:6); amphioxus (*Branchiostoma floridae*) 2A sequence (SEQ ID NO:7 or SEQ ID NO:8), porcine teschovirus-1 2A sequence (SEQ ID NO:9), Thoseaasigna virus 2A sequence (SEQ ID NO:10), equine rhinitis A virus 2A sequence (SEQ ID NO:11) or a synthetic sequence that includes the 2A consensus sequence D-X-E-X-N-P-G-P (SEQ ID NO:12), in which X is any amino acid residue, or any homolog thereof.

The invention further provides a vector or vectors comprising the construct or constructs of any of the foregoing embodiments. The vector or vectors may be selected from the group consisting of a DNA, an RNA, a plasmid, a lentivirus vector, adenoviral vector, a retrovirus vector, and an in vitro transcribed vector The invention additionally provides a recombinant cell comprising the nucleic acid construct or constructs or the vector or vectors according to any of the foregoing embodiments.

In some embodiments, the recombinant cell may be an immune cell, optionally a primary mammalian immune cell, optionally a primary human immune cell.

In some embodiments, the recombinant cell may be selected from a T lymphocyte, a B lymphocyte, a natural killer cell, an eosinophil, an NK/T cell, a macrophage, a cell of myeloid lineage, a dendritic cell, a neutrophilic granulocyte, and a monocyte, optionally selected from primary cells obtained from a human donor or donors.

In some embodiments, the recombinant cell may be selected from a T cell, a T cell progenitor, a CD4$^+$ T cell, a CD8+ T cell, a naive T (TN) cell, an immature T cell, an effector T (TEFF) cell, a memory T cell, a stem cell memory T (TSCM) cell, a central memory T (TCM) cell, an effector memory T (TEM) cell, a terminally differentiated effector memory T cell, a tumor-infiltrating lymphocyte (TIL), an immature T cell, a mature T cell, a helper T cell, a cytotoxic T lymphocyte (CTL), a mucosa-associated invariant T (MATT) cell, a regulatory T (Treg) cell, a helper T cell, a TH1 cell, a TH2 cell, a TH3 cell, a TH17 cell, a TH9 cell, a TH22 cell, a follicular helper T cell, an α/β T cell, a δ/γ T cell, a Natural Killer (NK) cell, a Natural Killer T (NKT) cell, a cytokine-induced killer (CIK) cell, and a lymphokine-activated killer (LAK) cell.

In some embodiments, the recombinant cell may be further engineered to:
  i. eliminate or reduce the expression or functionality of the T cell's endogenous T cell receptor (TCR);
  ii. express the dominant negative form of the transforming growth factor β (TGFβ) receptor (DNR);
  iii. overexpress pro-survival signals, reverse anti-survival signals, overexpress Bcl-xL, over-express BCL-2, inhibit the function of cell death genes (optionally Bak or Bax), overexpress hTERT, and/or eliminate Fas expression;
  iv. evade immunosuppressive mediators;
  v. inactivate the expression or functionality of a human leukocyte antigen (HLA) gene or HLA regulator gene product;
  vi. comprise a homing mechanism;
  vii. express a protein that may be capable of triggering cell suicide or elimination; and/or
  viii. express a protein whose expression allows for selection of cells comprising the nucleic acid construct or constructs or the vector or vectors of any of the foregoing embodiments.

In some embodiments, the recombinant cell may be engineered to express a second nucleic acid construct comprising another CAR, wherein said other CAR comprises an antigen binding domain or receptor, a transmembrane domain, and one or more of an immune signaling or costimulatory endodomain.

The invention further provides a therapeutic or pharmaceutical composition comprising a therapeutically or diagnostically effective amount of a recombinant cell according to any of the foregoing embodiments. In some embodiments, the composition may further comprise a pharmaceutically acceptable carrier, diluent or excipient.

The invention additionally provides a method of immune therapy comprising administering to a subject a therapeutically effective amount of a nucleic acid construct or constructs, a vector or vectors, a recombinant cell or a composition according to any of the foregoing embodiments.

In some embodiments, the method may be used in the treatment of a condition selected from:
  i. a proliferative disease or disorder, optionally cancer;
  ii. an infectious disease or disorder;
  iii. an inflammatory disease or disorder; and
  iv. an immune disease or disorder, optionally autoimmunity.

In some embodiments, the condition may be cancer.

In some embodiments, the cancer may be cancer of the colon, liver, cervix, lung, pancreas, prostate, leukemia, lymphoma, a gastrointestinal stromal tumor, prohemocytic leukemia, B-cell lymphoma, monocytic lymphoma, erythro leukemia, Burkitt's lymphoma, chronic myelogenous leukemia (CML), T and B lymphomas, myeloid leukemias, melanomas, carcinomas, large T SV40 antigen-transformed cells, acute nonlymphoblastic leukemia (ANLL), acute lymphoblastic leukemia (ALL), and non-Hodgkin's and Hodgkin's lymphoma, T-ALL, and marginal zone lymphoma.

In some embodiments, the cancer cells express B7-H6.

In some embodiments, administering the treatment to the subject may comprise adoptive cell therapy (ACT) using immune cells harvested from the subject or from one or more donors.

In some embodiments, ACT may comprise isolating primary immune cells from the subject or from one or more donors, transducing the primary immune cells with the nucleic acid construct or constructs of any of the foregoing embodiments, expressing the CAR and/or the transcription factor in the transduced primary immune cells, and delivering the transduced immune cells into the subject. ACT may further comprise stimulating and/or expanding the immune cells prior to delivering the transduced immune cells to the subject.

In some embodiments, the condition may be an infectious disease or disorder.

The invention also provides a method for treating cancer comprising delivering to a subject in need of treatment an effective amount of the nucleic acid construct or constructs, a vector or vectors, or a recombinant cell according to any of the foregoing embodiments, thereby treating the cancer. In some embodiments, the treatment of cancer may be measured by a decrease in tumor cell burden or by an increase in survival.

The invention additionally provides a kit comprising the nucleic acid constructs, vectors, recombinant cells, or compositions of any of the foregoing embodiments.

The invention also provides a method of manufacturing a chimeric antigen receptor (CAR) immune cell, comprising:
i. obtaining immune cells; and
ii. transducing the immune cells with a vector containing a nucleic acid that encodes the CAR and further transducing the same immune cells with a nucleic acid encoding a transcription factor according to any one of the foregoing embodiments, wherein the nucleic acid encoding the transcription factor may be on the same or a different vector as the CAR, wherein such transduction results in immune cells which express the CAR and the transcription factor, optionally wherein the immune cell may be a T or NK cell, e.g. a primary human T or NK cell.

In some embodiments, the resultant immune cells may constitutively or inducibly express or overexpress the transcription factor encoded by said nucleic acid.

BRIEF DESCRIPTION OF THE SEVERAL VIEWS OF THE DRAWINGS

FIG. 1A illustrates that the genes for the CAR and the transcription factor medicating pro-inflammatory cytokine expression may be on the same or different nucleic acid constructs, signified by the dashed line. FIG. 1B shows an anti-B7-H6 CAR construct including an anti-B7-H6 scFv ($V_H$ domain-linker-$V_L$ domain) fused in frame to a CD28 hinge (H), transmembrane domain (TM), and endodomain/cytoplasmic domain (CYP), also fused in frame to a CD3-ζ endodomain or signaling domain (CYP). FIG. 1C depicts an anti-B7-H6-CD28-CD3-ζ nucleic acid construct separated by a T2A linker sequence encoding the self-cleaving peptide 2A to a gene encoding mouse transcription factor T-bet.

FIG. 2B lists the amino acids indicated in FIG. 2A, along with their possible modifications and physiological effects.

FIGS. 3A-3B show that the coexpression of transcription factor T-bet and TZ.47 (anti-B7-H6 scFv) CAR molecules increases the secretion of various cytokines by CD4+ sorted T cells cocultured with RMA cells expressing B7-H6. FIG. 3A demonstrates a statistically significant increase in secretion of GM-CSF, IL-3, MIP-1a, and IFNγ by T-bet CAR T cells compared to CAR T cells which do not coexpress T-bet. FIG. 3B demonstrates a statistically significant increase in secretion of IL-2, IL-10, and TNF-α, but not IL-13 by T-bet CART cells compared to CART cells which do not coexpress T-bet.

FIGS. 4A-4C show the results of flow cytometry analyses of ConA-stimulated T cells (which were not CD4 sorted). TZ.47 expression is therefore based on the whole T cell population (CD4 and CD8 cells). Negative controls include T cells transduced with Pfb-neo alone (left panel) and T cells transduced with Pfb-TZ.47-28-3z alone (no T-bet, middle panel), which are compared to T cells transduced with Pfb-TZ.47-28-3z-MsTBET (right panel). FIG. 4A show CD8 expression. FIG. 4B shows MsT-bet (mouse T-bet) expression. FIG. 4C shows CAR expression. Coexpression of the TZ.47 CAR construct with T-bet increases CD8 expression, MsT-bet expression, and CAR expression compared to the Pfb-neo alone and CAR alone controls.

FIG. 5A shows CD3 and CD8 expression for cells transduced with Pfb-TZ.47-28-3z (left panel) or Pfb-TZ.47-28-3z-MsTBET (right panel). FIG. 5B shows MsT-bet expression for cells transduced with Pfb-TZ.47-28-3z (left panel) or Pfb-TZ.47-28-3z-MsTBET (right panel). FIG. 5C shows CAR expression for cells transduced with Pfb-TZ.47-28-3z (left panel) or Pfb-TZ.47-28-3z-MsTBET (right panel).

FIG. 6A shows that one mutant has a stop codon inserted at nucleotide position 214 (214 to 217 changed to TGA): this is the "TBET-STOP" mutant FIG. 6A also depicts the "TBET-Tbox Del" mutant, with the Tbox nucleotides 403 to 978 deleted, creating a truncated T-bet protein (T-box deletion region represented by gray box). The T-bet mutants were inserted into Pfb-TZ.47-28-3z vectors to create the constructs: Pfb-TZ.47-28-3z-AG23 (TBET-STOP) and Pfb-TZ.47-28-3z-AG24 (TBET-Tbox Del). MFI values for the two mutants, as compared to vectors Pfb-neo, Pfb-TZ.47-28-3z, and Pfb-TZ.47-28-3z-MsTBET are provided in FIG. 6B.

FIG. 8 shows interferon-γ (IFNγ) production of CD4+ T cells transduced with pfb-neo (white bars), pfb-TZ.47-28-3z (black bars), pfb-TZ.47-28-3z-MsTBET (gray bars), pfb-TZ.47-28-3z-TBET-STOP (bars with vertical lines), and pfb-TZ.47-28-3z-Tbox-Del (bars with diagonal lines). The left panel shows expression of IFNγ after exposure to mouse RMA cells. The right panel shows expression of IFNγ after exposure to RMA cells expressing B7-H6, the target of the TZ.47 CAR constructs.

FIG. 9A shows the results of the luciferase assay for RMA cells that do not express B7H6. FIG. 9B shows the results of the luciferase assay for RMA cells that express B7H6. Survival of tumor cells was assessed for CD4+ CAR T cells cocultured with tumor cell lines at E:T ratios of 0.2:1, 1:1, and 5:1 for 24H. The RLU values are shown +/−SD. ANOVA Dunnett's Test was used to measure significance. P(*)<0.01 for B7H6-specific CAR cells vs Mock, P(V)<0.01 B7H6-specific CAR/TBET (DTBOX) vs Mock.

FIG. 10 shows the Kaplan Meier survival curves of RMA B7H6 bearing mice treated with CAR T cells (n=12 per group). Treatment groups were: CD4+ Mock T cells+ConA stimulated T cells (mock group); CD4+ B7H6-specific CAR T cells+ConA stimulated T cells (no Tbet group); and CD4+ B7H6-specific CAR/T-bet (Delta-TBOX)+ConA stimulated T cells. Data are combined from two independent experiments. Log-Rank Mantel-Cox Test P(*)<0.01 compared to no Tbet and mock groups. Results indicate that CD4+ CAR T cells expressing T-bet (Delta-TBOX) promote survival against lymphoma-bearing mice.

DETAILED DESCRIPTION

Figure 1A:
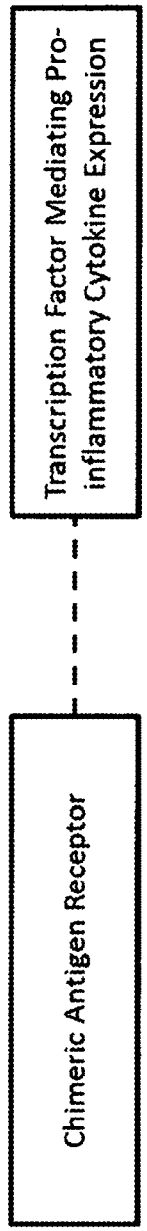
FIGS. 1A-1C schematically depicts exemplary CAR and transcription factor nucleic acid constructs.

Before describing the invention in detail, the following definitions are provided.

Definitions

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.0.1% from the specified value, as such variations are appropriate to perform the disclosed methods.

"Activation", as used herein, refers to the state of a T cell that has been sufficiently stimulated to induce detectable cellular proliferation. Activation can also be associated with induced cytokine production, and detectable effector functions. The term "activated T cells" refers to, among other things, T cells that are showing some response which by way of example may include these cells producing a cytokine, eliciting cytotoxicity, expressing or not expressing certain gene or genes such as activation makers such as CD69, and/or proliferating in an antigen-specific manner.

The term "adoptive cell therapy" or "adoptive T-cell therapy" or "ACT" as used herein means the transfer of cells into a patient, where the cells have been engineered to or otherwise altered prior to transfer into the subject. ACT is also referred to as adoptive T-cell immunotherapy, etc. An example of ACT is the harvesting from a subject's blood or tumor, an immune cell, such as a T cell. These immune cells are then stimulated ex vivo, in culture and expanded. The cells are then transduced with one or more nucleic acid constructs that allow the cell to express new molecules, such as a CAR, providing the engineered immune cells with a new mechanism for combating a disease, for instance a cancer. In some instances, the CAR will comprise an antigen binding domain that specifically recognizes an antigen expressed by a tumor or cancer. Typical immune cells utilized in ACT procedures include tumor-infiltrating lymphocytes (TIL) or T cells. Immune cells used in ACT can be derived from the patient/subject themselves, or from a universal donor. ACT may also be accompanied by the optional step of lymphodepletion of the subject's own lymphocytes that may compete with the recombinant cells infused back into the subject. For example, in some embodiments, ACT may comprise harvesting autologous or allogeneic T cells and transducing these T cells with one or more nucleic acid constructs, so that the T cells express a CAR and a transcription factor mediating pro-inflammatory cytokine expression, and then infusing the cells into a subject in need thereof.

The term "allogeneic" or "donor-derived" refers to any material derived from a different animal of the same species as the individual to whom the material is introduced. Two or more individuals are said to be allogeneic to one another when the genes at one or more loci are not identical. In some aspects, allogeneic material from individuals of the same species may be sufficiently unlike genetically to interact antigenically.

The term "anti-tumor effect" or "anti-tumor cytotoxicity" as used herein, refers to a biological effect which can be manifested by a decrease in tumor volume, a decrease in the number of tumor cells, a decrease in the number of metastases, an increase in life expectancy, or amelioration of various physiological symptoms associated with the cancerous condition. An "anti-tumor effect" can also be manifested by the ability of the peptides, polynucleotides, cells and antibodies of the invention in prevention of the occurrence of tumor in the first place. The term may also refer to any cytocidal activity against target tumor cells resulting from the exposure of these target cells to cells bearing the nucleic acid constructs described herein. This activity may be measured by known cytotoxicity assays, including, e.g., IFN-γ production assays and luciferase assays.

The term "antibody," as used herein, refers to an immunoglobulin molecule which specifically binds with an antigen. For example, in one aspect, the antigen is B7-H6. Antibodies can be intact immunoglobulins derived from natural sources or from recombinant sources and can be immunoreactive portions of intact immunoglobulins. The term is used in the broadest sense and includes polyclonal and monoclonal antibodies, including intact antibodies and functional (antigen-binding) antibody fragments, including fragment antigen binding (Fab) fragments, F(ab')$_2$ fragments, Fab' fragments, Fv fragments, recombinant IgG (rIgG) fragments, single chain antibody fragments, including single chain variable fragments (scFv), diabodies, and single domain antibodies (e.g., sdAb, sdFv, nanobody) fragments. The term encompasses genetically engineered and/or otherwise modified forms of immunoglobulins, such as intrabodies, peptibodies, chimeric antibodies, fully human antibodies, humanized antibodies, and heteroconjugate antibodies, multispecific (e.g., bispecific) antibodies, diabodies, triabodies, and tetrabodies, tandem di-scFv, tandem tri-scFv. Unless otherwise stated, the term "antibody" should be understood to encompass functional antibody fragments thereof. The term also encompasses intact or full-length antibodies, including antibodies of any class or sub-class, including IgG and sub-classes thereof, IgM, IgE, IgA, and IgD.

The term "antibody fragment" refers to a portion of an intact antibody and refers to the antigenic determining variable regions of an intact antibody. Examples of antibody fragments include, but are not limited to, fragment antigen binding (Fab) fragments, F(ab')$_2$ fragments, Fab' fragments, Fv fragments, recombinant IgG (rIgG) fragments, single chain antibody fragments, including single chain variable fragments (scFv), single domain antibodies (e.g., sdAb, sdFv, nanobody) fragments, diabodies, and multispecific antibodies formed from antibody fragments. In a specific embodiment, the antibody fragment may be an scFv.

An "antibody heavy chain," as used herein, refers to the larger of the two types of polypeptide chains present in all antibody molecules in their naturally occurring conformations.

An "antibody light chain," as used herein, refers to the smaller of the two types of polypeptide chains present in all antibody molecules in their naturally occurring conformations. Kappa and lambda light chains refer to the two major antibody light chain isotypes.

The term "antigen" or "Ag" refers to a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to encode polypeptides that elicit the desired immune response. Moreover, a skilled artisan will understand that an antigen need not be encoded by a "gene" at all. It is readily apparent that an antigen can be generated, synthesized, or can be derived from a biological sample, or might be macromolecule besides a polypeptide. Such a biological sample can include, but is not limited to a tissue sample, a tumor sample, a cell or a fluid with other biological components.

The term "antigen binding domain" refers to one or more extracellular domains of the chimeric antigen receptor which have specificity for a particular antigen.

The term "apheresis" as used herein refers to the art-recognized extracorporeal process by which the blood of a donor or patient is removed from the donor or patient and passed through an apparatus that separates out selected particular constituent(s) and returns the remainder to the circulation of the donor or patient, e.g., by retransfusion. Thus, in the context of "an apheresis sample" refers to a sample obtained using apheresis.

The term "auto-antigen" means, in accordance with the present invention, any self-antigen which is recognized by the immune system as being foreign. Auto-antigens comprise, but are not limited to, cellular proteins, phosphoproteins, cellular surface proteins, cellular lipids, nucleic acids, glycoproteins, including cell surface receptors.

The term "autologous" refers to any material derived from the same individual to whom it is later to be re-introduced.

The terms "B7H6", "B7-H6", and "NCR3LG1" refer to natural killer cell cytotoxicity receptor 3 ligand 1, a specific ligand for the NK cell-activating receptor NKp30. This protein is expressed on various types of primary human tumors, including leukemia, lymphoma, and gastrointestinal stromal tumors, but it is not constitutively expressed on normal tissues. In some embodiments, the nucleic acid construct or constructs of the invention encode a CAR that specifically binds to B7H6.

The term "bind" refers to an attractive interaction between two molecules that results in a stable association in which the molecules are in close proximity to each other. The result of molecular binding is sometimes the formation of a molecular complex in which the attractive forces holding the components together are generally non-covalent, and thus are normally energetically weaker than covalent bonds.

The term "cancer" refers to a disease characterized by the uncontrolled growth of aberrant cells. Cancer cells can spread locally or through the bloodstream and lymphatic system to other parts of the body. Examples of various cancers are described herein and include, but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer, cancer of the colon, liver, cervix, lung, pancreas, prostate, leukemia, lymphoma, gastrointestinal stromal tumor, prohemocytic leukemia, B-cell lymphoma, monocytic lymphoma, erythro leukemia, Burkitt's lymphoma, chronic myelogenous leukemia (CML), T and B lymphomas, myeloid leukemias, melanomas, carcinomas, large T SV40 antigen-transformed cells, acute nonlymphoblastic leukemia (ANLL), acute lymphoblastic leukemia (ALL), and non-Hodgkin's and Hodgkin's lymphoma, T-ALL, marginal zone lymphoma, and the like.

The term "CD28" refers to the protein Cluster of Differentiation 28, one of the proteins expressed on T cells that provide co-stimulatory signals required for T cell activation and survival. The protein may have at least 85, 90, 95, 96, 97, 98, 99 or 100% identity to NCBI Reference No: NP_006130 or a fragment thereof that has stimulatory activity.

The term "CD3ζ" or alternatively, "zeta", "zeta chain", "CD3-zeta" or "TCR-zeta" is defined as the protein provided as GenBan Acc. No. BAG36664.1, or the equivalent residues from a non-human species, e.g., mouse, rodent, monkey, ape and the like, and a "CD3t intracellular signaling domain" or alternatively a "zeta intracellular signaling domain" or a "TCR-zeta intracellular signaling domain" is defined as the amino acid residues from the cytoplasmic domain of the CD3ζ chain, or functional derivatives thereof, that are sufficient to functionally transmit an initial signal necessary for T cell activation.

As used herein, the term "chimeric antigen receptor" or "CAR" means a protein that when expressed on the surface of a cell allows a CAR expressing cell to recognize its specific protein (antigen), such as on tumor cells, infected cells or cells mediating autoimmune or inflammatory diseases or disorders. Such receptors are also known as chimeric T cell receptors, chimeric immunoreceptors, or artificial T cell receptors. Upon transduction of a cell with a nucleic acid construct encoding a CAR, the cell will recognize the antigen specified by the CAR. A CAR is typically comprised of an ectodomain (extracellular domain) and an endodomain (cytoplasmic domain), separated by a transmembrane domain. The ectodomain, expressed on the surface of the cell, comprises an antigen binding domain or receptor domain, optionally a signal peptide that directs the antigen binding domain into the endoplasmic reticulum for processing, and optionally a spacer (or hinge) region. The antigen binding domain (or receptor domain) comprises peptides that specifically recognize a target antigen. As a non-limiting example, the antigen binding domain can be a single chain antibody, such as an scFv. The spacer region links the antigen binding domain to the transmembrane domain and is designed to be sufficiently flexible to allow the antigen binding domain to orient in a manner that allows antigen recognition. Examples of spacer domains include, but are not limited to, the hinge region from IgG, the $CH_2CH_3$ region of an immunoglobulin, and portions of CD3 molecules. The transmembrane domain is a hydrophobic alpha helix, typically, that spans across the lipid bilayer of the cell membrane. An example of a transmembrane domain is the transmembrane domain from CD28, explained in more detail, infra. The endodomain of the CAR is composed of a signal transmitting peptide that transmits an activation signal intracellularly to the cell cytoplasm, thereby stimulating the cell expressing the CAR. The endodomain may include multiple such signaling domains, as explained, infra. In some embodiments, a CAR comprises at least an extracellular antigen binding domain, a transmembrane domain and a cytoplasmic signaling domain (also referred to herein as "an intracellular signaling domain") comprising a functional signaling domain derived from a stimulatory molecule and/ or costimulatory molecule as defined below. In some aspects, the set of polypeptides encoding the CAR are contiguous with each other. In some embodiments, the set of polypeptides include a dimerization switch that, upon the presence of a dimerization molecule, can couple the polypeptides to one another, e.g., can couple an antigen binding domain to an intracellular signaling domain. In one aspect, the stimulatory molecule is the zeta chain associated with the T cell receptor complex. In one aspect, the cytoplasmic signaling domain further comprises one or more functional signaling domains derived from at least one costimulatory molecule as defined below. In one aspect, the CAR comprises a chimeric fusion protein comprising an extracellular antigen binding domain, a transmembrane domain and an intracellular signaling domain comprising a functional signaling domain derived from a stimulatory molecule. In one aspect, the CAR comprises a chimeric fusion protein comprising an extracellular antigen binding domain, a transmembrane domain and an intracellular signaling domain comprising a functional signaling domain derived from a costimulatory molecule and a functional signaling domain derived from a stimulatory molecule. In one aspect, the CAR comprises a chimeric fusion protein comprising an extracellular antigen binding domain, a transmembrane domain and an intracellular signaling domain comprising two functional signaling domains derived from one or more costimulatory molecule(s) and a functional signaling domain derived from a stimulatory molecule. In one aspect the CAR comprises an optional leader sequence at the amino-terminus (N-ter) of the CAR fusion protein. In one aspect, the CAR further comprises a leader sequence at the N-terminus of the extracellular antigen binding domain, wherein the leader sequence is optionally cleaved from the antigen binding domain (e.g., an scFv) during cellular processing and localization of the CAR to the cellular membrane.

The term "compete", as used herein with regard to an antibody, means that a first antibody, or an antigen binding fragment (or portion) thereof, binds to an epitope in a manner sufficiently similar to the binding of a second antibody, or an antigen binding portion thereof, such that the result of binding of the first antibody with its cognate epitope is detectably decreased in the presence of the second antibody compared to the binding of the first antibody in the absence of the second antibody. The alternative, where the binding of the second antibody to its epitope is also detectably decreased in the presence of the first antibody, can, but need not be the case. That is, a first antibody can inhibit the binding of a second antibody to its epitope without that second antibody inhibiting the binding of the first antibody to its respective epitope. However, where each antibody detectably inhibits the binding of the other antibody with its cognate epitope or ligand, whether to the same, greater, or lesser extent, the antibodies are said to "cross-compete" with each other for binding of their respective epitope(s). Both competing and cross-competing antibodies are encompassed by the description herein. Regardless of the mechanism by which such competition or cross-competition occurs (e.g., steric hindrance, conformational change, or binding to a common epitope, or portion thereof), the skilled artisan would appreciate, based upon the teachings provided herein, that such competing and/or cross-competing antibodies are encompassed and can be useful for the methods disclosed herein.

The terms "complementarity determining region," and "CDR," synonymous with "hypervariable region" or "HVR," are known in the art to refer to non-contiguous sequences of amino acids within antibody variable regions, which confer antigen specificity and/or binding affinity. In general, there are three CDRs in each heavy chain variable region (CDR-H1, CDR-H2, CDR-H3) and three CDRs in each light chain variable region (CDR-L1, CDR-L2, CDR-L3). "Framework regions" and "FR" are known in the art to refer to the non-CDR portions of the variable regions of the heavy and light chains. In general, there are four FRs in each full-length heavy chain variable region (FR-H1, FR-H2, FR-H3, and FR-H4), and four FRs in each full-length light chain variable region (FR-L1, FR-L2, FR-L3, and FR-L4).

As used herein, the term "co-stimulatory ligand," includes a molecule on an antigen presenting cell (e.g., an APC, dendritic cell, B cell, and the like) that specifically binds a cognate co-stimulatory molecule on a T cell, thereby providing a signal which, in addition to the primary signal provided by, for instance, binding of a TCR/CD3 complex with an MHC molecule loaded with peptide, mediates a T cell response, including, but not limited to, proliferation, activation, differentiation, and the like. A co-stimulatory ligand can include, but is not limited to, CD7, B7-1 (CD80), B7-2 (CD86), PD-L1, PD-L2, 4-1BBL, OX40L, inducible costimulatory ligand (ICOS-L), intercellular adhesion molecule (ICAM), CD30L, CD40, CD70, CD83, HLA-G, MICA, MICB, HVEM, lymphotoxin β receptor, 3/TR6, ILT3, ILT4, HVEM, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as, but not limited to, CD27, CD28, 4-1BB, OX40, CD30, CD40, PD-1, ICOS, lymphocyte function-associated antigen-1 (LFA-1), CD2, CD7, LIGHT, NKG2C, B7-H3, and a ligand that specifically binds with CD83.

The term "costimulatory molecule" refers to a cognate binding partner on a T cell that specifically binds with a costimulatory ligand, thereby mediating a costimulatory response by the T cell, such as, but not limited to, proliferation. Costimulatory molecules are cell surface molecules other than antigen receptors or their ligands that are contribute to an efficient immune response. Costimulatory molecules include, but are not limited to a protein selected from the group consisting of an MHC class I molecule, TNF receptor proteins, Immunoglobulin-like proteins, cytokine receptors, integrins, signaling lymphocytic activation molecules (SLAM proteins), activating NK cell receptors, a Toll ligand receptor, B7-H3, BAFFR, BTLA, BLAME (SLAMF8), CD2, CD4, CD5, CD7, CD8α, CD8β, CD11a, LFA-1 (CD11a/CD18), CD11b, CD11c, CD11d, CD18, CD19, CD19a, CD27, CD28, CD29, CD30, CD40, CD49a, CD49D, CD49f, CD69, CD84, CD96 (Tactile), CD100 (SEMA4D), CD103, OX40 (CD134), 4-1BB (CD137), SLAM (SLAMF1, CD150, IPO-3), CD160 (BY55), SELPLG (CD162), DNAM1 (CD226), Ly9 (CD229), SLAMF4 (CD244, 2B4), ICOS (CD278), CEACAM1, CDS, CRTAM, DAP10, GADS, GITR, HVEM (LIGHTR), IA4, ICAM-1, IL2R β, IL2R γ, IL7R α, ITGA4, ITGA6, ITGAD, ITGAE, ITGAL, ITGAM, ITGAX, ITGB1, ITGB2, ITGB7, KIRDS2, LAT, LFA-1, LIGHT, LTBR, NKG2C, NKG2D, NKp30, NKp44, NKp46, NKp80 (KLRF1), PAG/Cbp, PD-1, PSGL1, SLAMF6 (NTB-A, Ly108), SLAMF7, SLP-76, TNFR2, TRANCE/RANKL, VLA1, VLA-6, and a ligand that specifically binds with CD83.

As used herein, the term "co-stimulatory signal", refers to a signal, which in combination with a primary signal, such as TCR/CD3 ligation, leads to T cell proliferation and/or upregulation or down regulation of key molecules.

As used herein, the term "cytokine" means a secreted, low-molecular-weight (about 5 to 20 kDa) protein expressed by cells that regulate the nature, intensity, and duration of an immune response by exerting a biological effect on immune cells that express receptors that bind the cytokine. Cytokines are often pleiotropic, possessing different biological effects when bound by different cell types and can modulate the balance between the humoral and the cell-based (innate) immune response. Cytokines play an important role in activating and stimulating cells of the immune system. Cytokines are generally divided into four structural families including the hematopoietin family, interferon (IFN) family, chemokine family, and tumor necrosis factor (TNF) family. The term cytokine encompasses interleukins, lymphokines, monokines, interferons, colony stimulating factors, and chemokines. Examples of cytokines include, but are not limited to, IL-1, IL-2, IL-4, IL-7, IL-9, IL-13, IL-15, IL-3, IL-5, granulocyte macrophage colony-stimulating factor (GM-CSF), IL-6, IL-11, IL-12, G-CSF, leukemia inhibitory factor (LIF), IL-10, IL-20, IL-14, INF-α, INF-β, INF-γ, TNF, CD154, LT-β, TNF-α, TNF-β, 4-1BBL, APRIL, CD70, CD153, CD178, GITRL, LIGHT, OX40L, TALL-1, TRAIL, TWEAK, TRANCE, TGF-β, Epo, Tpo, Flt-3L, Stem Cell Factor (SCF), M-CSF, and MSP. (See, Cameron et al., Madame Curie Bioscience Database [Internet]; Austin (Tex.): Landes Bioscience; 2000-2013). Cytokines may be involved in autocrine signalling, paracrine signalling and/or endocrine signalling as immunomodulating agents. Cytokines are produced by a broad range of cells, including immune cells like macrophages, B lymphocytes, T lymphocytes and mast cells, as well as endothelial cells, fibroblasts, and various stromal cells. "Chemokines" are a family of cytokines generally involved in mediating chemotaxis.

As used herein, the term "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

An "effective amount", "an amount effective to treat" or a "therapeutically effective amount" refers to the amount of the subject compound that will elicit the biological or medical response of a tissue, system, or subject that is being sought by the researcher, veterinarian, medical doctor or other clinician. In some embodiments, this refers to a dose that is adequate to prevent or treat a disease, condition, or disorder in an individual. In some embodiments, this amount includes that amount of a compound that, when administered, is sufficient to prevent development of, or alleviate to some extent, one or more of the signs or symptoms of the disorder or disease being treated. Amounts effective for a therapeutic or prophylactic use will depend on, for example, the stage and severity of the disease or disorder being treated, the age, weight, and general state of health of the patient, and the judgment of the prescribing physician. The size of the dose will also be determined by the active selected, method of administration, timing and frequency of administration, the existence, nature, and extent of any adverse side-effects that might accompany the administration of a particular active, and the desired physiological effect. It will be appreciated by one of skill in the art that various diseases or disorders could require prolonged treatment involving multiple administrations, perhaps using the inventive CAR materials in each or various rounds of administration.

As used herein, the term "encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein "endogenous" refers to any material from or produced inside an organism, cell, tissue or system. For example an "endogenous" TCR is one normally or naturally expressed on the surface of a primary T cell.

As used herein, the term "exogenous" refers to any material introduced from or produced outside an organism, cell, tissue or system.

As used herein, the term "expression" is defined as the transcription and/or translation of a particular nucleotide sequence driven by its promoter.

As used herein, the term "expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

The term "hinge", "spacer", or "linker" refers to an amino acid sequence of variable length typically encoded between two or more domains of a polypeptide construct to confer flexibility, improved spatial organization, proximity, etc.

As used herein, the term "homologous" refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared×100. For example, if 6 of 10 of the positions in two sequences are identical or homologous then the two sequences are 60% identical or homologous. By way of example, the DNA sequences ATTGCC and TATGGC share 50% homology or sequence identity. Generally, a comparison is made when two sequences are aligned to give maximum homology or sequence identity.

As used herein, "human antibody" means an antibody having an amino acid sequence corresponding to that of an antibody produced by a human and/or which has been made using any of the techniques for making human antibodies known to those skilled in the art or disclosed herein. This definition of a human antibody includes antibodies comprising at least one human heavy chain polypeptide or at least one human light chain polypeptide. One such example is an antibody comprising murine light chain and human heavy chain polypeptides. Human antibodies can be produced using various techniques known in the art. In one embodiment, the human antibody is selected from a phage library, where that phage library expresses human antibodies (Vaughan et al., *Nature Biotechnology*, 14:309-314, 1996; Sheets et al., *Proc. Natl. Acad. Sci.* (USA) 95:6157-6162, 1998; Hoogenboom and Winter, *J. Mol. Biol.*, 227:381, 1991; Marks et al., *J. Mol. Biol.*, 222:581, 1991). Human antibodies can also be made by immunization of animals into which human immunoglobulin loci have been transgenically introduced in place of the endogenous loci, e.g., mice in which the endogenous immunoglobulin genes have been partially or completely inactivated. This approach is described in U.S. Pat. Nos. 5,545,807; 5,545,806; 5,569,825; 5,625,126; 5,633,425; and 5,661,016. Alternatively, the human antibody may be prepared by immortalizing human B lymphocytes that produce an antibody directed against a target antigen (such B lymphocytes may be recovered from an individual or from single cell cloning of the cDNA, or may have been immunized in vitro). See, e.g., Cole et al. Monoclonal Antibodies and Cancer Therapy, Alan R. Liss, p. 77, 1985; Boerner et al., *J. Immunol.*, 147 (1):86-95, 1991; and U.S. Pat. No. 5,750,373.

An "iCAR" is a chimeric antigen receptor which contains inhibitory receptor signaling domains. These domains may be based, for example, on protectin D1 (PD1) or CTLA-4 (CD152). In some embodiments, the CAR expressing cells of the invention are further transduced to express an iCAR. In one aspect, this iCAR is added to restrict the CAR expressing cell's functional activity to tumor cells.

As used herein, "immune cell" refers to a cell of hematopoietic origin functionally involved in the initiation and/or execution of innate and/or adaptive immune response.

The term "immunoglobulin" or "Ig," as used herein is defined as a class of proteins, which function as antibodies. Antibodies expressed by B cells are sometimes referred to as the BCR (B cell receptor) or antigen receptor. The five members included in this class of proteins are IgA, IgG, IgM, IgD, and IgE. IgA is a primary antibody that is often present in body secretions, such as saliva, tears, breast milk, gastrointestinal secretions and mucus secretions of the respiratory and genitourinary tracts. IgG is the most common circulating antibody. IgM is the main immunoglobulin produced in the primary immune response in most subjects. It is the most efficient immunoglobulin in agglutination, complement fixation, and other antibody responses, and is important in defense against bacteria and viruses. IgD is the immunoglobulin that has no known antibody function, but may serve as an antigen receptor. IgE is the immunoglobulin that mediates immediate hypersensitivity by causing release of mediators from mast cells and basophils upon exposure to allergen.

As used herein, an "instructional material" includes a publication, a recording, a diagram, or any other medium of expression which can be used to communicate the usefulness of the compositions and methods of the invention. The instructional material of the kit of the invention may, for example, be affixed to a container which contains the nucleic acid, peptide, and/or composition of the invention or be shipped together with a container which contains the nucleic acid, peptide, and/or composition. Alternatively, the instructional material may be shipped separately from the container with the intention that the instructional material and the compound be used cooperatively by the recipient.

An "intracellular signaling domain," as the term is used herein, refers to an intracellular portion of a molecule. The intracellular signaling domain generates a signal that promotes an immune effector function of the cell transduced with a nucleic acid sequence comprising a CAR, e.g., a CART cell. Examples of immune effector function, e.g., in a CAR T cell, include cytolytic activity and helper activity, including the secretion of cytokines. Intracellular signaling domains include an intracellular signaling domain of a lymphocyte receptor chain, a TCR/CD3 complex protein, an Fc receptor subunit, an IL-2 receptor subunit, CD3ζ, FcR γ, FcR β, CD3 γ, CD3 δ, CD3 ε, CD5, CD22, CD79a, CD79b, CD66d, CD278(ICOS), FcεRI, DAP10, and DAP12.

An "isolated" biological component (such as an isolated chimeric antigen receptor or cell or vector or protein or nucleic acid) refers to a component that has been substantially separated or purified away from its environment or other biological components in the cell of the organism in which the component naturally occurs, for instance, other chromosomal and extra-chromosomal DNA and RNA, proteins, and organelles. Nucleic acids and proteins that have been "isolated" include nucleic acids and proteins purified by standard purification methods. The term also embraces nucleic acids and proteins prepared by recombinant technology as well as chemical synthesis. An isolated nucleic acid or protein can exist in substantially purified form, or can exist in a non-native environment such as, for example, a host cell.

A "lentivirus" as used herein refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses. Vectors derived from lentiviruses offer the means to achieve significant levels of gene transfer into living cells. Exemplary vectors of the invention are derived from lentiviruses.

The term "linker" as used in the context of an scFv refers to a peptide linker that consists of amino acids such as glycine and/or serine residues used alone or in combination, to link variable heavy and variable light chain regions together. In one embodiment, the flexible polypeptide linker is a Gly/Ser linker and comprises one or more repeats of the amino acid sequence Gly-Gly-Gly-Gly-Ser. In one embodiment, the flexible polypeptide linker includes, but is not limited to, $(Gly_4Ser)_3$.

The term "masked CAR" refers to a CAR expressing cell that further comprises a masking peptide. This masking peptide may prevent off-target cell killing. The masking peptide is often N-terminal to the CAR construct and may block the cell's ability to bind to unintended targets. The masking peptide may be cleaved from the CAR expressing cell when it encounters a tumor thereby allowing the CAR expressing cell to attack its target without killing off-target cells. The nucleic acid constructs of the invention may optionally encode masked CARs.

The term "nucleic acid" and "polynucleotide" refer to RNA or DNA that is linear or branched, single or double stranded, or a hybrid thereof. The term also encompasses RNA/DNA hybrids. The following are non-limiting examples of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes and primers. A polynucleotide may comprise modified nucleotides, such as methylated nucleotides and nucleotide analogs, uracil, other sugars and linking groups such as fluororibose and thiolate, and nucleotide branches. The sequence of nucleotides may be further modified after polymerization, such as by conjugation, with a labeling component. Other types of modifications included in this definition are caps, substitution of one or more of the naturally occurring nucleotides with an analog, and introduction of means for attaching the polynucleotide to proteins, metal ions, labeling components, other polynucleotides or solid support. The polynucleotides can be obtained by chemical synthesis or derived from a microorganism. The term "gene" is used broadly to refer to any segment of polynucleotide associated with a biological function. Thus, genes include introns and exons as in genomic sequence, or just the coding sequences as in cDNAs and/or the regulatory sequences required for their expression. For example, gene also refers to a nucleic acid fragment that expresses mRNA or functional RNA, or encodes a specific protein, and which includes regulatory sequences. In the context of the present invention, the following abbreviations for the commonly occurring nucleic acid bases are used, "A" refers to adenosine, "C" refers to cytosine, "G" refers to guanosine, "T" refers to thymidine, and "U" refers to uridine.

As used herein, the term "nucleic acid construct" refers to a nucleic acid molecule or polynucleotide, which includes a nucleic acid encoding a chimeric antigen receptor and at least one nucleic acid encoding a transcription factor. The transcription factor can be one that mediates cell differentiation resulting in proinflammatory cytokine expression. In some embodiments, the nucleic acid construct is a linear naked molecule or a vector, e.g., a plasmid, a bacmid, a phagemid, a cosmid, a phage, a virus or an artificial chromosome.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or RNA may also include introns to the extent that the nucleotide sequence encoding the protein may in some version contain an intron(s).

The term "overexpressed" tumor antigen or "overexpression" of the tumor antigen is intended to indicate an abnormal level of expression of the tumor antigen in a cell from a disease area like a solid tumor within a specific tissue or organ of the patient relative to the level of expression in a normal cell from that tissue or organ. Patients having solid tumors or a hematological malignancy characterized by overexpression of the tumor antigen can be determined by standard assays known in the art.

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

As used herein, "parenteral administration" of a pharmaceutical composition includes any route of administration characterized by physical breaching of a tissue of a subject and administration of the pharmaceutical composition through the breach in the tissue, thus generally resulting in the direct administration into the blood stream, into muscle, or into an internal organ. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal, intravenous, intraarterial, intrathecal, intraventricular, intraurethral, intracranial, intratumoral, intrasynovial injection or infusions; and kidney dialytic infusion techniques. In a preferred embodiment, parenteral administration of the compositions of the present invention comprises subcutaneous or intraperitoneal administration.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

A "pharmaceutically acceptable carrier" or "excipient" refers to compounds or materials conventionally used in immunogenic compositions during formulation and/or to permit storage.

As used herein the phrase "primary immune cells" or "primary T cells" refers to immune cells, e.g., T cells derived from donors, e.g., human donors which are allogeneic or autologous relative to a recipient which may be modified, e.g., in order to express a CAR, to delete or disrupt TCR expression or function, and the like, and which cells are useful in human therapy. These cells may be passaged during culturing and modification. Such primary immune cells and modified forms thereof may be distinguished from cell lines, e.g., immortalized T cell lines which are unsuitable for use in human therapy.

By "proinflammatory cytokine" as used herein, is meant any one or more cytokines that function in cell signaling and promote system inflammation, which are produced mainly by macrophages and other innate cell responses involved in upregulation of the inflammatory response. A proinflammatory cytokine encompasses cytokines that activate T helper cells (T$_H$1 and T$_H$2 cells). Proinflammatory cytokines include, but are not limited to, for example, IL-1, TNF-α, TL1A (tumor necrosis factor-like ligand), IL-12, INF-γ, IL-6, MCP-1, and CD40-L.

The term "promoter", as used herein, is defined as a DNA sequence recognized by the synthetic machinery of the cell, or introduced synthetic machinery, required to initiate the specific transcription of a polynucleotide sequence. A "constitutive" promoter is a nucleotide sequence which, when operably linked with a polynucleotide which encodes or specifies a gene product, causes the gene product to be produced in a cell under most or all physiological conditions of the cell. An "inducible" promoter is a nucleotide sequence which, when operably linked with a polynucleotide which encodes or specifies a gene product, causes the gene product to be produced in a cell substantially only when an inducer which activates or "turns on" the promoter is present in the cell. A "tissue-specific" promoter is a nucleotide sequence which, when operably linked with a polynucleotide encodes or specified by a gene, causes the gene product to be produced in a cell substantially only if the cell is a cell of the tissue type corresponding to the promoter.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

The term "recombinant" means a polynucleotide with semisynthetic or synthetic origin which either does not occur in nature or is linked to another polynucleotide in an arrangement not found in nature.

The term "scFv" refers to a fusion protein comprising at least one antibody fragment comprising a variable region of a light chain and at least one antibody fragment comprising a variable region of a heavy chain, wherein the light and heavy chain variable regions are contiguously linked, e.g., via a synthetic linker, e.g., a short flexible polypeptide linker, and capable of being expressed as a single chain polypeptide, and wherein the scFv retains the specificity of the intact antibody from which it is derived. Unless specified, as used herein an scFv may have the V$_L$ and V$_H$ variable regions in either order, e.g., with respect to the N-terminal and C-terminal ends of the polypeptide, the scFv may comprise V$_L$-linker-V$_H$ or may comprise V$_H$-linker-V$_L$. The linker may comprise portions of the framework sequences.

A "signal peptide" (also referred to as a signal sequence, targeting signal, localization signal, localization sequence, transit peptide, leader sequence or leader peptide) is a short peptide present at the N-terminus of the majority of newly synthesized proteins that are destined towards the secretory pathway. The core of the signal peptide may contain a long stretch of hydrophobic amino acids. The signal peptide may or may not be cleaved from the mature polypeptide.

The term "signaling domain" refers to the functional portion of a protein which acts by transmitting information within the cell to regulate cellular activity via defined signaling pathways by generating second messengers or functioning as effectors by responding to such messengers.

By the term "specifically binds," as used herein with respect to an antibody, is meant an antibody which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

By the term "stimulation," is meant a primary response induced by binding of a stimulatory molecule (e.g., a TCR/CD3 complex) with its cognate ligand thereby mediating a signal transduction event, such as, but not limited to, signal transduction via the TCR/CD3 complex. Stimulation can mediate altered expression of certain molecules, such as downregulation of TGF-.β., and/or reorganization of cytoskeletal structures, and the like.

A "stimulatory ligand," as used herein, means a ligand that when present on an antigen presenting cell (e.g., an APC, a dendritic cell, a B-cell, and the like) can specifically bind with a cognate binding partner (referred to herein as a "stimulatory molecule") on a T cell, thereby mediating a primary response by the T cell, including, but not limited to, activation, initiation of an immune response, proliferation, and the like. Stimulatory ligands are well-known in the art and encompass, inter alia, an MHC Class I molecule loaded with a peptide, an anti-CD3 antibody, a superagonist anti-CD28 antibody, and a superagonist anti-CD2 antibody.

The term "stimulatory molecule," refers to a molecule expressed by an immune cell (e.g., T cell, NK cell, B cell) that provides the cytoplasmic signaling sequence(s) that regulate activation of the immune cell in a stimulatory way for at least some aspect of the immune cell signaling pathway. In one aspect, the signal is a primary signal that is initiated by, for instance, binding of a TCR/CD3 complex with an MHC molecule loaded with peptide, and which leads to mediation of a T cell response, including, but not limited to, proliferation, activation, differentiation, and the like. A primary cytoplasmic signaling sequence (also referred to as a "primary signaling domain") that acts in a stimulatory manner may contain a signaling motif which is known as an immunoreceptor tyrosine-based activation motif or ITAM. Examples of an ITAM containing cytoplasmic signaling sequence that are of particular use in the invention include, but are not limited to, those derived from CD3ζ, common FcRγ (FCER1G), FcγRIIa, FcRβ (Fc E R1b), CD3γ, CD3δ, CD3ε, CD79a, CD79b, DAP10, and DAP12.

As used herein, a "substantially purified" cell is a cell that is substantially not associated with, or which is removed from one or more other moieties with which it is normally associated, e.g., it may be free or essentially free of other cell types. By substantially free is intended that the other moieties, e.g., other cells, may still be present, albeit in lesser amounts or percentages absent purification. A substantially purified cell also refers to a cell which has been separated or substantially separated from other cell types with which it is normally associated in its naturally occurring state, i.e., the isolated cell or cells are present in relatively greater numbers or percentages in the composition relative to the cells which are removed as a consequence of the purification. In some instances, a population of substantially purified cells refers to a homogenous population of cells. In other instances, this term refers simply to cell that have been separated from the cells with which they are naturally associated in their natural state. In some embodiments, the cells are cultured in vitro. In other embodiments, the cells are not cultured in vitro.

The term "subject" is intended to include living organisms in which an immune response can be elicited (e.g., mammals). Examples of subjects include humans, dogs, cats, mice, rats, and transgenic species thereof. The terms "patient," "subject," "individual," and the like are used interchangeably herein, and refer to any animal or cells thereof whether in vitro or in situ, amenable to the methods described herein. In certain non-limiting embodiments, the patient, subject or individual is a human.

By the term "synthetic antibody" as used herein, is meant an antibody which is generated using recombinant DNA technology, such as, for example, an antibody expressed by a yeast. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The term "T cell" as used herein encompasses any known T cell. For example, T cells are lymphocytes that express a T cell receptor (TCR, CD4). T cells mature in the thymus from thymocytes. The term T cell encompasses, for example, helper T cells ($T_H$ cells) such as $T_H1$, $T_H2$, $T_H3$, $T_H17$, $T_H9$, and $T_{FH}$ cells; cytotoxic T lymphocyte cells ($T_C$ or CTL) that express CD8 on their cell surface; memory T cells, such as central memory T cells, effector memory T cells, and resident memory T cells ($T_{CM}$ cells, $T_{EM}$ cells, $T_{EMRA}$ cells, and $T_{RM}$ cells, respectively); suppressor T cells, a type of regulatory T cell ($T_{reg}$ cell); natural killer cells (NKT cells); mucosal associated invariant T cells (MAITs); and γ-δ T cells, for example. T cells can be obtained from a subject, making them a primary T cell. T cells can be immature, allogeneic, autologous, xenogeneic, mortal or immortal.

The "T2A ribosome skip sequence" refers to an amino acid sequence that, when translated, causes cleavage of a nascent polyprotein on the ribosome, allowing for co-expression of multiple genes.

The terms "T-bet", "Tbet", "TBX21", "T-PET", "TBLYM", and "T-box 21" refer to the protein T-box transcription factor TBX21. T-bet has effects on various immune cells including dendritic cells (DCs), natural killer (NK) cells, ILC's, NKT cells, B cells, CD8$^+$ T cells, CD4$^+$ T cells, and γδ T cells. The effects it exerts on DCs include promoting $T_H1$ cell priming, suppression of TNF expression, and the homing of mast cell progenitors; on NK cells it promotes terminal differentiation and inhibits early differentiation; on ILCs it affects (upregulates) IFNδ, plasticity of ROR6t$^+$ subset, downregulates IL-7α, and promotes the development of NKp46$^+$ cell subset; on NKT cells it upregulates CD122 and IL-15Rβ and promotes cell survival; on B cells it promotes IgG2a switching and the survival of memory B cells; on CD8$^+$ T cells it promotes IFNγ expression, granzyme B and terminal differentiation; on CD4$^+$ T cells it promotes $T_H1$ cell differentiation, downregulates $T_H2$, $T_H17$ and $T_{FH}$ cell differentiation and promotes T-BET$^+$ $T_{REG}$ cell migration; and on γδ T cells it promotes IFNγ production. In some embodiments, the nucleic acid construct or constructs of the invention comprise nucleic acid sequences encoding T-bet or a variant thereof.

The term "therapeutic" as used herein means a treatment and/or prophylaxis. A therapeutic effect is obtained by suppression, remission, or eradication of a disease state.

The term "transcription factor" as used herein means a protein that possesses a biological function including regulation of transcription of genes. That is, a transcription factor is a protein that possesses a DNA-binding domain (DBD) that allows the protein to bind a specific sequence of DNA (an enhancer element or promoter sequence). Upon binding the enhancer or promoter element, the transcription factor's presence can aide in initiation of transcription by stabilizing transcription initiation complex formation and/or activity, for example. Transcription factors also bind to regulatory DNA sequences, such as enhancer sequences, that can be many hundreds of base pairs downstream or upstream from the transcribed gene. Transcription factors are also referred to as sequence-specific DNA-binding factors. Transcription factors can perform the transcription controlling function either alone or in combination with other proteins, i.e. by forming an activation complex, and can aide in recruiting RNA polymerase and related proteins to the transcription initiation start site. (See, Nevins, Science 258, 424-429 (1992); Dalton, EMBO J. 11, 11797 (1992); Yee et al. ibid. 6, 2061 (1987), Weintraub et al., Nature 358, 259-261 (1992), Pagano et al., Science 255, 1144-1147 (1992)). For a complete list of known eukaryotic transcription factors, see Fulton et al., Genome Biology, 10:R29, 2009 "TFCat: the curated catalog of mouse and human transcription factors." Examples of transcription factors include, but are not limited to, T-box 21 (T-bet), T-box 1, T-Brain 1, T-box 2, T-box 6, signal transducer and activator of transcription 1 (STAT1), STAT2, STAT3, STAT4, STAT5, STAT6, Runx1, Runx3, and Eomesodermin, for example. Transcription factors also include those that regulate T helper type 1 (Th1) cell differentiation, for example.

The term "transfected" or "transformed" or "transduced" refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny. The exogenous nucleic acid may be introduced stably or transiently into the host cell. Transfection can be achieved any number of known methods, such as retroviral infection and the like.

By the term "transmembrane domain", what is implied is any three-dimensional protein structure which is thermodynamically stable in a membrane. This may be a single alpha helix, a transmembrane beta barrel, a beta-helix of gramicidin A, or any other structure. Transmembrane helices are usually about 20 amino acids in length. Typically, the transmembrane domain denotes a single transmembrane alpha helix of a transmembrane protein, also known as an integral protein.

As used herein, the terms "treat", "treatment" and "treating" refer to the reduction or amelioration of the progression, severity and/or duration of a proliferative disorder, or the amelioration of one or more symptoms (preferably, one or more discernible symptoms) of a proliferative disorder resulting from the administration of one or more therapies (e.g., one or more therapeutic agents such as a CAR of the invention). In specific embodiments, the terms "treat", "treatment" and "treating" refer to the amelioration of at least one measurable physical parameter of a proliferative disorder, such as growth of a tumor, not necessarily discernible by the patient. In other embodiments the terms "treat", "treatment" and "treating"-refer to the inhibition of the progression of a proliferative disorder, either physically by, e.g., stabilization of a discernible symptom, physiologically by, e.g., stabilization of a physical parameter, or both. In other embodiments the terms "treat", "treatment" and "treating" refer to the reduction or stabilization of tumor size or cancerous cell count. Additionally, the terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount of any level of treatment or prevention of cancer in a mammal. Furthermore, the treatment or prevention provided by the inventive method can include treatment or prevention of one or more conditions or symptoms of the disease, e.g., cancer, being treated or prevented. Also, for purposes herein, "prevention" can encompass delaying the onset of the disease, or a symptom or condition thereof.

The phrase "under transcriptional control" or "operatively linked" as used herein means that the promoter is in the correct location and orientation in relation to a polynucleotide to control the initiation of transcription by RNA polymerase and expression of the polynucleotide.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. The four major types of vectors include plasmids, viral vectors, cosmids, and artificial chromosomes. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

The term "xenogeneic" refers to a graft derived from an animal of a different species.

Nucleic Acid Constructs and Chimeric Antigen Receptors (CARs) Encoded Thereby

Disclosed are nucleic acid constructs that comprise genes encoding a chimeric antigen receptor (CAR) and a transcription factor. Such nucleic acid constructs can be transduced into immune cells to create an immune cell that expresses the CAR and expresses the transcription factor. As shown in the examples provided herein, an immune cell that co-expresses a CAR and a transcription factor, such as a regulator for $T_H1$ differentiation, induces the expression of molecules associated with proinflammatory responses in purified CD4$^+$ T cells when cultured with ligand expressing tumor target cells. Such properties are beneficial in T-cell-based immunotherapy. Thus, disclosed herein are nucleic acid constructs useful in immune cell-based immunotherapy, such as, for instance, adoptive cell transfer, and the like. (See, Rosenberg et al., Nat. Rev. Cancer., 8(4):299-308, 2008, and Perica et al., Ram. Maim. Med. J., 6(1):e0004, 2015). Disclosed herein are the nucleic acid constructs encoding the CAR molecules and transcription factors, vectors comprising the same, recombinant cells comprising the same, kits and compositions comprising the same, and methods of use thereof.

As set forth in the Examples section, infra, a B7-H6-specific CAR 2A expression construct was prepared, which also expressed murine T-bet. Purified human CD4$^+$ T cells that were transduced with the nucleic acid construct and that expressed the genes encoded by the construct were found to produce greater amounts of cytokines (e.g., GM-CSF, TNF-α, IL-2, IFN-γ, IL-3, IL-15, MIP-1a, MIP-1B) when cultured with B7-H6-expressing tumor target cells as compared to the same CD4$^+$ T cells transduced with the CAR vector alone.

Therefore, disclosed are nucleic acid constructs, vectors, and immune host cells that harbor nucleic acids encoding a CAR and one or more nucleic acids encoding one or more transcription factors. The transcription factor can be one that mediates cell differentiation and proinflammatory cytokine expression, and use of the same in immunotherapy, e.g., to treat cancer and/or infectious disease. For the purposes of this invention, "nucleic acids" refer to single or double stranded nucleic acid molecules, which are isolated and provided in the form of RNA, a complementary polynucleotide (cDNA), a genomic polynucleotide and/or a composite polynucleotide (e.g., a combination of the above). As used herein, the term "nucleic acid construct" refers to a nucleic acid molecule, which includes nucleic acids encoding a CAR and nucleic acids encoding a transcription factor that mediates cell differentiation resulting in proinflammatory cytokine expression. In some embodiments, the nucleic acid construct is a linear naked molecule or a vector, e.g., a plasmid, a bacmid, a phagemid, a cosmid, a phage, a virus or an artificial chromosome.

In accordance with the present invention, the nucleic acid construct is transformed, transduced, transfected or otherwise introduced into a T cell and is transcribed and translated to produce a product (e.g., a chimeric receptor and/or a suicide protein). Thus, the nucleic acid construct further includes at least one or more elements encoding, for example, a promoter for directing transcription of the CAR and transcription factor. According to some embodiments, nucleic acids encoding the CAR and transcription factor are operably linked to at least one promoter sequence. A coding nucleic acid is "operably linked" to a regulatory sequence (e.g., promoter) if the regulatory sequence is capable of exerting a regulatory effect on the coding sequence linked thereto. The nucleic acid encoding the CAR can be controlled by the same promoter, or by a promoter different from the promoter that controls expression of the transcription factor. Other elements that the nucleic acid construct can encode include other regulatory elements, such as a transcription enhancer; a self-cleaving peptide located between the CAR and the transcription factor; a nucleic acid encoding a protein that is capable of triggering cell suicide or elimination; one or more internal ribosomal entry sites; a gene encoding a protein whose expression allows for selection of a cell comprising the vector; and/or one or more cis-acting hydrolase elements.

A nucleic acid construct according to the present invention can be produced by any means known in the art. Nucleic acids encoding the CAR can be prepared and assembled into a complete coding sequence by standard techniques of molecular cloning (genomic library screening, PCR, primer-assisted ligation, site-directed mutagenesis, etc.). Nucleic acids encoding the other moieties (e.g., transcription factor, IRES or CHYSEL) may be similarly prepared. The resulting nucleic acids are preferably inserted into an expression vector and used to transform suitable mammalian host cells, preferably T lymphocyte cells as described herein, as well as other immune cells such as NK cells and LAK cells, LIK cells and stem cells or other progenitor cells that differentiate into these T lymphocyte cells.

The chimeric antigen receptor, also known as a CAR, artificial T cell receptor, chimeric T cell receptor, or chimeric immunoreceptor expressed by a construct according to the invention will generally comprise a fusion protein composed of an antigen targeting domain or recognition domain attached to an extracellular spacer/hinge domain, a transmembrane region that anchors the antigen targeting domain to the cell surface, and at least one signaling endodomain or cytoplasmic domain.

Antigen Targeting Domain

The terms "antigen targeting domain", "antigen binding domain", and "antigen recognition domain" are used interchangeably herein. Antigen targeting or antigen recognition by CAR molecules most commonly involves the use of a single chain variable fragment (scFv) that has been assembled from a monoclonal antibody. However, alternative targeting moieties include ligands (Altenschmidt, et al. (1996) Clin. Cancer Res. 2:1001-8; Muniappan, et al. (2000) Cancer Gene Ther. 7:128-134), peptides (Pameijer, et al. (2007) Cancer Gene Ther. 14:91-97), chimeric ligands (Davies, et al. (2012) Mol. Med. 18:565-576), receptor derivatives (Scholler, et al. (2012) Sci. Translation. Med. 4:Article IDS 132ra53; Zhang, et al. (2012) J. Immunol. 189:2290-9), and single domain antibodies (Sharifzadeh, et al. (2012) Cancer Res. 72:1844-52). Any desired antibody or antibody fragment thereof that specifically recognizes and binds a target antigen, such as a tumor antigen, may be incorporated in a CAR according to the invention. Antigens that are commonly expressed by diverse solid and hematological malignancies and have been shown to be amenable to CAR-directed targeting include proteins, carbohydrates, gangliosides, and the like. In particular, such molecules include CD19 (Brentjens, et al. (2007) Clin. Can. Res. 13:5426-5435; Loskog, et al. (2006) Leukemia 20:1819-1828; Brentjens, et al. (2003) Nat. Med. 9:279-286; Kochenderfer, et al. (2009) J. Immunol. 32:689-702; Cooper, et al. (2003) Blood 101:1637-44), CD20 (Wang, et al. (2004) Mol. Ther. 9:577-86), CD22 (James, et al. (2008) J. Immunol. 180:7028-7038), k light chain (Vera, et al. (2006) Blood 108:3890-7), CD38 (Mihara, et al. (2010) Br. J. Haematol. 151:37-46; Mihara, et al. (2009) J. Immunother. 32:737-43), and receptor-tyrosine-kinase-like orphan receptor 1 (ROR1) for treating B cell malignancies (Hudecek, et al. (2010) Blood 116:4532-41); CD30 for treating Hodgkin's and non-Hodgkin's lymphomas (Di Stasi, et al. (2009) Blood 113:6392-6402; Savoldo, et al. (2007) Blood 110: 2620-30); CD33 (Dutour, et al. (2012) Adv. Hematol. Article ID 683065) or CD123 (Thokala, et al. (2011) Blood 118, abstract 1908) for treating myeloid malignancies; epithelial glycoprotein (EGP) 40 for targeting colon cancer (Daly, et al. (2000) Cancer Gene Ther. 7:284-291); tumor-associated glycoprotein 72 for treating gastrointestinal cancer (Hombach, et al. (1997) Gastroenterol. 113:1163-70); prostate-specific membrane antigen (Maher, et al. (2002) Nat. Biotechnol. 20:70-75; Gong, et al. (1999) Neoplasia 1:123-127) or prostate stem cell antigen (Morgenroth, et al. (2007) Prostate 67:1121-1131) for treating prostate cancer; ganglioside (GD) 3 (Abken, et al. (2001) Rec. Results Cancer Res. 158:249-264), high molecular weight melanoma-associated antigen (Westwood, et al. (2005) Proc. Natl. Acad. Sci. USA 102:19051-19056) or HLA-A1 MAGE A1 (Willemsen, et al. (2005) J Immunol. 174:7853-8) for treating melanoma; ErbB2 (Altenschmidt, et al. (1996) Clin. Cancer Res. 2:1001-8) or mucin (MUC) 1 (Wilkie, et al. (2008) J. Immunol. 180:4901-9) for treating breast cancer; MUC1 (Wilkie, et al. (2008) J. Immunol. 180:4901-9), MUC16 (Chekmasova, et al. (2010) Clin. Cancer Res. 16:3594-3606), folate receptor-α for treating ovarian cancer (Hwu, et al. (1995) Cancer Res. 55:3369-73; Kershaw, et al. (2002) Nat. Biotechnol. 20:1221-7), CD44v7/8 for treating cervical cancer (Dall, et al. (2005) Cancer Immunol. Immunother. 54:51-60); carbonic anhydrase 9 (Weijtens, et al. (1996) J. Immunol. 157:836-43) or G250/CAIX (Lamers, et al. (2006) J. Clin. Oncol. 24:e20-22) for treating renal cell carcinoma; GD2 (Krause, et al. (1998) J. Exp. Med. 188: 619-26; Rossig, et al. (2001) Int. J. Cancer 94:228-236; Kailayangiri, et al. (2012) Br. J. Cancer 106:1123-33), CD171 (Park, et al. (2007)Mol. Ther. 15:825-33) or nerve cell adhesion molecule (Gilham, et al. (2002) J. Immunol. 25:139-51) for treating neuroblastoma; Foetal acetylcholine receptor for treating rhabdomyosarcoma (Gattenlohner, et al. (2006) Cancer Res. 66:24-28); or ErB3/4 (Altenschmidt, et al. (1996) Clin. Cancer Res. 2:1001-8; Muniappan, et al. (2000) Cancer Gene Ther. 7:128-134), epidermal growth factor receptor vIII (Morgan, et al. (2012) Human Gene Ther. 23:1043-53), carcinoembryonic antigen (Haynes, et al. (2001) J. Immunol. 166:182-7; Haynes, et al. (2002) J. Immunol. 169:5780-6; Darcy, et al. (2000) J. Immunol. 164:3705-12), EGP2 (Ren-Heidenreich, et al. (2000) Human Gene Ther. 11:9-19), mesothelin (Carpenito, et al. (2009) Proc. Natl. Acad. Sci. USA 106:3360-5; Lanitis, et al. (2012) Mol. Ther. 20:633-43), natural killer group 2 member D ligands (Zhang, et al. (2005) Blood 106:1544-51), B7-H6 (Zhang, et al. (2012) J. Immunol. 189:2290-9), IL-13 receptor α2 (Kong, et al. (2012) Clin. Cancer Res. 18:5949-60; Kahlon, et al. (2004) Cancer Res. 64:9160-6; Brown, et al. (2012) Clin. Cancer Res. 18:2199-2209), Lewis Y (Westwood, et al. (2005) Proc. Natl. Acad. Sci. USA 102:19051-6), HLA-A2 NY-ESO-1 (Schuberth, et al. (2013) Gene Ther. 20:386-95), CD44v6 (Hekele, et al. (1996) Internatl. J. Cancer 68:232-8), $\alpha_v\beta_6$ integrin (Pameijer, et al. (2007) Cancer Gene Ther. 14:91-7), 8H9 (Cheung, et al. (2003) Hybrid. Hybrid. 22:209-218), vascular endothelial growth factor receptors (Niederman, et al. (2002) Proc. Natl. Acad. Sci. USA 99:7009-14; Kershaw, et al. (2000) Human Gene Ther. 11:2445-52), or 5T4 (Jiang, et al. (2006) J. Immunol. 177:4288-98) to treat a variety of cancers including, but not limited to, breast cancer, glioma, colon cancer, ovarian cancer, and multiple myeloma. In addition to antigen-specific approaches, two "universal" CAR systems have been described. These generic CARs containing avidin (Urbanska, et al. (2012) Cancer Res. 72:1844-52) or antifluorescein isothiocyanate (FITC) scFv (Ang, et al. (2011) Mol. Ther. 19:abstract 353; Chmielewski, et al. (2004) J. Immunol. 173:7647-7653), enabling their use in conjunction with separate targeting moieties that have been biotinylated or conjugated to FITC, respectively.

In embodiments wherein the antigen targeting domain is an scFv, the scFv can be derived from the variable heavy chain ($V_H$) and variable light chain ($V_L$) regions of an antigen-specific mAb linked by a flexible linker. The scFv retains the same specificity and a similar affinity as the full antibody from which it was derived (Muniappan, et al. (2000) Cancer Gene Ther. 7:128-134). Various methods for preparing an scFv can be used including methods described in U.S. Pat. No. 4,694,778; Bird, et al. (1988) *Science* 242:423-442; Ward, et al. (1989) *Nature* 334:54454; and Skerra, et al. (1988) *Science* 242:1038-1041. In certain embodiments, the scFv is humanized or is a fully human scFv. In a specifically preferred embodiment, the scFv may be the TZ.47 scFv as disclosed in Wu et al., *J. Immunol.,* 194(11):5305-5311, 2015 (incorporated by reference herein).

Non-scFv antigen targeting domains include, e.g., the CD27 receptor (Shaffer, et al. (2011) *Blood* 117:4304-4314), the heregulin molecule (a ligand for Her3 and Her4 receptors) (Muniappan, et al. (2000) *Cancer Gene Ther.* 7:128), interleukin (IL)-13 mutein (Kahlon, et al. (2004) *Cancer Res.* 64:9160-6), vascular endothelial growth factor (anti-VEGFR2) (Niedeman, et al. (2002) *Proc. Natl. Acad. Sci. USA* 99:7009-14), a chimeric NKp30 CAR targeting B7-H6 (NKp30 ligand) (Zhang, et al. (2012) *J. Immunol.* 189:2290-2299), variable regions of a T cell receptor (e.g., TCRα, TCRβ, TCRγ, or TCR δ), CD8α, CD8β, CD11A, CD11B, CD11C, CD18, CD29, CD49A, CD49B, CD49D, CD49E, CD49F, CD61, CD41, and CD51.

Particularly preferred antigens include those of the B7 family, such as B7-H6. NKp30 recognizes B7-H6 and BAT-3 (Brandt et al., 2009; Pogge von Strandmann et al., 2007). B7-H6 is a member of the B7 family (which includes ligands for stimulatory/inhibitory T cell co-receptors CD28/CTLA4) and is poorly expressed on normal cells, but up-regulated in different tumor cell lines. (See, Vitale, C., Mingari, M. C., Vitale, M., Balsamo, M. and Zambello, R., 2012, Physiological and Pathological Aspects of Human NK Cells. INTECH Open Access Publisher).

For example, B7-H6 was found to be expressed at the surface of several tumor cell lines including T and B lymphomas, myeloid leukemias, melanomas, carcinomas, and large T SV4 antigen-transformed cells. (See, Brandt et al., *JEM,* 206(7):1495-1503, 2009). In a broader survey, B7-H6 expression was detected on 24 of 110 cancer cell lines (Id.). The surface expression of B7-H6 was also tested on primary tumor blood and bone marrow cells obtained at diagnosis from 43 individuals with a variety of hematological malignancies, including acute nonlymphoblastic leukemia (ANLL; n=20), acute lymphoblastic leukemia (ALL; n=11), and non-Hodgkin's and Hodgkin's lymphoma (n=12) and B7-H6 expression was observed on circulating tumor cells from three patients with ANLL, two patients with T-ALL, and one patient with marginal zone lymphoma. (See, Brandt et al., *JEM,* 206(7):1495-1503, 2009). Brandt et al. concluded that B7-H6 is a major NKp30 ligand on tumor cells of various origins, including K562, a prototypical model of tumor NK cell target. The absence of B7-H6 mRNA in normal tissues, coupled with its relative abundance among tumor cells, indicates that its expression is up-regulated by tumor transformation. The amino acid and nucleic acid sequences of B7-H6 are available to the public through the GenBank database and are hereby incorporated by reference.

Other specific examples of targeting domains include C-type lectin-like NK cell receptors that bind MIC-A, MIC-B, heat shock proteins, ULBP binding proteins (e.g., ULPBs 1-4), and non-classical HLA molecules such as HLA-E and HLA-G. Exemplary NK cell receptors of this type include, but are not limited to, Dectin-1 (GENBANK accession number AJ312373 or AJ312372), Mast cell function-associated antigen (GENBANK accession number AF097358), HNKR-PIA (GENBANK accession number U11276), LLT1 (GENBANK accession number AF133299), CD69 (GENBANK accession number NM_001781), CD69 homolog, CD72 (GENBANK accession number NM_001782), CD94 (GENBANK accession number NM_002262 or NM_007334), KLRF1 (GENBANK accession number NM_016523), Oxidised LDL receptor (GENBANK accession number NM_002543), CLEC-1, CLEC-2 (GENBANK accession number NM_016509), NKG2D (GENBANK accession number BC039836; Zhang, et al. (2006) *Cancer Res.* 66:5927-5933; Song, et al. (2013) *Hum. Gene Ther.* 24:295-305; Lehner, et al. (2012) *PLoS One* 7:e31210; U.S. Pat. No. 7,994,298), NKG2C (GENBANK accession number AJ001684), NKG2A (GENBANK accession number AF461812), NKG2E (GENBANK accession number AF461157), WUGSC:H_DJ0701016.2, or Myeloid DAP12-associating lectin (MDL-1; GENBANK accession number AJ271684). Similar type I receptors, which can be used in the CAR of this invention, include NKp46 (e.g., GENBANK accession number AJ001383), NKp30 (e.g., GENBANK accession number AB055881), or NKp44 (e.g., GENBANK accession number AJ225109).

A protein associated with a C-type lectin-like NK cell receptor protein can also be used in the CAR of the invention. In general, proteins associated with C-type lectin-like NK cell receptor are defined as proteins that interact with the receptor and transduce signals therefrom. Suitable human proteins that function in this manner include, but are not limited to DAP10 (e.g., GENBANK accession number AF072845; U.S. Pat. No. 8,252,914) and DAP12 (e.g., GENBANK accession number AF019562).

A CAR of the invention can also include an antigen targeting domain capable of binding to an antigen derived from Retroviridae (e.g., human immunodeficiency viruses such as HIV-1 and HIV-LP), Picornaviridae (e.g., poliovirus, hepatitis A virus, enterovirus, human coxsackievirus, rhinovirus, and echovirus), rubella virus, coronavirus, vesicular stomatitis virus, rabies virus, Ebola virus, parainfluenza virus, mumps virus, measles virus, respiratory syncytial virus, influenza virus, hepatitis B virus, parvovirus, Adenoviridae, Herpesviridae (e.g., type 1 and type 2 herpes simplex virus (HSV), varicella-zoster virus, cytomegalovirus (CMV), and herpes virus), Poxviridae (e.g., smallpox virus, vaccinia virus, and pox virus), or hepatitis C virus. For example, CARs for the treatment of hepatitis C virus, hepatitis C virus and influenza virus have been described. See, e.g., Sautto, et al. (2015) Gut doi:10.1136/gutjn1-2014-308316; Krebs, et al. (2013) *Gastroenterol.* 145:456-65; and Talbot, et al. (2013) *Open Virol. J.* 7:28-36.

Further, a CAR of the invention can also include an antigen binding domain the binds to an antigen derived from a bacterial strain of Staphylococci, *Streptococcus, Escherichia coli, Pseudomonas,* or *Salmonella.* Particularly, there is provided a CAR capable of binding to an antigen derived from an infectious bacterium, for example, *Helicobacter pyloris, Legionella pneumophilia,* a bacterial strain of *Mycobacteria* sps. (e.g., *M. tuberculosis, M. avium, M. intracellulare, M. kansasii,* or *M. gordonea*), *Staphylococcus aureus, Neisseria gonorrhoeae, Neisseria meningitides, Listeria monocytogenes, Streptococcus pyogenes,* Group A *Streptococcus,* Group B *Streptococcus (Streptococcus agalactiae), Streptococcus pneumoniae,* or *Clostridium tetani.*

Further, a CAR of the invention can also include an antigen binding domain the binds to an autoantigen or self-antigen, an allergen, or an antigen or receptor expressed by cells involved in triggering autoimmunity or inflammation.

The antigen binding domain may be derived from a polypeptide that binds to a target antigen. In some embodiments, the polypeptide may be a receptor or a portion of a receptor that binds to an antigen. In another embodiment, the antigen binding domain may be derived from ligands that bind to an antigen.

In another embodiment, the antigen binding domain may be derived from an antibody or antigen binding fragment thereof that binds to an antigen. Examples of antibody fragments include, but are not limited to, fragment antigen binding (Fab) fragments, F(ab')$_2$ fragments, Fab' fragments, FAT fragments, recombinant IgG (rIgG) fragments, single chain antibody fragments, single chain variable fragments (scFv), single domain antibodies (e.g., sdAb, sdFv, nanobody) fragments, diabodies, and multi-specific antibodies formed from antibody fragments. In particular embodiments, the antibodies are single-chain antibody fragments comprising a variable heavy chain region and/or a variable light chain region, such as scFvs.

Single-domain antibodies are antibody fragments comprising all or a portion of the heavy chain variable domain or all or a portion of the light chain variable domain of an antibody. In certain embodiments, a single-domain antibody is a human single-domain antibody.

Antibody fragments can be made by various techniques, including but not limited to proteolytic digestion of an intact antibody as well as production by recombinant host cells. In some embodiments, the antibodies are recombinantly-produced fragments, such as fragments comprising arrangements that do not occur naturally, such as those with two or more antibody regions or chains joined by synthetic linkers, e.g., peptide linkers, and/or that may not be produced by enzyme digestion of a naturally-occurring intact antibody. In some aspects, the antibody fragments are scFvs.

In some aspects, the antigen binding domain may be derived from an antibody or antigen-binding fragment thereof that has one or more specified functional features, such as binding properties, including binding to particular epitopes, such as epitopes that are similar to or overlap with those of other antibodies, the ability to compete for binding with other antibodies, and/or particular binding affinities.

In some embodiments, the antigen binding domain binds to an epitope containing one or more amino acids within (or is entirely within) an extracellular domain of a target antigen and/or within (or is entirely within) a membrane-proximal region of the extracellular portion of a target antigen.

In some embodiments, the antigen binding domain, the CARs comprising such, and the cells comprising such CARs display a binding preference for target antigen-expressing cells as compared to target antigen-negative cells. In some embodiments, the binding preference is observed where a significantly greater degree of binding is measured to the antigen-expressing, as compared to the non-expressing, cells. In some cases, the total degree of observed binding to the target antigen or to the antigen-expressing cells is approximately the same, at least as great, or greater than that observed for non-antigen specific domains, CARs, or cells. In any of the provided embodiments, comparison of binding properties, such as affinities or competition, may be via measurement by the same or similar assay.

In some embodiments, the antigen binding domain comprises an scFv comprising the CDR sequences of a target antigen binding antibody. CDRs may be determined using conventional methods, The precise amino acid sequence boundaries of a given CDR or FR can be readily determined using any of a number of well-known schemes, including those described by Kabat et al. (1991), "Sequences of Proteins of Immunological Interest," 5th Ed. Public Health Service, National Institutes of Health, Bethesda, Md. ("Kabat" numbering scheme), Al-Lazikani et al., (1997) *JMB* 273, 927-948 ("Chothia" numbering scheme), MacCallum et al., *J. Mol. Biol.* 262:732-745 (1996), "Antibody-antigen interactions: Contact analysis and binding site topography," *J. Mol. Biol.* 262, 732-745." ("Contact" numbering scheme), Lefranc M P et al., "IMGT unique numbering for immunoglobulin and T cell receptor variable domains and Ig superfamily V-like domains," *Dev Comp Immunol*, 2003 January; 27(1):55-77 ("IMGT" numbering scheme), and Honegger A and Pluckthun A, "Yet another numbering scheme for immunoglobulin variable domains: an automatic modeling and analysis tool," *J. Mol Biol*, 2001 Jun. 8; 309(3):657-70, ("Aho" numbering scheme).

In an embodiment, the sequence comprising the antigen binding domain further comprises a leader sequence or signal sequence. In embodiments where the antigen binding domain comprises an scFv, the leader sequence may be positioned at the amino terminus of the scFv. In some embodiments, when the heavy chain variable region is N-terminal, the leader sequence may be positioned at the amino terminus of the heavy chain variable region. In some embodiments, when the light chain variable region is N-terminal, the leader sequence may be positioned at the amino terminus of the light chain variable region. The leader sequence may comprise any suitable leader sequence.

Hinge

In some embodiments, the CAR comprises a linker, spacer, or hinge sequence between the antigen binding domain and the transmembrane domain and/or between the transmembrane domain and the cytoplasmic domain. A linker, spacer, or hinge refers to any oligopeptide or polypeptide that serves to link the transmembrane domain with the antigen targeting domain and/or the transmembrane domain with the intracellular signaling endodomain. The spacer domain can be up to 300 amino acids, preferably 10 to 100 amino acids, 25 to 50 amino acids or 2 to 10 amino acids in length. One of ordinary skill in the art will appreciate that a hinge sequence is a short sequence of amino acids that facilitates flexibility (see, e.g., Woof et al., *Nat. Rev. Immunol.*, 4(2): 89-99 (2004)). The hinge sequence can be any suitable sequence derived or obtained from any suitable molecule. In some embodiments, the length of the hinge sequence may be optimized based on the distance between the CAR and the binding epitope, e.g., longer hinges may be optimal for membrane proximal epitopes.

In some embodiments, the CAR, such as the antigen binding portion thereof, further includes a hinge, linker or spacer. The hinge may be derived from or include at least a portion of an immunoglobulin Fc region, for example, an IgG1 Fc region, an IgG2 Fc region, an IgG3 Fc region, an IgG4 Fc region, an IgE Fc region, an IgM Fc region, or an IgA Fc region. In certain embodiments, the spacer domain includes at least a portion of an IgG1, an IgG2, an IgG3, an IgG4, an IgE, an IgM, or an IgA immunoglobulin Fc region that falls within its CH2 and CH3 domains. In some embodiments, the spacer domain may also include at least a portion of a corresponding immunoglobulin hinge region. In some embodiments, the hinge is derived from or includes at least a portion of a modified immunoglobulin Fc region, for example, a modified IgG1 Fc region, a modified IgG2 Fc region, a modified IgG3 Fc region, a modified IgG4 Fc region, a modified IgE Fc region, a modified IgM Fc region, or a modified IgA Fc region. The modified immunoglobulin Fc region may have one or more mutations (e.g., point mutations, insertions, deletions, duplications) resulting in one or more amino acid substitutions, modifications, or deletions that cause impaired binding of the spacer domain to an Fc receptor (FcR). In some aspects, the modified immunoglobulin Fc region may be designed with one or more mutations which result in one or more amino acid substitutions, modifications, or deletions that cause impaired binding of the spacer domain to one or more FcR including, but not limited to, FcγRI, FcγR2A, FcγR2B1, FcγR2B2, FcγR3A, FcγR3B, FcγRI, FccR2, FcαRI, Fcα/μR, or FcRn.

In some aspects, a portion of the immunoglobulin constant region serves as a spacer region between the antigen binding domain, e.g., scFv, and transmembrane domain. The spacer can be of a length that provides for increased responsiveness of the cell following antigen binding, as compared to in the absence of the spacer. In some examples, the spacer is at or about 12 amino acids in length or is no more than 12 amino acids in length. Exemplary spacers include those having at least about 10 to 229 amino acids, about 10 to 200 amino acids, about 10 to 175 amino acids, about 10 to 150 amino acids, about 10 to 125 amino acids, about 10 to 100 amino acids, about 10 to 75 amino acids, about 10 to 50 amino acids, about 10 to 40 amino acids, about 10 to 30 amino acids, about 10 to 20 amino acids, or about 10 to 15 amino acids, and including any integer between the endpoints of any of the listed ranges. In some embodiments, a spacer region has about 12 amino acids or less, about 119 amino acids or less, or about 229 amino acids or less. Exemplary spacers include a CD28 hinge, IgG4 hinge alone, IgG4 hinge linked to CH2 and CH3 domains, or IgG4 hinge linked to the CH3 domain. Exemplary spacers include, but are not limited to, those described in Hudecek et al. (2013) *Clin. Cancer Res.*, 19:3153, international patent application publication number WO2014031687, U.S. Pat. No. 8,822,647 or published app. No. US2014/0271635.

The spacer domain preferably has a sequence that promotes binding of a CAR with an antigen and enhances signaling in a cell. Examples of an amino acid that is expected to promote the binding include cysteine, a charged amino acid, and serine and threonine in a potential glycosylation site, and these amino acids can be used as an amino acid constituting the spacer domain.

As the spacer domain, all or a part of residues 118 to 178 of CD8a (GENBANK Accession No. NP_001759.3), residues 135 to 195 of CD8r3 (GENBANK Accession No. AAA35664), residues 315 to 396 of CD4 (GENBANK Accession No. NP_000607.1), or residues 137 to 152 of CD28 (GENBANK Accession No. NP_006130.1) can be used. Also, as the spacer domain, a part of a constant region of an antibody H chain or L chain ($C_{H1}$ region or $C_L$ region) can be used. Further, the spacer domain may be an artificially synthesized sequence.

Transmembrane Domain

With respect to the transmembrane domain, the CAR can be designed to comprise a transmembrane domain that is fused to the antigen binding domain of the CAR. In one embodiment, the transmembrane domain that naturally is associated with one of the domains in the CAR is used. In some instances, the transmembrane domain can be selected or modified by amino acid substitution to avoid binding of such domains to the transmembrane domains of the same or different surface membrane proteins to minimize interactions with other members of the receptor complex.

The transmembrane domain may be derived either from a natural or from a synthetic source. Where the source is natural, the domain may be derived from any membrane-bound or transmembrane protein. Typically, the transmembrane domain denotes a single transmembrane a helix of a transmembrane protein, also known as an integral protein. Transmembrane regions of particular use in this invention may be derived from (i.e. comprise at least the transmembrane region(s) of) CD28, CD3 ε, CD4, CD5, CD8, CD9, CD16, CD22, CD33, CD37, CD45, CD64, CD80, CD86, CD134, CD137, CD154, TCRα, TCR β, H2-Kb, FcεRIγ, GITR or CD3 ζ and/or transmembrane regions containing functional variants thereof such as those retaining a substantial portion of the structural, e.g., transmembrane, properties thereof can be used. See, e.g., Kahlon, et al. (2004) *Cancer Res.* 64:9160-9166; Schambach, et al. (2009) *Methods Mol. Biol.* 506:191-205; Jensen, et al. (1998) *Biol. Blood Marrow Transplant* 4:75-83; Patel, et al. (1999) *Gene Ther.* 6:412; Song, et al. (2012) *Blood* 119:696-706; Carpenito, et al. (2009) *Proc. Natl. Acad. Sci. USA* 106:3360-5; Hombach, et al. (2012) *Oncoimmunology* 1:458-66) and Geiger, et al. (2001) *Blood* 98:2364-71.

Alternatively, the transmembrane domain may be synthetic, in which case it will comprise predominantly hydrophobic residues such as leucine and valine. Preferably a triplet of phenylalanine, tryptophan and valine will be found at each end of a synthetic transmembrane domain. A transmembrane domain of the invention is thermodynamically stable in a membrane. It may be a single alpha helix, a transmembrane beta barrel, a beta-helix of gramicidin A, or any other structure. Transmembrane helices are usually about 20 amino acids in length.

In one embodiment, the transmembrane domain is composed of residues 153 to 180 of CD28 (GENBANK Accession No. NP_006130, sequence provided, infra). As another embodiment, the transmembrane domain is composed of residues 162 to 183 of a GITR (GENBANK Accession No. NP_004186). Preferably, the spacer region and transmembrane domain are obtained from the corresponding domains in the CD28 sequences.

Optionally, a short oligo- or polypeptide linker, preferably between 2 and 10 amino acids in length may form the linkage between the transmembrane domain and the intracellular signaling domain(s) of the CAR. A glycine-serine doublet may provide a suitable linker.

Intracellular Signaling Domain

The intracellular signaling domain or otherwise the cytoplasmic domain of the CAR of the invention triggers or elicits activation of at least one of the normal effector functions of the immune cell in which the CAR has been placed. The term "effector function" refers to a specialized function of a cell. Effector function of a T cell, for example, may be cytolytic activity or helper activity including the secretion of cytokines. Thus, the term "intracellular signaling domain" refers to the portion of a protein which transduces the effector function signal and directs the cell to perform a specialized function. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the intracellular signaling domain sufficient to transduce the effector function signal.

In some embodiments, the intracellular signaling endodomain transmits a signal into a cell when the extracellular antigen targeting domain present within the same molecule binds to (interacts with) an antigen. Natural T cell-activation is transmitted by two different kinds of cytoplasmic signaling endodomains, that is, a sequence for initiating antigen-dependent primary activation via a TCR complex (primary cytoplasmic signaling endodomain) and a sequence for acting antigen-independently to provide a secondary or costimulatory signal (secondary cytoplasmic signaling endodomain or costimulatory endodomain). Therefore, while some embodiments embrace a CAR with only a primary cytoplasmic signaling endodomain, in other embodiments, a CAR of the invention includes a primary signaling endodomain and a secondary cytoplasmic signaling endodomain.

The primary cytoplasmic signaling endodomain regulates primary activation of a TCR complex. The primary cytoplasmic signaling sequence that stimulates the activation may include a signal transduction motif known as an immunoreceptor tyrosine-based activation motif (ITAM) (Asp/Glu)-Xaa-Xaa-Tyr*-Xaa-Xaa-(Ile/Leu)-Xaa$_{6-8}$-Tyr*-Xaa-Xaa-(Ile/Leu) (SEQ ID NO:1) (Reth, et al. (1989) *Nature* 338:383-384). On the other hand, the primary cytoplasmic signaling endodomain that acts in an inhibitory way includes a signal transduction motif known as an immunoreceptor tyrosine-based inhibition motif (ITIM) (Burshtyn, et al. (1999) *J. Immunol.* 162:897-902). In the present invention, an intracellular signaling endodomain having an ITAM or an ITIM can be used.

Examples of ITAM-containing primary cytoplasmic signaling sequences that are of particular use in the invention include those derived from an intracellular signaling domain of a lymphocyte receptor chain, a TCR/CD3 complex protein, an Fc receptor subunit, an IL-2 receptor subunit, CD3 ζ, FcR γ, FcR β, CD3 γ, CD3 δ, CD3 ε, CD5, CD22, CD79a, CD79b, CD66d, CD278(ICOS), FcεRI, DAP10, and DAP12. It is particularly preferred that the intracellular signaling domain in the CAR of the invention comprises a cytoplasmic signaling sequence derived from CD3. Specifically, examples of the ITAM include residues 51 to 164 of CD3ζ (GENBANK Accession No. NP_932170), residues 45 to 86 of FcεRIγ (GENBANK Accession No. NP_004097), residues 201 to 244 of FcεRIβ (GENBANK Accession No. NP_000130), residues 139 to 182 of CD3γ (GENBANK Accession No. NP_000064), residues 128 to 171 of CD36 (GENBANK Accession No. NP_000723), residues 153 to 207 of CD3E (GENBANK Accession No. NP_000724), residues 402 to 495 of CD5 (GENBANK Accession No. NP_055022), residues 707 to 847 of CD22 (GENBANK Accession No. NP_001762), residues 166 to 226 of CD79a (GENBANK Accession No. NP_001774), residues 182 to 229 of CD79b (GENBANK Accession No. NP_000611), and residues 177 to 252 of CD66d (GENBANK Accession No. NP_001806), and their variants having the same function as these peptides have. The referenced residues are based on amino acid sequence information from GENBANK and is based on the full length of the precursor (including a signal peptide sequence etc.) of each protein.

Preferred examples of intracellular signaling domains for use in the CAR of the invention include the cytoplasmic sequences of the T cell receptor (TCR) and co-receptors that act in concert to initiate signal transduction following antigen receptor engagement, as well as any derivative or variant of these sequences and any synthetic sequence that has the same functional capability.

In a preferred embodiment, the cytoplasmic domain of the CAR can be designed to comprise the CD3-ζ signaling domain by itself or combined with any other desired cytoplasmic domain(s) useful in the context of the CAR of the invention. For example, the cytoplasmic domain of the CAR can comprise a CD3 ζ chain portion and a costimulatory signaling region. The costimulatory signaling region refers to a portion of the CAR comprising the intracellular domain of a costimulatory molecule. A costimulatory molecule is a cell surface molecule other than an antigen receptor or their ligands that is required for an efficient response of lymphocytes to an antigen.

Various co-stimulatory domains have been reported to confer differing properties. For example, the 4-1BB co-stimulatory domain showed enhanced persistence in in vivo xenograph models (Milone et al. *Mol Ther* 2009; 17:1453-1464; Song et al. *Cancer Res* 2011; 71:4617-4627) whereas CARs that associate with DAP10 are associated with a decreased persistence in vivo (Barber et al. *Gene Ther* 2011; 18:509-516). Additionally, these different co-stimulatory domains produce different cytokine profiles which, in turn, may produce effects on target cell-mediated cytotoxicity and the tumor microenvironment. Indeed, DAP10 signaling in NK cells has been associated with an increase in Th1 and inhibition of Th2 type cytokine production in CD8+ T cells (Barber et al. *Blood* 2011; 117:6571-6581).

Examples of co-stimulatory molecules include an MHC class I molecule, TNF receptor proteins, immunoglobulin-like proteins, cytokine receptors, integrins, signaling lymphocytic activation molecules (SLAM proteins), activating NK cell receptors, a Toll ligand receptor, B7-H3, BAFFR, BTLA, BLAME (SLAMF8), CD2, CD4, CD5, CD7, CD8α, CD8β, CD11a, LFA-1 (CD11a/CD18), CD11b, CD11c, CD11d, CD18, CD19, CD19a, CD27, CD28, CD29, CD30, CD40, CD49a, CD49D, CD49f, CD69, CD84, CD96 (Tactile), CD100 (SEMA4D), CD103, CRTAM, OX40 (CD134), 4-1BB (CD137), SLAM (SLAMF1, CD150, IPO-3), CD160 (BY55), SELPLG (CD162), DNAM1 (CD226), Ly9 (CD229), SLAMF4 (CD244, 2B4), ICOS (CD278), CEACAM1, CDS, CRTAM, DAP10, GADS, GITR, HVEM (LIGHTR), IA4, ICAM-1, IL2R β, IL2R γ, IL7Rα, ITGA4, ITGA6, ITGAD, ITGAE, ITGAL, ITGAM, ITGAX, ITGB1, ITGB2, ITGB7, KIRDS2, LAT, LFA-1, LIGHT, LTBR, NKG2C, NKG2D, NKp30, NKp44, NKp46, NKp80 (KLRF1), PAG/Cbp, PD-1, PSGL1, SLAMF6 (NTB-A, Ly108), SLAMF7, SLP-76, TNFR2, TRANCE/RANKL, VLA1, VLA-6, a ligand that specifically binds with CD83, and the like.

Specific examples of secondary cytoplasmic signaling endodomains or costimulatory endodomains that can be used in the present invention include residues 236 to 351 of CD2 (GENBANK Accession No. NP_001758), residues 421 to 458 of CD4 (GENBANK Accession No. NP_000607), residues 402 to 495 of CD5 (GENBANK Accession No. NP_055022), residues 207 to 235 of CD8a (GENBANK Accession No. NP_001759), residues 196 to 210 of CD83 (GENBANK Accession No. AAA35664), residues 181 to 220 of CD28 (GENBANK Accession No. NP_006130), residues 214 to 255 of CD137 (4-1BB, GENBANK Accession No. NP_001552), residues 241 to 277 of CD134 (OX40, GENBANK Accession No. NP_003318), and residues 166 to 199 of ICOS (GENBANK Accession No. NP_036224), and their variants having the same function as these peptides have. In some embodiments, the costimulatory endodomain is from CD28, 41BB, OX40, ICOS, or a combination thereof. All of the above disclosed sequences are incorporated herein by reference for all purposes.

While any suitable endodomain can be used in the CAR of the invention, in certain embodiments, the invention specifically contemplates the use of all or a part of the endodomains of CD28 and CD3 ζ. In specific embodiments, intracellular signaling endodomains are those of the T cell antigen receptor complex, e.g., CD28, DAP10, CD137, CD2, which are used either alone or in a series with CD3 ζ. One or multiple endodomains may be employed, as so-called third generation CARs have at least 2 or 3 signaling domains fused together for additive or synergistic effect, for example.

The cytoplasmic signaling sequences within the intracellular signaling domain of the CAR of the invention may be linked to each other in a random or specified order. In a CAR containing more than one intracellular endodomain, an oligopeptide linker, as described above, or a polypeptide linker can be inserted between the intracellular endodomains to link the domains. Optionally, a short oligo- or polypeptide linker, preferably between 2 and 10 amino acids in length may form the linkage. A glycine-serine doublet or continuous sequence provides a particularly suitable linker.

Signal Peptide

In addition to the antigen targeting domain, extracellular spacer/hinge domain, transmembrane domain, and signaling endodomain, the CAR of the invention can also include a signal peptide sequence linked to the N-terminus of the CAR. Signal peptide sequences exist at the N-terminus of many secretory proteins and membrane proteins, and have a length of 15 to 30 amino acids. Since many of the protein molecules mentioned above have signal peptide sequences, these signal peptides can be used as a signal peptide for the CAR of this invention.

Transcription Factors

Several transcription factors, in coordination, can induce full differentiation of $T_H1$ cells and mediate proinflammatory cytokine expression. The master regulator for Th1 differentiation, the T-box 21 transcription factor (T-bet or TBX21; GENBANK Accession No. NP_037483, sequence provided, infra), is defined not only by its ability to activate the set of genes to promote differentiation of a particular phenotype, but also by being able to suppress the development of opposing cell lineages (Afkarian, et al. (2002) *Nat. Immunol.* 3:549-57; Lugo-Villarino, et al. (2003) *Proc. Natl. Acad. Sci. USA* 100:7749-54). T-bet is a principal transcription factor, as it significantly enhances the production of IFNγ, and plays an important role in suppressing the development of Th2 and Th17 (Lugo-Villarino, et al. (2003) *Proc. Natl. Acad. Sci. USA* 100:7749-54; Lazarevic, et al. (2011) *Nat. Immunol.* 12:96-104). T-bet expression has been found to be strongly dependent on signal transducer and activator of transcription 1 (STAT1), rather than on IL-12-dependent STAT4 (Afkarian, et al. (2002) *Nat. Immunol.* 3:549-57; Lighvani, et al. (2001) *Proc. Natl. Acad. Sci. USA* 98:15137-42). STAT1, is in turn activated by IFNγ. T-bet further induces IFNγ production by the differentiating cells, thereby amplifying T-bet expression and upregulating the expression of IL-12Rβ2. T-bet suppresses development of Th2 cell by inhibiting the crucial IL-4 gene and impairing the function of the Th2 master regulator GATA3 (Diuretic, et al. (2007) *Nat. Immunol.* 8:145-53; Hwang, et al. (2005) *Science* 307:430-3). Th17 lineage is inhibited by the interaction of T-bet with Rorc promoter, which encodes RORγt, the principal transcription factor of Th17 (Lazarevic, et al. (2011) *Nat. Immunol.* 12:96-104).

Signal transducer and activator of transcription 1 (STAT1; GenBank Accession No. P42224, sequence provided, infra) is also an important transcription factor encoded by the STAT1 gene, encoding a 91 kDa protein. STAT1 is involved in upregulation of genes through signaling by IFN. In response to IFN stimulation (IFN-γ, IFN-α, EGF, PDGF, and IL-6), STAT1 is phosphorylated and will form a homodimer or heterodimer with STAT3 and bind to Interferon-Gamma-Activated Sequence (GAS) promoter elements, or Interferon Stimulated Response Elements (ISRE) in the cell, which activates transcription of some genes, such as IFN-stimulated genes, which drive the cell in an antiviral state, and repression of other genes, being a pleiotropic transcription modulator. (See, Ramana et al., *Oncogene*, 19(21):2619-2627, 2000).

IL12-induced signal transducer and activator of transcription 4 (STAT4; GENBANK Accession No. NP_003142, sequence provided, infra) is another important transcription factor involved in the Th1 cell differentiation and proinflammatory cytokine expression (Thierfelder, et al. (1996) *Nature* 382:171-4). STAT4 induces IFNγ production, thereby creating a positive feedback loop for further T-bet and IL-12Rβ2 expression. STAT4 and T-bet are involved directly in the transcription of IFNγ locus through the creation of activating marks at the locus, while STAT6 and GATA3 in Th2 differentiation establish repressive histone marks at said locus. For complete Th1 cell differentiation, these-lineage specific transcription factors need to operate in coordination with one another (Thieu, et al. (2008) *Immunity* 29:679-90). In later stages of differentiation, IL-12/STAT4 pathway upregulates IL-18Rα. IL12 along with IL18 induces IFNγ production independent of TCR activation, thus creating a pathway for enhancing Th1 response.

Accordingly, in some embodiments, the nucleic acid construct of the invention includes nucleic acids encoding T-bet, STAT1, or STAT4 preferably T-bet or a mutated form thereof. Said transcription factors are shown to overcome or alleviate the limited capacity of T lymphocytes (including adoptively transferred tumor-specific T lymphocytes) to expand and differentiate within a tumor microenvironment. In particular, the overexpression of such transcription factors is proven to promote $T_H1$ cell differentiation and induces the expression of molecules associated with a proinflammatory response (e.g., TNFα, IFNγ, GM-CSF, IL-2, IL-3, IL-15, MIP-1A, MIP-1B and the like).

Particularly preferred are genes encoding human or murine T-bet, STAT1, and STAT4 or mutated forms of any of the foregoing.

```
The mouse T-bet polypeptide sequence is as follows
(NCBI Ref Seq. NP_062380.2, RefSeq accession NM_019597.2):
                                                        (SEQ ID NO: 22)
MGIVEPGCGDMLTGTEPMPSDEGRGPGADQQHRFFYPEPGAQDPTDRRAGSSLGTPYSGGALVPAAPGR

FLGSFAYPPRAQVAGFPGPGEFFPPPAGAEGYPPVDGYPAPDPRAGLYPGPREDYALPAGLEVSGKLRV

ALSNHLLWSKFNQHQTEMIITKQGRRMFPFLSFTVAGLEPTSHYRMFVDVVLVDQHHWRYQSGKWVQCG

KAEGSMPGNRLYVHPDSPNTGAHWMRQEVSFGKLKLTNNKGASNNVTQMIVLQSLHKYQPRLHIVEVND
```

```
GEPEAACSASNTHVFTFQETQFIAVTAYQNAEITQLKIDNNPFAKGFRENFESMYASVDTSVPSPPGPN

CQLLGGDPFSPLLSNQYPVPSRFYPDLPGQPKDMISQPYWLGTPREHSYEAEFRAVSMKPTLLPSAPGP

TVPYYRGQDVLAPGAGWPVAPQYPPKMSPAGWFRPMRTLPMDPGLGSSEEQGSSPSLWPEVTSLQPEPS

DSGLGEGDTKRRRISPYPSSGDSSSPAGAPSPFDKETEGQFYNYFPN
```

GenBank Accession Number NP_037483 provides the corresponding human T-bet sequence:

(SEQ ID NO: 23)
```
MGIVEPGCGDMLTGTEPMPGSDEGRAPGADPQHRYFYPEPGAQDADERRGGGSLGSPYPGGALVPAPPS

RFLGAYAYPPRPQAAGFPGAGESFPPPADAEGYQPGEGYAAPDPRAGLYPGPREDYALPAGLEVSGKLR

VALNNHLLWSKFNQHQTEMIITKQGRRMFPFLSFTVAGLEPTSHYRMFVDVVLVDQHHWRYQSGKWVQC

GKAEGSMPGNRLYVHPDSPNTGAHWMRQEVSFGKLKLTNNKGASNNVTQMIVLQSLHKYQPRLHIVEVN

DGEPEAACNASNTHIFTFQETQFIAVTAYQNAEITQLKIDNNPFAKGFRENFESMYTSVDTSIPSPPGP

NCQFLGGDHYSPLLPNQYPVPSRFYPDLPGQAKDVVPQAYWLGAPRDHSYEAEFRAVSMKPAFLPSAPG

PTMSYYRGQEVLAPGAGWPVAPQYPPKMGPASWFRPMRTLPMEPGPGGSEGRGPEDQGPPLVWTEIAPI

RPESSDSGLGEGDSKRRRVSPYPSSGDSSSPAGAPSPFDKEAEGQFYNYFPN
```

GenBank Accession Number P42224 provides the following human STAT1 peptide sequence:

(SEQ ID NO: 18)
```
MSQWYELQQLDSKFLEQVHQLYDDSFPMEIRQYLAQWLEKQDWEHAANDVSFATIRFHDLLSQLDDQYS

RFSLENNFLLQHNIRKSKRNLQDNFQEDPIQMSMIIYSCLKEERKILENAQRFNQAQSGNIQSTVMLDK

QKELDSKVRNVKDKVMCIEHEIKSLEDLQDEYDFKCKTLQNREHETNGVAKSDQKQEQLLLKKMYLMLD

NKRKEVVHKIIELLNVTELTQNALINDELVEWKRRQQSACIGGPPNACLDQLQNWFTIVAESLQQVRQQ

LKKLEELEQKYTYEHDPITKNKQVLWDRTFSLFQQLIQSSFVVERQPCMPTHPQRPLVLKTGVQFTVKL

RLLVKLQELNYNLKVKVLFDKDVNERNTVKGFRKFNILGTHTKVMNMEESTNGSLAAEFRHLQLKEQKN

AGTRTNEGPLIVTEELHSLSFETQLCQPGLVIDLETTSLPVVVISNVSQLPSGWASILWYNMLVAEPRN

LSFFLTPPCARWAQLSEVLSWQFSSVTKRGLNVDQLNMLGEKLLGPNASPDGLIPWTRFCKENINDKNF

PFWLWIESILELIKKHLLPLWNDGCIMGFISKERERALLKDQQPGTFLLRFSESSREGAITFTWVERSQ

NGGEPDFHAVEPYTKKELSAVTFPDIIRNYKVMAAENIPENPLKYLYPNIDKDHAFGKYYSRPKEAPEP

MELDGPKGTGYIKTELISVSEVHPSRLQTTDNLLPMSPEEFDEVSRIVGSVEFDSMMNTV
```

GenBank Accession No. AAA19454 provides the corresponding mouse peptide sequence for STAT1, as follows:

(SEQ ID NO: 19)
```
MSQWFELQQLDSKFLEQVHQLYDDSFPMEIRQYLAQWLEKQDWEHAAYDVSFATIRFHDLLSQLDDQYS

RFSLENNFLLQHNIRKSKRNLQDNFQEDPVQMSMIIYNCLKEERKILENAQRFNQAQEGNIQNTVMLDK

QKELDSKVRNVKDQVMCIEQEIKTLEELQDEYDFKCKTSQNREGEANGVAKSDQKQEQLLLHKMFLMLD

NKRKEIIHKIRELLNSIELTQNTLINDELVEWKRRQQSACIGGPPNACLDQLQTWFTIVAETLQQIRQQ

LKKLEELEQKFTYEPDPITKNKQVLSDRTFLLFQQLIQSSFVVERQPCMPTHPQRPLVLKTGVQFTVKS

RLLVKLQESNLLTKVKCHFDKDVNEKNTVKGFRKFNILGTHTKVMNMEESTNGSLAAELRHLQLKEQKN

AGNRTNEGPLIVTEELHSLSFETQLCQPGLVIDLETTSLPVVVISNVSQLPSGWASILWYNMLVTEPRN

LSFFLNPPCAWWSQLSEVLSWQFSSVTKRGLNADQLSMLGEKLLGPNAGPDGLIPWTRFCKENINDKNF

SFWPWIDTILELIKNDLLCLWNDGCIMGFISKERERALLKDQQPGTFLLRFSESSREGAITFTWVERSQ

NGGEPDFHAVEPYTKKELSAVTFPDIIRNYKVMAAENIPENPLKYLYPNIDKDHAFGKYYSRPKEAPEP

MELDDPKRTGYIKTELISVSEVHPSRLQTTDNLLPMSPEEFDEMSRIVGPEFDSMMSTV
```

-continued

GenBank Accession Number AAH31212 provides the following human STAT4
peptide sequence:
(SEQ ID NO: 20)
MSQWNQVQQLEIKFLEQVDQFYDDNFPMEIRHLLAQWIENQDWEAASNNETMATILLQNLLIQLDEQLG

RVSKEKNLLLIHNLKRIRKVLQGKFHGNPMHVAVVISNCLREERRILAAANMPVQGPLEKSLQSSSVSE

RQRNVEHKVAAIKNSVQMTEQDTKYLEDLQDEFDYRYKTIQTMDQSDKNSAMVNQEVLTLQEMLNSLDF

KRKEALSKMTQIIHETDLLMNTMLIEELQDWKRRQQIACIGGPLHNGLDQLQNCFTLLAESLFQLRRQL

EKLEEQSTKMTYEGDPIPMQRTHMLERVTFLIYNLFKNSFVVERQPCMPTHPQRPLVLKTLIQFTVKLR

LLIKLPELNYQVKVKASIDKNVSTLSNRRFVLCGTNVKAMSIEESSNGSLSVEFRHLQPKEMKSSAGGK

GNEGCHMVTEELHSITFETQICLYGLTIDLETSSLPVVMISNVSQLPNAWASIIWYNVSTNDSQNLVFF

NNPPPATLSQLLEVMSWQFSSYVGRGLNSDQLHMLAEKLTVQSSYSDGHLTWAKFCKEHLPGKSFTFWT

WLEAILDLIKKHILPLWIDGYVMGFVSKEKERLLLKDKMPGTFLLRFSESHLGGITFTWVDHSESGEVR

FHSVEPYNKGRLSALPFADILRDYKVIMAENIPENPLKYLYPDIPKDKAFGKHYSSQPCEVSRPTERGD

KGYVPSVFIPISTIRSDSTEPHSPSDLLPMSPSVYAVLRENLSPTTIETAMKSPYSAE

GenBank Accession No. AAA19453 provides the corresponding mouse
peptide sequence for STAT4, as follows:
(SEQ ID NO: 21)
MSQWNQVQQLEIKFLEQVDQFYDDNFPMEIRHLLAQWIETQDWEVASNNETMATILLQNLLIQLDEQLG

RVSKEKNLLLIHNLKRIRKVLQGKFHGNPMHVAVVISNCLREERRILAAANMPIQGPLEKSLQSSSVSE

RQRNVEHKVSAIKNSVQMTEQDTKYLEDLQDEFDYRYKTIQTMDQGDKNSILVNQEVLTLLQEMLNSLD

FKRKEALSKMTQIVNETDLLMNSMLLEELQDWKKRQQIACIGGPLHNGLDQLQNCFTLLAESLFQLRQQ

LEKLQEQSTKMTYEGDPIPAQRAHLLERATFLIYNLFKNSFVVERQPCMPTHPQRPMVLKTLIQFTVKL

RLLIKLPELNYQVKVKASIDKNVSTLSNRRFVLCGTHVKAMSSEESSNGSLSVEFRHLQPKEMKCSTGS

KGNEGCHMVTEELHSITFETQICLYGLTINLETSSLPVVMISNVSQLPNAWASIIWYNVSTNDSQNLVF

FNNPPSVTLGQLLEVMSWQFSSYVGRGLNSEQLNMLAEKLTVQSNYNDGHLTWAKFCKEHLPGKTFTFW

TWLEAILDLIKKHILPLWIDGYIMGFVSKEKERLLLKDKMPGTFLLRFSESHLGGITFTWVDQSENGEV

RFHSVEPYNKGRLSALAFADILRDYKVIMAENIPENPLKYLYPDIPKDKAFGKHYSSQPCEVSRPTERG

DKGYVPSVFIPISTIRSDSTEPQSPSDLLPMSPSAYAVLRENLSPTTIETAMNSPYSAE

Expression of the CAR and Transcription Factor

In the nucleic acid expression construct of the invention, at least one promoter directs transcription of the CAR and the transcription factor. According to some embodiments, nucleic acids encoding the CAR and transcription factor are independently expressed via different promoters, i.e., nucleic acids encoding the CAR are operably linked to a first promoter and nucleic acids encoding the transcription factor are operably linked to a second promoter, which promoters may be the same or different.

According to certain embodiments of the invention, nucleic acids encoding the CAR and transcription factor are co-expressed via a single promoter, i.e., nucleic acids encoding the CAR and nucleic acids encoding the transcription factor are in tandem and operably linked to a single promoter. A coding nucleic acid is "operably linked" to a regulatory sequence (e.g., promoter) if the regulatory sequence is capable of exerting a regulatory effect on the coding sequence linked thereto. In other words, the promoter(s) of the invention is positioned so as to promote transcription of the messenger RNA from the DNA encoding the CAR and transcription factor.

The promoter(s) of the invention can be of genomic origin or synthetically generated. A variety of promoters for use in T cells have been described in the art. For example, the CD4 promoter is disclosed by Marodon, et al. ((2003) *Blood* 101 (9): 3416-23). The promoter can be constitutive or inducible, where induction is associated with the specific cell type, a specific level of maturation, or drug (e.g., tetracycline or doxorubicin). Alternatively, a number of viral promoters are also suitable. Promoters of interest include the β-actin promoter, SV40 early and late promoters, immunoglobulin promoter, human cytomegalovirus promoter, retrovirus promoter, and the Friend spleen focus-forming virus promoter. The promoters may or may not be associated with enhancers, wherein the enhancers may be naturally associated with the particular promoter or associated with a different promoter.

The simultaneous or co-expression of a CAR and transcription factor via a single promoter may be achieved by the use of an internal ribosomal entry site (IRES) or cis-acting hydrolase element. The term "internal ribosome entry site" or "IRES" defines a sequence motif that promotes attachment of ribosomes to that motif on internal mRNA sequences. Consequently, an mRNA containing an IRES sequence motif results in two translational products, one initiating from the 5'-end of the mRNA and the other by an internal translation mechanism mediated by the IRES. A number of IRES have been described and can be used in the nucleic acid construct of this invention. See, e.g., U.S. Pat. No. 8,192,984; WO 2010/119257; and US 2005/0112095.

A "cis-acting hydrolase element" or "CHYSEL" refers to a peptide sequence that causes a ribosome to release the growing polypeptide chain that it is being synthesized without dissociation from the mRNA. In this respect, the ribosome continues translating and therefore produces a second polypeptide. Peptides such as the foot and mouth disease virus (FMDV) 2A sequence (GSGSRVTELLY-RMKRAETYC PRPLLAIHPT EARHKQKIV APVKQLLNFDLLKLAGDVESNPGP, SEQ ID NO:2), sea urchin (*Strongylocentrotus purpuratus*) 2A sequence (DGFCILYLLLILLMRSGDVETNPGP, SEQ ID NO:3); Sponge (*Amphimedon queenslandica*) 2A sequence (LLCFMLLLLLSGDVELNPGP, SEQ ID NO:4; or HHFMFLLLLL AGDIELNPGP, SEQ ID NO:5); acorn worm (*Saccoglossus kowalevskii*) 2A sequence (WFLVLLSFILSGDIEVNPGP, SEQ ID NO: 6); amphioxus (*Branchiostoma floridae*) 2A sequence (KN-CAMYMLLLSGDVETNPGP, SEQ ID NO:7; or MVISQLMLKLAGDVEENPGP, SEQ ID NO:8); porcine teschovirus-1 (GSGATNFSLLKQAGDVEENPGP, SEQ ID NO:9) 2A sequence; Thosea asigna virus (GSGEGRGSLL TCGDVEENPGP, SEQ ID NO:10) 2A sequence; and equine rhinitis A virus (GSGQCTNYALLKLAGDVESNPGP, SEQ ID NO:11) 2A sequence are CHYSELs of use in this invention. In some embodiments, the 2A sequence is a naturally occurring or synthetic sequence that includes the 2A consensus sequence D-X-E-X-NPGP (SEQ ID NO:12), in which X is any amino acid residue.

The sequence of the open reading frames encoding the CAR and transcription factor can be obtained from a genomic DNA source, a cDNA source, or can be synthesized (e.g., via PCR), or combinations thereof. Depending upon the size of the genomic DNA and the number of introns, it may be desirable to use cDNA or a combination thereof as it is found that introns stabilize the mRNA or provide T cell-specific expression (Barthel and Goldfeld (2003) *J. Immunol.* 171(7):3612-9). Also, it may be further advantageous to use endogenous or exogenous non-coding regions to stabilize the mRNA.

For expression of a CAR or transcription factor, the naturally occurring or endogenous transcriptional initiation region of the nucleic acid sequence encoding N-terminal component of the CAR or transcription factor can be used to generate the CAR or transcription factor in the target host. Alternatively, an exogenous transcriptional initiation region can be used which allows for constitutive or inducible expression, wherein expression can be controlled depending upon the target host, the level of expression desired, the nature of the target host, and the like.

The termination region(s) of the construct may be provided by the naturally occurring or endogenous transcriptional termination regions of the nucleic acids encoding the C-terminal component of the last gene. Alternatively, the termination region may be derived from a different source. For the most part, the source of the termination region is generally not considered to be critical to the expression of a recombinant protein and a wide variety of termination regions can be employed without adversely affecting expression.

Exemplary Constructs

Particularly preferred embodiments employ the use of, for example, the CD28 spacer region and transmembrane domain and cytoplasmic signaling domain. This endodomain may be followed in sequence, or fused with, for example, the endodomain of CD3-ζ. Sequences for CD28 and CD3-ζ are available to the public on various databases such as GenBank, etc.

For instance, GenBank Accession Number AAI12086 provides the following human CD28 peptide sequence:
(SEQ ID NO: 14)
MLRLLLALNLFPSIQVTGNKILVKQSPMLVAYDNAVNLSCKYSYNLFSRE

FRASLHKGLDSAVEVCVVYGNYSQQLQVYSKTGFNCDGKLGNESVTFYLQ

NLYVNQTDIYFCKIEVMYPPPYLDNEKSNGTIIHVKGKHLCPSPLFPGPS

KPFWVLVVVGGVLACYSLLVTVAFIIFWVRSKRSRLLHSDYMNMTPRRPG

PTRKHYQPYAPPRDFAAYRS

GenBank Accession No. AAH64058 provides the corresponding mouse peptide sequence for CD28, as follows:
(SEQ ID NO: 15)
MTLRLLFLALNFFSVQVTENKILVKQSPLLVVDSNEVSLSCRYSYNLLAK

EFRASLYKGVNSDVEVCVGNGNFTYQPQFRSNAEFNCDGDFDNETVTFRL

WNLHVNHTDIYFCKIEFMYPPPYLDNERSNGTIIHIKEKHLCHTQSSPKL

FWALVVVAGVLFCYGLLVTVALCVIWTNSRRNRLLQSDYMNMTPRRPGLT

RKPYQPYAPARDFAAYRP

GenBank Accession No. P20963 provides the human peptide sequence for CD3-ζ, as follows:
(SEQ ID NO: 16)
MKWKALFTAAILQAQLPITEAQSFGLLDPKLCYLLDGILFIYGVILTALF

LRVKFSRSADAPAYQQGQNQLYNELNLGRREEYDVLDKRRGRDPEMGGKP

QRRKNPQEGLYNELQKDKMAEAYSEIGMKGERRRGKGHDGLYQGLSTATK

DTYDALHMQALPPR

GenBank Accession No. AAH52824 provides the corresponding mouse peptide sequence for CD3-ζ, as follows:
(SEQ ID NO: 17)
MKWKVSVLACILHVRFPGAEAQSFGLLDPKLCYLLDGILFIYGVIITALY

LRAKFSRSAETAANLQDPNQLYNELNLGRREEYDVLEKKRARDPEMGGKQ

QRRRNPQEGVYNALQKDKMAEAYSEIGTKGERRRGKGHDGLYQGLSTATK

DTYDALHMQTLAPR

In one embodiment, the CAR of the invention comprises the nucleic acid sequence of the TZ.47 scFv (SEQ ID NO:24). In one embodiment, the CAR of the invention comprises the nucleic acid sequence that encodes the amino acid sequence of SEQ ID NO: 13. In one embodiment, the CAR of the invention comprises the amino acid sequence of SEQ ID NO: 13.

In one embodiment, the CAR of the invention comprises the nucleic acid sequence of Tz.47-28-3z (SEQ ID NO:26). In one embodiment, the CAR of the invention comprises the nucleic acid sequence that encodes the amino acid sequence of SEQ ID NO: 25. In one embodiment, the CAR of the invention comprises the amino acid sequence of SEQ ID NO: 25.

In one embodiment, the transcription factor of the invention comprises the nucleic acid sequence of the T-bet STOP mutant (SEQ ID NO:30). In one embodiment, the transcription factor of the invention comprises the nucleic acid sequence that encodes the amino acid sequence of SEQ ID NO:29. In one embodiment, the transcription factor comprises the amino acid sequence of SEQ ID NO:29.

In one embodiment, the transcription factor of the invention comprises the nucleic acid sequence of the T-bet TBOX Del mutant (SEQ ID NO:32). In one embodiment, the transcription factor of the invention comprises the nucleic acid sequence that encodes the amino acid sequence of SEQ ID NO:31. In one embodiment, the transcription factor comprises the amino acid sequence of SEQ ID NO:31.

In one embodiment, the nucleic acid construct or constructs of the invention comprise the nucleic acid sequence of Tz.47-28-3z-MsTBET (SEQ ID NO:35). In one embodiment, the nucleic acid construct or constructs of the invention comprise the nucleic acid sequence that encodes the amino acid sequence of SEQ ID NO:34.

In one embodiment, the nucleic acid construct or constructs of the invention comprise the nucleic acid sequence of Tz.47-28-3z-MsTBET-STOP (SEQ ID NO:37). In one embodiment, the nucleic acid construct or constructs of the invention comprise the nucleic acid sequence that encodes the amino acid sequence of SEQ ID NO:36.

In one embodiment, the nucleic acid construct or constructs of the invention comprise the nucleic acid sequence of Tz.47-28-3z-MsTBET-TBOX Del (SEQ ID NO:39). In one embodiment, the nucleic acid construct or constructs of the invention comprise the nucleic acid sequence that encodes the amino acid sequence of SEQ ID NO:38.

In one embodiment, the CAR of the invention comprises a CD28 hinge-transmembrane-endodomain having the amino acid sequence of SEQ ID NO:51. In one embodiment, the CAR of the invention comprises a CD3ζ endodomain having the amino acid sequence of SEQ ID NO:50. In one embodiment, the CAR of the invention comprises a G4S linker having the amino acid sequence of SEQ ID NO:53.

Further Modifications

The nucleic acid constructs, vectors, polypeptides, CARs, transcription factors, and cells of the invention may be further modified, engineered, optimized, or appended in order to provide or select for various features. These features may include, but are not limited to, efficacy, persistence, target specificity, reduced immunogenicity, multi-targeting, enhanced immune response, expansion, growth, reduced off-tumor effect, reduced subject toxicity, improved target cytotoxicity, improved tumor infiltration, detection, selection, targeting, and the like. For example, the cells may be engineered to express another CAR, a suicide mechanism, and may be modified to remove or modify expression of an endogenous receptor or molecule such as a TCR and/or MHC molecule.

As will be appreciated by one of skill in the art, in some instances, a few amino acids at the ends of each domain can be deleted, usually not more than 10, more usually not more than 5 residues. Also, it may be desirable to introduce a small number of amino acids at the borders, usually not more than 10, more usually not more than 5 residues. The deletion or insertion of amino acids will usually be as a result of the needs of the construction, providing for convenient restriction sites, ease of manipulation, improvement in levels of expression, or the like. In addition, the substitution of one or more amino acids with a different amino acid can occur for similar reasons, usually not substituting more than about five amino acids in any one domain.

In some embodiments, the vector or nucleic acid sequence may encode multiple genes. The vector or nucleic acid sequence may be constructed to allow for the co-expression of multiple genes using a multitude of techniques including co-transfection of two or more plasmids, the use of multiple or bidirectional promoters, or the creation of bicistronic or multicistronic vectors. The construction of multicistronic vectors may include the encoding of IRES elements or 2A peptides, such as T2A, P2A, E2A, or F2A. In a particular embodiment, the nucleic acid sequence or vector encoding the CAR further encodes a transcription factor with the use of a T2A ribosomal skip sequence.

The CAR expressing cell may further comprise a disruption to one or more endogenous genes. In some embodiments, the endogenous gene encodes TCRα, TCRβ, CD52, glucocorticoid receptor (GR), deoxycytidine kinase (dCK), or an immune checkpoint protein such as, for example, programmed death-1 (PD-1).

Efficacy in Solid Tumors

The CARs of the present invention and cells expressing these CARs may be further modified to improve efficacy against solid tumors. This increased efficacy may be measured by an increase in tumor cytotoxicity, tumor infiltration, and evasion of or resistance to tumor immunosuppressive mediators. In some embodiments, enhanced anti-tumor efficacy may be characterized by increased TCR signaling, increased cytokine release, enhanced killing of tumor cells, increased T cell infiltration of established tumors, improved tumor trafficking, attenuated tumor-induced hypofunction, and improved migration and chemotaxis.

In one aspect, the CAR expressing cells are further modified to evade or neutralize the activity of immunosuppressive mediators, including, but not limited to prostaglandin E2 (PGE2) and adenosine. In some embodiments, this evasion or neutralization is direct. In other embodiments, this evasion or neutralization is mediated via the inhibition of protein kinase A (PKA) with one or more binding partners, for example ezrin. In a specific embodiment, the CAR-expressing cells further express the peptide "regulatory subunit I anchoring disruptor"(RIAD). RIAD is thought to inhibit the association of protein kinase A (PKA) with ezrin, which thus prevents PKA-mediated inhibition of TCR activation (Newick et al. *Cancer Res* 2016 August; 76(15 Suppl):Abstract nr B27).

In some embodiments, the CAR expressing cells of the invention may induce a broad antitumor immune response consistent with epitope spreading.

In some embodiments, the CAR expressing cells of the invention further comprise a homing mechanism. For example, the cell may transgenically express one or more stimulatory chemokines or cytokines or receptors thereof. In particular embodiments, the cells are genetically modified to express one or more stimulatory cytokines. In certain embodiments, one or more homing mechanisms are used to render the inventive cells resistant to an inhibitory tumor microenvironment. In some embodiments, the CAR expressing cells are further modified to release inducible cytokines upon CAR activation, e.g., to attract or activate innate immune cells to a targeted tumor (so-called fourth generation CARs or TRUCKS). In some embodiments, CARs may co-express homing molecules, e.g., CCR4 or CCR2b, to increase tumor trafficking.

Controlling CAR Expression

In some instances, it may be advantageous to regulate the activity of the CAR or CAR-expressing cells. For example, inducing apoptosis using, e.g., a caspase fused to a dimerization domain (see, e.g., Di et al., *N Engl. J. Med.* 2011 Nov. 3; 365(18):1673-1683), can be used as a safety switch in the CAR therapy of the instant invention. In another example, CAR-expressing cells can also express an inducible Caspase-9 (iCaspase-9) molecule that, upon administration of a dimerizer drug (e.g., rimiducid (also called AP1903 (Bellicum Pharmaceuticals) or AP20187 (Ariad)) leads to activation of the Caspase-9 and apoptosis of the cells. The iCaspase-9 molecule contains a chemical inducer of dimerization (CID) binding domain that mediates dimerization in the presence of a CID. This results in inducible and selective depletion of CAR-expressing cells. In some cases, the iCaspase-9 molecule is encoded by a nucleic acid molecule separate from the CAR-encoding vector(s). In some cases, the iCaspase-9 molecule is encoded by the same nucleic acid molecule as the CAR-encoding vector. The iCaspase-9 can provide a safety switch to avoid any toxicity of CAR-expressing cells. See, e.g., Song et al. *Cancer Gene Ther.* 2008; 15(10):667-75; Clinical Trial Id. No. NCT02107963; and Di Stasi et al. *N Engl. J. Med.* 2011; 365:1673-83.

Alternative strategies for regulating the CAR therapy of the instant invention include utilizing small molecules or antibodies that deactivate or turn off CAR activity, e.g., by deleting CAR-expressing cells, e.g., by inducing antibody dependent cell-mediated cytotoxicity (ADCC). For example, CAR-expressing cells described herein may also express an antigen that is recognized by molecules capable of inducing cell death, e.g., ADCC or compliment-induced cell death. For example, CAR expressing cells described herein may also express a receptor capable of being targeted by an antibody or antibody fragment. Examples of such receptors include EpCAM, VEGFR, integrins (e.g., integrins αvβ3, α4, αI3/4β3, α4β7, α5β1, αvβ3, αv), members of the TNF receptor superfamily (e.g., TRAIL-R1, TRAIL-R2), PDGF Receptor, interferon receptor, folate receptor, GPNMB, ICAM-1, HLA-DR, CEA, CA-125, MUC1, TAG-72, IL-6 receptor, 5T4, GD2, GD3, CD2, CD3, CD4, CD5, CD11, CD11a/LFA-1, CD15, CD18/ITGB2, CD19, CD20, CD22, CD23/IgE Receptor, CD25, CD28, CD30, CD33, CD38, CD40, CD41, CD44, CD51, CD52, CD62L, CD74, CD80, CD125, CD147/basigin, CD152/CTLA-4, CD154/CD40L, CD195/CCR5, CD319/SLAMF7, and EGFR, and truncated versions thereof (e.g., versions preserving one or more extracellular epitopes but lacking one or more regions within the cytoplasmic domain). For example, CAR-expressing cells described herein may also express a truncated epidermal growth factor receptor (EGFR) which lacks signaling capacity but retains the epitope that is recognized by molecules capable of inducing ADCC, e.g., cetuximab (ERBITUX®), such that administration of cetuximab induces ADCC and subsequent depletion of the CAR-expressing cells (see, e.g., WO2011/056894, and Jonnalagadda et al., *Gene Ther.* 2013; 20(8)853-860).

In some embodiments, the CAR cell comprises a polynucleotide encoding a suicide polypeptide, such as for example RQR8. See, e.g., WO2013153391A, which is hereby incorporated by reference in its entirety. In CAR cells comprising the polynucleotide, the suicide polypeptide may be expressed at the surface of a CAR cell. The suicide polypeptide may also comprise a signal peptide at the amino terminus. Another strategy includes expressing a highly compact marker/suicide gene that combines target epitopes from both CD32 and CD20 antigens in the CAR-expressing cells described herein, which binds rituximab, resulting in selective depletion of the CAR-expressing cells, e.g., by ADCC (see, e.g., Philip et al., *Blood.* 2014; 124(8)1277-1287). Other methods for depleting CAR-expressing cells described herein include administration of CAMPATH, a monoclonal anti-CD52 antibody that selectively binds and targets mature lymphocytes, e.g., CAR-expressing cells, for destruction, e.g., by inducing ADCC. In other embodiments, the CAR-expressing cell can be selectively targeted using a CAR ligand, e.g., an anti-idiotypic antibody. In some embodiments, the anti-idiotypic antibody can cause effector cell activity, e.g., ADCC or ADC activities, thereby reducing the number of CAR-expressing cells. In other embodiments, the CAR ligand, e.g., the anti-idiotypic antibody, can be coupled to an agent that induces cell killing, e.g., a toxin, thereby reducing the number of CAR-expressing cells. Alternatively, the CAR molecules themselves can be configured such that the activity can be regulated, e.g., turned on and off, as described below.

In some embodiments of the invention, a nucleic acid construct or cell harboring the nucleic acid construct includes a nucleic acid encoding a protein that is capable of triggering cell death or elimination. Examples of such proteins include suicide proteins such as thymidine kinase (TK) of the HSV virus (herpesvirus) type I (Bonini, et al. (1997) *Science* 276:1719-1724), a Fas-based "artificial suicide gene" (Thomis, et al. (2001) *Blood* 97:1249-1257), *E. coli* cytosine deaminase gene or caspase-9, which are activated by ganciclovir, AP1903, 5-fluorocytosine or a specific chemical inducer of dimerization (CID), respectively.

The nucleic acid encoding the protein for cell death or elimination is advantageously provided in the nucleic acid construct of the invention to allow for the opportunity to ablate the transduced T cells in case of toxicity and to destroy the chimeric construct once a tumor has been reduced or eliminated. The use of suicide genes for eliminating transformed or transduced cells is known in the art. For example, Bonini, et al. ((1997) *Science* 276:1719-1724) teach that donor lymphocytes transduced with the HSV-TK suicide gene provide antitumor activity in patients for up to one year and elimination of the transduced cells is achieved using ganciclovir. Further, Gonzalez, et al. ((2004) *J. Gene Med.* 6:704-711) describe the targeting of neuroblastoma with cytotoxic T lymphocyte clones genetically modified to express a chimeric scFvFc:ζ immunoreceptor specific for an epitope on L1-CAM, wherein the construct further expresses the hygromycin thymidine kinase (HyTK) suicide gene to eliminate the transgenic clones.

The nucleic acid encoding the protein for cell death or elimination can be expressed from the same promoter as the CAR and/or transcription factor or from a different promoter. Generally, the nucleic acid encoding the protein for cell death or elimination, CAR and transcription factor will reside on the same construct or vector. Expression of the protein for cell death or elimination from the same promoter as the CAR and/or transcription factor can be accomplished using the IRES or CHYSEL sequences described herein. Generally it is expressed by a different promoter, often an inducible promoter.

In some embodiments, a regulatable CAR (RCAR) where the CAR activity can be controlled is desirable to optimize the safety and efficacy of a CAR therapy. In some embodiments, a RCAR comprises a set of polypeptides, typically two in the simplest embodiments, in which the components of a standard CAR described herein, e.g., an antigen binding domain and an intracellular signaling domain, are partitioned on separate polypeptides or members. In some embodiments, the set of polypeptides include a dimerization switch that, upon the presence of a dimerization molecule, can couple the polypeptides to one another, e.g., can couple an antigen binding domain to an intracellular signaling domain. Additional description and exemplary configurations of such regulatable CARs are provided herein and in International Publication No. WO 2015/090229, hereby incorporated by reference in its entirety.

In an aspect, an RCAR comprises two polypeptides or members: 1) an intracellular signaling member comprising an intracellular signaling domain, e.g., a primary intracellular signaling domain described herein, and a first switch domain; 2) an antigen binding member comprising an antigen binding domain, e.g., that specifically binds a tumor antigen described herein, as described herein and a second switch domain. Optionally, the RCAR comprises a transmembrane domain described herein. In an embodiment, a transmembrane domain can be disposed on the intracellular signaling member, on the antigen binding member, or on both. Unless otherwise indicated, when members or elements of an RCAR are described herein, the order can be as provided, but other orders are included as well. In other words, in an embodiment, the order is as set out in the text, but in other embodiments, the order can be different. E.g., the order of elements on one side of a transmembrane region can be different from the example, e.g., the placement of a switch domain relative to an intracellular signaling domain can be different, e.g., reversed.

In some embodiments, the CAR expressing immune cell may only transiently express a CAR. For example, the cells of the invention may be transduced with mRNA comprising a nucleic acid sequence encoding an inventive CAR. In this vein, the present invention also includes an RNA construct that can be directly transfected into a cell. A method for generating mRNA for use in transfection involves in vitro transcription (IVT) of a template with specially designed primers, followed by polyA addition, to produce a construct containing 3' and 5' untranslated sequences ("UTRs"), a 5' cap and/or Internal Ribosome Entry Site (IRES), the nucleic acid to be expressed, and a polyA tail, typically 50-2000 bases in length. RNA so produced can efficiently transfect different kinds of cells. In one embodiment, the template includes sequences for the CAR. In an embodiment, an RNA CAR vector is transduced into a cell by electroporation.

Target Specificity

The CAR expressing cells of the present invention may further comprise one or more additional CARs. These additional CARs may or may not be specific for the same antigen. In some embodiments, the one or more additional CARs may act as inhibitory or activating CARs. In some embodiments, the cells further include inhibitory CARs (iCARs, see Fedorov et al., Sci. Transl. Medicine, 2013 December; 5(215): 215ra172), such as a CAR recognizing an antigen other than the antigen of the first CAR, whereby an activating signal delivered through the first CAR is diminished or inhibited by binding of the inhibitory CAR to its ligand, e.g., to reduce off-target effects.

In some embodiments, the CAR expressing cells of the present invention may further comprise one or more additional CARs, and each of these CARs may target one or more antigens selected from the group of: BCMA; BCR-Ab1; BST2; CAIX; CD19; CD20; CD22; CD123; CD171; CD30; CD33; CD38; CD44v6; CD44v7/8; CEA; CLL-1; EGFRvIII; EGP-2; EGP-40; ERBB2 (Her2/neu); EPCAM; fetal acetylcholine receptor; FBP; FLT3; Folate receptor α; GD2; GD3; Her3 (ErbB3); Her4 (ErbB4); k-light chain; KDR; MAD-CT-1; MAD-CT-2; MAGE-A1; MARTI; ML-IAP; MYCN; Oncofetal antigen (h5T4); NKG2D ligands PDK1; PDL1; PSCA; PSMA; PRSS21; ROR1; SLAMF7; TAG-72; Tn Ag; TSLPR; B7H3 (CD276); KIT (CD117); IL-13Ra2; Mesothelin; IL-11Ra; VEGFR2; LeY; CD24; PDGFR-β; SSEA-4; CD20; MUC1; EGFR; NCAM; Prostase; PAP; ELF2M; Ephrin B2; FAP; IGF-I receptor; CAFX; LMP2; gp100; tyrosinase; EphA2; Fucosyl GM1; sLe; ganglioside GM3; TGS5; HMWMAA; OAcGD2; OR51E2; Folate receptor β; TEM1/CD248; TEM7R; CLDN6; TSHR; GloboH; GPR20; GPRCSD; CXORF61; CD97; CD179a; ADRB3; ALK; Polysialic acid; PANX3; PLAC1; NY-BR-1; NY-ESO-1; UPK2; TIM-1; HAVCR1; LY6K; TARP; WT1; LAGE-la; ETV6-AML; SPA17; XAGE1; Tie 2; Fos-related antigen 1; p53; p53 mutant; prostein; surviving; telomerase; PCTA-1; Rat sarcoma Ras mutant; hTERT; sarcoma translocation breakpoints; ERG; NA17; PAX3; Androgen receptor; Cyclin Bl; RhoC; TRP-2; CYP1B1; BORIS, SART3; PAX5; OY-TES1; LCK; AKAP-4; SSX2; RAGE-1; RU1; RU2; legumain; HPV E6; HPV E7; intestinal carboxyl esterase; mut hsp70-2; CD79a; CD79b; CD72; LAIR1; CD89; LILRA2; CD300LF; CLEC12A; EMR2; FCRL5; GPC3; IGLL1; and LY75.

In some embodiments, the antigen binding domain of the inventive CAR is affinity tuned. In particular, the affinity of the CAR antigen binding domain may be adjusted to discriminate cells overexpressing an antigen, e.g. tumor cells, from normal tissues which express the antigen at physiological levels. This may be accomplished, e.g., through the use of a CAR-expressing T cell with target antigen affinities varying over three orders of magnitude (Liu et al. *Cancer Res* 2015 September; 75(17):3596-607). Additionally, in vivo xenograft models may be used to evaluate the toxicity of affinity tuned CARs on normal human tissue (Johnson et al. *Sci Transl Med* 2015 February; 7(275):275ra22).

In some embodiments, the antigen binding domain of the CAR is or is part of an immunoconjugate, in which the antigen binding domain is conjugated to one or more heterologous molecule(s), such as, but not limited to, a cytotoxic agent, an imaging agent, a detectable moiety a multimerization domain or other heterologous molecule. Cytotoxic agents include, but are not limited to, radioactive isotopes (e.g., At211, 1131, 1125, Y90, Re186, Re188, Sm153, Bi212, P32, Pb212 and radioactive isotopes of Lu); chemotherapeutic agents (e.g., methotrexate, adriamycin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins. In some embodiments, the antigen binding domain is conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

Other

In some embodiments, the CAR expressing cells of the invention may be further genetically modified to express the dominant negative form of the transforming growth factor (TGF) β receptor (DNR).

In another embodiment, the CAR expressing cell may be specific for another antigen, including a tumor antigen in some cases. In some embodiments, the transformed host cells may be selected for specificity for one or more strong viral antigens or may be transformed to exhibit specificity for these antigens. In specific embodiments, the cells are pp65CMV-specific T cells, CMV-specific T cells, EBV-specific T cells, Varicella Virus-specific T cells, Influenza Virus-specific T cells and/or Adenovirus-specific T cells.

To increase persistence, the cells of the invention may be further modified to overexpress pro-survival signals, reverse anti-survival signals, overexpress Bcl-xL, overexpress hTERT, lack Fas, or express a TGFβ dominant negative receptor. Persistence may also be facilitated by the administration of cytokines, e.g., IL-2, IL-7, and IL-15.

Vectors

The present invention also provides vectors in which a DNA of the present invention is inserted. Vectors derived from retroviruses are suitable tools to achieve long-term gene transfer since they allow for genetic stability and high expression, in addition to having a flexible genome. Furthermore, clinical experience with retroviral vectors provides guidance for optimizing efficacy and safety in their use. Lentiviral vectors are an appealing tool for transgenesis because of their ability to incorporate into genomic DNA with high efficiency, especially in cells that are not actively dividing and because lentiviral vector-mediated transgene expression can be maintained for long periods of time.

Both lentiviruses and retroviruses have been widely used as gene transfer vectors, and they compose the vector system that is currently used in the majority of clinical gene therapy trials for cancer (Sinn, et al. (2005) Gene Ther. 12:1089-1098). However, the lentiviral vectors have become more widely used and are advantageous because they mediate the efficient transduction of cells, can be used with both dividing and non-dividing cells, result in long-term, stable transgene expression and appear to be less prone to gene silencing (Sinn, et al. (2005) Gene Ther. 12:1089-1098).

A variety of viral vectors (e.g., a retroviral vector, adenoviral vector, adeno-associated viral vector, or lentiviral vector) can be used to introduce the nucleic acid construct of the invention into immune cells. Suitable vectors for use in accordance with the method of the invention are those that do not replicate in the engineered recombinant immune cells. A large number of vectors are known that are based on viruses, where the copy number of the virus maintained in the cell is low enough to maintain the viability of the cell. Illustrative vectors include the pFB-neo vectors (STRATAGENE), as well as vectors based on HIV, SV40, EBV, HSV or BPV. Especially preferred embodiments employ the pFB-neo vector, as described infra. Other preferred embodiments of the above methods contemplate transduction or transfection of immune cells which are CD4+ T cells.

In brief summary, the expression of natural or synthetic nucleic acids encoding CARs is typically achieved by operably linking a nucleic acid encoding the CAR polypeptide or portions thereof to a promoter, and incorporating the construct into an expression vector. The vectors can be suitable for replication and integration in eukaryotes. Typical cloning vectors contain transcription and translation terminators, initiation sequences, and promoters useful for regulation of the expression of the desired nucleic acid sequence.

The expression constructs of the present invention may also be used for nucleic acid immunization and gene therapy, using standard gene delivery protocols. Methods for gene delivery are known in the art. See, e.g., U.S. Pat. Nos. 5,399,346, 5,580,859, 5,589,466, incorporated by reference herein in their entireties. In another embodiment, the invention provides a gene therapy vector.

The nucleic acid can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the expression vector may be provided to a cell in the form of a viral vector. Viral vector technology is well known in the art and is described, for example, in Sambrook et al. (2001, Molecular Cloning: A Laboratory Manual, Cold Spring Harbor Laboratory, New York), and in other virology and molecular biology manuals. Viruses, which are useful as vectors include, but are not limited to, retroviruses, gammaretroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, adenovirus vectors are used. A number of adenovirus vectors are known in the art. In one embodiment, retrovirus vectors are used. In some embodiments, the retroviral vector is pFSG or pFB.

It is contemplated that the nucleic acid construct can be introduced into the T cells as naked DNA or in a suitable vector. Methods of stably transfecting or transducing immune cells by electroporation of nucleic acid constructs are known in the art. See, e.g., U.S. Pat. No. 6,410,319. Naked DNA generally refers to the DNA encoding the nucleic acid constructs of the invention can be encoded by an expression vector in proper orientation for expression, and electroporation can be used to transduce the target immune cells to be engineered.

Nonviral gene transfer technologies are also applicable to the presently disclosed methods. For example, one approach includes the electrotransfer of DNA plasmids using the Sleeping Beauty (SB) transposon/transposase system into primary human T cells, which has been shown to provide efficient and stable CD19-specific CAR gene expression (Singh, et al. (2008) Cancer Res. 68:2961-71; Maiti, et al. (2013) J. Immunother. 36:112-123). An alternative non-viral approach that does not rely on transgene integration, which uses RNA electroporation, results in transient CAR expression, precluding effective T-cell persistence beyond a week (Zhao, et al. (2006) Mol. Ther. 13:151-159). The use of transient CART cells, which require multiple injections to provide meaningful tumor responses, may reduce the destruction of normal tissues or prevent T-cell accumulations to levels that increase the risk of cytokine storms (Zhao, et al. (2010) Cancer Res. 70:9053-61). Moreover, mRNA CAR T cells have been shown to mediate antitumor activity in patients with advanced solid tumors (Beatty, et al. (2014) Cancer Immunology Res. 2:112-20).

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

Various promoter sequences may be used, including, but not limited to the immediate early cytomegalovirus (CMV)

promoter, Elongation Growth Factor-1α (EF-1α), simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

In order to assess the expression of a CAR polypeptide or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

In certain embodiments of the invention, a nucleic acid construct or cell harboring the nucleic acid construct uses a detectable marker so that the cell that harbors the nucleic acid construct is identifiable, for example for qualitative and/or quantitative purposes. The detectable marker may be detectable by any suitable means in the art, including by flow cytometry, fluorescence, spectrophotometry, and so forth. An example of a detectable marker is one that encodes a nonfunctional gene product but that is still detectable by flow cytometry means, for example, or can be used to select transgenic cells by flow cytometry or magnetic selection. In addition to detection, the marker protein can be used as a means to eliminate the transduced cells in vivo via an antibody that recognizes the marker protein. Examples of marker proteins of use in cell elimination include, e.g., truncated CD19 (Tey, et al. (2007) *Biol. Blood Marrow Transplant* 13:913-24), the extracellular region of CD20 (Introna, et al. (2000) *Hum. Gene Ther.* 11:611-20; Griffioen, et al. (2009) *Haematologica* 94:1316-20), and the extracellular region of EGFR (Terakura, et al. (2012) *Blood* 119: 72-82). See also, Lang, et al. (2004) *Blood* 103:3982-5. Incorporation of these proteins into gene-modified T cells renders the cells susceptible to elimination by clinically used anti-CD19 antibodies, anti-CD20 antibodies, and anti-EGFR antibodies (e.g., cetuximab).

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, β-galactosidase, chloramphenicol acetyl transferase, secreted alkaline phosphatase, or the green fluorescent protein gene (e.g., Ui-Tei et al., 2000 *FEBS Letters* 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Transduction

Methods of introducing genes into a cell and expressing genes in a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2001, Molecular Cloning: A Laboratory Manual, Cold Spring Harbor Laboratory, New York). A preferred method for the introduction of a polynucleotide into a host cell is calcium phosphate transfection.

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Choi") can be obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20 degrees Celsius. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 *Glycobiology* 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce exogenous nucleic acids into a host cell or otherwise expose a cell to the inhibitor of the present invention, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

After it is established that the transfected or transduced T cell is capable of expressing the nucleic acid construct with the desired regulation and at a desired level, it can be determined whether the CAR and/or transcription factor are functional in the mammalian cell to provide for the desired signal induction. Subsequently, the transduced T cells are reintroduced or administered to the subject to activate antitumor and anti-infectious agent responses in the subject.

Cells of the Invention

Also provided are cells, cell populations, and compositions containing the cells. The nucleic acid constructs of the present invention or vectors containing can be transduced into an immune cell, e.g., a human T cell, thereby creating a recombinant immune cell engineered to express the encoded CAR and transcription factor molecules. Among the compositions are pharmaceutical compositions and formulations for administration, such as for adoptive cell therapy. Also provided are therapeutic methods for administering the cells and compositions to subjects, e.g., patients.

Cell Types

Thus also provided are cells expressing the CARs and transcription factors. The cells generally are eukaryotic cells, such as mammalian cells, and typically are human cells, more typically primary human cells, e.g., allogeneic or autologous donor cells. The cells for introduction of the nucleic acid constructs described herein may be isolated from a sample, such as a biological sample, e.g., one obtained from or derived from a subject. In some embodiments, the subject from which the cell is isolated is one having the disease or condition or in need of a cell therapy or to which cell therapy will be administered. The subject in some embodiments is a human in need of a particular therapeutic intervention, such as the adoptive cell therapy for which cells are being isolated, processed, and/or engineered. In some embodiments, the cells are derived from the blood, bone marrow, lymph, or lymphoid organs, are cells of the immune system, such as cells of the innate or adaptive immune systems, e.g., myeloid or lymphoid cells, including lymphocytes, typically T cells and/or NK cells. Other exemplary cells include stem cells, such as multipotent and pluripotent stem cells, including induced pluripotent stem cells (iPSCs). The cells typically are primary cells, such as those isolated directly from a subject and/or isolated from a subject and frozen. In some embodiments, the cells include one or more subsets of T cells or other cell types, such as whole T cell populations, $CD4^+$ cells, $CD8^+$ cells, and subpopulations thereof, such as those defined by function, activation state, maturity, potential for differentiation, expansion, recirculation, localization, and/or persistence capacities, antigen-specificity, type of antigen receptor, presence in a particular organ or compartment, marker or cytokine secretion profile, and/or degree of differentiation.

With reference to the subject to be treated, the cells may be allogeneic and/or autologous. Among the methods included are off-the-shelf methods. In some aspects, such as for off-the-shelf technologies, the cells are pluripotent and/or multipotent, such as stem cells, induced pluripotent stem cells (iPSCs), or T cells that either lack or are engineered to be deficient in T cell receptor function. In some embodiments, the methods include isolating cells from the subject, preparing, processing, culturing, and/or engineering them, as described herein, and re-introducing them into the same patient, before or after cryopreservation.

Among the sub-types and subpopulations of T cells and/or of CD4+ and/or of CD8+ T cells are naïve T (TN) cells, effector T cells (TEFF), memory T cells and sub-types thereof, such as stem cell memory T (TSCM), central memory T (TCM), effector memory T (TEM), or terminally differentiated effector memory T cells, tumor-infiltrating lymphocytes (TIL), immature T cells, mature T cells, helper T cells, cytotoxic T cells, mucosa-associated invariant T (MATT) cells, naturally occurring and adaptive regulatory T (Treg) cells, helper T cells, such as TH1 cells, TH2 cells, TH3 cells, TH17 cells, TH9 cells, TH22 cells, follicular helper T cells, α/β T cells, and δ/γ T cells.

In some embodiments, the cells are natural killer (NK) cells, Natural Killer T (NKT) cells, cytokine-induced killer (CIK) cells, tumor-infiltrating lymphocytes (TIL), lymphokine-activated killer (LAK) cells, or the like. In some embodiments, the cells are monocytes or granulocytes, e.g., myeloid cells, macrophages, neutrophils, dendritic cells, mast cells, eosinophils, and/or basophils.

In some embodiments, the cells are derived from cell lines, e.g., T cell lines. The cells in some embodiments are obtained from a xenogeneic source, for example, from mouse, rat, non-human primate, and pig.

Suitable immune cells that can be used in the invention include autologous T lymphocyte cells, allogeneic T cells, xenogeneic T cells, progenitors of any of the foregoing, transformed tumor or xenogenic immunologic effector cells, tumor infiltrating lymphocytes (TIL), cytotoxic lymphocytes or other cells that are capable of killing target cells when activated. These cells may be isolated from human or non-human subjects or may be derived from stem cells, e.g., embryonic stem cells, induced pluripotent stem cells, adult stem cells or other reprogrammed cells. As is known to one of skill in the art, various methods are readily available for isolating immune cells from a subject. For example, using cell surface marker expression or using commercially available kits (e.g., ISOCELL from Pierce, Rockford, IL.).

Cell Acquisition

Prior to expansion and genetic modification, a source of cells can be obtained from a subject through a variety of non-limiting methods. Cells can be obtained from a number of non-limiting sources, including peripheral blood mononuclear cells, bone marrow, lymph node tissue, cord blood, thymus tissue, tissue from a site of infection, ascites, pleural effusion, spleen tissue, and tumors. In some embodiments, any number of T cell lines available and known to those skilled in the art, may be used. In some embodiments, cells can be derived from a healthy donor, from a patient diagnosed with cancer, from a patient diagnosed with an autoimmune or inflammatory disorder or from a patient diagnosed with an infection. In some embodiments, cells can be part of a mixed population of cells which present different phenotypic characteristics.

Accordingly, the cells in some embodiments are primary cells, e.g., primary human cells. The samples include tissue, fluid, and other samples taken directly from the subject, as well as samples resulting from one or more processing steps, such as separation, centrifugation, genetic engineering (e.g. transduction with viral vector), washing, and/or incubation. The biological sample can be a sample obtained directly from a biological source or a sample that is processed. Biological samples include, but are not limited to, body fluids, such as blood, plasma, serum, cerebrospinal fluid, synovial fluid, urine and sweat, tissue and organ samples, including processed samples derived therefrom.

In some aspects, the sample from which the cells are derived or isolated is blood or a blood-derived sample, or is or is derived from an apheresis or leukapheresis product. Exemplary samples include whole blood, peripheral blood mononuclear cells (PBMCs), leukocytes, bone marrow, thymus, tissue biopsy, tumor, leukemia, lymphoma, lymph node, gut associated lymphoid tissue, mucosa associated lymphoid tissue, spleen, other lymphoid tissues, liver, lung, stomach, intestine, colon, kidney, pancreas, breast, bone, prostate, cervix, testes, ovaries, tonsil, or other organ, and/or cells derived therefrom. Samples include, in the context of cell therapy, e.g., adoptive cell therapy, samples from autologous and allogeneic sources.

In some examples, cells from the circulating blood of a subject are obtained, e.g., by apheresis or leukapheresis. The samples, in some aspects, contain lymphocytes, including T cells, monocytes, granulocytes, B cells, other nucleated white blood cells, red blood cells, and/or platelets, and in some aspects contain cells other than red blood cells and platelets.

Also provided herein are cell lines obtained from a transformed cell according to any of the above-described methods. Also provided herein are modified cells resistant to an immunosuppressive treatment. In some embodiments, an isolated cell according to the invention comprises a polynucleotide encoding a CAR and a transcription factor.

Cell Purification

In some embodiments, isolation of the cells includes one or more preparation and/or non-affinity based cell separation steps. In some examples, cells are washed, centrifuged, and/or incubated in the presence of one or more reagents, for example, to remove unwanted components, enrich for desired components, lyse or remove cells sensitive to particular reagents. In some examples, cells are separated based on one or more property, such as density, adherent properties, size, sensitivity and/or resistance to particular components.

In some embodiments, the blood cells collected from the subject are washed, e.g., to remove the plasma fraction and to place the cells in an appropriate buffer or media for subsequent processing steps. In some embodiments, the cells are washed with phosphate buffered saline (PBS). In some embodiments, the wash solution lacks calcium and/or magnesium and/or many or all divalent cations. In some aspects, a washing step is accomplished by a semi-automated "flow-through" centrifuge (for example, the Cobe 2991 cell processor, Baxter) according to the manufacturer's instructions. In some aspects, a washing step is accomplished by tangential flow filtration (TFF) according to the manufacturer's instructions. In some embodiments, the cells are resuspended in a variety of biocompatible buffers after washing, such as, for example, $Ca^{++}/Mg^{++}$ free PBS. In certain embodiments, components of a blood cell sample are removed and the cells directly resuspended in culture media.

In some embodiments, the isolation methods include the separation of different cell types based on the expression or presence in the cell of one or more specific molecules, such as surface markers, e.g., surface proteins, intracellular markers, or nucleic acid. In some embodiments, any known method for separation based on such markers may be used. In some embodiments, the separation is affinity- or immunoaffinity-based separation. For example, the isolation in some aspects includes separation of cells and cell populations based on the cells' expression or expression level of one or more markers, typically cell surface markers, for example, by incubation with an antibody or binding partner that specifically binds to such markers, followed generally by washing steps and separation of cells having bound the antibody or binding partner, from those cells having not bound to the antibody or binding partner.

Such separation steps can be based on positive selection, in which the cells having bound the reagents are retained for further use, and/or negative selection, in which the cells having not bound to the antibody or binding partner are retained. In some examples, both fractions are retained for further use. In some aspects, negative selection can be particularly useful where no antibody is available that specifically identifies a cell type in a heterogeneous population, such that separation is best carried out based on markers expressed by cells other than the desired population.

In some embodiments, multiple rounds of separation steps are carried out, where the positively or negatively selected fraction from one step is subjected to another separation step, such as a subsequent positive or negative selection. In some examples, a single separation step can deplete cells expressing multiple markers simultaneously, such as by incubating cells with a plurality of antibodies or binding partners, each specific for a marker targeted for negative selection. Likewise, multiple cell types can simultaneously be positively selected by incubating cells with a plurality of antibodies or binding partners expressed on the various cell types.

For example, in some aspects, specific subpopulations of T cells, such as cells positive or expressing high levels of one or more surface markers, e.g., $CD28^+$, $CD62L^+$, $CCR7^+$, $CD27^+$, $CD127^+$, $CD4^+$, $CD8^+$, $CD45RA^+$, and/or $CD45RO^+$ T cells, are isolated by positive or negative selection techniques. For example, $CD3^+$ T cells can be expanded using CD3 conjugated magnetic beads (e.g., DYNABEADS® M-450 CD3/CD28 T Cell Expander).

In some embodiments, isolation is carried out by enrichment for a particular cell population by positive selection, or depletion of a particular cell population, by negative selection. In some embodiments, positive or negative selection is accomplished by incubating cells with one or more antibodies or other binding agent that specifically bind to one or more surface markers expressed or expressed ($marker^+$) at a relatively higher level ($marker^{high}$) on the positively or negatively selected cells, respectively.

In some embodiments, T cells are separated from a PBMC sample by negative selection of markers expressed on non-T cells, such as B cells, monocytes, or other white blood cells, such as CD14. In some aspects, a $CD4^+$ or $CD8^+$ selection step is used to separate $CD4^+$ helper and $CD8^+$ cytotoxic T cells. Such $CD4^+$ and $CD8^+$ populations can be further sorted into sub-populations by positive or negative selection for markers expressed or expressed to a relatively higher degree on one or more naive, memory, and/or effector T cell subpopulations.

In some embodiments, $CD8^+$ cells are further enriched for or depleted of naïve, central memory, effector memory, and/or central memory stem cells, such as by positive or negative selection based on surface antigens associated with the respective subpopulation. In some embodiments, enrichment for central memory T ($T_{CM}$) cells is carried out to increase efficacy, such as to improve long-term survival, expansion, and/or engraftment following administration, which in some aspects is particularly robust in such subpopulations. See Terakura et al. (2012) *Blood*. 1:72-82; Wang et al. (2012) *J. Immunother* 35(9):689-701. In some embodiments, combining $T_{CM}$-enriched $CD8^+$ T cells and $CD4^+$ T cells further enhances efficacy.

In embodiments, memory T cells are present in both $CD62L^+$ and $CD62L^-$ subsets of CD8+ peripheral blood lymphocytes. PBMC can be enriched for or depleted of $CD62L^-CD8^+$ and/or $CD62L^+CD8$ fractions, such as using anti-CD8 and anti-CD62L antibodies.

In some embodiments, the enrichment for central memory T ($T_{CM}$) cells is based on positive or high surface expression of CD45RO, CD62L, CCR7, CD28, CD3, and/or CD127; in some aspects, it is based on negative selection for cells expressing or highly expressing CD45RA and/or granzyme B. In some aspects, isolation of a $CD8^+$ population enriched for $T_{CM}$ cells is carried out by depletion of cells expressing CD4, CD14, CD45RA, and positive selection or enrichment for cells expressing CD62L. In one aspect, enrichment for central memory T ($T_{CM}$) cells is carried out starting with a negative fraction of cells selected based on CD4 expression, which is subjected to a negative selection based on expression of CD14 and CD45RA, and a positive selection based on CD62L. Such selections in some aspects are carried out simultaneously and in other aspects are carried out sequentially, in either order. In some aspects, the same CD4 expression-based selection step used in preparing the $CD8^+$ cell population or subpopulation, also is used to generate the $CD4^+$ cell population or subpopulation, such that both the positive and negative fractions from the $CD4^-$ based separation are retained and used in subsequent steps of the methods, optionally following one or more further positive or negative selection steps.

In some aspects, the sample or composition of cells to be separated is incubated with small, magnetizable or magnetically responsive material, such as magnetically responsive particles or microparticles, such as paramagnetic beads (e.g., such as Dynabeads or MACS beads). The magnetically responsive material, e.g., particle, generally is directly or indirectly attached to a binding partner, e.g., an antibody, that specifically binds to a molecule, e.g., surface marker, present on the cell, cells, or population of cells that it is desired to separate, e.g., that it is desired to negatively or positively select.

In some embodiments, the magnetic particle or bead comprises a magnetically responsive material bound to a specific binding member, such as an antibody or other binding partner. There are many well-known magnetically responsive materials used in magnetic separation methods. Suitable magnetic particles include those described in Molday, U.S. Pat. No. 4,452,773, and in European Patent Specification EP 452342 B, which are hereby incorporated by reference. Colloidal sized particles, such as those described in Owen U.S. Pat. No. 4,795,698, and Liberti et al., U.S. Pat. No. 5,200,084 are other examples.

The incubation generally is carried out under conditions whereby the antibodies or binding partners, or molecules, such as secondary antibodies or other reagents, which specifically bind to such antibodies or binding partners, which are attached to the magnetic particle or bead, specifically bind to cell surface molecules if present on cells within the sample.

In some aspects, the sample is placed in a magnetic field, and those cells having magnetically responsive or magnetizable particles attached thereto will be attracted to the magnet and separated from the unlabeled cells. For positive selection, cells that are attracted to the magnet are retained; for negative selection, cells that are not attracted (unlabeled cells) are retained. In some aspects, a combination of positive and negative selection is performed during the same selection step, where the positive and negative fractions are retained and further processed or subject to further separation steps.

In certain embodiments, the magnetically responsive particles are coated in primary antibodies or other binding partners, secondary antibodies, lectins, enzymes, or streptavidin. In certain embodiments, the magnetic particles are attached to cells via a coating of primary antibodies specific for one or more markers. In certain embodiments, the cells, rather than the beads, are labeled with a primary antibody or binding partner, and then cell-type specific secondary antibody- or other binding partner (e.g., streptavidin)-coated magnetic particles, are added. In certain embodiments, streptavidin-coated magnetic particles are used in conjunction with biotinylated primary or secondary antibodies.

In some embodiments, the magnetically responsive particles are left attached to the cells that are to be subsequently incubated, cultured and/or engineered; in some aspects, the particles are left attached to the cells for administration to a patient. In some embodiments, the magnetizable or magnetically responsive particles are removed from the cells. Methods for removing magnetizable particles from cells are known and include, e.g., the use of competing non-labeled antibodies, magnetizable particles or antibodies conjugated to cleavable linkers, etc. In some embodiments, the magnetizable particles are biodegradable.

In certain embodiments, the isolation or separation is carried out using a system, device, or apparatus that carries out one or more of the isolation, cell preparation, separation, processing, incubation, culture, and/or formulation steps of the methods. In some aspects, the system is used to carry out each of these steps in a closed or sterile environment, for example, to minimize error, user handling and/or contamination. In one example, the system is a system as described in International Patent Application, Publication Number WO2009/072003, or US 20110003380 A1.

In some embodiments, the system or apparatus carries out one or more, e.g., all, of the isolation, processing, engineering, and formulation steps in an integrated or self-contained system, and/or in an automated or programmable fashion. In some aspects, the system or apparatus includes a computer and/or computer program in communication with the system or apparatus, which allows a user to program, control, assess the outcome of, and/or adjust various aspects of the processing, isolation, engineering, and formulation steps.

In some embodiments, a cell population described herein is collected and enriched (or depleted) via flow cytometry, in which cells stained for multiple cell surface markers are carried in a fluidic stream. In some embodiments, a cell population described herein is collected and enriched (or depleted) via preparative scale (FACS)-sorting. In certain embodiments, a cell population described herein is collected and enriched (or depleted) by use of microelectromechanical systems (MEMS) chips in combination with a FACS-based detection system (see, e.g., WO 2010/033140, Cho et al. (2010) *Lab Chip* 10, 1567-1573; and Godin et al. (2008) *J Biophoton.* 1(5):355-376. In both cases, cells can be labeled with multiple markers, allowing for the isolation of well-defined T cell subsets at high purity.

In some embodiments, the antibodies or binding partners are labeled with one or more detectable marker, to facilitate separation for positive and/or negative selection. For example, separation may be based on binding to fluorescently labeled antibodies. In some examples, separation of cells based on binding of antibodies or other binding partners specific for one or more cell surface markers are carried in a fluidic stream, such as by fluorescence-activated cell sorting (FACS), including preparative scale (FACS) and/or microelectromechanical systems (MEMS) chips, e.g., in combination with a flow-cytometric detection system. Such methods allow for positive and negative selection based on multiple markers simultaneously.

In some embodiments, the methods include density-based cell separation methods, such as the preparation of white blood cells from peripheral blood by lysing the red blood cells and centrifugation through a Percoll or Ficoll gradient.

In any of the aforementioned separation steps, the separation need not result in 100% enrichment or removal of a particular cell population or cells expressing a particular marker. For example, positive selection of or enrichment for cells of a particular type, such as those expressing a marker, refers to increasing the number or percentage of such cells, but need not result in a complete absence of cells not expressing the marker. Likewise, negative selection, removal, or depletion of cells of a particular type, such as those expressing a marker, refers to decreasing the number or percentage of such cells, but need not result in a complete removal of all such cells.

Cell Preparation and Expansion

In some embodiments, the provided methods include cultivation, incubation, culture, and/or genetic engineering steps. For example, in some embodiments, provided are methods for incubating and/or engineering the depleted cell populations and culture-initiating compositions.

Thus, in some embodiments, the cell populations are incubated in a culture-initiating composition. The incubation and/or engineering may be carried out in a culture vessel, such as a unit, chamber, well, column, tube, tubing set, valve, vial, culture dish, bag, or other container for culture or cultivating cells.

In some embodiments, the cells are incubated and/or cultured prior to or in connection with genetic engineering. The incubation steps can include culture, cultivation, stimulation, activation, and/or propagation.

In some embodiments, the compositions or cells are incubated in the presence of stimulating conditions or a stimulatory agent. Such conditions include those designed to induce proliferation, expansion, activation, and/or survival of cells in the population, to mimic antigen exposure, and/or to prime the cells for genetic engineering, such as for the introduction of a recombinant antigen receptor. The cells of the invention can be activated and expanded, either prior to or after genetic modification of the cells, using methods as generally described, for example without limitation, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005. The conditions can include one or more of particular media, temperature, oxygen content, carbon dioxide content, time, agents, e.g., nutrients, amino acids, antibiotics, ions, and/or stimulatory factors, such as cytokines, chemokines, antigens, binding partners, fusion proteins, recombinant soluble receptors, and any other agents designed to activate the cells.

T cells can be expanded in vitro or in vivo. Generally, the T cells of the invention can be expanded, for example, by contact with an agent that stimulates a CD3 TCR complex and a co-stimulatory molecule on the surface of the T cells to create an activation signal for the T cell. For example, chemicals such as calcium ionophore A23187, phorbol 12-myristate 13-acetate (PMA), or mitogenic lectins like phytohemagglutinin (PHA) can be used to create an activation signal for the T cell.

In some embodiments, T cell populations may be stimulated in vitro by contact with, for example, an anti-CD3 antibody, or antigen-binding fragment thereof, or an anti-CD2 antibody immobilized on a surface, or by contact with a protein kinase C activator (e.g., bryostatin) in conjunction with a calcium ionophore. In some embodiments, the T cell populations may be stimulated in vitro by contact with Muromonab-CD3 (OKT3). For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. Conditions appropriate for T cell culture include an appropriate media (e.g., Minimal Essential Media or RPMI Media 1640 or, X-vivo 5, (Lonza)) that may contain factors necessary for proliferation and viability, including serum (e.g., fetal bovine or human serum), interleukin-2 (IL-2), insulin, IFN-γ, IL-4, IL-7, GM-CSF, IL-10, IL-2, IL-15, IL-21, TGFβ, and TNF, or any other additives for the growth of cells known to the skilled artisan. In a preferred embodiment, T cells are stimulated in vitro by exposure to OKT3 and IL-2. Other additives for the growth of cells include, but are not limited to, surfactant, Plasmanate, and reducing agents such as N-acetyl-cysteine and 2-mercaptoethanol. Media can include RPMI 1640, AIM-V, DMEM, MEM, a-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37 degrees Celsius) and atmosphere (e.g., air plus 5% $CO_2$). T cells that have been exposed to varied stimulation times may exhibit different characteristics.

In some embodiments, the isolated cells of the invention can be expanded by co-culturing with tissue or cells. The cells can also be expanded in vivo, for example in the subject's blood after administrating the cell into the subject.

In some embodiments, the T cells are expanded by adding to the culture-initiating composition feeder cells, such as non-dividing peripheral blood mononuclear cells (PBMC), (e.g., such that the resulting population of cells contains at least about 5, 10, 20, or 40 or more PBMC feeder cells for each T lymphocyte in the initial population to be expanded); and incubating the culture (e.g. for a time sufficient to expand the numbers of T cells). In some aspects, the non-dividing feeder cells can comprise gamma-irradiated PBMC feeder cells. In some embodiments, the PBMC are irradiated with gamma rays in the range of about 3000 to 3600 rads to prevent cell division. In some aspects, the feeder cells are added to culture medium prior to the addition of the populations of T cells.

In some embodiments, the preparation methods include steps for freezing, e.g., cryopreserving, the cells, either before or after isolation, incubation, and/or engineering. In some embodiments, the freeze and subsequent thaw step removes granulocytes and, to some extent, monocytes in the cell population. In some embodiments, the cells are suspended in a freezing solution, e.g., following a washing step to remove plasma and platelets. Any of a variety of known freezing solutions and parameters in some aspects may be used. One example involves using PBS containing 20% DMSO and 8% human serum albumin (HSA), or other suitable cell freezing media. This is then diluted 1:1 with media so that the final concentration of DMSO and HSA are 10% and 4%, respectively. The cells are then frozen to −80 degrees Celsius at a rate of 1 degree per minute and stored in the vapor phase of a liquid nitrogen storage tank.

Therapeutic Applications

Isolated cells obtained by the methods described above, or cell lines derived from such isolated cells, can be used as a medicament in the treatment of a disease, disorder, or condition in a subject. In some embodiments, such a medicament can be used for treating cancer.

Treatments according to the present invention do not necessarily imply 100% or complete treatment. Rather, there are varying degrees of treatment of which one of ordinary skill in the art recognizes as having a potential benefit or therapeutic effect. In this respect, the inventive method can provide any amount of any level of treatment. Furthermore, the treatment provided by the inventive method can include the treatment of one or more conditions or symptoms of the disease being treated.

Cell Origin

For purposes of the inventive methods, wherein host cells or populations of cells are administered, the cells can be cells that are xenogeneic, allogeneic or autologous to the subject. Generally, the cells are autologous to the subject.

In some embodiments, the cell therapy, e.g., adoptive cell therapy, e.g., adoptive T cell therapy, is carried out by autologous transfer, in which the cells are isolated and/or otherwise prepared from the subject who is to receive the cell therapy, or from a sample derived from such a subject. Thus, in some aspects, the cells are derived from a subject, e.g., patient, in need of a treatment and the cells, following isolation and processing are administered to the same subject.

In some embodiments, the cell therapy, e.g., adoptive cell therapy, e.g., adoptive T cell therapy, is carried out by allogeneic transfer, in which the cells are isolated and/or otherwise prepared from a subject other than a subject who is to receive or who ultimately receives the cell therapy, e.g., a first subject. In such embodiments, the cells then are administered to a different subject, e.g., a second subject, of the same species. In some embodiments, the first and second subjects are genetically identical. In some embodiments, the first and second subjects are genetically similar. In some embodiments, the second subject expresses the same HLA class or supertype as the first subject.

Subject

The subject referred to herein may be any living subject. In a preferred embodiment, the subject is a mammal. The mammal referred to herein can be any mammal. As used herein, the term "mammal" refers to any mammal, including, but not limited to, mammals of the order Rodentia, such as mice and hamsters, and mammals of the order Logomorpha, such as rabbits. The mammals may be from the order Carnivora, including Felines (cats) and Canines (dogs). The mammals may be from the order Artiodactyla, including Bovines (cows) and Swines (pigs) or of the order Perssodactyla, including Equines (horses). The mammals may be of the order Primates, Ceboids, or Simoids (monkeys) or of the order Anthropoids (humans and apes)

In some embodiments, the subject, to whom the cells, cell populations, or compositions are administered is a primate, such as a human. In some embodiments, the primate is a monkey or an ape. The subject can be male or female and can be any suitable age, including infant, juvenile, adolescent, adult, and geriatric subjects. In some examples, the patient or subject is a validated animal model for disease, adoptive cell therapy, and/or for assessing toxic outcomes such as cytokine release syndrome (CRS).

In some embodiments, the subject has persistent or relapsed disease, e.g., following treatment with another immunotherapy and/or other therapy, including chemotherapy, radiation, and/or hematopoietic stem cell transplantation (HSCT), e.g., allogenic HSCT. In some embodiments, the administration effectively treats the subject despite the subject having become resistant to another therapy. In some embodiments, the subject has not relapsed but is determined to be at risk for relapse, such as at a high risk of relapse, and thus the compound or composition is administered prophylactically, e.g., to reduce the likelihood of or prevent relapse.

In some embodiments, the methods include administration of CAR expressing cells or a composition containing the cells to a subject, tissue, or cell, such as one having, at risk for, or suspected of having a disease, condition or disorder. In some embodiments, the cells, populations, and compositions are administered to a subject having the particular disease or condition to be treated, e.g., via adoptive cell therapy, such as adoptive T cell therapy. In some embodiments, the cells or compositions are administered to the subject, such as a subject having or at risk for the disease or condition. In some aspects, the methods thereby treat, e.g., ameliorate one or more symptom of the disease or condition.

Functional Activity

In one embodiment, the present invention includes a type of cellular therapy where isolated cells are genetically modified to express CARs and transcription factors and the CAR cell is infused into a subject in need thereof. Such administration can promote activation of the cells (e.g., T cell activation) in a target-specific manner, such that the cells of the disease or disorder are targeted for destruction. In the case where the cell is a T cell, CAR T cells, unlike antibody therapies, are able to replicate in vivo resulting in long-term persistence that may lead to sustained control of targeted diseases, disorders, or conditions.

In one embodiment, the isolated cells of the invention can undergo in vivo expansion and can persist for an extended amount of time. In another embodiment, where the isolated cell is a T cell, the isolated T cells of the invention evolve into specific memory T cells that can be reactivated to inhibit any additional target cell growth. CAR T cells may differentiate in vivo into a central memory-like state upon encounter and subsequent elimination of target cells expressing the surrogate antigen.

Without wishing to be bound by any particular theory, the anti-tumor immunity response elicited by the isolated CAR-modified immune cells may be an active or a passive immune response. In addition, the CAR mediated immune response may be part of an adoptive immunotherapy approach in which CAR-modified immune cells induce an immune response specific to the antigen binding domain in the CAR.

In certain embodiments, CAR expressing cells are modified in any number of ways, such that their therapeutic or prophylactic efficacy is increased. For example, the CAR may be conjugated either directly or indirectly through a linker to a targeting moiety. The practice of conjugating compounds, e.g., the CAR, to targeting moieties is known in the art. See, for instance, Wadhwa et al., *J. Drug Targeting* 1995; 3(2):111-127, and U.S. Pat. No. 5,087,616.

Once the cells are administered to a subject (e.g., a human), the biological activity of the engineered cell populations and/or antibodies in some aspects is measured by any of a number of known methods. Parameters to assess include specific binding of an engineered or natural T cell or other immune cell to antigen, in vivo, e.g., by imaging, or ex vivo, e.g., by ELISA or flow cytometry. In certain embodiments, the ability of the engineered cells to destroy target cells can be measured using any suitable method known in the art, such as cytotoxicity assays described in, for example, Kochenderfer et al., *J. Immunotherapy*, 32(7): 689-702 (2009), and Herman et al. *J. Immunological Methods*, 285 (1): 25-40 (2004). In certain embodiments, the biological activity of the cells also can be measured by assaying expression and/or secretion of certain cytokines, such as GM-CSF, IL-3, MIP-1a, TNF-α, IL-10, IL-13, IFN-γ, or IL-2.

In some aspects the biological activity is measured by assessing clinical outcome, such as reduction in tumor burden or load, stabilization of tumor, progression free survival, or overall survival.

Target Cancer Cells

The recombinant cells of this invention especially find application in the treatment of subjects having or suspected of having cancer by reducing the size of a tumor or preventing the growth or re-growth or re-occurrence of a tumor in these subjects. Accordingly, the invention further relates to a method for reducing growth, preventing tumor formation or treating cancer or preventing the growth or re-growth or re-occurrence of a tumor in a subject by delivering to a subject in need of treatment an effective amount of the nucleic acid construct of this invention. The step of delivering the nucleic acid construct to the subject generally involves introducing a nucleic acid construct of the invention into an isolated immune cell (e.g., an autologous immune cell isolated from peripheral blood mononuclear cells (PBMC) or immune cells derived from an allogeneic third party-derived immune cell donor) and introducing into the subject the transformed immune cell, thereby effecting anti-tumor responses to reduce or eliminate tumors in the subject, as in an adoptive T cell therapy method. For example, the immune cell may comprise a T cell and the subject is suffering from, or is believed to be suffering from, or is diagnosed as having tumor or cancer, e.g., a B7-H6-expressing cancer. For example, the B7-H6 scFv-containing CAR molecules encoded by exemplary nucleic acid constructs of the present invention may be administered to the subject in the form of a recombinant immune cell engineered to express the anti-B7-H6 scFv CAR molecule and one or more transcription factors, such as T-bet, STAT1, and/or STAT4.

Cancers that may be treated include tumors that are not vascularized, or not yet substantially vascularized, as well as vascularized tumors. The cancers may comprise non-solid tumors (such as hematological tumors, for example, leukemias and lymphomas) or may comprise solid tumors. Types of cancers to be treated with the CARs of the invention include, but are not limited to, carcinoma, blastoma, and sarcoma, and certain leukemia or lymphoid malignancies, benign and malignant tumors, and malignancies e.g., sarcomas, carcinomas, and melanomas. Adult tumors/cancers and pediatric tumors/cancers are also included.

Hematologic cancers are cancers of the blood or bone marrow. Examples of hematological (or hematogenous) cancers include leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

Solid tumors are abnormal masses of tissue that usually do not contain cysts or liquid areas. Solid tumors can be benign or malignant. Different types of solid tumors are named for the type of cells that form them (such as sarcomas, carcinomas, and lymphomas). Examples of solid tumors, such as sarcomas and carcinomas, include fibrosarcoma, myxosarcoma, liposarcoma, chondrosarcoma, osteosarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, and CNS tumors (such as a glioma (such as brainstem glioma and mixed gliomas), glioblastoma (also known as glioblastoma multiforme) astrocytoma, CNS lymphoma, germinoma, medulloblastoma, Schwannoma craniopharyogioma, ependymoma, pinealoma, hemangioblastoma, acoustic neuroma, oligodendroglioma, menangioma, neuroblastoma, retinoblastoma and brain metastases).

Methods of testing a CAR for the ability to recognize target cells and for antigen specificity are known in the art. For instance, Clay et al., *J. Immunol.*, 163: 507-513 (1999), teaches methods of measuring the release of cytokines (e.g., interferon-γ, granulocyte/monocyte colony stimulating factor (GM-CSF), tumor necrosis factor α (TNF-α) or interleukin 2 (IL-2)). In addition, CAR function can be evaluated by measurement of cellular cytotoxicity, as described in Zhao et al., *J. Immunol.*, 174: 4415-4423 (2005).

A biopsy is the removal of tissue and/or cells from an individual. Such removal may be to collect tissue and/or cells from the individual in order to perform experimentation on the removed tissue and/or cells. This experimentation may include experiments to determine if the individual has and/or is suffering from a certain condition or disease-state. The condition or disease may be, e.g., cancer. With respect to detecting the presence of antigen-expressing tumor cells in a host, the sample comprising cells of the host can be a sample comprising whole cells, lysates thereof, or a fraction of the whole cell lysates, e.g., a nuclear or cytoplasmic fraction, a whole protein fraction, or a nucleic acid fraction. If the sample comprises whole cells, the cells can be any cells of the host, e.g., the cells of any organ or tissue, including blood cells or endothelial cells.

Other Targets

The nucleic acid constructs and recombinant immune cells of this invention also find application in the treatment of infections caused by infectious agents such as viruses, fungi, yeast, parasites, and bacteria. Thus, the invention also relates to a method for reducing growth of, or preventing infection by, an infectious agent (e.g., a virus, fungus, yeast, parasite or bacterium) or treating an infection in a subject by delivering to a subject in need of treatment an effective amount of the nucleic acid construct of this invention. The step of delivering the nucleic acid construct to the subject generally involves introducing a nucleic acid construct of the invention into an isolated T cell (e.g., an autologous, allogeneic, xenogeneic or third party-derived T cell) and introducing the transformed T cell into the subject, thereby reducing or eliminating the growth of the infectious agent in the subject and/or treating the infection.

In embodiments where it is sought to inhibit the activity or growth of, or deplete, a patient's B7-H6-positive cells, the ability of the anti-B7-H6 scFv-containing CAR molecules expressed by the engineered immune cells, for example, to inhibit proliferation of or deplete a patient's B7-H6-positive cells is assessed. If the B7-H6-positive cells are depleted by the anti-B7-H6 scFv-containing CAR molecules expressed by the engineered immune cells, the patient is determined to be responsive to therapy with an engineered immune cell expressing an anti-B7-H6 CAR molecule and transcription factor.

The subject engineered immune cells may be used in treating or diagnosing human or animal subjects. Animal subjects include, but are not limited to, animal models, such as, mammalian models of conditions or disorders associated with elevated or excessive MICA expression such as the cancers, autoimmune diseases, inflammatory conditions and infections described herein.

In some embodiments, the recombinant cells of the invention may be used to treat an inflammatory, immune or autoimmune disorder or disease.

The conditions that can be treated with the present compositions and methods include, but are not limited to: inflammatory skin diseases including psoriasis and dermatitis (e.g., atopic dermatitis); dermatomyositis; systemic scleroderma and sclerosis; conditions associated with inflammatory bowel disease (such as Crohn's disease and ulcerative colitis); colitis; gastritis; respiratory distress syndrome (including adult respiratory distress syndrome and ARDS); dermatitis; meningitis; encephalitis; uveitis; glomerulonephritis; allergic conditions such as eczema and asthma and other conditions involving infiltration of T cells and chronic inflammatory responses; atherosclerosis; leukocyte adhesion deficiency; rheumatoid arthritis; systemic lupus erythematosus (SLE); diabetes mellitus (e.g., Type I diabetes mellitus); multiple sclerosis; Reynaud's syndrome; autoimmune thyroiditis; allergic encephalomyelitis; Sjögren's syndrome; juvenile onset diabetes; and immune responses associated with acute and delayed hypersensitivity mediated by cytokines and T-lymphocytes typically found in tuberculosis, sarcoidosis, polymyositis, granulomatosis and vasculitis; Wegener's disease; pernicious anemia (Addison's disease); diseases involving leukocyte diapedesis; central nervous system (CNS) inflammatory disorder; multiple organ injury syndrome; hemolytic anemia (including, but not limited to cryoglobinemia or Coombs positive anemia); myasthenia gravis; antigen-antibody complex mediated diseases; anti-glomerular basement membrane disease; antiphospholipid syndrome; allergic neuritis; Graves' disease; Lambert-Eaton myasthenic syndrome; pemphigoid bullous; pemphigus; autoimmune polyendocrinopathies; vitiligo; Reiter's disease; stiff-man syndrome; Behçet's disease; giant cell arteritis; immune complex nephritis; IgA nephropathy; IgM polyneuropathies; immune thrombocytopenic purpura (ITP) or autoimmune thrombocytopenia and autoimmune hemolytic diseases; Hashimoto's thyroiditis; autoimmune hepatitis; autoimmune hemophilia; autoimmune lymphoproliferative syndrome (ALPS); autoimmune uveoretinitis; Guillain-Barre syndrome; Goodpasture's syndrome; mixed connective tissue disease; autoimmune-associated infertility; polyarteritis nodosa; alopecia areata; idiopathic myxedema; graft versus host disease; muscular dystrophy (Duchenne, Becker, Myotonic, Limb-girdle, Facioscapulohumeral, Congenital, Oculopharyngeal, Distal, and Emery-Dreifuss); diabetes mellitus (e.g., Type I diabetes mellitus); and juvenile onset diabetes.

In some embodiments, the recombinant cells of the invention may be used to treat an infectious disease, e.g., one caused by bacteria, protozoa, fungi, or viruses.

Infectious bacteria include, but are not limited to, gram negative and gram positive bacteria. Gram positive bacteria include, but are not limited to *Pasteurella* species, Staphylococci species, and *Streptococcus* species. Gram negative bacteria include, but are not limited to, *Escherichia coli*, *Pseudomonas species*, and *Salmonella* species. Specific examples of infectious bacteria include but are not limited to: *Helicobacter pyloris, Borrelia burgdorferi, Legionella pneumophilia, Mycobacteria* sps (e.g., *M. tuberculosis, M. avium, M. intracellulare, M. kansasii, M. gordonae*), *Staphylococcus aureus, Pseudomonas aeruginosa, Neisseria gonorrhoeae, Neisseria meningitidis, Listeria monocytogenes, Streptococcus pyogenes* (Group A *Streptococ-* cus), *Streptococcus agalactiae* (Group B *Streptococcus*), *Streptococcus* (*viridans* group), *Streptococcus faecalis, Streptococcus bovis, Streptococcus* (anaerobic species), *Streptococcus pneumoniae*, pathogenic *Campylobacter* sp., *Enterococcus* sp., *Haemophilus influenzae, Bacillus anthracis, Corynebacterium diphtheriae, Corynebacterium* sp., *Erysipelothrix rhusiopathiae, Clostridium perfringens, Clostridium tetani, Enterobacter aerogenes, Klebsiella pneumoniae, Pasteurella multocida, Bacteroides* sp., *Fusobacterium nucleatum, Streptobacillus moniliformis, Treponema pallidum, Treponema pertenue, Leptospira, Rickettsia*, and *Actinomyces israelli*. Viruses include, but are not limited to, enteroviruses, rotaviruses, adenovirus, hepatitis virus. Specific examples of viruses that have been found in humans include but are not limited to: Retroviridae (e.g., human immunodeficiency viruses (HIV); Picornaviridae (e.g., polio viruses, hepatitis A virus; enteroviruses, human Coxsackie viruses, rhinoviruses, echoviruses); Calciviridae (e.g., strains that cause gastroenteritis); Togaviridae (e.g., equine encephalitis viruses, rubella viruses); Flaviviridae (e.g., dengue viruses, encephalitis viruses, yellow fever viruses); Coronaviridae (e.g., coronaviruses); Rhabdoviridae (e.g., vesicular stomatitis viruses, rabies viruses); Filoviridae (e.g., ebola viruses); Paramyxoviridae (e.g., parainfluenza viruses, mumps virus, measles virus, respiratory syncytial virus); Orthomyxoviridae (e.g., influenza viruses); Bungaviridae (e.g., Hantaan viruses, bunga viruses, phleboviruses and Nairo viruses); Arenaviridae (hemorrhagic fever viruses); Reoviridae (e.g., reoviruses, orbiviurses and rotaviruses); Birnaviridae; Hepadnaviridae (Hepatitis B virus); Parvoviridae (parvoviruses); Papovaviridae (papillomaviruses, polyoma viruses); Adenoviridae (most adenoviruses); Herpesviridae (herpes simplex virus (HSV) 1 and 2, varicella zoster virus, cytomegalovirus (CMV)); Poxviridae (variola viruses, vaccinia viruses, pox viruses); Iridoviridae (e.g., African swine fever virus); and unclassified viruses (e.g., the etiological agents of spongiform encephalopathies, the agent of delta δhepatitis, the agents of non-A, non-B hepatitis; Norwalk and related viruses, and astroviruses).

Protozoan infections that may be treated include, but are not limited to, infections caused by Sarcodina (e.g., *Entamoeba*); *Mastigophora* (e.g., *Giardia, Leishmania*); *Ciliophora* (e.g., *Balantidium*); and Sporozoa (e.g., *Plasmodium, Cryptosporidium*).

Modes of Administration

To facilitate administration, the transduced immune cells, for example recombinant/engineered T cells, preferably CD4$^+$ T cells, according to the invention can be made into a pharmaceutical composition or made implant-appropriate for administration in vivo, with appropriate carriers or diluents, which further can be pharmaceutically acceptable. The means of making such a composition or an implant have been described in the art (see, for instance, Remington: *The Science and Practice of Pharmacy*, Lippincott Williams & Wilkins, 21st edition (2005). Where appropriate, the transduced immune cells can be formulated into a preparation in semisolid or liquid form, such as a capsule, solution, injection, inhalant, or aerosol, in the usual ways for their respective route of administration. Means known in the art can be used to prevent or minimize release and absorption of the composition until it reaches the target tissue or organ, or to ensure timed-release of the composition. Desirably, however, a pharmaceutically acceptable form is employed which does not adversely affect the desired immune potentiating effects of recombinant cells according to the invention. For example transduced T cells can be made into a pharmaceutical composition containing a balanced salt solution, preferably Hanks' balanced salt solution, or normal saline. Additional examples of carriers or diluents include fats, oils, water, saline solutions, lipids, liposomes, resins, binders, fillers and the like, or combinations thereof. The composition may also include various antioxidants to retard oxidation of one or more component.

The compositions of the present invention may be administered in a number of ways depending upon whether local or systemic treatment is desired.

In the case of adoptive cell therapy, methods for administration of cells for adoptive cell therapy are known and may be used in connection with the provided methods and compositions. For example, adoptive T cell therapy methods are described, e.g., in US Patent Application Publication No. 2003/0170238 to Gruenberg et al; U.S. Pat. No. 4,690,915 to Rosenberg; Rosenberg (2011) Nat Rev Clin Oncol. 8(10): 577-85). See, e.g., Themeli et al. (2013) Nat Biotechnol. 31(10): 928-933; Tsukahara et al. (2013) Biochem Biophys Res Commun 438(1): 84-9; Davila et al. (2013) PLoS ONE 8(4): e61338.

One skilled in the art will recognize that, although more than one route can be used for administration, a particular route can provide a more immediate and more effective reaction than another route. For example, intradermal delivery may be advantageously used over inhalation for the treatment of melanoma. Local or systemic delivery can be accomplished by administration comprising application or instillation of the formulation into body cavities, inhalation or insufflation of an aerosol, or by parenteral introduction, comprising intramuscular, intravenous, intraportal, intrahepatic, peritoneal, subcutaneous, or intradermal administration.

Although systemic (intravenous, IV) injection is favored in clinical applications because of its ease of administration, several preclinical studies (Carpenito, et al. (2009) *Proc. Natl. Acad. Sci. USA* 106:3360-3365; Song, et al. (2011) *Cancer Res.* 71:4617-4627; Parente-Pereira, et al. (2011) *J. Clin. Immunol.* 31:710-718) suggest that the regional (intratumoral, IT or intraperitoneal, IP) administration of T cells may provide optimal therapeutic effects, which may be in part due to increased T-cell trafficking to the tumor. For example, it has been shown that CAR T cells remain at the site of inoculation with minimal systemic absorption when delivered via IP or IT routes (Parente-Pereira, et al. (2011) *J. Clin. Immunol.* 31:710-718). In contrast, after IV administration, CAR T cells initially reach the lungs and then are redistributed to the spleen, liver, and lymph nodes. In addition, RNA CAR-electroporated T cells may be particularly suitable for regional administration, due to the transient nature of the CAR expression on the T cells (Zhao, et al. (2010) *Cancer Res.* 70:9053-9061). Furthermore, clinical studies have shown the feasibility and safety of both the intratumoral and intraperitoneal injection of T cells (Canevari, et al. (1995) *J. Natl. Cancer Inst.* 87:1463-1469; Duval, et al. (2006) *Clin. Cancer Res.* 12:1229-123680). Overall, a local route of administration of the recombinant T cells may provide the optimal therapeutic effect and decrease the potential for the "on-target, off-organ" toxicity discussed below.

In general, administration may be topical, parenteral, or enteral.

The compositions of the invention are typically suitable for parenteral administration. As used herein, "parenteral administration" of a pharmaceutical composition includes any route of administration characterized by physical breaching of a tissue of a subject and administration of the pharmaceutical composition through the breach in the tissue, thus generally resulting in the direct administration into the blood stream, into muscle, or into an internal organ. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal, intravenous, intraarterial, intrathecal, intraventricular, intraurethral, intracranial, intratumoral, intrasynovial injection or infusions; and kidney dialytic infusion techniques. In a preferred embodiment, parenteral administration of the compositions of the present invention comprises subcutaneous or intraperitoneal administration.

Formulations of a pharmaceutical composition suitable for parenteral administration generally comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampoules or in multi-dose containers containing a preservative. Formulations for parenteral administration include, but are not limited to, suspensions, solutions, emulsions in oily or aqueous vehicles, pastes, and the like. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition. Parenteral formulations also include aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water. Exemplary parenteral administration forms include solutions or suspensions in sterile aqueous solutions, for example, aqueous propylene glycol or dextrose solutions. Such dosage forms can be suitably buffered, if desired. Other parentally-administrable formulations which are useful include those which comprise the active ingredient in microcrystalline form, or in a liposomal preparation. Formulations for parenteral administration may be formulated to be immediate and/or modified release. Modified release formulations include delayed-, sustained-, pulsed-, controlled-, targeted and programmed release.

A composition suitable for parenteral administration conveniently includes a sterile aqueous preparation of the inventive composition, which preferably is isotonic with the blood of the recipient. This aqueous preparation can be formulated according to known methods using suitable dispersing or wetting agents and suspending agents. The sterile injectable preparation also can be a sterile injectable solution or suspension in a non-toxic parenterally-acceptable diluent or solvent, for example, as a solution in 1,3-butane diol. Among the acceptable vehicles and solvents that can be employed are water, Ringer's solution, and isotonic sodium chloride solution. In addition, sterile, fixed oils are conventionally employed as a solvent or suspending medium. For this purpose any bland, fixed oil can be employed, such as synthetic mono- or di-glycerides. In addition, fatty acids such as oleic acid can be used in the preparation of injectables. Carrier formulations suitable for oral, subcutaneous, intravenous, intramuscular, etc. administrations can be found in Remington's Pharmaceutical Sciences, Mack Publishing Co., Easton, PA.

Preferably, the formulated composition comprising isolated CAR-expressing cells is suitable for administration via injection.

The terms "oral", "enteral", "enterally", "orally", "non-parenteral", "non-parenterally", and the like, refer to administration of a compound or composition to an individual by a route or mode along the alimentary canal. Examples of "oral" routes of administration of a composition include, without limitation, swallowing liquid or solid forms of a composition from the mouth, administration of a composition through a nasojejunal or gastrostomy tube, intraduodenal administration of a composition, and rectal administration, e.g., using suppositories for the lower intestinal tract of the alimentary canal.

Pharmaceutical compositions and formulations for topical administration may include transdermal patches, ointments, lotions, creams, gels, drops, suppositories, sprays, liquids, semi-solids, monophasic compositions, multiphasic compositions (e.g., oil-in-water, water-in-oil), foams, microsponges, liposomes, nanoemulsions, aerosol foams, polymers, fullerenes, and powders. Conventional pharmaceutical carriers, aqueous, powder or oily bases, thickeners and the like may be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal, or intraventricular administration may include sterile aqueous solutions that may also contain buffers, diluents and other suitable additives such as, but not limited to, penetration enhancers, carder compounds and other pharmaceutically acceptable carriers or excipients.

The pharmaceutical composition can contain suitable buffering agents, including, for example, acetic acid in a salt, citric acid in a salt, boric acid in a salt, and phosphoric acid in a salt. The pharmaceutical compositions also optionally can contain suitable preservatives, such as benzalkonium chloride, chlorobutanol, parabens, and thimerosal.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical compositions of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, liquid syrups, soft gels, suppositories, aerosols, and enemas. The compositions of the present invention may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product. Agents that enhance uptake of oligonucleotides at the cellular level may also be added to the pharmaceutical and other compositions of the present invention. For example, cationic lipids, such as lipofectin (U.S. Pat. No. 5,705,188), cationic glycerol derivatives, and polycationic molecules, such as polylysine (WO 97/30731), also enhance the cellular uptake of oligonucleotides.

The compositions of the present invention may additionally contain other adjunct components conventionally found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Formulations comprising populations of CAR-expressing cells may include pharmaceutically acceptable excipient(s). Excipients included in the formulations will have different purposes depending, for example, on the CAR construct, the subpopulation of cells used, and the mode of administration. Examples of generally used excipients include, without limitation: saline, buffered saline, dextrose, water-for-infection, glycerol, ethanol, and combinations thereof, stabilizing agents, solubilizing agents and surfactants, buffers and preservatives, tonicity agents, bulking agents, and lubricating agents. The formulations comprising populations of CAR-expressing cells will typically have been prepared and cultured in the absence of any non-human components, such as animal serum (e.g., bovine serum albumin).

The composition of the invention includes a carrier, desirably a pharmaceutically acceptable carrier. The pharmaceutically acceptable carrier can be any suitable pharmaceutically acceptable carrier. The term pharmaceutically acceptable carrier, as used herein, means one or more compatible solid or liquid fillers, diluents, other excipients, or encapsulating substances, which are suitable for administration into a human or veterinary patient (e.g., a physiologically acceptable carrier or a pharmacologically acceptable carrier). The term carrier denotes an organic or inorganic ingredient, natural or synthetic, with which the active ingredient is combined to facilitate the application. The pharmaceutically acceptable carrier can be co-mingled with one or more of the active components and with each other, when more than one pharmaceutically acceptable carrier is present in the composition in a manner so as not to substantially impair the desired pharmaceutical efficacy.

Pharmaceutically acceptable materials typically are capable of administration to a patient without the production of significant undesirable physiological effects such as nausea, dizziness, rash, or gastric upset. It is, for example, desirable for a composition comprising a pharmaceutically acceptable carrier not to be immunogenic when administered to a human patient for therapeutic purposes.

The formulation or composition may also contain more than one active ingredient useful for the particular indication, disease, or condition being treated with the binding molecules or cells, preferably those with activities complementary to the binding molecule or cell, where the respective activities do not adversely affect one another. Such active ingredients are suitably present in combination in amounts that are effective for the purpose intended. Thus, in some embodiments, the pharmaceutical composition further includes other pharmaceutically active agents or drugs, such as chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc. In some embodiments, the pharmaceutically active agents or drugs may comprise immune checkpoint inhibitors, e.g., drugs that target PD-1, PD-L1, PD-L2, LAG3, CTLA4, KIR, CD244, B7-H3, B7-H4, BTLA, HVEM, GALS, TIM3, and/or A2aR. Examples of these inhibitors include, but are not limited to, pidilizumab, nivolumab, pembrolizumab, atezolizumab, MDX-1105, BMS-936559, MEDI4736, MPDL3280A, MSB0010718C, tremelimumab, and ipilimumab, which may be administered alone or in combination with other agents, e.g., GM-CSF.

The foregoing methods of treatment can further include therapeutic regimens wherein another therapeutic agent is administered which is useful for treating the particular disorder. These therapeutic agents may be separately or jointly administered. In some instances the combination may elicit a synergistic benefit on immunity.

A pharmaceutical composition of the invention can be used alone or in combination with other well-established agents useful for treating cancer or an infectious disease. Whether delivered alone or in combination with other agents, the pharmaceutical composition of the invention can be delivered via various routes and to various sites in a mammalian, particularly human, body to achieve a particular effect. One skilled in the art will recognize that, although more than one route can be used for administration, a particular route can provide a more immediate and more effective reaction than another route. For example, intradermal delivery may be advantageously used over inhalation for the treatment of melanoma. Local or systemic delivery can be accomplished by administration comprising application or instillation of the formulation into body cavities, inhalation or insufflation of an aerosol, or by parenteral introduction, comprising intramuscular, intravenous, intraportal, intrahepatic, peritoneal, subcutaneous, or intradermal administration.

For example, when the disorder to be treated involves a B7-H6-expressing cancer, the method can further include co-administration of a cytotoxic, cystostatic, or anti-angiogenic agent suitable for treating the cancer. If the cancer is a B-cell lymphoma, the method can further include, for example, co-administration of rituximab, alemtuzumab, or a CHOP chemotherapeutic regimen. When the disorder is a viral infection, the method can further include co-administration of antiviral therapies, including but not limited to nucleotide and nucleoside analogues (Lamivudine, Adefovir dipivoxil, Tenofovir, and Entecavir) and other immune modulatory drugs (steroids, rituximab, interferon-α-2b and pegylated interferon-a-2a). When the disorder is an inflammatory condition, the method can further include co-administration of immunomodulatory therapies, including but not limited to azathioprine, basiliximab, cyclosporine A, daclizumab, mycophenolic acid, mycophenolate mofetil, prednisone, sirolimus, and tacrolimus.

The pharmaceutical composition in some aspects can employ time-released, delayed release, and sustained release delivery systems such that the delivery of the composition occurs prior to, and with sufficient time to cause, sensitization of the site to be treated. Many types of release delivery systems are available and known. Such systems can avoid repeated administrations of the composition, thereby increasing convenience to the subject and the physician.

Many types of release delivery systems are available and known to those of ordinary skill in the art. Suitable release delivery systems include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are lipids including sterols such as cholesterol, cholesterol esters, and fatty acids or neutral fats such as mono-di- and tri-glycerides; hydrogel release systems; silastic systems; peptide based systems; wax coatings; compressed tablets using conventional binders and excipients; partially fused implants; and the like. Specific examples include, but are not limited to erosional systems in which the active composition is contained in a form within a matrix such as those described in U.S. Pat. Nos. 4,452,775, 4,667,014, 4,748,034, and 5,239,660; and diffusional systems in which an active component permeates at a controlled rate from a polymer such as described in U.S. Pat. Nos. 3,832,253 and 3,854,480. In addition, pump-based hardware delivery systems can be used, some of which are adapted for implantation.

Dosing

The pharmaceutical composition in some embodiments contains the CAR cells in amounts effective to treat or prevent the disease or condition, such as a therapeutically effective or prophylactically effective amount. Therapeutic or prophylactic efficacy in some embodiments is monitored by periodic assessment of treated subjects. For repeated administrations over several days or longer, depending on the condition, the treatment is repeated until a desired suppression of disease symptoms occurs. However, other dosage regimens may be useful and can be determined. The desired dosage can be delivered by a single bolus administration of the composition, by multiple bolus administrations of the composition, or by continuous infusion administration of the composition.

Desirably an effective amount or sufficient number of the isolated transduced T cells is present in the composition and introduced into the subject such that long-term, specific, anti-tumor or anti-infectious agent responses are established to reduce the size or regrowth of a tumor or growth of an infectious agent than would otherwise result in the absence of such treatment. Desirably, the amount of transduced T cells reintroduced into the subject causes a 10%, 20%, 30%, 40%, 50%, 60%, 70%, 80%, 90%, 95%, 98%, or 100% decrease in tumor size when compared to otherwise same conditions, wherein the transduced T cells are not present.

Accordingly, the amount of transduced T cells administered should take into account the route of administration and should be such that a sufficient number of the transduced T cells will be introduced so as to achieve the desired therapeutic response. Furthermore, the amounts of each active agent included in the compositions described herein (e.g., the amount per each cell to be contacted or the amount per certain body weight) can vary in different applications. In general, the concentration of transduced T cells desirably should be sufficient to provide in the subject being treated at least from about $1\times10^6$ to about $1\times10^9$ transduced T cells, even more desirably, from about $1\times10^7$ to about $5\times10^8$ transduced T cells, although any suitable amount can be utilized either above, e.g., greater than $5\times10^8$ cells, or below, e.g., less than $1\times10^7$ cells. The dosing schedule can be based on well-established cell-based therapies (see, e.g., Topalian & Rosenberg (1987) *Acta Haematol.* 78 Suppl 1:75-6; U.S. Pat. No. 4,690,915) or an alternate continuous infusion strategy can be employed.

In certain embodiments, in the context of genetically engineered cells expressing the CARs, a subject is administered the range of about one million to about 100 billion cells, such as, e.g., 1 million to about 50 billion cells (e.g., about 5 million cells, about 25 million cells, about 500 million cells, about 1 billion cells, about 5 billion cells, about 20 billion cells, about 30 billion cells, about 40 billion cells, or a range defined by any two of the foregoing values), such as about 10 million to about 100 billion cells (e.g., about 20 million cells, about 30 million cells, about 40 million cells, about 60 million cells, about 70 million cells, about 80 million cells, about 90 million cells, about 10 billion cells, about 25 billion cells, about 50 billion cells, about 75 billion cells, about 90 billion cells, or a range defined by any two of the foregoing values), and in some cases about 100 million cells to about 50 billion cells (e.g., about 120 million cells, about 250 million cells, about 350 million cells, about 450 million cells, about 650 million cells, about 800 million cells, about 900 million cells, about 3 billion cells, about 30 billion cells, about 45 billion cells) or any value in between these ranges, and/or such a number of cells per kilogram of body weight of the subject. For example, in some embodiments the administration of the cells or population of cells can comprise administration of about $10^3$ to about $10^9$ cells per kg body weight including all integer values of cell numbers within those ranges.

A composition of the invention can be provided in unit dosage form wherein each dosage unit, e.g., an injection, contains a predetermined amount of the composition, alone or in appropriate combination with other active agents. The term unit dosage form, as used herein, refers to physically discrete units suitable as unitary dosages for human and animal subjects, each unit containing a predetermined quantity of the composition of the invention, alone or in combination with other active agents, calculated in an amount sufficient to produce the desired effect, in association with a pharmaceutically acceptable diluent, carrier, or vehicle, where appropriate. The specifications for the novel unit dosage forms of the invention depend on the particular pharmacodynamics associated with the pharmaceutical composition in the particular subject.

The cells or population of cells can be administrated in one or more doses. In some embodiments, said effective amount of cells can be administrated as a single dose. In some embodiments, said effective amount of cells can be administrated as more than one dose over a period time. Timing of administration is within the judgment of managing physician and depends on the clinical condition of the patient. The cells or population of cells may be obtained from any source, such as a blood bank or a donor. While individual needs vary, determination of optimal ranges of effective amounts of a given cell type for a particular disease or conditions within the skill of the art. An effective amount means an amount which provides a therapeutic or prophylactic benefit. The dosage administrated will be dependent upon the age, health and weight of the recipient, kind of concurrent treatment, if any, frequency of treatment and the nature of the effect desired. In some embodiments, an effective amount of cells or composition comprising those cells are administrated parenterally. In some embodiments, administration can be an intravenous administration. In some embodiments, administration can be directly done by injection within a tumor.

For purposes of the invention, the amount or dose of the inventive CAR material administered should be sufficient to effect a therapeutic or prophylactic response in the subject or animal over a reasonable time frame. For example, the dose of the inventive CAR material should be sufficient to bind to antigen, or detect, treat or prevent disease in a period of from about 2 hours or longer, e.g., about 12 to about 24 or more hours, from the time of administration. In certain embodiments, the time period could be even longer. The dose will be determined by the efficacy of the particular inventive CAR material and the condition of the animal (e.g., human), as well as the body weight of the animal (e.g., human) to be treated.

For purposes of the invention, an assay, which comprises, for example, comparing the extent to which target cells are lysed or IFN-γ is secreted by T cells expressing the inventive CAR, polypeptide, or protein upon administration of a given dose of such T cells to a mammal, among a set of mammals of which is each given a different dose of the T cells, could be used to determine a starting dose to be administered to a mammal. The extent to which target cells are lysed or IFN-γ is secreted upon administration of a certain dose can be assayed by methods known in the art.

In some embodiments, the cells are administered as part of a combination treatment, such as simultaneously with or sequentially with, in any order, another therapeutic intervention, such as an antibody or engineered cell or receptor or agent, such as a cytotoxic or therapeutic agent. The cells or antibodies in some embodiments are co-administered with one or more additional therapeutic agents or in connection with another therapeutic intervention, either simultaneously or sequentially in any order. In some contexts, the cells are co-administered with another therapy sufficiently close in time such that the cell populations enhance the effect of one or more additional therapeutic agents, or vice versa. In some embodiments, the cells or antibodies are administered prior to the one or more additional therapeutic agents. In some embodiments, the cells or antibodies are administered after to the one or more additional therapeutic agents.

In some embodiments, a lymphodepleting chemotherapy is administered to the subject prior to, concurrently with, or after administration (e.g., infusion) of CAR cells. In an example, the lymphodepleting chemotherapy is administered to the subject prior to administration of the cells. For example, the lymphodepleting chemotherapy ends 1~4 days (e.g., 1, 2, 3, or 4 days) prior to CAR cell infusion. In embodiments, multiple doses of CAR cells are administered, e.g., as described herein. In embodiments, a lymphodepleting chemotherapy is administered to the subject prior to, concurrently with, or after administration (e.g., infusion) of a CAR-expressing cell described herein. Examples of lymphodepletion include, but may not be limited to, nonmyeloablative lymphodepleting chemotherapy, myeloablative lymphodepleting chemotherapy, total body irradiation, etc. Examples of lymphodepleting agents include, but are not limited to, antithymocyte globulin, anti-CD3 antibodies, anti-CD4 antibodies, anti-CD8 antibodies, anti-CD52 antibodies, anti-CD2 antibodies, TCRαβ blockers, anti-CD20 antibodies, anti-CD19 antibodies, Bortezomib, rituximab, anti-CD154 antibodies, rapamycin, CD3 immunotoxin, fludarabine, cyclophosphamide, busulfan, melphalan, Mabthera, Tacrolimus, alefacept, alemtuzumab, OKT3, OKT4, OKT8, OKT11, fingolimod, anti-CD40 antibodies, anti-BR3 antibodies, Campath-1H, anti-CD25 antibodies, calcineurin inhibitors, mycophenolate, and steroids, which may be used alone or in combination.

Kits

Any of the compositions described herein may be included in a kit provided by the present invention. The kits will thus include, in suitable container means, recombinant/engineered cells of the present invention, and/or vectors encoding the nucleic acid constructs of the present invention, and/or nucleic acid constructs or related reagents of the present invention. In some embodiments, the kit further includes an additional agent for treating cancer or an infectious disease, and the additional agent may be combined with the nucleic acid construct(s) or cells, or other components of the kit of the present invention or may be provided separately in the kit. In some embodiments, means of taking a sample from an individual and/or of assaying the sample may be provided in the kit. In certain embodiments the kit includes cells, buffers, cell media, vectors, primers, restriction enzymes, salts, and so forth, for example.

The components of the kits may be packaged either in aqueous media or in lyophilized form. The container means of the kits will generally include at least one vial, test tube, flask, bottle, syringe or other container means, into which a component may be placed, and preferably, suitably aliquoted. Where there is more than one component in the kit, the kit also will generally contain a second, third or other additional container into which the additional components may be separately placed. However, various combinations of components may be comprised in a vial. Such containers may include injection or blow-molded plastic containers into which the desired vials are retained.

When the components of the kit are provided in one and/or more liquid solutions, the liquid solution is an aqueous solution, with a sterile aqueous solution being particularly preferred. The compositions may also be formulated into a syringe compatible composition. In which case, the container means may itself be a syringe, pipette, and/or other such like apparatus, from which the formulation may be applied to an infected area of the body, injected into an animal, and/or even applied to and/or mixed with the other components of the kit. However, the components of the kit may be provided as dried powder(s). When reagents and/or components are provided as a dry powder, the powder can be reconstituted by the addition of a suitable solvent. It is envisioned that the solvent may also be provided in another container means.

Variations

Included in the scope of the invention are functional portions of the inventive CARs and transcription factors described herein. The term "functional portion" when used in reference to a CAR refers to any part or fragment of the CAR of the invention, which part or fragment retains the biological activity of the CAR of which it is a part (the parent CAR). Functional portions encompass, for example, those parts of a CAR that retain the ability to recognize target cells, or detect, treat, or prevent a disease, to a similar extent, the same extent, or to a higher extent, as the parent CAR. In reference to the parent CAR, the functional portion can comprise, for instance, about 10%, 25%, 30%, 50%, 68%, 80%, 90%, 95%, or more, of the parent CAR.

The functional portion can comprise additional amino acids at the amino or carboxy terminus of the portion, or at both termini, which additional amino acids are not found in the amino acid sequence of the parent CAR. Desirably, the additional amino acids do not interfere with the biological function of the functional portion, e.g., recognize target cells, detect cancer, treat or prevent cancer, etc. More desirably, the additional amino acids enhance the biological activity, as compared to the biological activity of the parent CAR.

Included in the scope of the invention are functional variants of the inventive CARs and transcription factors described herein. The term "functional variant" as used herein refers to a polypeptide (CAR, transcription factor, or protein) having substantial or significant sequence identity or similarity to a parent polypeptide, which functional variant retains the biological activity of the polypeptide of which it is a variant. Functional variants encompass, for example, those variants of the CARs described herein (the parent CAR) that retain the ability to recognize target cells to a similar extent, the same extent, or to a higher extent, as the parent CAR. In reference to the parent CAR, the functional variant can, for instance, be at least about 30%, 50%, 75%, 80%, 90%, 98% or more identical in amino acid sequence to the parent CAR.

A functional variant can, for example, comprise the amino acid sequence of the parent polypeptide with at least one conservative amino acid substitution. Alternatively or additionally, the functional variants can comprise the amino acid sequence of the parent polypeptide with at least one non-conservative amino acid substitution. In this case, it is preferable for the non-conservative amino acid substitution to not interfere with or inhibit the biological activity of the functional variant. The non-conservative amino acid substitution may enhance the biological activity of the functional variant, such that the biological activity of the functional variant is increased as compared to the parent polypeptide.

Amino acid substitutions of the polypeptides described herein are preferably conservative amino acid substitutions. Conservative amino acid substitutions are known in the art, and include amino acid substitutions in which one amino acid having certain physical and/or chemical properties is exchanged for another amino acid that has the same or similar chemical or physical properties. For instance, the conservative amino acid substitution can be an acidic/negatively charged polar amino acid substituted for another acidic/negatively charged polar amino acid (e.g., Asp or Glu), an amino acid with a nonpolar side chain substituted for another amino acid with a nonpolar side chain (e.g., Ala, Gly, Val, Ile, Leu, Met, Phe, Pro, Trp, Cys, Val, etc.), a basic/positively charged polar amino acid substituted for another basic/positively charged polar amino acid (e.g. Lys, His, Arg, etc.), an uncharged amino acid with a polar side chain substituted for another uncharged amino acid with a polar side chain (e.g., Asn, Gln, Ser, Thr, Tyr, etc.), an amino acid with a beta-branched side-chain substituted for another amino acid with a beta-branched side-chain (e.g., Ile, Thr, and Val), an amino acid with an aromatic side-chain substituted for another amino acid with an aromatic side chain (e.g., His, Phe, Trp, and Tyr), etc.

Also, amino acids may be added or removed from the sequence based on vector design.

The polypeptide (CAR, transcription factor, protein) can consist essentially of the specified amino acid sequence or sequences described herein, such that other components, e.g., other amino acids, do not materially change the biological activity of the functional variant.

The polypeptides of embodiments of the invention (including functional portions and functional variants) can be of any length, i.e., can comprise any number of amino acids, provided that the polypeptides (or functional portions or functional variants thereof) retain their biological activity, e.g., the ability to specifically bind to antigen, detect diseased cells in a mammal, or treat or prevent disease in a mammal, etc. For example, the polypeptide can be about 50 to about 5000 amino acids long, such as 50, 70, 75, 100, 125, 150, 175, 200, 300, 400, 500, 600, 700, 800, 900, 1000 or more amino acids in length.

The polypeptides of embodiments of the invention (including functional portions and functional variants of the invention) can comprise synthetic amino acids in place of one or more naturally-occurring amino acids. Such synthetic amino acids are known in the art, and include, for example, aminocyclohexane carboxylic acid, norleucine, α-amino n-decanoic acid, homoserine, S-acetylaminomethyl-cysteine, trans-3- and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, α-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine, α-aminocyclopentane carboxylic acid, a-aminocyclohexane carboxylic acid, α-aminocycloheptane carboxylic acid, a-(2-amino-2-norbornane)-carboxylic acid, α,γ-diaminobutyric acid, α,β-diaminopropionic acid, homophenylalanine, and α-tert-butylglycine.

The polypeptides of embodiments of the invention (including functional portions and functional variants) can be glycosylated, amidated, carboxylated, phosphorylated, esterified, N-acylated, cyclized via, e.g., a disulfide bridge, or converted into an acid addition salt and/or optionally dimerized or polymerized, or conjugated.

The polypeptides of embodiments of the invention (including functional portions and functional variants thereof) can be obtained by methods known in the art. The polypeptides may be made by any suitable method of making polypeptides or proteins. Suitable methods of de novo synthesizing polypeptides and proteins are described in references, such as Chan et al., Fmoc Solid Phase Peptide Synthesis, Oxford University Press, Oxford, United Kingdom, 2000; Peptide and Protein Drug Analysis, ed. Reid, R., Marcel Dekker, Inc., 2000; Epitope Mapping, ed. Westwood et al., Oxford University Press, Oxford, United Kingdom, 2001; and U.S. Pat. No. 5,449,752. Also, polypeptides and proteins can be recombinantly produced using the nucleic acids described herein using standard recombinant methods. See, for instance, Sambrook et al., Molecular Cloning: A Laboratory Manual, 3rd ed., Cold Spring Harbor Press, Cold Spring Harbor, N.Y. 2001; and Ausubel et al., Current Protocols in Molecular Biology, Greene Publishing Associates and John Wiley & Sons, N Y, 1994. Further, some of the polypeptides of the invention (including functional portions and functional variants thereof) can be isolated and/or purified from a source, such as a plant, a bacterium, an insect, a mammal, e.g., a rat, a human, etc. Methods of isolation and purification are well-known in the art. Alternatively, the polypeptides described herein (including functional portions and functional variants thereof) can be commercially synthesized by companies. In this respect, the polypeptides described herein can be synthetic, recombinant, isolated, and/or purified.

The following examples are put forth in order to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

The following examples are put forth in order to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

EXAMPLES

Example 1: Generation of CAR Constructs and CAR-T Cells

Generation of CAR Constructs

Figure 1B:
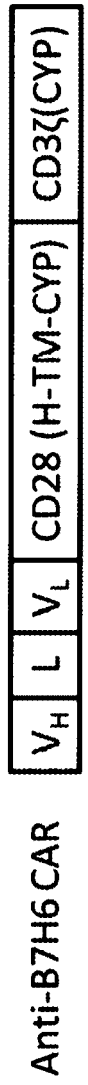

A CAR construct having anti-B7H6 specificity and two endodomains was constructed using molecular biology and genetics techniques known in the art. The B7-H6-specific monoclonal antibody clone 47.39 was used as the basis for the antigen receptor, fused in frame to the endodomains of CD28 and CD3 zeta. (See, WO 2013/0169691; Wu et al., *Gene Ther.*, 22(8):675-684, 2015; Wu et al., *J. Immunol.*, 194(11):5305-5311, 2015; and Zhang et al., *J. Immunol.*, 189(5):2290-2299, 2012; the disclosures of which are specifically incorporated herein by references for all purposes). A polynucleotide encoding an scFv fragment of the anti-B7H6 monoclonal antibody clone 47.39 (TZ.47) was created and fused to polynucleotides encoding CD28 and CD3 ζ, as disclosed in Wu et al. (See FIG. 1B.)

Briefly, the B7H6-specific CAR was constructed by fusing the single chain variable fragment (scFv) of an anti-B7H6 hybridoma, clone 47.39, in frame to the human CD28 hinge (H), transmembrane (TM), and cytoplasmic (CYP) domains (corresponding to amino acids ("aa") 135-220 of human CD28) and a human CD3 ζ endodomain (aa 52-164 of CD3 ζ). The anti-B7H6 scFv (amino acid SEQ ID NO:13, nucleic acid sequence SEQ ID NO:24) was generated by fusing the variable regions of the 47.39 antibody heavy chain ($V_H$, aa 1-134) and light chain ($V_L$, aa 23-129) in frame with a 15 amino acid glycine (G)-serine (S) linker. This linker has the amino acid sequence $(G_4S)_3$, i.e. 3 repeats of GGGGS. The B7H6-specific CAR construct (the "TZ.47 CAR", Tz.47-28-3z, amino acid SEQ ID NO: 25, nucleic acid SEQ ID NO: 26) was then cloned into a retroviral vector pFB-neo (Stratagene, Palo Alto, CA), to create "Pfb-TZ.47-28-3z". As known to those skilled in the art, pFB-neo plasmid vectors are designed for retroviral gene delivery and expressed, and are derived from the Moloney murine leukemia virus (MMLV). Such vectors also contain the bacterial origin of replication and ampicillin-resistance gene from pBR322, as well as a multiple cloning site. The vector pFB-neo also provides a cassette consisting of the internal ribosome entry site (IRES) from encephalomyocarditis virus (EMCV) and the neomycin-resistance gene (neo'). Retroviral transduction of T cells was performed as previously described in Zhang et al., *J. Immunol.*, 189(5): 2290-2299, 2012.

Figure 1C:
Figure 2A:
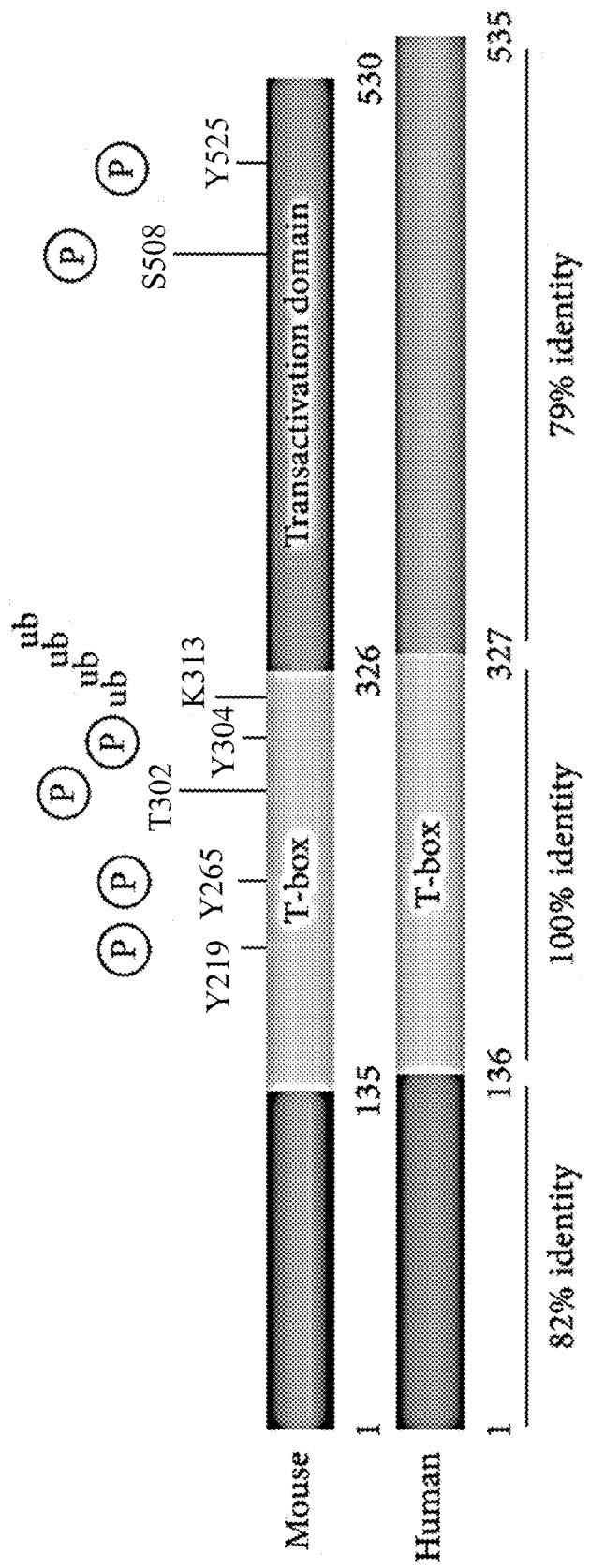
FIG. 2A shows the domains of the mouse and human T-bet proteins along with various amino acids that may be phosphorylated or ubiquitinated. Sequence similarities between the domains of the human and mouse homologues are also indicated.

A second CAR construct similar to the TZ.47 CAR construct was generated like Pfb-TZ.47-28-3z, in which the vector also includes a polynucleotide encoding the mouse T-bet transcription factor, to create vector "Pfb-TZ.47-28-3z-MsTBET". Briefly, a polynucleotide encoding the full length mouse transcription factor T-bet was inserted into the Pfb-TZ.47-28-3z construct described above. A schematic of the generated construct is provided in FIG. 1C.

The CAR and transcription factor are separated by a T2A linker sequence encoding the self-cleaving peptide 2A, allowing efficient expression of both proteins from a single vector. (See, Kim et al., *PLoS ONE*, 6(4):e18556; and Chang et al., *mAbs*, 7(2):403-412, 2015). The CAR and transcription factor T-bet are under control of a retroviral LTR promoter.

Transduction

Primary human T cells were transduced with either construct TZ.47 CAR or TZ.47 CAR+MsTBET. Transduction of CAR plasmids into packaging 293T cells was performed using LIPOFECTAMINE™ 2000 (Life Technology, Carlsbad, CA) following the manufacturer's protocols. Cell-free media containing viral particles was collected after 3 days and used to transduce packaging cell lines to produce stable virus producing cells.

Transduction of murine primary T cells was conducted using ecotropic viruses collected from vector-transduced GP+E86 cells, whereas dualtropic retroviral viruses generated from vector-transduced PT67 cells were used to infect human primary T cells. Primary T cells from spleens of B6 mice were infected 18-24 hours after concanavalin A (ConA, 1 µL/mL) stimulation. Two days after infection, transduced primary T cells ($\sim$0.5-1×10$^6$/ml) were selected in RPMI-10 media containing G418 (1 mg/ml) plus 25 U/ml rHuIL-2 for additional 3 days. Viable cells were isolated using HISTOPAQUE-1083 (Sigma, St. Louise, MO), washed extensively, and expanded for 2 days without G418 before functional analyses or intravenous injection.

CD4$^+$ T cells were obtained from mouse spleen cells by known methods. These CD4$^+$ T cells were transduced with Pfb-TZ.47-28-3z or Pfb-TZ.47-28-3z-MsTBET using known methods, as disclosed above. Cells were activated with anti-CD3 monoclonal antibody OKT3 (40 ng/mL; eBioscience, San Diego, CA) and anti-CD28 monoclonal antibody for 48 hours prior to examination. Cells were examined on day 8.

Primary human T cells from cell clones were activated with anti-CD3 mAb OKT3 (40 ng/mL; eBioscience) plus IL-2 (50 U/mL) for 3 days before transduction. G418 selection and T cell expansion were done following similar procedures for culturing mouse T cells.

Example 2: Characterization of CAR-T Cell Cytokine Secretion

Mouse RMA/S tumor cells expressing B7H6 were positively sorted in Miltenyi magnetic columns with CD4 microbeads based on the manufacturer's protocol. RMA/S cells are known to possess decreased cell surface expression of major histocompatibility complex (MHC) class I molecules and be deficient in presenting endogenously synthesized influenza virus nucleoprotein (NP) to cytotoxic T cells (CTL). (See, Esquivel et al., *JEM*, 175(1):163-168, 1992). RMA/S tumor cells expressing B7H6 were generated by transducing the parental cell line with a dualtropic retrovirus containing the full length human B7H6 gene, followed by selection with 1 mg/mL G418 (Corning, Cambridge, MA) or 2 μg/mL Puromycin (Sigma-Aldrich, Saint Louis, MO) selection for 7 days.

Cell-free media was isolated after the 24-hour incubation and cytokine production of transduced T cells cultured with RMA-B7H6 cells was determined by multiplex analysis using known methods.

Results are shown in FIG. 3A and FIG. 3B. As can be seen from the Figures, T cells expressing TZ.47 CAR with MsTBET produced significantly more of the $T_H1$ cytokines GM-CSF, IL-3, MIP-1a, IFNγ, IL-2, IL-10, and TNFα as compared to the same construct expressed on the T cells without MsTBET. Only IL-13, a $T_H2$ cytokine, was expressed at higher levels in T cells expressing the TZ.47 CAR alone, as compared to the construct that co-expresses MsTBET.

Figure 4A:
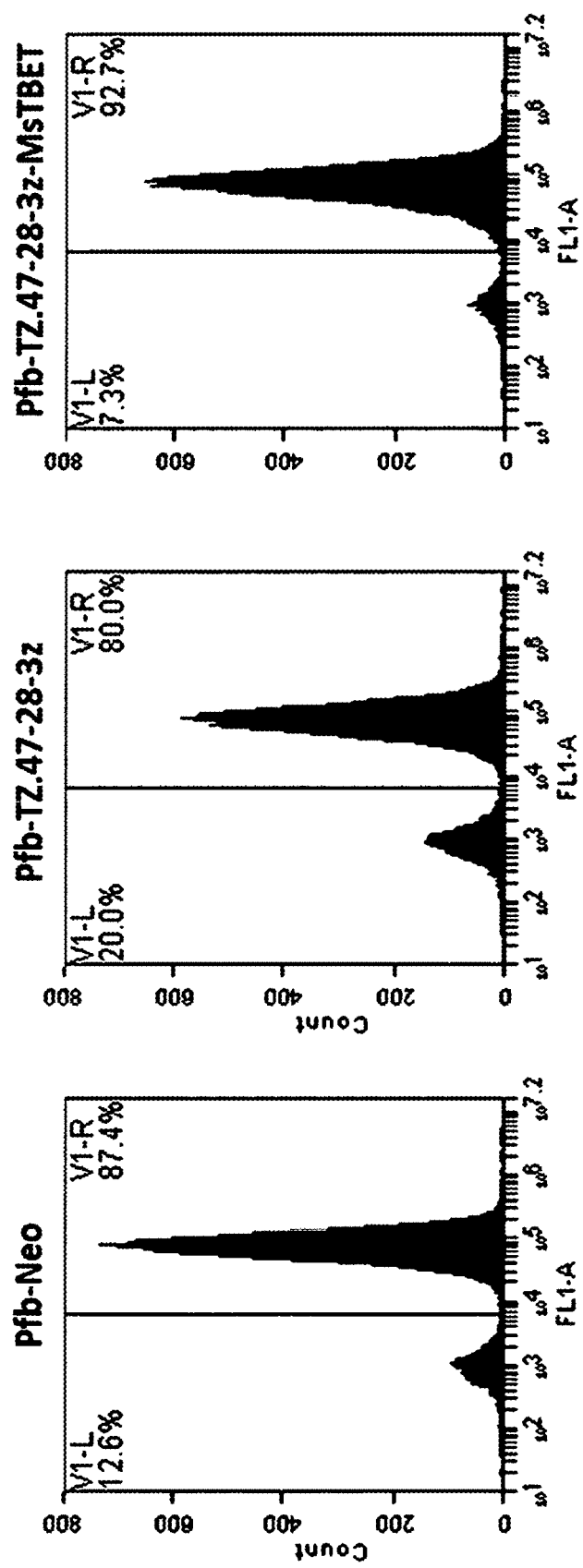

Example 3: Expression of TZ.47 CAR in ConA-Stimulated Mouse Splenocytes with or without TBET Mouse splenocytes were obtained by known methods. Cells were transduced with Pfb-Neo vector alone, Pfb-TZ.47-28-3z or Pfb-TZ.47-28-3z-MsTBET, using known methods, as disclosed above, and then activated with the mitogen concanavalin A (ConA) for 24 hours (FIGS. 4A-4C, left, middle, and right panels, respectively). Cells were then analyzed on day 8 for CD8 expression (FIG. 4A), MsTBET expression (FIG. 4B), and CAR expression (FIG. 4C). Cells were gated on live cells and the percent above background was plotted as shown in FIGS. 4A-4C.

The data show that co-expression of transcription factor T-bet markedly increased CAR expression in mouse CART cells activated with ConA. More specifically, 3.7% of T cells transduced with vector alone (Pfb-neo) measured positive for anti-B7H6 CAR expression (background), 11.2% of T cells transduced with vector Pfb-TZ.47-28-3z measured positive for anti-B7H6 CAR expression, and 31.6% of T cells transduced with both vector Pfb-TZ.47-28-3z measured positive for anti-B7H6 CAR expression (FIG. 4C, left, middle, and right panels, respectively).

Example 4: Expression of TZ.47 CAR in CD4+ T Cells with or without TBET

CD4+ T cells were obtained from mouse spleen cells by known methods. These CD4+ T cells were transduced with Pfb-TZ.47-28-3z or Pfb-TZ.47-28-3z-MsTBET using known methods, as disclosed above. Cells were activated with plate bound anti-CD3 monoclonal antibody OKT3 (40 ng/mL; eBioscience, San Diego, CA) and soluble anti-CD28 monoclonal antibodies for 48 hours prior to transduction. T cells were examined on day 8.

Figure 5A:
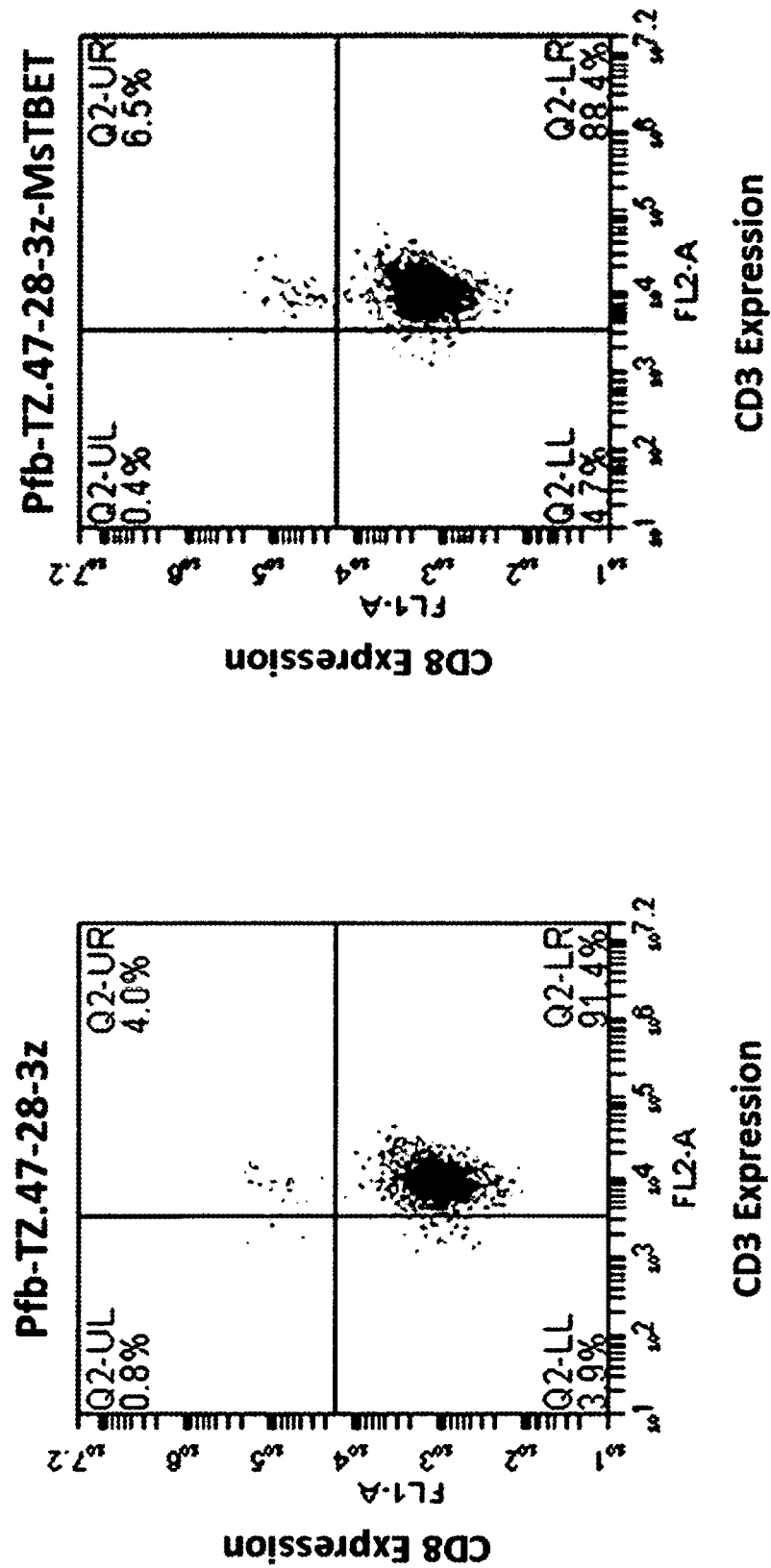
FIGS. 5A-5C show that expression of TZ.47 CAR on CD4+ T cells is increased when co-expressed with MsT-bet. CD4+ sorted T cells were transduced with Pfb-TZ.47-28-3z or Pfb-TZ.47-28-3z-MsTBET and activated with anti-CD3 monoclonal antibody and anti-CD28 monoclonal antibody. Cells were gated on live cells.
Figure 5B:
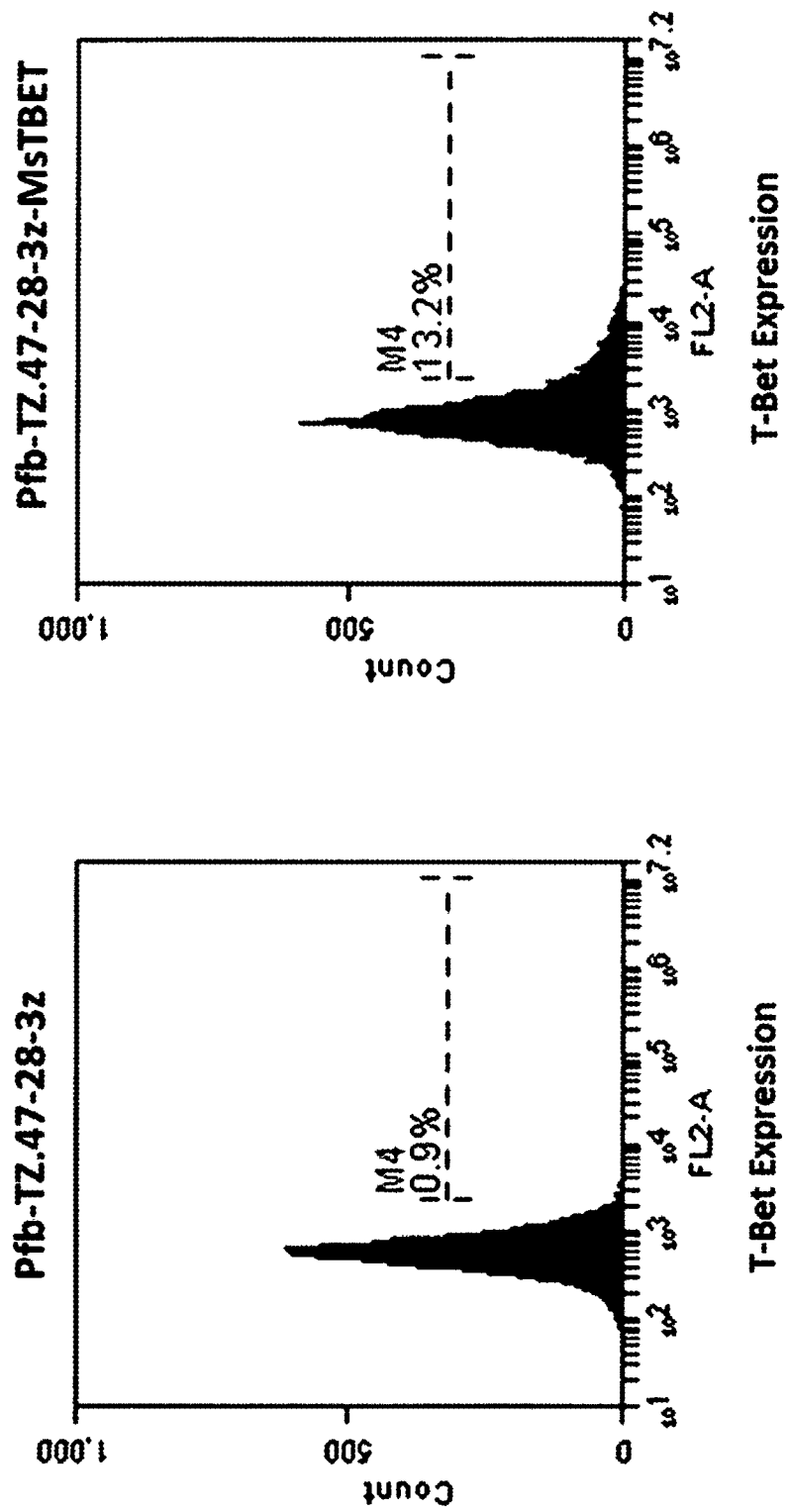
Figure 5C:
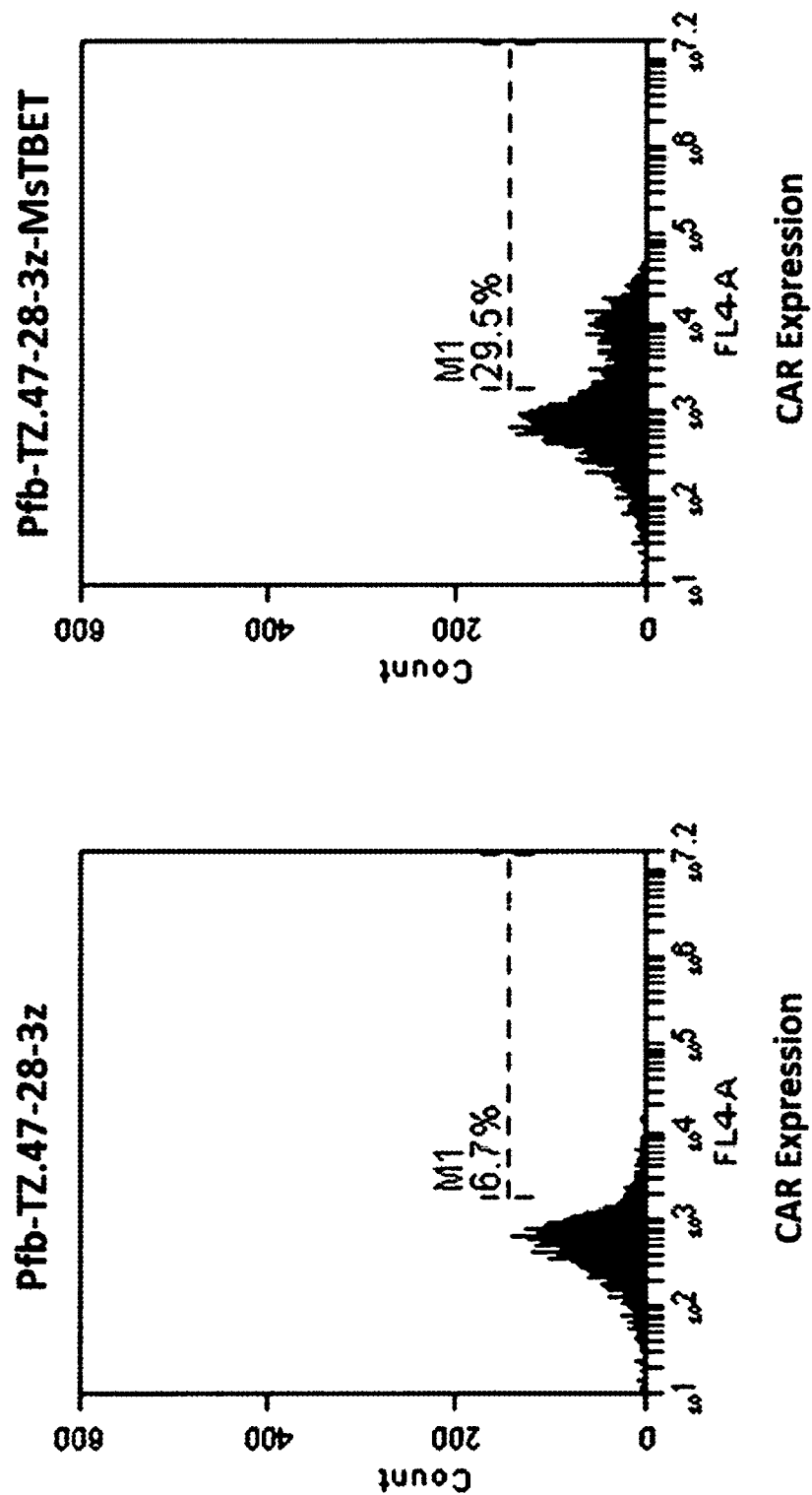

Cells were gated on live cells and the percent above background was plotted as shown in FIGS. 5A-5C. FIG. 5A shows CD8 expression for cells transduced with Pfb-TZ.47-28-3z (left panel) or Pfb-TZ.47-28-3z-MsTBET (right panel). FIG. 5B shows MsT-bet expression for cells transduced with Pfb-TZ.47-28-3z (left panel) or Pfb-TZ.47-28-3z-MsTBET (right panel). FIG. 5C shows CAR expression for cells transduced with Pfb-TZ.47-28-3z (left panel) or Pfb-TZ.47-28-3z-MsTBET (right panel). The data show that co-expression of transcription factor T-bet markedly increased CAR expression on activated mouse CD4+ T cells.

Example 5: Expression of TZ.47 CAR in CD4+ T Cells with T-Bet Mutants

Figures 6A, 6B:
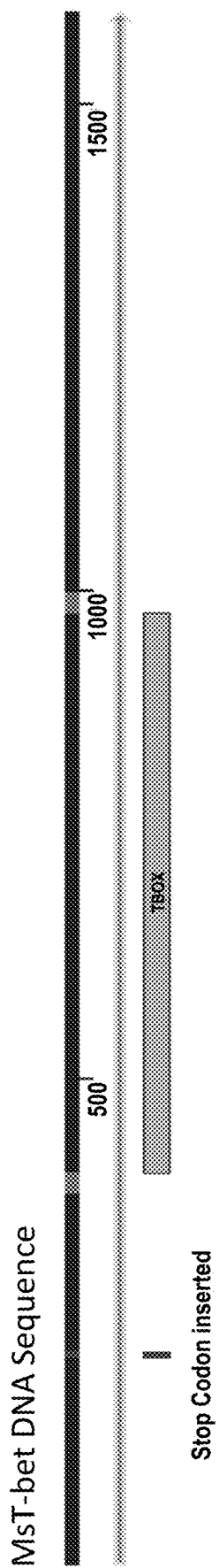
FIGS. 6A-6B depict T-bet mutations and provide Mean Fluorescence Intensity (MFI) data for the mutations, respectively.

Two mutants of T-bet were generated to determine their impact on CAR expression. In the "TBET-STOP" mutant (amino acid SEQ ID NO:29, and nucleic acid SEQ ID NO:30), a stop codon is inserted at nucleotide position 214 (214 to 217 changed to TGA, FIG. 6A, stop codon position noted). In the "TBET-Tbox Del" mutant (amino acid SEQ ID NO:31, and nucleic acid SEQ ID NO:32), the Tbox nucleotides 403 to 978 are deleted, creating a truncated T-bet protein (FIG. 6A, T-box deletion region represented by gray box).

Nucleic acids encoding T-bet mutants were generated using known methods. Briefly, the polynucleotide encoding the mouse T-bet gene was cloned into vector. DNA cloning primers were designed to create mutant T-bet constructs. Primers to design Pfb-TZ.47-28-3z-AG23(TBET-STOP) encoded a stop codon at nucleotide positions 214-217. Primers for Pfb-TZ.47-28-3z-AG24 (TBET-Tbox Del) were designed to exclude the T-box domain. For each construct, two fragments were initially cloned using Pfb-TZ.47-28-3z-MsTBET as a template. The fragments were subsequently joined through overlapping PCR and the products were ligated into Pfb Vectors.

The T-bet mutants were inserted into Pfb-TZ.47-28-3z vectors to create the constructs: Pfb-TZ.47-28-3z-AG23 (TBET-STOP) and Pfb-TZ.47-28-3z-AG24 (TBET-Tbox Del). Mean Fluorescence Intensity (MFI) values for the two mutants, as compared to vectors Pfb-neo, Pfb-TZ.47-28-3z, and Pfb-TZ.47-28-3z-MsTBET are provided in FIG. 6B. The CAR construct for the TBET-STOP mutant has the amino acid sequence of SEQ ID NO:36, encoded by the nucleic acid sequence of SEQ ID NO:37. The CAR construct for the TBET-Tbox Del mutant has the amino acid sequence of SEQ ID NO:38, encoded by the nucleic acid sequence of SEQ ID NO:39.

CD4+ T cells were obtained from CD8KO mice, which are deficient in CD8a expression. CD4+ cells were transduced with the constructs noted above and activated with anti-CD3 monoclonal antibody OKT3 (40 ng/mL; eBioscience, San Diego, CA) and anti-CD28 monoclonal antibody for seven days. Flow cytometry was performed on day 8.

Figure 7A:
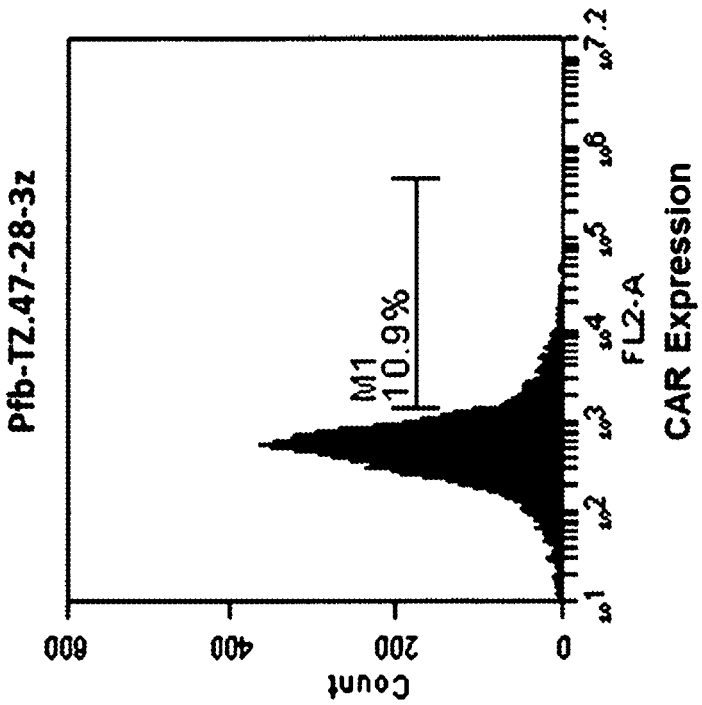
FIGS. 7A-7E show that co-expression of T-bet and T-bet mutants increases the expression of chimeric antigen receptors. CD4+ cells were obtained from CD8KO mice and transduced with the control and various TZ.47 CAR vectors. TZ.47 expression was detected for pfb-neo (FIG. 7A), pfb-TZ.47-28-3z (FIG. 7B), pfb-TZ.47-28-3z-MsTBET (FIG. 7C), pfb-TZ.47-28-3z-TBET-STOP (FIG. 7D), and pfb-TZ.47-28-3z-Tbox-Del (FIG. 7E).
Figure 7B:
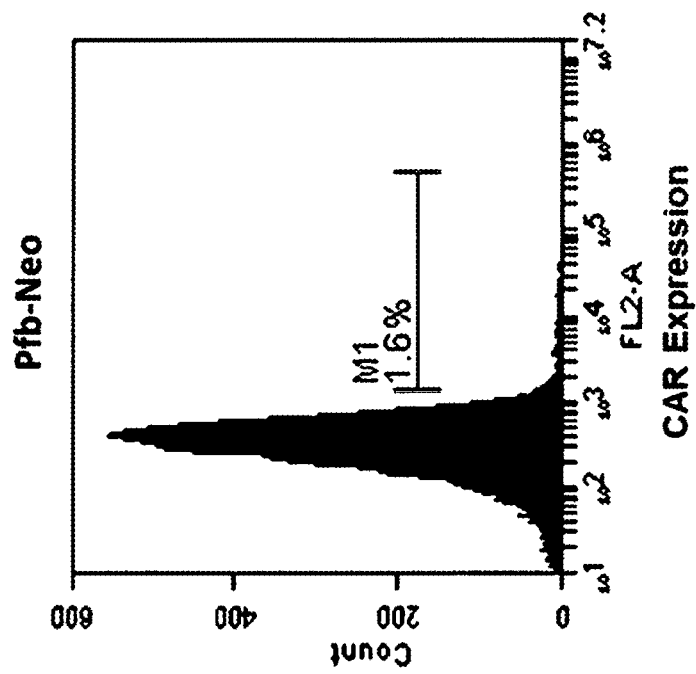
Figure 7C:
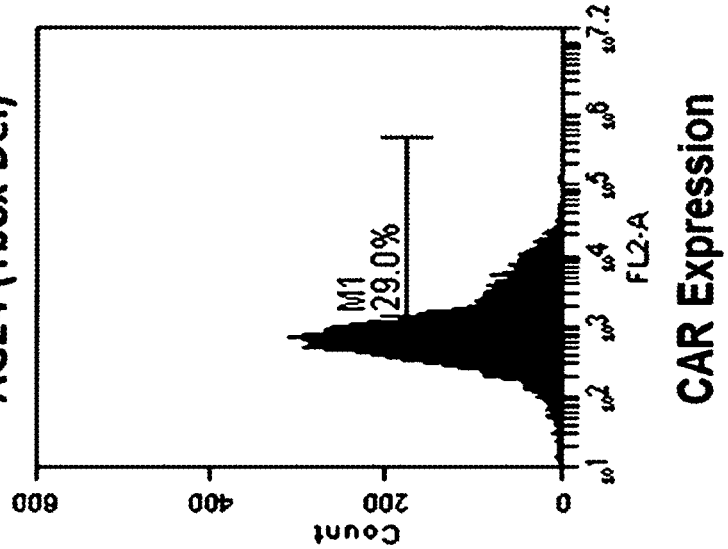
Figure 7D:
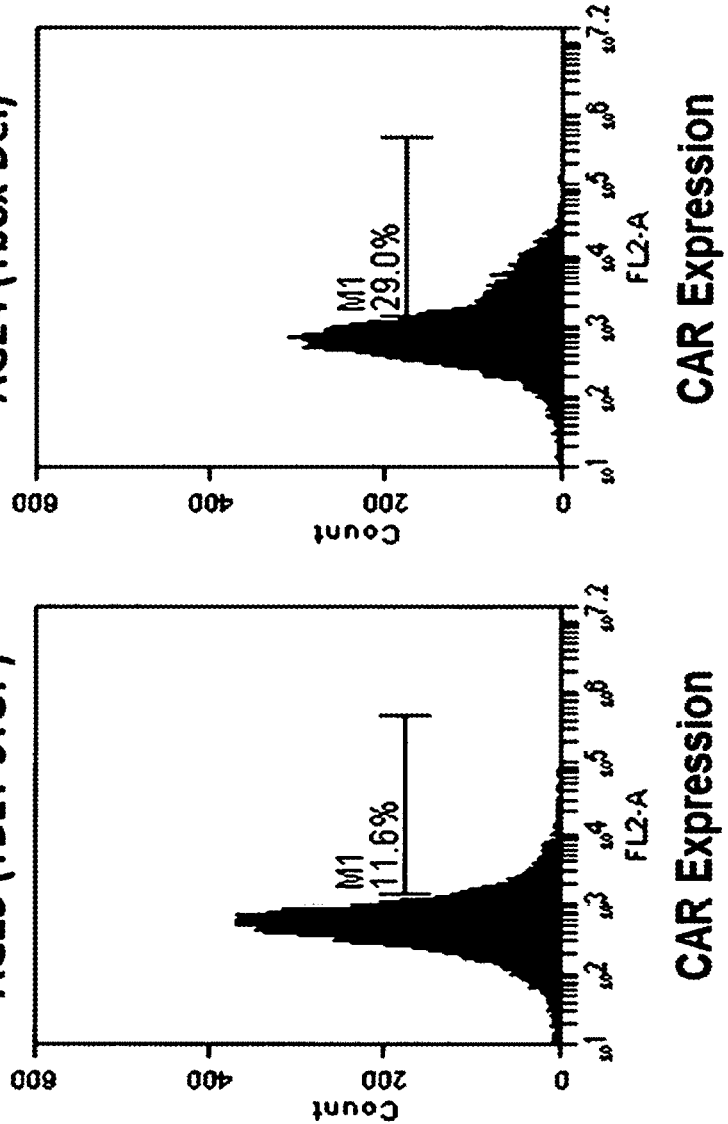
Figure 7E:
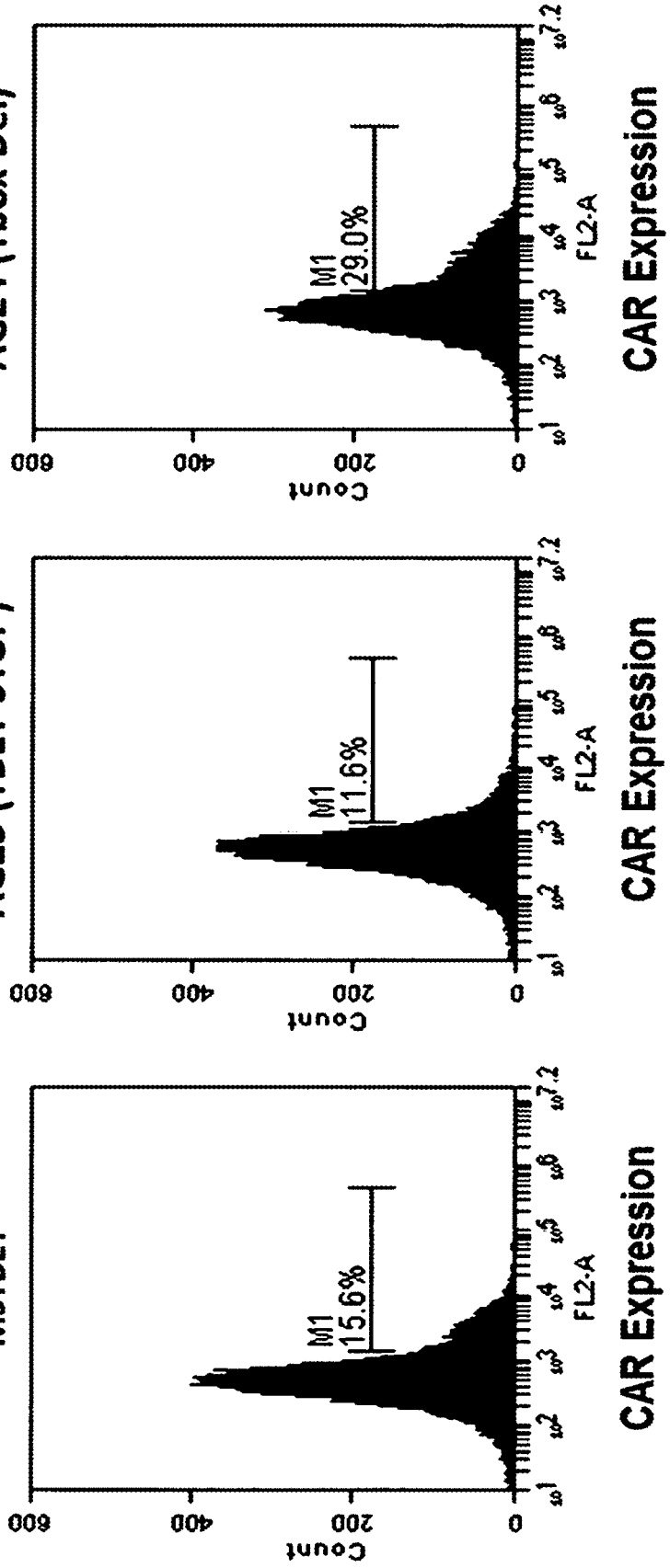

Controls included CD8KO cells transduced with Pfb-Neo alone and Pfb-TZ.47-28-3z alone, the results of which are depicted in FIG. 7A and FIG. 7B, respectively. Additional data shown in FIGS. 7C-E, reflect the results obtained from CD8KO cells transduced with each of Pfb-TZ.47-28-3z-MsTBET (full length T-bet transcription factor), Pfb-TZ.47-28-3z-AG23 (T-bet with a stop codon at nucleotide 214), and Pfb-TZ.47-28-3z-AG24 (T-bet with a truncation at nucleotide 403), respectively. Results indicate that the expression of T-bet (FIG. 7C) or the T-box deletion mutant (TBET-Tbox Del, FIG. 7E) increased CAR expression in T cells compared to CAR alone (FIG. 7B) or CAR with truncated T-bet (TBET Stop, FIG. 7D). Thus, TZ.47 CAR expression and CD4+-dependent cytokine secretion is enhanced by T-bet expression and T-box deletion mutant T-bet expression.

Example 6: IFNγ Production by CAR-T Cells

Cells transduced with the constructs noted above were examined for IFNγ secretion after exposure to RMA cells or RMA cells expressing B7H6. CD4+ T cells were obtained from CD8KO mice and transduced with the constructs as noted above. The cells were stimulated by exposure to anti-CD3 monoclonal antibody and anti-CD28 monoclonal antibody as described above. At the end of the transduction/expansion period, T cells were then co-cultured with either RMA cells or RMA cells expressing B7H6 (as described above).

Amounts of IFNγ in cell-free conditioned media were analyzed with ELISA. As shown in FIG. 8, left panel (RMA), little or no IFNγ was secreted by cells exposed only to RMA cells. However, anti-B7H6 CAR T cells exposed to RMA cells expressing ligand B7-H6 (right panel, RMA B7H6) secreted IFNγ. Particularly, T-bet transduced cells (FIG. 8, Tz-47-28-3z-TBET, right panel, gray bar) secreted more IFNγ than cells transduced with CAR alone (Tz-47-28-3z, black bar) when exposed to RMA cells expressing B7-H6. The T cells expressing CAR and T-box mutants (TBOX Del(AG24), bar with vertical lines) produced more IFNγ than CAR alone, and produced approximately the same amount of IFNγ as native T-bet (gray bar).

Therefore, the experimental results disclosed in the examples demonstrate that engineering primary T cells to express a CAR and a transcription factor, e.g., T-bet or a mutated form thereof, elicits one or more of the following effects: (i) increases the expression of CARs by said T cells, (ii) promotes the differentiation of CD4+ T cells into $T_H1$ cells, (iii) promotes the production of proinflammatory ($T_H1$) cytokines such as IL-2, IFN-γ, and TNF-α, (iv) suppresses the production of $T_H2$ cytokines such as IL-13 and/or (v) suppresses the development of other $T_H$ (non $T_H1$) cells. Based on these results CAR-T cells according to the invention should be well suited for use in human or non-human immunotherapy, e.g., for the treatment of cancer, infectious disease, allergy, autoimmunity or inflammatory conditions.

Example 7: Luciferase Survival Assay

A luciferase survival assay was used to test the ability of antigen-specific CAR T cells (with and without transcription factor expression) to kill antigen-expressing tumor cells at various effector:target (E:T) ratios.

Figure 9A:
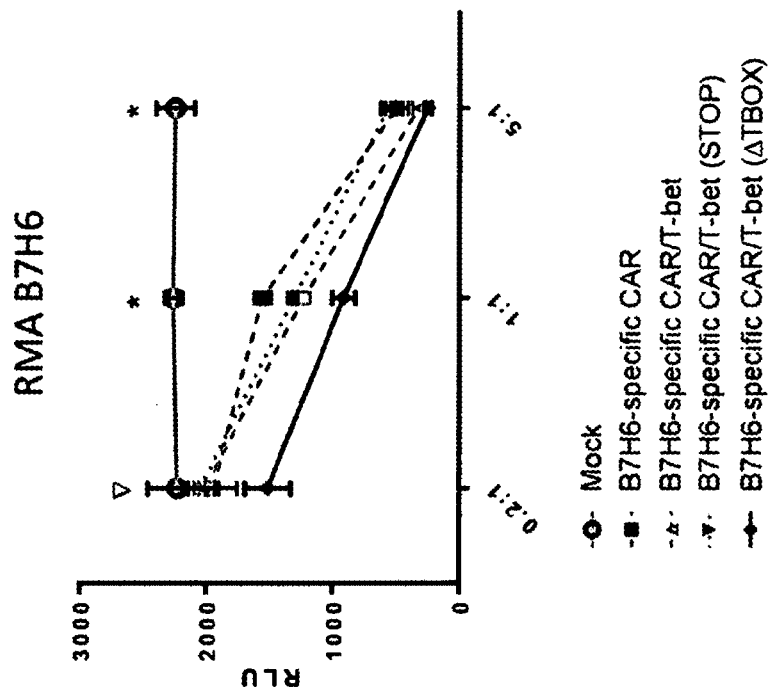
FIGS. 9A-9B show the results of luciferase assays confirming that purified CD4+ T cells that express a B7H6-specific CAR with or without the addition of T-bet or a T-bet variant can kill RMA-B7H6 but not RMA tumor cells.
Figure 9B:
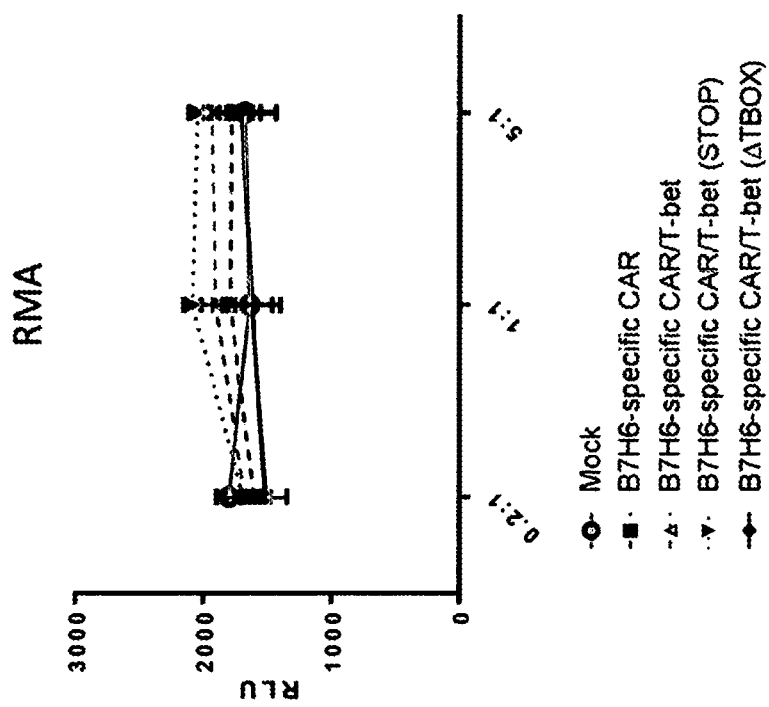

Purified CD4+ T cells were transduced with the vectors described in Example 5: mock, B7H6-specific CAR, B7H6-specific CAR/T-bet, B7H6-specific CART-bet (STOP), and B7H6-specific CAR/T-bet (ΔTBOX). These cells were co-cultured with luciferase-expressing RMA and RMA-B7H6 cells for 24 hours at E:T ratios of 0.2:1, 1:1, and 5:1, and RLU values were measured. None of the five groups of transduced CD4+ T cells killed RMA cells that do not express B7H6 (FIG. 9A). However, all of the B7H6-specific CAR-expressing CD4+ T cells killed RMA cells that expressed B7H6 (FIG. 9B). In particular, at an E:T ratio of 0.2:1, the CART cells that also expressed T-bet (ΔTBOX) showed a significant increase in target cell killing compared to the mock group. At 1:1 and 5:1 E:T ratios, all four B7H6-specific CAR T cells showed significant cell killing compared to the mock group.

Example 8: In Vivo Efficacy of CAR T Cells

The B7H6-specific CAR T cells were tested in an in vivo tumor model. C57Bl/6 mice (n=12 per group) were injected with $1 \times 10^5$ RMA-B7H6 cells (tumor cells expressing B7H6) intravenously. Mice were then administered transduced T cells intravenously, seven days post tumor injection. Each mouse received $2.5 \times 10^6$ ConA-stimulated B7H6-specific CART cells. The three treatment group were additionally administered $5 \times 10^6$ purified CD4+ T cells that were transduced with: Mock, B7H6-specific CAR, or B7H6-specific CART-bet (ΔTBOX). Each mouse thus received $7.5 \times 10^6$ T cells total. Mice were monitored for 40 days post tumor injection to determine survival. Data were combined from two independent experiments The Kaplan Meier Survival Curve shows that CD4+ CAR T cells expressing T-bet (ΔTBOX) promote survival in lymphoma-bearing mice (FIG. 10).

It will be appreciated that the methods of the present invention can be incorporated in the form of a variety of embodiments, only a few of which are disclosed herein. It will be apparent for the specialist in the field that other embodiments exist and do not depart from the spirit of the invention. Thus, the described embodiments are illustrative and should not be construed as restrictive.

The publications and other materials used herein to illuminate the background of the invention, and in particular, to provide additional details with respect to its practice, are each individually incorporated herein by reference in their entirety for all purposes.

What is claimed is:

1. A nucleic acid construct or constructs comprised in a CD4$^+$ T cell, the nucleic acid construct or constructs comprising:
   (i) a nucleic acid encoding a chimeric antigen receptor (CAR); and
   (ii) at least one other nucleic acid encoding a mutated form of T-box transcription factor 21 (T-bet),
wherein (i) and (ii) are on the same or different constructs, and wherein the mutated form of T-bet lacks the T-box domain.

2. The construct or constructs of claim 1, wherein the mutated form of T-bet elicits one or more of the following effects:
   (i) enhances the expression of said CAR by said CD4$^+$ T cell,
   (ii) promotes the development of the CD4$^+$ T cell to a $T_H1$ cell,
   (iii) promotes the expression of IFNγ by the CD4$^+$ T cell or its progeny,
   (iv) suppresses the development of the CD4$^+$ T cell or its progeny into a non-$T_H1$ cells,
   (v) suppresses the expression of $T_H2$ cytokines by said CD4$^+$ T cell or its progeny; and/or
   (vi) enhances the CD4$^+$ T cell's killing of target cells expressing the antigen bound by the CAR.

3. The construct or constructs of claim 1, wherein the mutated form of T-bet is a mutated form of human or murine T-bet.

4. The construct or constructs of claim 1, wherein:
   (i) the nucleic acid encoding the mutated form of T-bet comprises a stop codon within nucleic acid residues corresponding to nucleic acid residues 200-250 of a nucleic acid encoding the amino acid sequence of SEQ ID NO: 22 or 23;
   (ii) the nucleic acid encoding the mutated form of T-bet comprises a stop codon at nucleic acid positions corresponding to nucleic acid residues 214-216 of a nucleic acid encoding the amino acid sequence of SEQ ID NO: 22 or 23;
   (iii) the nucleic acid encoding the mutated form of T-bet lacks nucleic acid residues corresponding to nucleic acid residues 300-400, 300-500, 400-600, 400-700, 500-800, 600-900, 400-1000, 400-1100, or 400-1200 of a nucleic acid encoding the amino acid sequence of SEQ ID NO: 22 or 23;
   (iv) the nucleic acid encoding the mutated form of T-bet lacks nucleic acid residues corresponding to nucleic acid residues 403-978 of a nucleic acid encoding murine T-bet comprising the amino acid sequence of SEQ ID NO: 22 or 23; and/or
   (v) the mutated form of T-bet further lacks the transactivation domain,
wherein the mutated form of T-bet is a mutated form of human or murine T-bet.

5. The construct or constructs of claim 1, which further comprises a nucleic acid encoding STAT-1 or STAT-4 or chimeric, truncated or mutated form thereof.

6. The construct or constructs of claim 1, wherein the CAR comprises an antigen binding domain or receptor, a transmembrane domain, and one or more immune signaling or costimulatory endodomains.

7. The construct or constructs of claim 1, further comprising nucleic acid sequences encoding or comprising one or more of:
   (i) a promoter;
   (ii) a transcription enhancer;
   (iii) a self-cleaving peptide cis-acting hydrolase element (CHVSEL) located between the CAR and the mutated form of T-bet;
   (iv) a protein that is capable of triggering cell suicide or elimination;
   (v) a suicide gene;
   (vi) one or more internal ribosomal entry sites (IRES);
   (vii) a gene encoding a protein whose expression allows for selection of a cell harboring the vector;
   (viii) one or more CHVSEL; or
   (ix) one or more IRES between the nucleic acid encoding the CAR and the nucleic acid encoding the mutated form of T-bet.

8. The construct or constructs of claim 1, wherein:
   (i) the CAR comprises an antigen binding domain that specifically recognizes any of: CD19, CD20, CD22, kappa light chain, CD38, receptor-tyrosine-kinase-like orphan receptor 1 (ROR1), CD30, CD33, epithelial glycoprotein (EGP) 40, tumor-associated glycoprotein 72, prostate-specific membrane antigen, prostate stem cell antigen, ganglioside (GD) 3, high molecular weight melanoma-associated antigen, HLA-A1 MAGEA1, ErbB2, mucin (MUC) 1, MUC16, folate receptor-α, CD44v7/8, carbonic anhydrase 9, G250/CAIX, GD2, CD171, nerve cell adhesion molecule, fetal acetylcholine receptor, ErB3/4, epidermal growth factor receptor VIII, carcinoembryonic antigen, EGP2, mesothelin, natural killer group 2 member D ligands, B7-H6, IL-13 receptor α2, HLA-A2 NY-ESO-1, CD44v6, $α_vβ_6$ integrin, 8H9, vascular endothelial growth factor receptors, or 5T4;
   (ii) the CAR comprises an antigen binding domain which specifically recognizes B7-H6;
   (iii) the CAR comprises a human, humanized, or chimeric antigen binding domain, optionally wherein the antigen binding domain comprises a human, humanized, or chimeric scFv; and/or
   (iv) the CAR comprises an antigen binding domain which specifically recognizes B7-H6 and comprises a heavy chain variable domain (VH) comprising a CDRH1, a CDRH2, and a CDRH3 and a light chain variable domain (VL) comprising a CDRL1, a CDRL2, and a CDRL3, wherein the amino acid sequences of the CDRH1, the CDRH2, the CDRH3, the CDRL1, the CDRL2, and the CDRL3 are those contained in TZ.47 scFv comprising the amino acid sequence of SEQ ID NO:13.

9. The construct or constructs of claim 1, wherein
(i) the CAR comprises a transmembrane domain derived from a protein selected from the group consisting of CD28, CD3 ε, CD4, CD5, CD8, CD9, CD16, CD22, CD33, CD37, CD45, CD64, CD80, CD86, CD134, CD137, CD154, TCRα, TCRβ, and CD3ζ;
(ii) the CAR comprises a transmembrane domain of CD28 and/or an endodomain of CD28;
(iii) the CAR comprises at least one of the endodomains of one or more of a lymphocyte receptor chain, a TCR/CD3 complex protein, an Fc receptor subunit, an IL-2 receptor subunit, FcRγ, FcRβ, CD3γ, CD3δ, CD3ε, CD5, CD22, CD79a, CD79b, CD66d, CD2, CD4, CD5, CD8α, CD8β, CD28, CD134, CD137, ICOS, CD122, CD132, CD40, CD154, FcεRI, DAP10, DAP12 or CD3ζ;
(iv) the CAR further comprises one or more costimulatory endodomains derived from a protein selected from the group consisting of an MHC class I molecule, TNF receptor proteins, Immunoglobulin-like proteins, cytokine receptors, integrins, signaling lymphocytic activation molecules (SLAM proteins), activating NK cell receptors, a Toll ligand receptor, B7-H3, BAFFR, BTLA, BLAME (SLAMF8), CD2, CD4, CD5, CD7, CD8α, CD8β, CD11a, LFA-1 (CD11a/CD18), CD11b, CD11c, CD11d, CD18, CD19, CD19a, CD27, CD28, CD29, CD30, CD40, CD49a, CD49D, CD49f, CD69, CD84, CD96 (Tactile), CD100 (SEMA4D), CD103, OX40 (CD134), 4-1BB (CD137), SLAM (SLAMF1, CD150, IPO-3), CD160 (BY55), SELPLG (CD162), DNAM1 (CD226), Ly9 (CD229), SLAMF4 (CD244, 2B4), ICOS (CD278), CEACAM1, CDS, CRTAM, DAP10, GADS, GITR, HVEM (LIGHTR), IA4, ICAM-1, IL2R β, IL2R γ, IL7R α, ITGA4, ITGA6, ITGAD, ITGAE, ITGAL, ITGAM, ITGAX, ITGB1, ITGB2, ITGB7, KIRDS2, LAT, LFA-1, LIGHT, LTBR, NKG2C, NKG2D, NKp30, NKp44, NKp46, NKp80 (KLRF1), PAG/Cbp, PD-1, PSGL1, SLAMF6 (NTB-A, Ly108), SLAMF7, SLP-76, TNFR2, TRANCE/RANKL, VLA1, VLA-6, and a ligand that specifically binds with CD83;
(v) the nucleic acid construct includes sequences encoding the endodomains of CD28 and CD3ζ; or
(vi) a combination of the foregoing.

10. The construct or constructs of claim 1, wherein the CAR comprises:
(a) a scFv which specifically binds to an antigen of interest, optionally CD19 or B7-H6;
(b) a transmembrane domain;
(c) a CD28 endodomain; and
(d) a CD3 ζ endodomain.

11. The construct or constructs of claim 1, wherein the nucleic acid encoding the CAR and the nucleic acid encoding the mutated form of T-bet are on the same vector or are on different vectors.

12. The construct or constructs of claim 1, wherein
(i) the nucleic acid encoding the CAR comprises a gene encoding a C-type lectin-like natural killer cell receptor and an immune signaling receptor containing an immunoreceptor tyrosine-based activation motif;
(ii) expression of the nucleic acid encoding the CAR and the nucleic acid encoding the mutated form of T-bet are regulated by different or the same constitutive or inducible promoter(s); and/or
(iii) the nucleic acid encoding the CAR and the nucleic acid encoding the mutated form of T-bet are separated by a self-cleaving peptide or CHYSEL.

13. A vector or vectors comprising the construct or constructs of claim 1, optionally wherein the vector or vectors are selected from the group consisting of a DNA vector, an RNA vector, a plasmid, a lentivirus vector, adenoviral vector, a retrovirus vector, and an in vitro transcribed vector.

14. A recombinant $CD4^+$ T cell or a cell population comprising the recombinant $CD4^+$ T cell, wherein the recombinant $CD4^+$ T cell comprises the nucleic acid construct or constructs of claim 1 or vector or vectors containing said nucleic acid construct or constructs, optionally wherein the recombinant $CD4^+$ T cell is: a primary human $CD4^+$ T cell; a T cell; a T cell progenitor cell; an immature T cell; an effector T (TEFF) cell; a memory T cell, optionally a stem cell memory T (TSCM) cell, a central memory T (TCM) cell, an effector memory T (TEM) cell, or a terminally differentiated effector memory T cell; a tumor-infiltrating lymphocyte (TIL); an immature T cell; a mature T cell; a regulatory T (Treg) cell; a TH1 cell; a TH2 cell; a TH3 cell; a TH17 cell; a TH9 cell; a TH22 cell; a follicular helper T cell; an α/β T cell; or a δ/γ T cell.

15. The recombinant $CD4^+$ T cell or cell population according to claim 14, wherein the $CD4^+$ T cell is further engineered to:
(i) eliminate or reduce the expression or functionality of the T cell's endogenous T cell receptor (TCR);
(ii) express the dominant negative form of the transforming growth factor β (TGFβ) receptor (DNR);
iii) overexpress pro-survival signals, reverse anti-survival signals, overexpress Bcl-xL, over-express BCL-2, inhibit the function of cell death genes (optionally Bak or Bax), overexpress hTERT, and/or eliminate Fas expression;
(iv) evade immunosuppressive mediators;
(v) inactivate the expression or functionality of a human leukocyte antigen (HLA) gene or HLA regulator gene product;
(vi) comprise a homing mechanism;
(vii) express a protein that is capable of triggering cell suicide or elimination; and/or
(viii) express a protein whose expression allows for selection of cells comprising the nucleic acid construct or constructs.

16. The recombinant $CD4^+$ T cell or cell population according to claim 14, wherein the recombinant $CD4^+$ T cell is engineered to express a second nucleic acid construct comprising another CAR, wherein said other CAR comprises an antigen binding domain or receptor, a transmembrane domain, and one or more of an immune signaling or costimulatory endodomain.

17. A therapeutic or pharmaceutical composition comprising a therapeutically or diagnostically effective amount of a recombinant $CD4^+$ T cell or cell population according to claim 14, optionally further comprising a pharmaceutically acceptable carrier, diluent or excipient.

18. The construct or constructs of claim 1, wherein the mutated form of T-bet comprises the amino acid sequence of human T-bet comprising SEQ ID NO: 23 except that it lacks the T-box domain.

19. The construct or constructs of claim 12, wherein, in (iii), the self-cleaving peptide or CHYSEL gene is selected from: foot-and-mouth disease virus (FMDV) self-cleaving polypeptide 2A sequence (SEQ ID NO: 2); sea urchin (*Strongylocentrotus purpuratus*) 2A sequence (SEQ ID NO: 3); sponge (*Amphimedon queenslandica*) 2A sequence (SEQ ID NO: 4 or SEQ ID NO: 5); acorn worm (*Saccoglossus kowalevskii*) 2A sequence (SEQ ID NO: 6); amphioxus (*Branchiostoma floridae*) 2A sequence (SEQ ID NO: 7 or SEQ ID NO: 8); porcine teschovirus-1 2A sequence (SEQ ID NO: 9); *Thoseaasigna* virus 2A sequence (SEQ ID NO: 10); equine rhinitis A virus 2A sequence (SEQ ID NO: 11); or a synthetic sequence that includes the 2A consensus sequence D-X-E-X-N-P-G-P (SEQ ID NO: 12), in which X is any amino acid residue, or any homolog thereof; or a combination of any of the foregoing.

20. The construct or constructs of claim 1, wherein the mutated form of T-bet comprises the amino acid sequence of human T-bet comprising SEQ ID NO: 23 except that it lacks the transactivation domain and the T-box domain.

\* \* \* \* \*